US009173645B2

(12) United States Patent
Overes et al.

(10) Patent No.: US 9,173,645 B2
(45) Date of Patent: Nov. 3, 2015

(54) ANCHOR ASSEMBLY INCLUDING EXPANDABLE ANCHOR

(75) Inventors: Tom Overes, Langendorf (CH); Daniel Vennard, West Chester, PA (US); Jamie Manos, West Chester, PA (US); Kevin Henrichsen, West Chester, PA (US); Wamis Singhatat, West Chester, PA (US); Scott Larsen, West Chester, PA (US); James Talbot, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 350 days.

(21) Appl. No.: 13/095,192

(22) Filed: Apr. 27, 2011

(65) Prior Publication Data

US 2011/0270278 A1 Nov. 3, 2011

Related U.S. Application Data

(60) Provisional application No. 61/328,251, filed on Apr. 27, 2010, provisional application No. 61/398,699, filed on Jun. 29, 2010, provisional application No. 61/432,755, filed on Jan. 14, 2011, provisional application No. 61/461,490, filed on Jan. 18, 2011, provisional application No. 61/443,142, filed on Feb. 15, 2011.

(51) Int. Cl.
*A61B 17/04* (2006.01)
*A61B 17/00* (2006.01)
(Continued)

(52) U.S. Cl.
CPC ......... *A61B 17/0057* (2013.01); *A61B 17/0487* (2013.01); *A61B 17/842* (2013.01);
(Continued)

(58) Field of Classification Search
CPC ............. A61B 17/0057; A61B 17/842; A61B 2017/00663; A61B 2017/00615
USPC ......................................... 606/232, 151, 228
See application file for complete search history.

(56) References Cited

U.S. PATENT DOCUMENTS 233,475 A 10/1880 Cook et al.
261,501 A 7/1882 Vandermark
(Continued)

FOREIGN PATENT DOCUMENTS

CN 101056587 10/2007
DE 4207854 9/1993
(Continued)

OTHER PUBLICATIONS

International Patent Application No. PCT/US05/34495: International Search Report dated Apr. 4, 2007, 2 pages.
(Continued)

*Primary Examiner* — Gregory Anderson
*Assistant Examiner* — Christina Lauer
(74) *Attorney, Agent, or Firm* — Baker & Hostetler LLP

(57) ABSTRACT

An anchor assembly can include at least one anchor member, such as a pair of anchor members that are configured to be implanted in a target anatomical location in a first configuration, and can subsequently be actuated to an expanded configuration that secures the anchor members in the target anatomy. The anchor assembly can further include a connector member that attaches the pair of anchor members together across a gap so as to approximate the anatomical defect.

37 Claims, 81 Drawing Sheets

(51) Int. Cl.
*A61B 17/84* (2006.01)
*A61B 17/06* (2006.01)

(52) U.S. Cl.
CPC .................. *A61B2017/00623* (2013.01); *A61B 2017/00663* (2013.01); *A61B 2017/0406* (2013.01); *A61B 2017/0409* (2013.01); *A61B 2017/0464* (2013.01); *A61B 2017/0475* (2013.01); *A61B 2017/0477* (2013.01); *A61B 2017/0496* (2013.01); *A61B 2017/06176* (2013.01)

(56) References Cited

U.S. PATENT DOCUMENTS

| | | |
|---|---|---|
| 330,087 A | 11/1885 | Binns |
| 400,743 A | 4/1889 | Brown |
| 2,490,364 A | 12/1949 | Livingston |
| 3,580,256 A | 5/1971 | Wilkinson et al. |
| 3,867,728 A | 2/1975 | Stubstad et al. |
| 3,908,677 A | 9/1975 | Beach |
| 3,987,806 A | 10/1976 | Gilbert |
| 4,006,747 A | 2/1977 | Kronenthal et al. |
| 4,235,238 A | 11/1980 | Ogiu et al. |
| 4,669,473 A | 6/1987 | Richards et al. |
| 4,741,330 A | 5/1988 | Hayhurst |
| 4,778,990 A | 10/1988 | Laughlin |
| 4,994,028 A | 2/1991 | Leonard et al. |
| 5,021,059 A | 6/1991 | Kensey et al. |
| 5,041,129 A | 8/1991 | Hayhurst et al. |
| 5,053,046 A | 10/1991 | Janese |
| 5,062,344 A | 11/1991 | Gerker |
| 5,120,596 A | 6/1992 | Yamada |
| 5,156,616 A | 10/1992 | Meadows et al. |
| 5,269,809 A | 12/1993 | Hayhurst et al. |
| 5,281,238 A | 1/1994 | Chin et al. |
| 5,403,348 A | 4/1995 | Bonutti |
| 5,417,691 A | 5/1995 | Hayhurst |
| 5,464,426 A | 11/1995 | Bonutti |
| 5,478,353 A | 12/1995 | Yoon |
| 5,507,754 A | 4/1996 | Green et al. |
| 5,522,846 A | 6/1996 | Bonutti |
| 5,527,343 A | 6/1996 | Bonutti |
| 5,540,703 A | 7/1996 | Barker et al. |
| 5,549,630 A | 8/1996 | Bonutti |
| 5,562,684 A | 10/1996 | Kammerer |
| 5,562,736 A | 10/1996 | Ray et al. |
| 5,571,189 A | 11/1996 | Kuslich |
| 5,584,862 A | 12/1996 | Bonutti |
| 5,601,557 A | 2/1997 | Hayhurst |
| 5,626,614 A | 5/1997 | Hart |
| 5,628,756 A | 5/1997 | Barker, Jr. et al. |
| 5,643,319 A | 7/1997 | Green et al. |
| 5,649,945 A | 7/1997 | Ray et al. |
| 5,699,657 A | 12/1997 | Paulson |
| 5,702,462 A | 12/1997 | Oberlander |
| 5,728,109 A | 3/1998 | Schulze et al. |
| 5,733,306 A | 3/1998 | Bonutti |
| 5,824,093 A | 10/1998 | Ray et al. |
| 5,906,626 A | 5/1999 | Carrillo |
| 5,941,900 A | 8/1999 | Bonutti |
| 5,944,739 A | 8/1999 | Zlock et al. |
| 5,951,590 A | 9/1999 | Goldfarb |
| 5,957,953 A | 9/1999 | DiPoto et al. |
| 5,970,697 A | 10/1999 | Jacobs et al. |
| 5,989,252 A | 11/1999 | Fumex |
| 6,056,773 A | 5/2000 | Bonutti |
| 6,077,292 A | 6/2000 | Bonutti |
| 6,110,183 A | 8/2000 | Cope |
| 6,113,611 A | 9/2000 | Allen et al. |
| 6,146,422 A | 11/2000 | Lawson |
| 6,179,860 B1 | 1/2001 | Fulton et al. |
| 6,187,048 B1 | 2/2001 | Milner et al. |
| 6,209,550 B1 | 4/2001 | Powell |
| 6,224,630 B1 | 5/2001 | Bao et al. |
| 6,245,107 B1 | 6/2001 | Ferree |
| 6,287,325 B1 | 9/2001 | Bonutti |
| 6,296,659 B1 | 10/2001 | Foerster |
| 6,306,159 B1 | 10/2001 | Schwartz et al. |
| 6,325,816 B1 | 12/2001 | Fulton et al. |
| 6,409,742 B1 | 6/2002 | Fulton et al. |
| 6,432,123 B2 | 8/2002 | Schwartz et al. |
| 6,482,235 B1 | 11/2002 | Lambrecht et al. |
| 6,508,839 B1 | 1/2003 | Lambrecht et al. |
| 6,511,498 B1 | 1/2003 | Fumex |
| 6,530,933 B1 | 3/2003 | Yeung et al. |
| 6,579,291 B1 | 6/2003 | Keith et al. |
| 6,592,625 B2 | 7/2003 | Cauthen |
| 6,656,182 B1 | 12/2003 | Hayhurst |
| 6,689,125 B1 | 2/2004 | Keith et al. |
| 6,719,797 B1 | 4/2004 | Ferree |
| 6,758,855 B2 | 7/2004 | Fulton et al. |
| 6,964,674 B1 | 11/2005 | Matsuura et al. |
| 6,972,027 B2 | 12/2005 | Fallin et al. |
| 6,984,247 B2 | 1/2006 | Cauthen |
| 6,986,775 B2 | 1/2006 | Morales et al. |
| 6,991,643 B2 | 1/2006 | Saadat |
| 6,997,956 B2 | 2/2006 | Cauthen |
| 7,004,970 B2 | 2/2006 | Cauthen, III et al. |
| 7,033,393 B2 | 4/2006 | Gainor et al. |
| 7,033,395 B2 | 4/2006 | Cauthen |
| 7,041,052 B2 | 5/2006 | Saadat et al. |
| 7,048,754 B2 | 5/2006 | Martin et al. |
| 7,052,516 B2 | 5/2006 | Cauthen et al. |
| 7,128,708 B2 | 10/2006 | Saadat et al. |
| 7,153,312 B1 | 12/2006 | Torrie et al. |
| 7,189,235 B2 | 3/2007 | Cauthen |
| 7,285,124 B2 | 10/2007 | Foerster |
| 7,303,575 B2 | 12/2007 | Ogle |
| 7,329,279 B2 | 2/2008 | Haug et al. |
| 7,335,221 B2 | 2/2008 | Collier et al. |
| 7,347,863 B2 | 3/2008 | Rothe et al. |
| 7,390,332 B2 | 6/2008 | Selvitelli et al. |
| 7,468,074 B2 | 12/2008 | Caborn et al. |
| 7,491,212 B2 | 2/2009 | Sikora et al. |
| 7,494,496 B2 | 2/2009 | Swain et al. |
| 7,601,165 B2 | 10/2009 | Stone |
| 7,615,076 B2 | 11/2009 | Cauthen, III et al. |
| 7,621,925 B2 | 11/2009 | Saadat et al. |
| 7,651,509 B2 | 1/2010 | Bojarski et al. |
| 7,658,750 B2 | 2/2010 | Li |
| 7,666,193 B2 | 2/2010 | Starksen et al. |
| 7,670,379 B2 | 3/2010 | Cauthen |
| 7,670,380 B2 | 3/2010 | Cauthen, III |
| 7,678,135 B2 | 3/2010 | Maahs et al. |
| 7,731,732 B2 | 6/2010 | Ken |
| 7,736,379 B2 | 6/2010 | Ewers et al. |
| 7,749,250 B2 | 7/2010 | Stone et al. |
| 7,749,273 B2 | 7/2010 | Cauthen, III et al. |
| 7,753,941 B2 | 7/2010 | Keith et al. |
| 7,776,096 B2 | 8/2010 | Cauthen |
| 7,828,850 B2 | 11/2010 | Cauthen, III et al. |
| 7,846,208 B2 | 12/2010 | Cauthen, III et al. |
| 7,857,830 B2 | 12/2010 | Stone et al. |
| 7,905,904 B2 | 3/2011 | Stone et al. |
| 7,905,923 B2 | 3/2011 | Keith et al. |
| 7,909,851 B2 | 3/2011 | Stone et al. |
| 7,909,879 B2 | 3/2011 | Cauthen |
| 7,922,768 B2 | 4/2011 | Cauthen, III et al. |
| 7,935,147 B2 | 5/2011 | Wales |
| 7,951,201 B2 | 5/2011 | Cauthen et al. |
| 7,959,650 B2 | 6/2011 | Kaiser et al. |
| 7,963,992 B2 | 6/2011 | Cauthen et al. |
| 7,985,257 B2 | 7/2011 | Cauthen et al. |
| 7,993,405 B2 | 8/2011 | Cauthen et al. |
| 8,034,112 B2 | 10/2011 | Cauthen et al. |
| 8,048,160 B2 | 11/2011 | Cauthen |
| 8,083,768 B2 | 12/2011 | Ginn et al. |
| 8,088,130 B2 | 1/2012 | Kaiser et al. |
| 8,088,165 B2 | 1/2012 | Cauthen et al. |
| 8,100,914 B2 | 1/2012 | Cauthen et al. |
| 8,118,836 B2 | 2/2012 | Denham et al. |
| 8,128,640 B2 | 3/2012 | Harris et al. |
| 8,128,658 B2 | 3/2012 | Kaiser et al. |

(56) References Cited

U.S. PATENT DOCUMENTS

| | | |
|---|---|---|
| 8,128,698 B2 | 3/2012 | Bentley et al. |
| 8,137,382 B2 | 3/2012 | Denham et al. |
| 8,216,253 B2 | 7/2012 | Saadat et al. |
| 8,216,260 B2 | 7/2012 | Lam et al. |
| 8,298,291 B2 | 10/2012 | Ewers et al. |
| 8,814,903 B2 | 8/2014 | Sengun et al. |
| 8,828,053 B2 | 9/2014 | DeMatteo et al. |
| 8,920,436 B2 | 12/2014 | Lam et al. |
| 8,926,634 B2 | 1/2015 | Rothe et al. |
| 2002/0065536 A1 | 5/2002 | Hart et al. |
| 2002/0115999 A1 | 8/2002 | McDevitt et al. |
| 2002/0143359 A1 | 10/2002 | Fulton et al. |
| 2002/0188301 A1 | 12/2002 | Dallara et al. |
| 2003/0167071 A1 | 9/2003 | Martin et al. |
| 2004/0097980 A1 | 5/2004 | Ferree |
| 2004/0153074 A1 | 8/2004 | Bojarski et al. |
| 2004/0162618 A1 | 8/2004 | Mujwid et al. |
| 2004/0225183 A1 | 11/2004 | Michlitsch et al. |
| 2004/0243171 A1 | 12/2004 | Fulton et al. |
| 2005/0080422 A1 | 4/2005 | Otte et al. |
| 2005/0228448 A1 | 10/2005 | Li |
| 2005/0251157 A1 | 11/2005 | Saadat |
| 2005/0251159 A1 | 11/2005 | Ewers et al. |
| 2005/0251177 A1 | 11/2005 | Saadat et al. |
| 2005/0251202 A1 | 11/2005 | Ewers et al. |
| 2005/0251205 A1 | 11/2005 | Ewers et al. |
| 2005/0251206 A1 | 11/2005 | Maahs et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0277966 A1 | 12/2005 | Ewers et al. |
| 2005/0277981 A1 | 12/2005 | Maahs et al. |
| 2005/0283192 A1 | 12/2005 | Torrie et al. |
| 2005/0283246 A1 | 12/2005 | Cauthen, III et al. |
| 2006/0064126 A1 | 3/2006 | Fallin et al. |
| 2006/0178680 A1 | 8/2006 | Nelson et al. |
| 2006/0190042 A1 | 8/2006 | Stone et al. |
| 2006/0259076 A1 | 11/2006 | Burkhart et al. |
| 2006/0265008 A1 | 11/2006 | Maruyama et al. |
| 2007/0010857 A1* | 1/2007 | Sugimoto et al. ............ 606/232 |
| 2007/0027476 A1 | 2/2007 | Harris et al. |
| 2007/0073320 A1 | 3/2007 | Mikkaichi et al. |
| 2007/0083236 A1 | 4/2007 | Sikora et al. |
| 2007/0100348 A1 | 5/2007 | Cauthen, III et al. |
| 2007/0129804 A1 | 6/2007 | Bentley et al. |
| 2007/0156245 A1 | 7/2007 | Cauthen, III et al. |
| 2007/0162054 A1 | 7/2007 | Horaguchi |
| 2007/0162120 A1 | 7/2007 | Bouffier |
| 2007/0185532 A1* | 8/2007 | Stone et al. ................ 606/232 |
| 2007/0255285 A1 | 11/2007 | Trieu |
| 2007/0276433 A1 | 11/2007 | Huss |
| 2008/0009888 A1 | 1/2008 | Ewers et al. |
| 2008/0015635 A1 | 1/2008 | Olsen et al. |
| 2008/0015636 A1 | 1/2008 | Olsen et al. |
| 2008/0033487 A1 | 2/2008 | Schwartz et al. |
| 2008/0086155 A1 | 4/2008 | Rothe et al. |
| 2008/0097484 A1 | 4/2008 | Lim et al. |
| 2008/0097522 A1 | 4/2008 | Chopra |
| 2008/0140092 A1 | 6/2008 | Stone et al. |
| 2008/0140093 A1 | 6/2008 | Stone et al. |
| 2008/0147086 A1 | 6/2008 | Pfister et al. |
| 2008/0147102 A1 | 6/2008 | Rotella et al. |
| 2008/0167658 A1 | 7/2008 | Kerr et al. |
| 2008/0177302 A1 | 7/2008 | Shumas |
| 2008/0177304 A1 | 7/2008 | Westra et al. |
| 2008/0188893 A1 | 8/2008 | Selvitelli et al. |
| 2008/0195145 A1 | 8/2008 | Bonutti et al. |
| 2008/0200930 A1 | 8/2008 | Saadat et al. |
| 2008/0208225 A1 | 8/2008 | Seibold et al. |
| 2008/0208226 A1 | 8/2008 | Seibold et al. |
| 2008/0228198 A1 | 9/2008 | Traynor et al. |
| 2008/0228266 A1 | 9/2008 | McNamara et al. |
| 2008/0228267 A1 | 9/2008 | Spence et al. |
| 2008/0243151 A1 | 10/2008 | Binmoeller et al. |
| 2008/0269781 A1 | 10/2008 | Funamura et al. |
| 2008/0281355 A1 | 11/2008 | Mayer et al. |
| 2008/0312689 A1 | 12/2008 | Denham et al. |
| 2008/0319524 A1 | 12/2008 | Yachia et al. |
| 2009/0018561 A1 | 1/2009 | Schwartz et al. |
| 2009/0030522 A1 | 1/2009 | Cauthen, III et al. |
| 2009/0036937 A1 | 2/2009 | Cauthen, III et al. |
| 2009/0036989 A1 | 2/2009 | Cauthen, III et al. |
| 2009/0036990 A1 | 2/2009 | Cauthen, III et al. |
| 2009/0062846 A1 | 3/2009 | Ken |
| 2009/0062847 A1 | 3/2009 | Ken |
| 2009/0062848 A1 | 3/2009 | Ken |
| 2009/0062850 A1 | 3/2009 | Ken |
| 2009/0062854 A1 | 3/2009 | Kaiser et al. |
| 2009/0069823 A1 | 3/2009 | Foerster et al. |
| 2009/0076547 A1 | 3/2009 | Sugimoto et al. |
| 2009/0082805 A1 | 3/2009 | Kaiser et al. |
| 2009/0157184 A1 | 6/2009 | Cauthen III et al. |
| 2009/0228042 A1 | 9/2009 | Koogle et al. |
| 2009/0259260 A1 | 10/2009 | Bentley et al. |
| 2009/0306711 A1 | 12/2009 | Stone et al. |
| 2010/0049212 A1 | 2/2010 | Caborn et al. |
| 2010/0069923 A1 | 3/2010 | Nguyen et al. |
| 2010/0094337 A1 | 4/2010 | Maiorino |
| 2010/0094425 A1 | 4/2010 | Bentley et al. |
| 2010/0121376 A1 | 5/2010 | Li |
| 2010/0292731 A1 | 11/2010 | Gittings et al. |
| 2011/0022083 A1* | 1/2011 | DiMatteo et al. ............. 606/228 |
| 2011/0022084 A1 | 1/2011 | Sengun et al. |
| 2011/0077667 A1 | 3/2011 | Singhatal et al. |
| 2011/0082472 A1 | 4/2011 | Harris et al. |
| 2011/0172701 A1 | 7/2011 | Wales et al. |
| 2011/0270278 A1 | 11/2011 | Overes et al. |
| 2012/0004669 A1 | 1/2012 | Overes et al. |
| 2012/0035654 A1 | 2/2012 | Belson |
| 2012/0046693 A1 | 2/2012 | Denham et al. |
| 2012/0053630 A1 | 3/2012 | Denham et al. |
| 2012/0109156 A1 | 5/2012 | Overes et al. |
| 2012/0130422 A1 | 5/2012 | Hootstein |
| 2012/0143215 A1 | 6/2012 | Corrao et al. |
| 2012/0150223 A1 | 6/2012 | Manos et al. |
| 2013/0110165 A1 | 5/2013 | Burkhart et al. |
| 2014/0336703 A1 | 11/2014 | Sengun et al. |
| 2015/0038992 A1 | 2/2015 | DiMatteo et al. |

FOREIGN PATENT DOCUMENTS

| | | |
|---|---|---|
| EP | 0834281 | 4/1998 |
| EP | 0838197 | 4/1998 |
| EP | 1938760 | 7/2008 |
| EP | 1964520 | 9/2008 |
| EP | 2238944 | 10/2010 |
| EP | 2663240 | 11/2013 |
| EP | 2663242 | 11/2013 |
| WO | WO 92/11810 | 7/1992 |
| WO | WO 99/22648 | 5/1999 |
| WO | WO 03/096910 | 11/2003 |
| WO | WO 2004/071307 | 8/2004 |
| WO | WO 2005/011463 | 2/2005 |
| WO | WO 2005/065553 | 7/2005 |
| WO | WO 2006/039296 | 4/2006 |
| WO | WO 2006/117398 | 11/2006 |
| WO | WO 2007/005394 | 1/2007 |
| WO | WO 2008/010738 | 1/2008 |
| WO | WO 2008/048667 | 4/2008 |
| WO | WO 2009/126781 | 10/2009 |
| WO | WO 2009/146402 | 12/2009 |
| WO | WO 2010/088561 | 8/2010 |
| WO | WO 2011/137159 | 11/2011 |
| WO | WO 2012/006161 | 1/2012 |
| WO | WO 2012/096706 | 7/2012 |
| WO | WO 2012/096707 | 7/2012 |

OTHER PUBLICATIONS

Snyder, S.J., "Shoulder Arthroscopy: Arthroscopic Treatment of the Acromioclavicular Joint", Chapter 13, 2nd Edition, 2003, 167-183.
U.S. Appl. No. 60/113,548, filed Dec 23, 1998, Schwartz.
U.S. Appl. No. 60/148,913, filed Aug. 13, 1999, Ferree.

(56) References Cited

OTHER PUBLICATIONS

U.S. Appl. No. 60/149,490, filed Aug. 18, 1999, Lambrecht.
U.S. Appl. No. 60/154,969, filed Sep. 20, 1999, Matsuura.
U.S. Appl. No. 60/161,085, filed Oct. 25, 1999, Lambrecht.
U.S. Appl. No. 09/453,120, filed Dec. 2, 1999, Torrie.
U.S. Appl. No. 60/263,343, filed Jan. 22, 2001, Keith.
Ahlgren et al., "Anular incision technique on the strength and multidirectional flexibility of the healing intervertebral disc," Spine, Apr. 15, 1994, 19(8), 948-954.
Ahlgren et al., "Effect of anular repair on the healing strength of the intervertebral disc: a sheep model," Spine, Sep. 1, 2000, 25(17), 2165-2170.
Arthrex, Inc., "Arthroscopic Meniscal Repair using the Meniscal Cinch: Surgical Technique," www.arthrex.com, © 2008, 6 pages.
Barrett et al., "T-Fix endoscopic meniscal repair: technique and approach to different types of tears," Arthroscopy: The Journal of Arthroscopic and Related Surgery, Apr. 1995, 11(2), 245-251.
Burg et al., "Modulation of Surface and Bulk Properties of Biomedical Polymers," Annals of the New York Academy of Sciences, Dec. 1997, 831, 217-222.
Caborn, D., "Meniscal Repair with the Fast T-Fix Suture System," Smith & Nephew Technique Plus Illustrated Guide, Mar. 2002, 10 pages.
Cauthen, J., "Annulotomy Study Table", Feb. 8, 1999, 1 page.
Cauthen, J., "Microsurgical Annular Reconstruction (Annuloplasty) Following Lumbar Microdiscectomy: A New Technique," Draft Abstract, Sep. 4, 1998, 4 pages.
Cauthen, J., "Microsurgical Annular Reconstruction (Annuloplasty) Following Lumbar Microdiscectomy: A New Technique," Abstract, AANS CNS Section on Disorders of the Spine and Peripheral Nerves Annual Meeting, 1999, 2 pages.
Cauthen,"Microsurgical Annular Reconstruction (Annuloplasty) Following Lumbar Microdiscectomy: Preliminary Report of a New Technique", CNS Boston Massachusetts, Spine & Peripheral Nerves Section (abstract only), http://abstracts.neurosurgeon.org/view.php?id=2790, accessed Oct. 6, 2010, 1999, 1 page.
Cobey, M., "Arthroplasties using compressed ivalon sponge ("intramedic sponge") long-term follow-up studies in 109 cases," Clinical Orthopaedics and Related Research, Sep.-Oct. 1967, 54, 139-144.
Coen et al., "An anatomic evaluation of T-Fix suture device placement for arthroscopic all-inside meniscal repair," Arthroscopy: The Journal of Arthroscopic and Related Surgery, Apr. 1999, 15(3), 275-280.
Dodge, Jr. et al., "Use of Polyvinyl Sponge in Neurosurgery," Journal of Neurosurgery, May 1954, 11(3), 258-261.
Edgerton et al., "Augmentation Mammaplasty: Psychiatric Implications and Surgical Indications," Plastic & Reconstructive Surgery, Apr. 1958, 21(4), 279-305.
Hampton et al., "Healing Potential of the Anulus Fibrosus," Spine, Apr. 1989, 14(4), 398-401.
International Patent Application No. PCT/US2011/034084: International Search Report and Written Opinion dated Jul. 1, 2011, 5 pages.
International Patent Application No. PCT/US2011/042384: International Search Report and Written Opinion dated Feb. 6, 2012, 26 pages.
International Patent Application No. PCT/US2011/058065: International Search Report and Written Opinion dated Apr. 5, 2012, 23 pages.
International Patent Application No. PCT/US2011/058071: International Search Report and Written Opinion dated Feb. 6, 2012, 14 pages.
Kambin et al., "Development of degenerative spondylosis of the lumbar spine after partial discectomy. Comparison of laminotomy, discectomy, and posterolateral discectomy," Spine, Mar. 1, 1995, 20(5), 599-607.
Kotilainen et al., "Microsurgical treatment of lumbar disc herniation: Follow-up of 237 patients," Acta Neurochirurgica, 1993, 120(3-4) 143-149.

Kroschwitz, J. I., "Concise Encyclopedia of Polymer Science and Engineering: Vinyl Alcohol Polymers," Wiley & Sons, 1990, 1233-1236.
Kusaka et al., "The Effect of Annulus Fibrosus Perforation on the Intradiscal Matrix Strain of the Axially Loaded Intervertebral Disc," Transactions of the 44th Annual Meeting, Orthopaedic Research Society, Mar. 16-19, 1998, New Orleans, Louisiana, 23(1), p. 190-32 (Abstract).
Lehmann et al., "Refinements in technique for open lumbar discectomy," International Society for the Study of the Lumbar Spine, 1997, 2 pages.
Liu et al., "Morphologic Characterization of Polyvinyl Sponge (Ivalon) Breast Prosthesis," Archives of Pathol. & Lab. Medicine, Sep. 1996, 120(9), 876-878.
Malemud, C. J., "The Role of Growth Factors in Cartilage Metabolism," Rheum. Dis. Clin. North Am., Aug. 1993, 19(3), 569-580.
Ordway et al., "Failure Properties of a Hydrogel Nucleus in the Intervertebral Disc," North American Spine Society, Oct. 22-25, 1997, 168-169.
Osti et al., "1990 Volvo Award in Experimental Studies: Anulus Tears and Intervertebral Disc Degeneration: An Experimental Study Using an Animal Model," Spine, Aug. 1990, 15(8), 762-767.
Osti et al., "Annular Tears and Disc Degeneration in the Lumbar Spine. A post-mortem study of 135 discs," The Journal of Bone and Joint Surgery, Sep. 1992, 74(5), 678-682.
Panjabi et al., "Intrinsic Disc Pressure as a Measure of Integrity of the Lumbar Spine," Spine, Aug. 1988, 13(8), 913-917.
Peters et al., "Ivalon Breast Prostheses: Evaluation 19 Years after Implantation," Plastic and Reconstructive Surgery, Apr. 1981, 67(4), 514-518.
PR Newswire, "Smith & Nephew Launches Fast-Fix™ AB Meniscal Repair System," http://www.prnewswire.com/news-releases/smith--nephew-launches-fast-fixtm-ab-menis . . . , Accessed Aug. 23, 2010, 1 page.
Ray, C. D., "Prosthetic Disc Nucleus Implants: Update," North American Spine Society 13th Annual Meeting, 1999, 252-253.
Sgaglione et al., "All-Inside Meniscal Repair with the ULTRA FAST-FIX™ Meniscal Repair System," Smith & Nephew Knee Series Technique Guide, Feb. 2008, 12 pages.
Silver et al., "Cartilage Wound Healing: An Overview," Otolaryngol. Clin. North Am., Oct. 1995, 28(5), 847-863.
Smith & Nephew Endoscopy, "Endoscopic Meniscal Repair Using the T-Fix™," Smith & Nephew, May 1996, 16 pages.
Smith & Nephew Endoscopy, "Fast-Fix Meniscal Repair System: Technique Information," http://endo.smith-nephew.com/no/node.asp?NodeId=3045, Accessed Apr. 26, 2011, 3 pages.
Southwick et al., "Prosthetic Replacement of Chest-Wall Defects: An Experimental and Clinical Study", A. M. A. Archives of Surgery, 1956, 72, 901-907.
Unipoint Industries, Inc., "Polyvinyl Alcohol Foam for Surgical and Industrial Use: Data Sheets," Jul. 15, 1989, 6 pages.
Urbaniak et al., "Replacement of intervertebral discs in chimpanzees by silicone-dacron implants: a preliminary report," J. Biomed. Mater. Res. Symposium, May 1973, 7(4), 165-186.
Wageck et al., "Arthroscopic meniscal suture with the "double-loop technique"," Arthroscopy: The Journal of Arthroscopic and Related Surgery, Feb. 1997, 13(1), 120-123.
Yasargil, M. G., "Microsurgical Operation of Herniated Lumbar Disc," Advances in Neurosurgery, Lumbar Disc Adult Hydrocephalus, Springer-Verlag, 1977, 4(81), p. 81.
U.S. Appl. No. 60/160,710, filed Oct. 20, 1999, Cauthen.
U.S. Appl. No. 09/484,706, filed Jan. 18, 2000, Cauthen.
U.S. Appl. No. 61/328,251, filed Apr. 27, 2010, Overes.
U.S. Appl. No. 61/398,699, filed Jun. 29, 2010, Overes et al.
U.S. Appl. No. 61/432,755, filed Jan. 14, 2011, Henrichsen et al.
U.S. Appl. No. 61/461,490, filed Jan. 14, 2011, Henrichsen et al.
U.S. Appl. No. 61/443,142, filed Feb. 15, 2011, Henrichsen et al.
Mitek Brochure, Rapid Loc, "Surgical Technique Guide for Repair of Meniscal Tears," 2001, 6 pages.
Biomet Maxfire Technique Guide, Meniscal Repair, 1994, 16 pages.
Brinckmann, et al., "A Laboratory Model of Lumbar Disc Protrusion," Spine, Jan. 1994, vol. 19, No. 2, 228-235.

(56) References Cited

OTHER PUBLICATIONS

Cayenne Medical, Crossfix Meniscal Repair System, Surgical Technique Guide, Jul. 2009, 4 pages.

Ahlgren et al., "Effect of Annular Repair on the Healing Strength of the Intervertebral Disc," Spine, Sep. 2000, vol. 25, No. 17, 2165-2170.

Hoffmann, et al., "Arthroscopic shoulder stabilization using Mitek anchors," Knee Surg., Sports Traumatol., Arthroscopy, Mar. 1995, vol. 3, Issue 1, 50-54.

Klinger, Proceedings of the 1976 Meeting of the Deutsche Gesellschaft fur Neurochirurgica in Berlin, ACTA Neurochirurgica, Sep. 1977, vol. 36, Issue 3-4, 265-294.

Mayer et al., "Percutaneous Endoscopic Lumbar Discectomy (PELD)," Neurosurg. Rev., Jun. 1993, 115-120.

Mayer et al, "Endoscopic Discectomy in Pediatric and Juvenile Lumbar Disc Herniations," Journal of Pediatric Orthopaedics, Part B, Jan. 1996, 39-43.

Abstracts of the $7^{th}$ Annual Meeting of the Japanese Society of Microsurgery, Oct. 1980, Niigata, Japan, 8 pages.

Maroon, et al., "Microdiscectomy versus Chemonucleoysis," Neurosurgery, May 1985, vol. 16, No. 5, 644-649.

Vuono-Hawkins, et al., "Mechanical Evaluation of a Canine Intervertebral Disc Spacer: In Situ and in Vivo Studies," Journal of Orthopaedic Research, Jan. 1994, 119-127.

European Patent Application No. 05802651.9: European Search Report, dated Aug. 31, 2009, 7 pages.

U.S. Appl. No. 12/509,112: Non-Final Office Action, dated Jul. 12, 2012, 8 pages.

U.S. Appl. No. 12/509,112: Restriction Requirement, dated Nov. 17, 2011, 8 pages.

U.S. Appl. No. 12/509,112: Restriction Requirement, dated Apr. 10, 2012, 6 pages.

U.S. Appl. No. 13/095,192: Restriction Requirement, dated Sep. 6, 2012, 10 pages.

European Patent Application No. 10251328.0; European Search Report dated Oct. 29, 2010.

\* cited by examiner

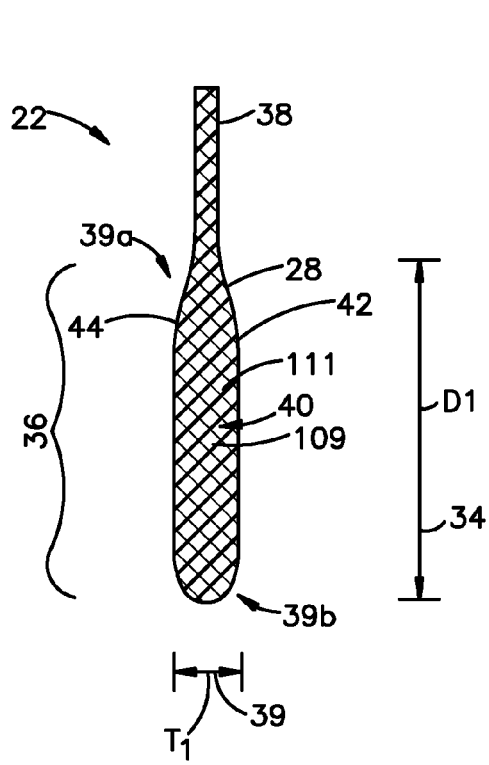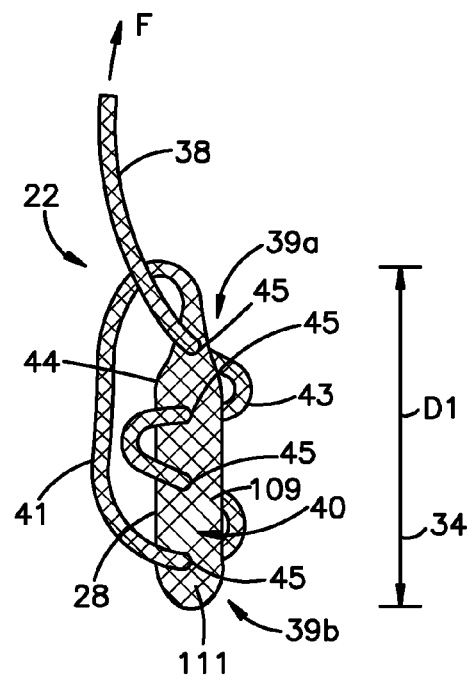
Fig.15A  Fig.15B
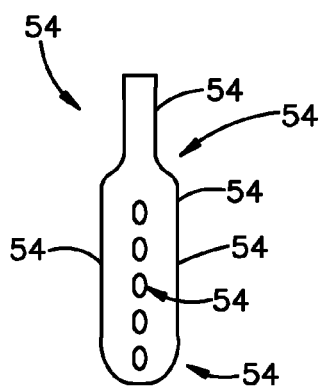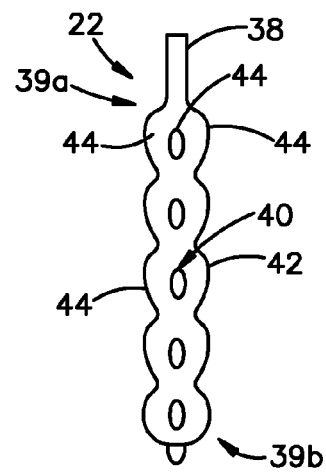
Fig.15C  Fig.15D

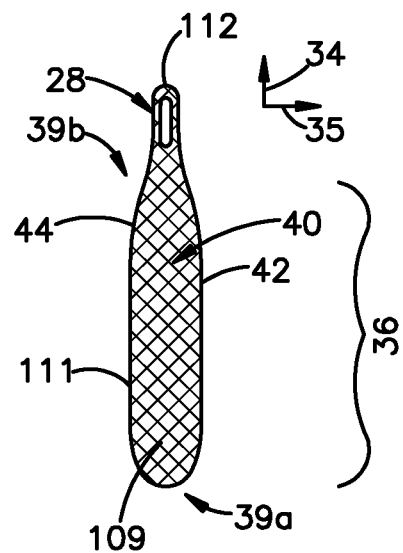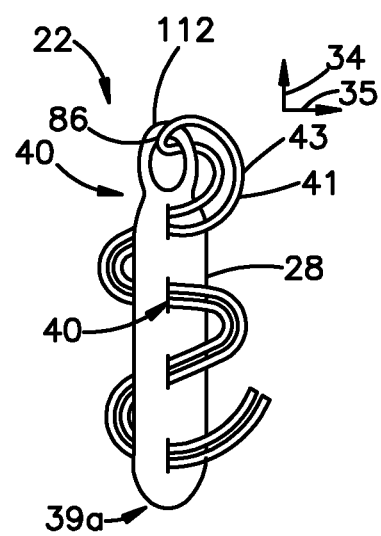
Fig.16A  Fig.16B
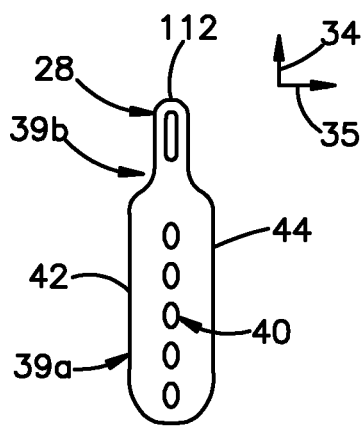
Fig.16C

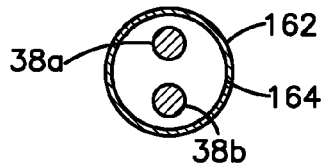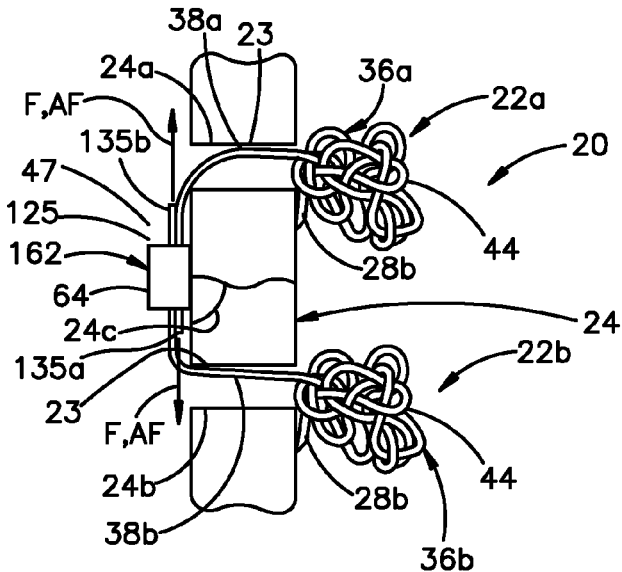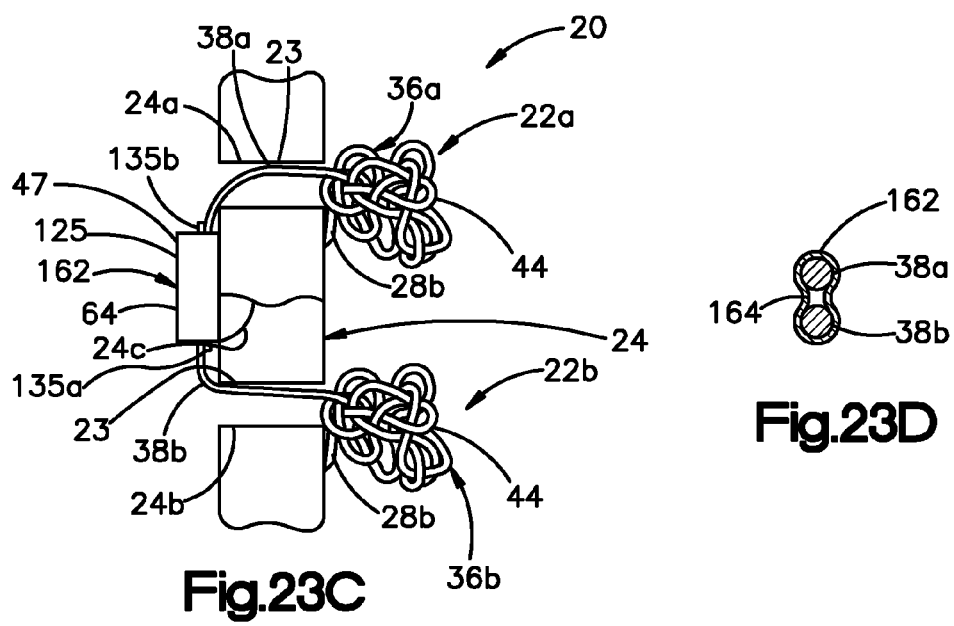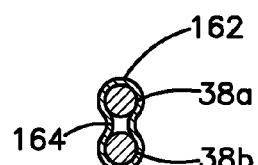

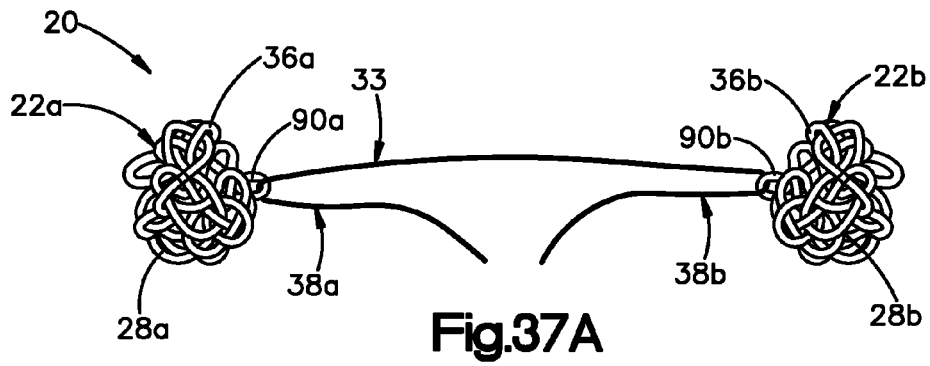
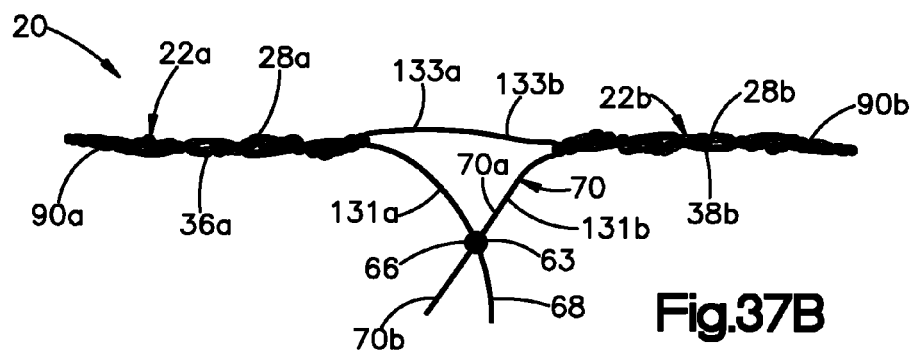
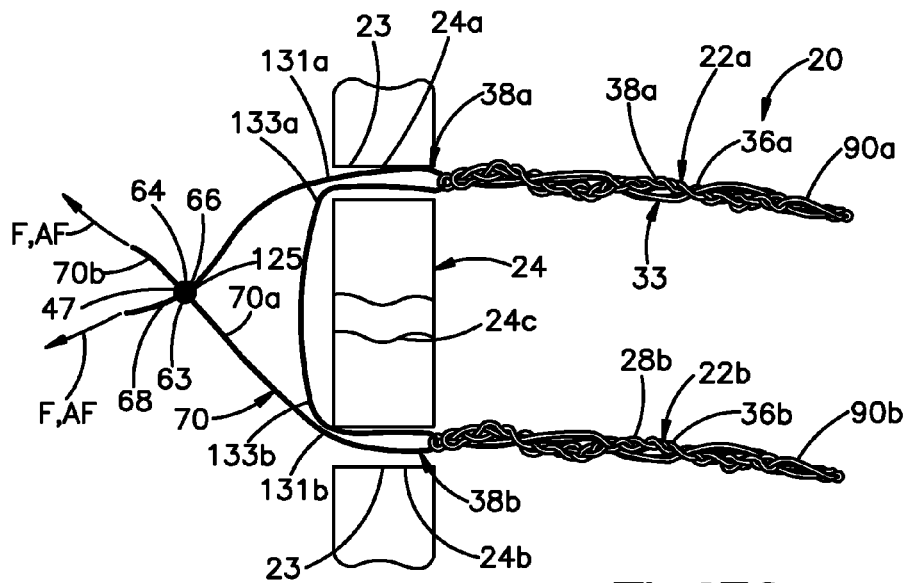

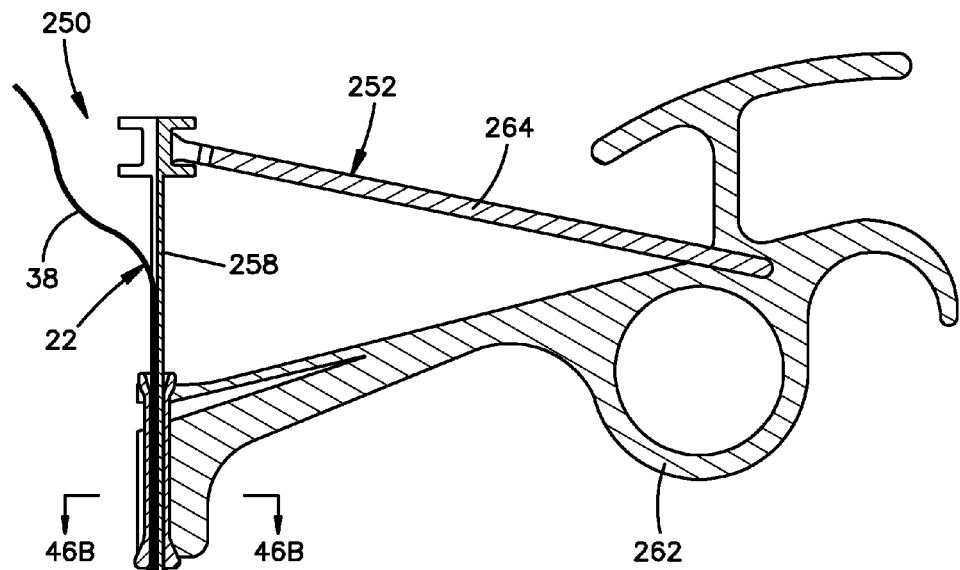
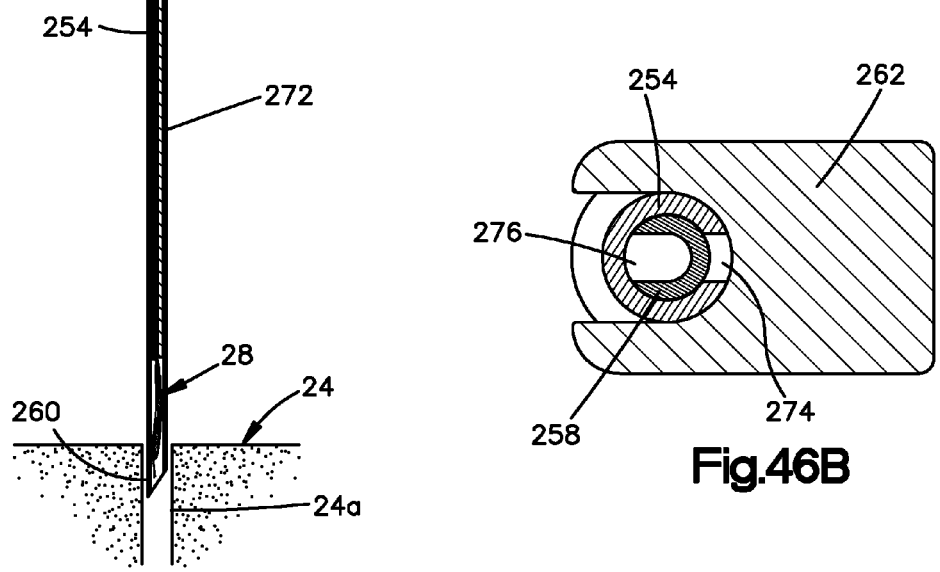
Fig.46A
Fig.46B

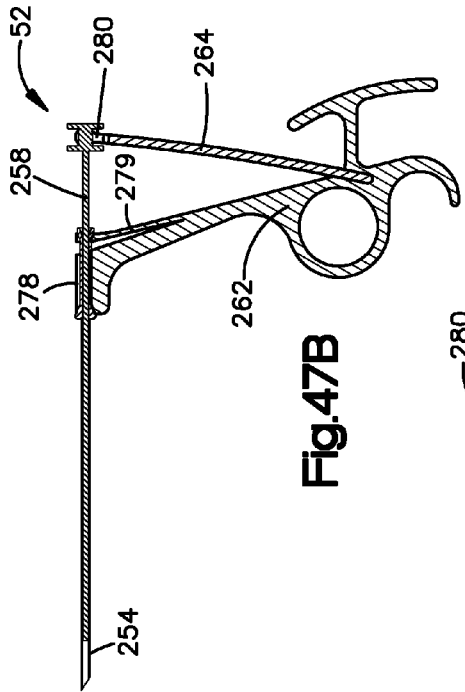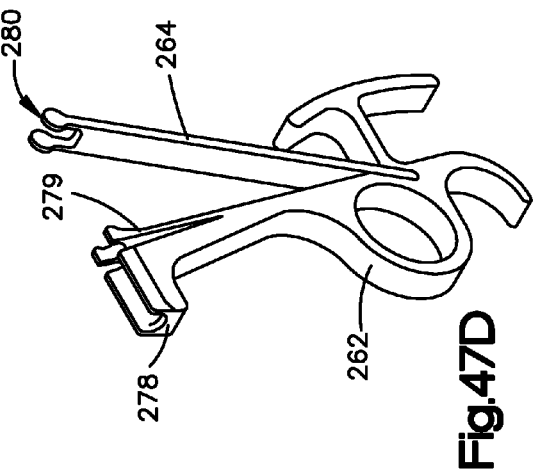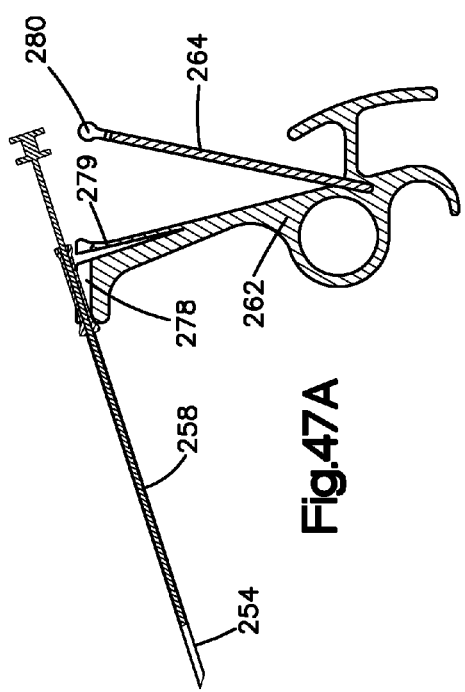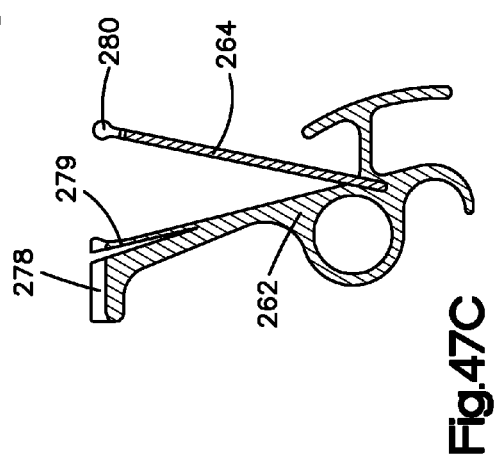

ANCHOR ASSEMBLY INCLUDING EXPANDABLE ANCHOR

CROSS-REFERENCE TO RELATED APPLICATIONS

This application claims the benefit of U.S. Patent Application Ser. No. 61/328,251 filed on Apr. 27, 2010 (Overes), U.S. Patent Application Ser. No. 61/398,699 filed on Jun. 29, 2010 (Overes, et al.), U.S. Patent Application Ser. No. 61/432,755 filed on Jan. 14, 2011 (Henrichsen, et al.), U.S. Patent Application Ser. No. 61/461,490 filed on Jan. 18, 2011 (Henrichsen, et al.), and U.S. Patent Application Ser. No. 61/443,142 filed on Feb. 15, 2011 (Overes), the disclosure of each of which is hereby incorporated by reference as if set forth in its entirety herein.

BACKGROUND

Orthopaedic surgical procedures often involve the use of a fixation device. Usually an access hole is produced in a bone or soft tissue wherein a suitable fixation device can be fastened. Apart from screws, expandable fixations devices can be used which are inserted into the hole in a collapsed state and transformed into an expanded state once being correctly positioned.

In one example orthopaedic surgical procedure, such as a lumbar microdiscectomy, radiculopathy is treated by surgically removing the herniated nucleus pulposus to achieve neural decompression. The lumbar microdiscectomy is one of the most common spinal surgeries performed today Many patients find relief with this procedure, but for others, the disc could re-herniate through the opening in the annulus resulting in continuing pain and potentially requiring additional surgery. Currently, the standard microdiscectomy technique does not involve closing the annular defect and presents the surgeon with a dilemma. The surgeon may elect to remove the herniated portion of the nucleus impinging on the nerves, which treats radiculopathy, but increases the risk of post-operative reherniation of the remaining nucleus through the existing defect of the annulus. Alternately, the surgeon may elect to perform extensive debulking, in which most of the remaining nucleus material is removed in addition to the herniated portion to minimize the risk of post-operative reherniation. However, the risk of post-operative disc height collapse and subsequent progression to lower back pain increase.

Conventional expandable implants include a sleeve with an expandable portion having plurality of fingers or expandable parts formed by intermediate slots or holes in the peripheral wall of the sleeve and a compression element extending through the central bore of the sleeve. The compression element can be coupled to the front end of the sleeve so that upon pulling said compression element towards the rear end of the sleeve said fingers or expandable parts are bent radially outwards so as to transform said expandable portion from its collapsed state to its expanded state.

SUMMARY

In accordance with one embodiment, an anchor assembly can be configured to be anchored to a target anatomical location. The anchor assembly includes an anchor that, in turn, includes an anchor body that defines an expandable portion. The expandable portion extends substantially along a direction of elongation when in a first configuration. The anchor defines a plurality of openings that extend through the anchor body and are spaced substantially along the direction of elongation. The anchor further includes an actuation member that extends through at least two of the openings. The actuation member is configured to receive an actuation force and, in response to the actuation force, actuate the expandable portion from the first configuration to an expanded configuration, wherein the expandable portion collapses along the direction of elongation and expands along a direction angularly offset with respect to the direction of elongation.

BRIEF DESCRIPTION OF THE DRAWINGS

The foregoing summary, as well as the following detailed description of an example embodiment of the application, will be better understood when read in conjunction with the appended drawings, in which there is shown in the drawings example embodiments for the purposes of illustration. It should be understood, however, that the application is not limited to the precise arrangements and instrumentalities shown. In the drawings:

FIG. 15A is a perspective view of an anchor including an anchor body in the form of a mesh, and an actuation strand integral with the mesh, showing the anchor body in a first configuration;

FIG. 15B is a perspective view of the anchor illustrated in FIG. 15A, showing the anchor body in a first configuration;

FIG. 15C is a perspective view of an anchor including an anchor body that defines a plurality of cut openings, and an actuation strand integral with the anchor body, showing the anchor body in a first configuration;

FIG. 15D is a perspective view of an anchor including a braided anchor body, and an actuation strand integral with the braided anchor body;

FIG. 16A is a perspective view of an anchor including an anchor body having an expandable portion in the form of a mesh, and an eyelet extending from the expandable portion; showing the expandable portion in a first configuration;

FIG. 16B is a perspective view of the anchor illustrated in FIG. 16A, including an actuation strand coupled to the expandable portion, showing the expandable portion in a first configuration;

FIG. 16C is a perspective view of an anchor including an anchor body that has an expandable portion defining a plurality of cut openings, and an eyelet extending from the expandable portion;

FIG. 23A is a sectional end elevation view of a portion of a anchor assembly constructed in accordance with another alternative embodiment FIG. 23B is a side elevation view of the anchor assembly illustrated in FIG. 23A, including first and second anchors shown in respective expanded configurations and implanted in an anatomical structure;

FIG. 23C is a side elevation view of the anchor assembly illustrated in FIG. 23B, showing the first and second anchors in respective expanded configurations;

FIG. 23D is a sectional end elevation view of a connector member of the anchor assembly as illustrated in FIG. 23C;

FIG. 37A is a side elevation view of an anchor assembly constructed in accordance with another alternative embodiment, including first and second anchors shown in respective first configurations;

FIG. 37B is a side elevation view of the anchor assembly illustrated in FIG. 37A, showing the first and second anchors in respective first configurations;

FIG. 37C is a side elevation view of an anchor assembly illustrated in FIG. 37B, shown implanted in a target anatomical structure;

FIG. 40A is a side elevation view of an anchor assembly constructed in accordance with another embodiment, including first and second anchors;

FIG. 40B is a side elevation view of an anchor assembly illustrated in FIG. 40A, shown implanted in a target anatomical structure and showing the first and second anchors in respective first configurations;

FIG. 40C is a side elevation view of an anchor assembly illustrated in FIG. 40B, shown in an approximated configuration;

FIG. 41A is a side elevation view of an anchor assembly constructed in accordance with another embodiment, including first and second anchors;

FIG. 41B is a side elevation view of an anchor assembly illustrated in FIG. 41A, shown implanted in a target anatomical structure and showing the first and second anchors in respective first configurations;

FIG. 41C is a side elevation view of an anchor assembly illustrated in FIG. 41B, showing the first and second anchors in respective expanded configurations;

FIG. 42A is a side elevation view of an anchor assembly constructed in accordance with another embodiment, including first and second anchors;

FIG. 42B is a side elevation view of an anchor assembly illustrated in FIG. 42A, shown implanted in a target anatomical structure and showing the first and second anchors in respective first configurations;

FIG. 42C is a side elevation view of an anchor assembly illustrated in FIG. 42B, showing the first and second anchors in respective expanded configurations;

FIG. 43A is a side elevation view of an anchor assembly constructed in accordance with another embodiment, including first and second anchors shown implanted in a target anatomical structure, and showing the first and second anchors in respective first configurations;

FIG. 43B is a side elevation view of the anchor assembly illustrated in FIG. 43A, showing the first and second anchors in respective expanded configurations;

FIG. 43C is a side elevation view of an anchor assembly constructed in accordance with another embodiment, including first and second anchors shown implanted in a target anatomical structure, and showing the first and second anchors in respective first configurations;

Figure 43A:
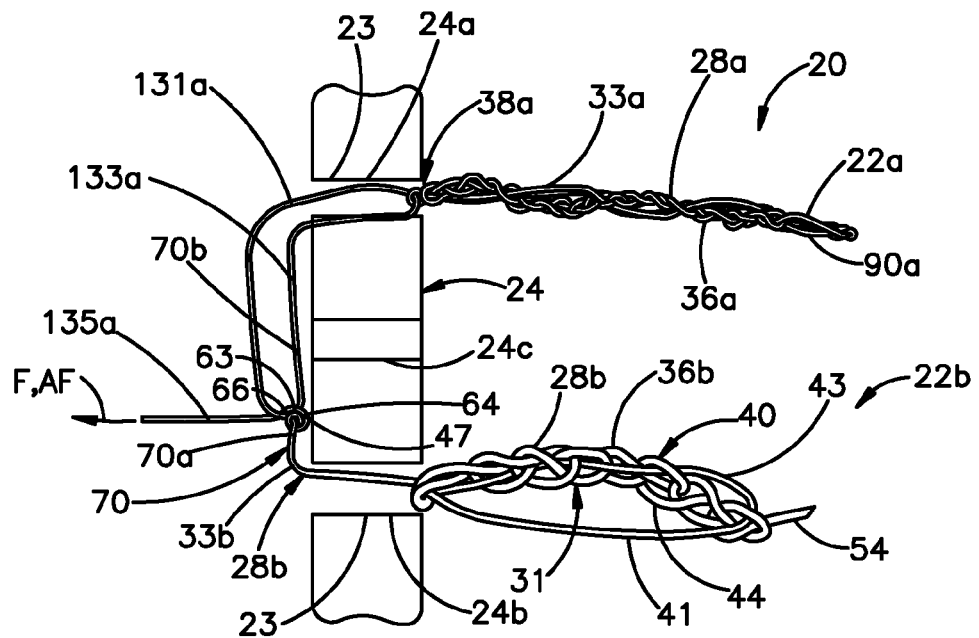
Figure 43B:
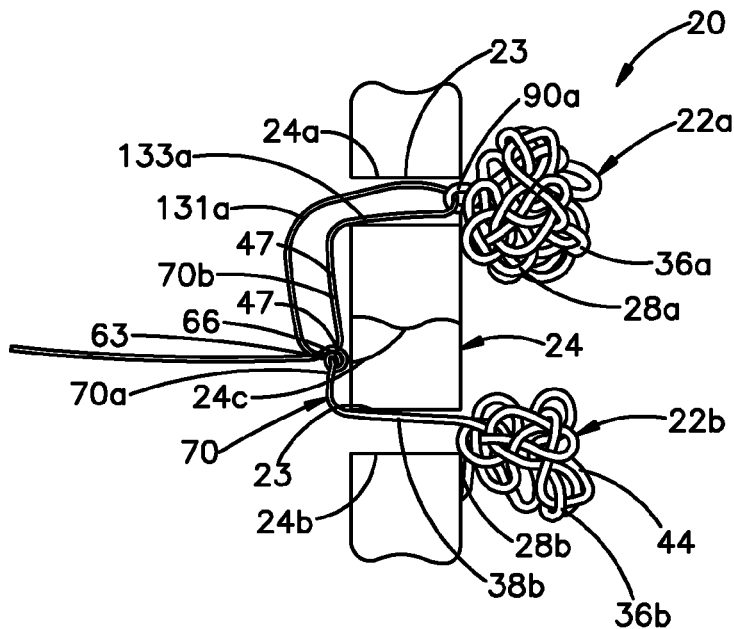
Figure 43C:
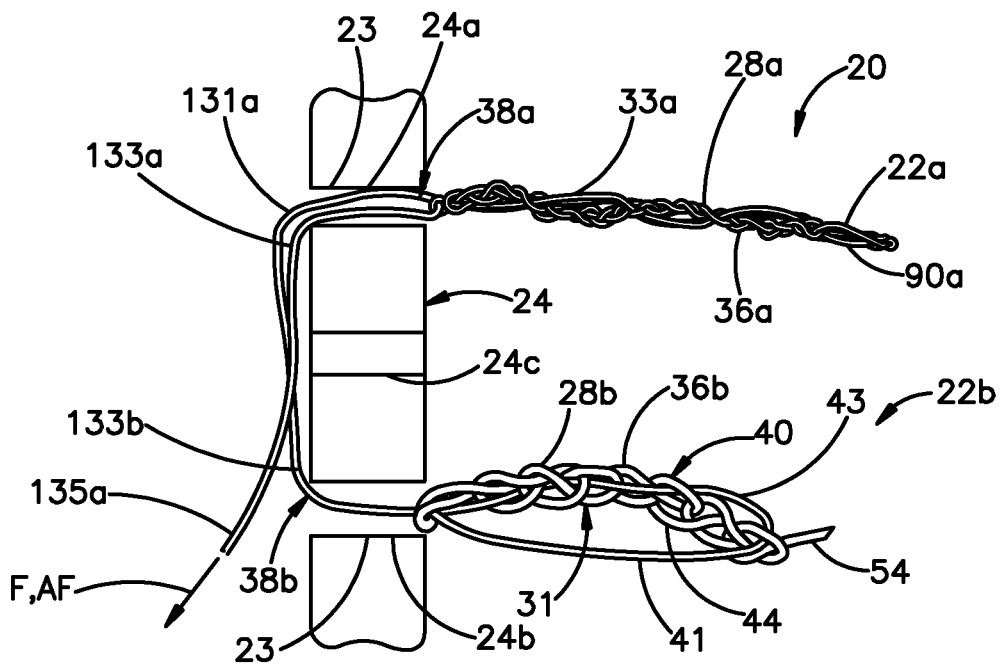
Figure 43D:
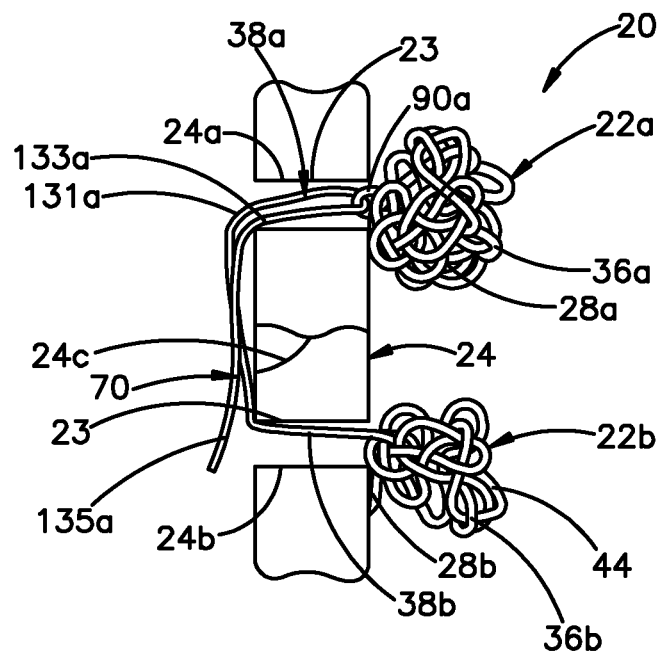
Figure 44A:
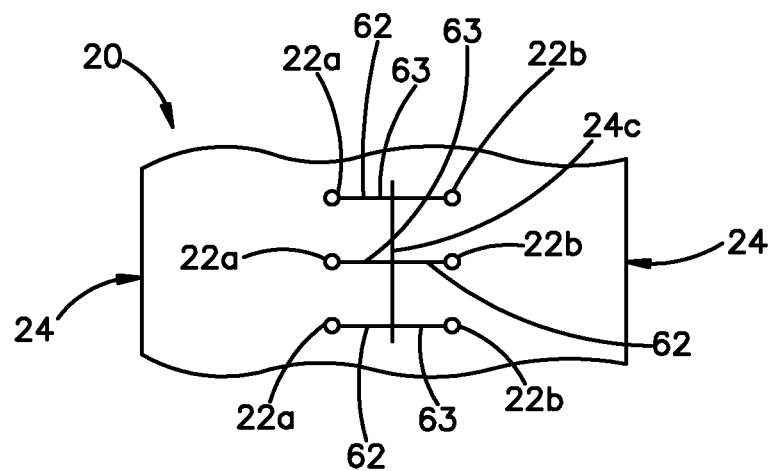
Figure 44B:
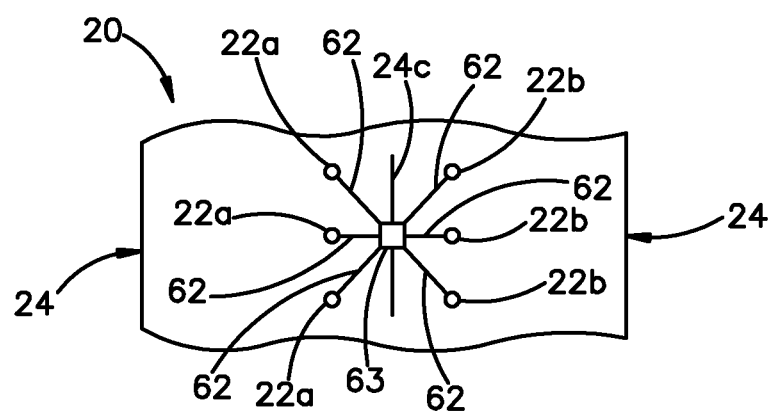
Figure 45A:
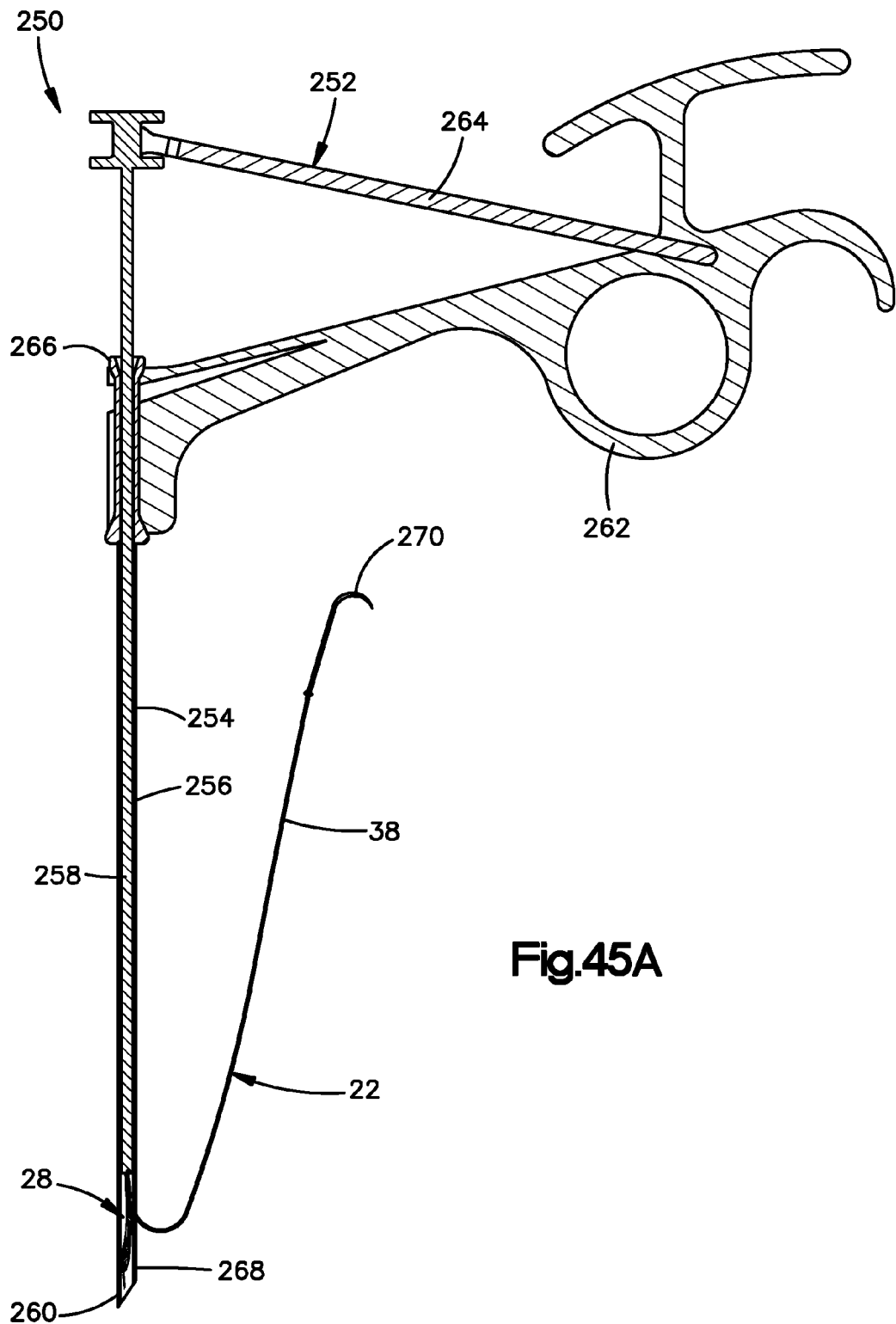
Figure 45B:
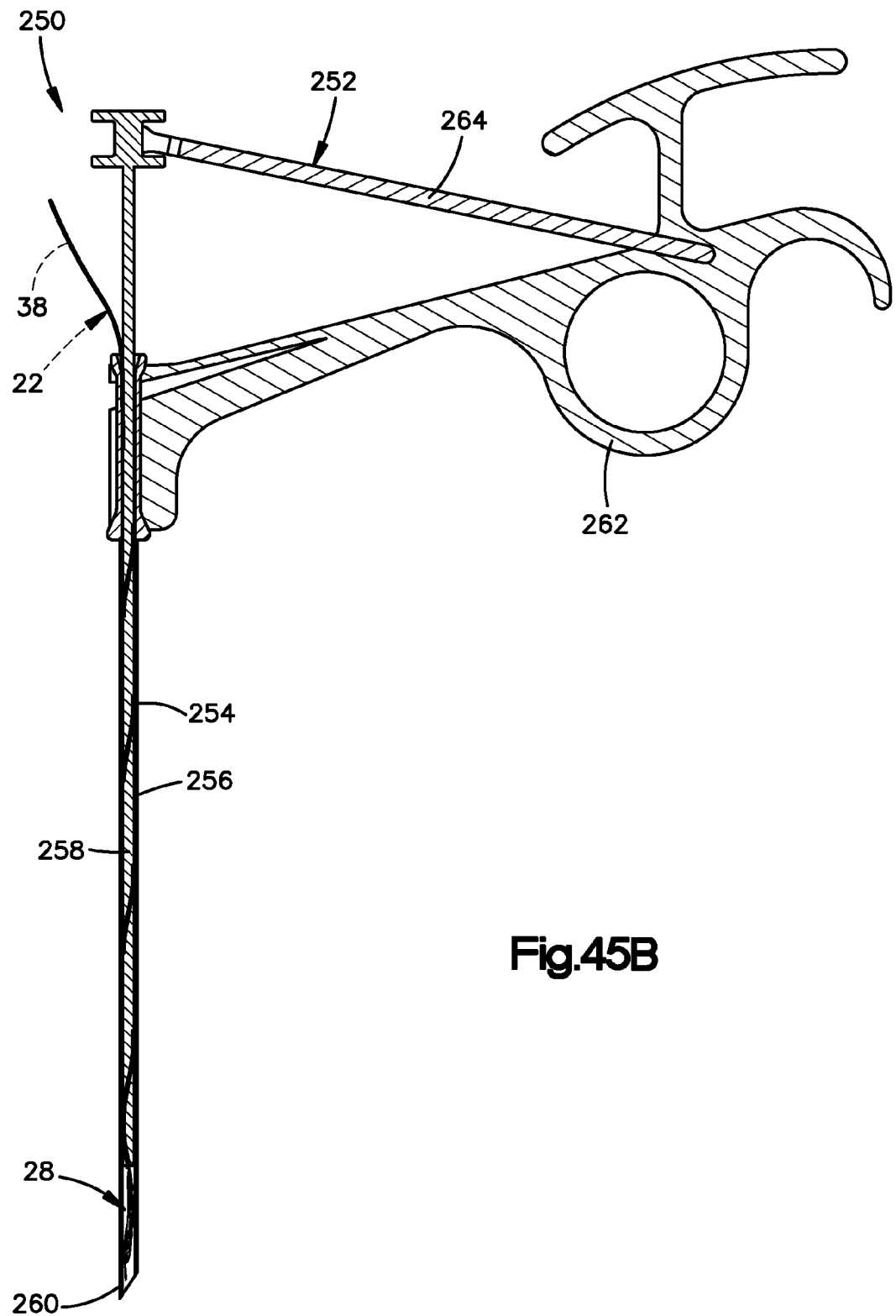
Figure 46C:
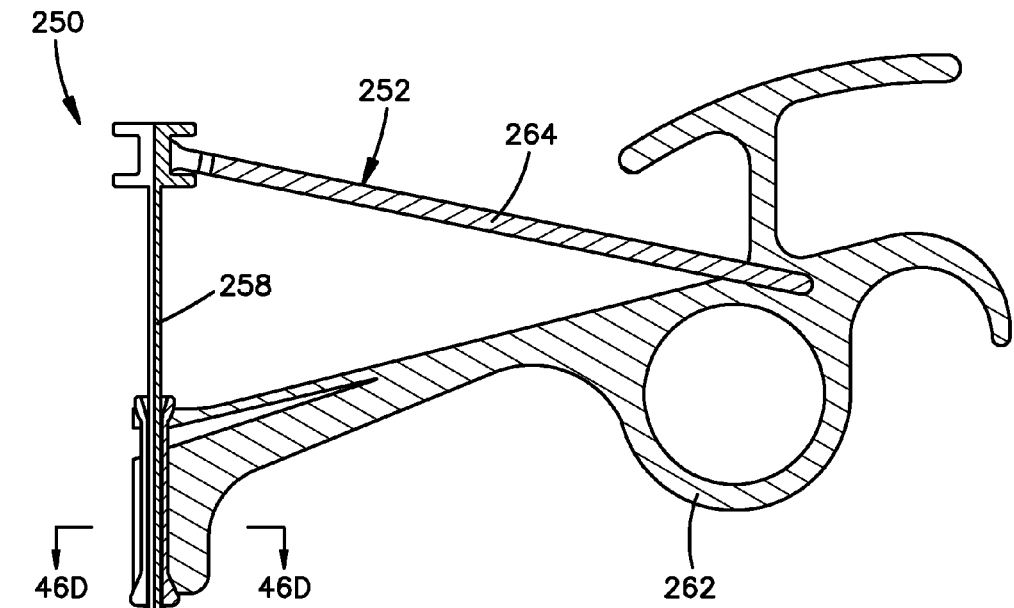
Figure 46D:
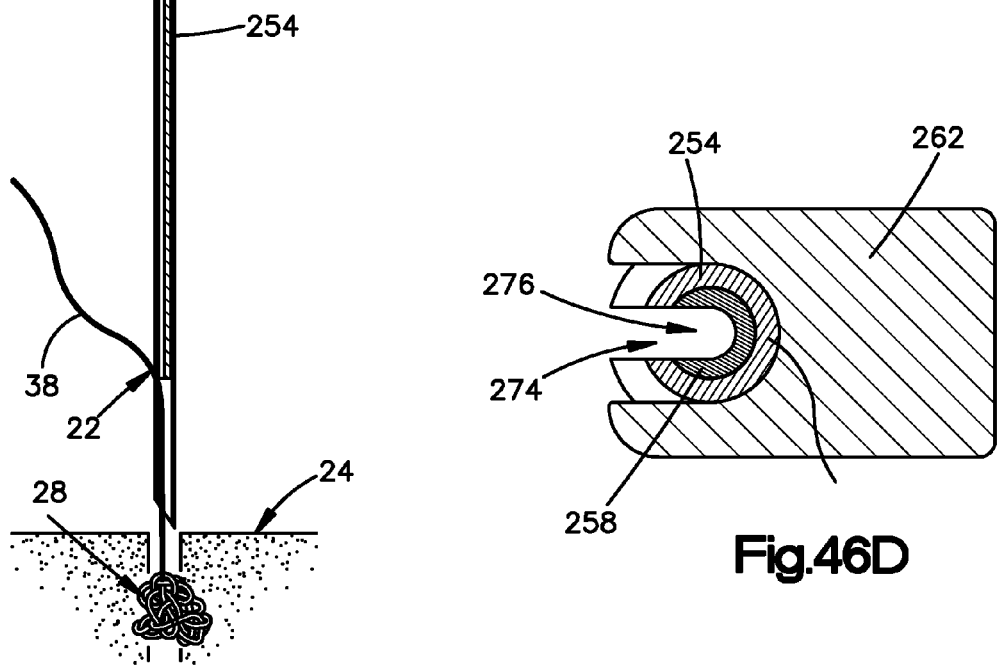

FIG. 43D is a side elevation view of the anchor assembly illustrated in FIG. 43C, showing the first and second anchors in respective expanded configurations;

FIG. 44A is a schematic top plan view of an anchor assembly constructed in accordance with an alternative embodiment, including multiple pairs of anchors attached to each other across an anatomical defect;

FIG. 44B is a schematic top plan view of an anchor assembly constructed in accordance with an alternative embodiment, including a plurality of anchors attached to each other across an anatomical defect at a common hub;

FIG. 45A is a side elevation view of a fixation kit including at least one anchor and an insertion instrument;

FIG. 45B is a sectional side elevation view of the fixation kit illustrated in FIG. 45A;

FIG. 46A is a sectional elevation view of a fixation kit constructed in accordance with an alternative embodiment, shown in a first rotative state;

FIG. 46B is a sectional side elevation view of the kit illustrated in FIG. 46A, taken along line 46B-46B;

FIG. 46C is a sectional side elevation view of the fixation kit as illustrated in FIG. 46A, but shown in a second rotative state whereby a pair of apertures is aligned;

FIG. 46D-sectional side elevation view of the fixation kit illustrated in FIG. 46C, taken along line 46D-46D;

FIG. 47A is a sectional side elevation view of an insertion instrument during assembly;

FIG. 47B is a sectional side elevation view of the insertion instrument illustrated in FIG. 47A, but shown assembled;

FIG. 47C is a sectional side elevation view of a handle of the insertion instrument illustrated in FIG. 47B;

FIG. 47D is a perspective view of the handle illustrated in FIG. 47C; and

Figure 48:
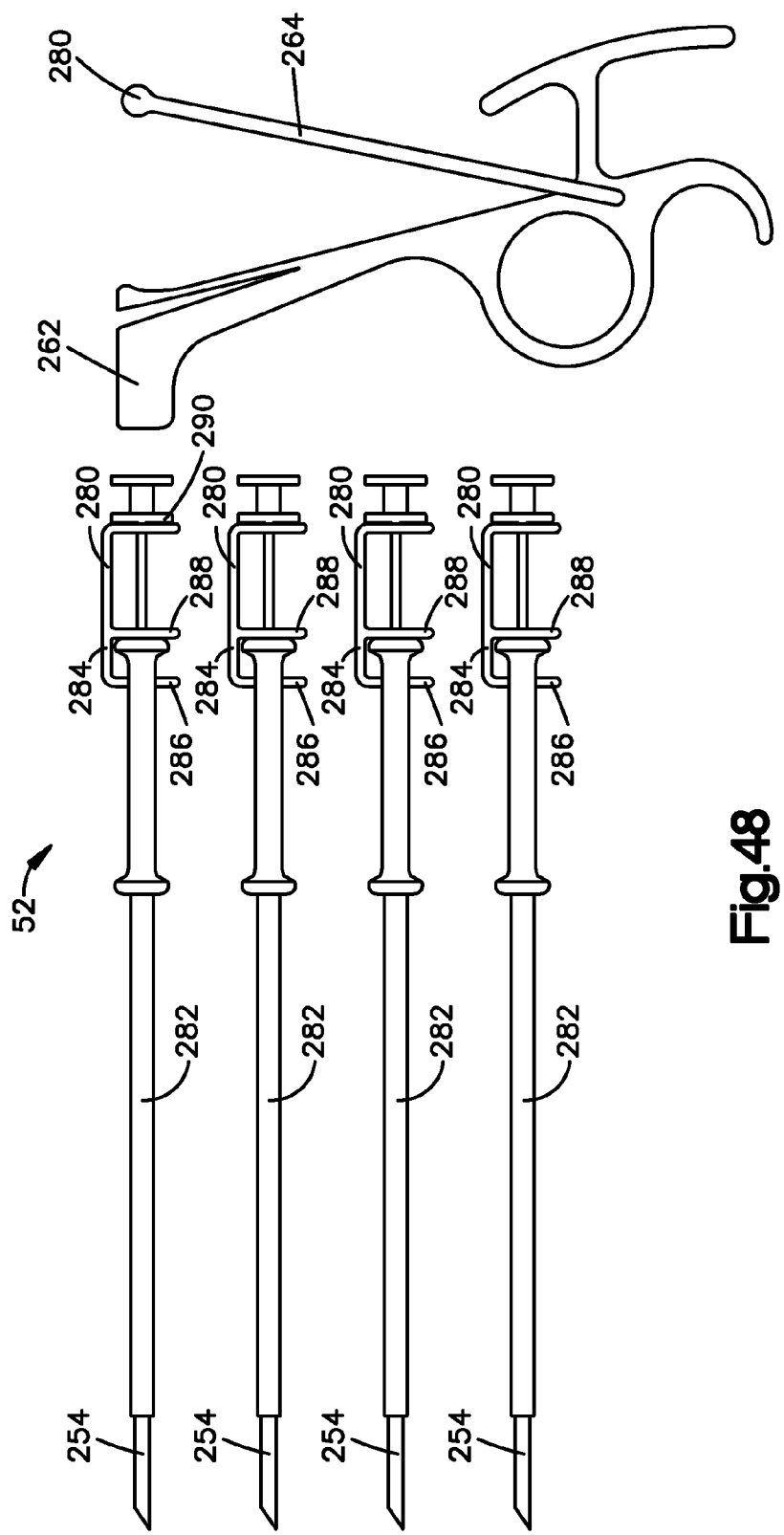

FIG. 48 is a side elevation view of the fixation kit constructed in accordance with another embodiment.

DETAILED DESCRIPTION

Figure 1A:
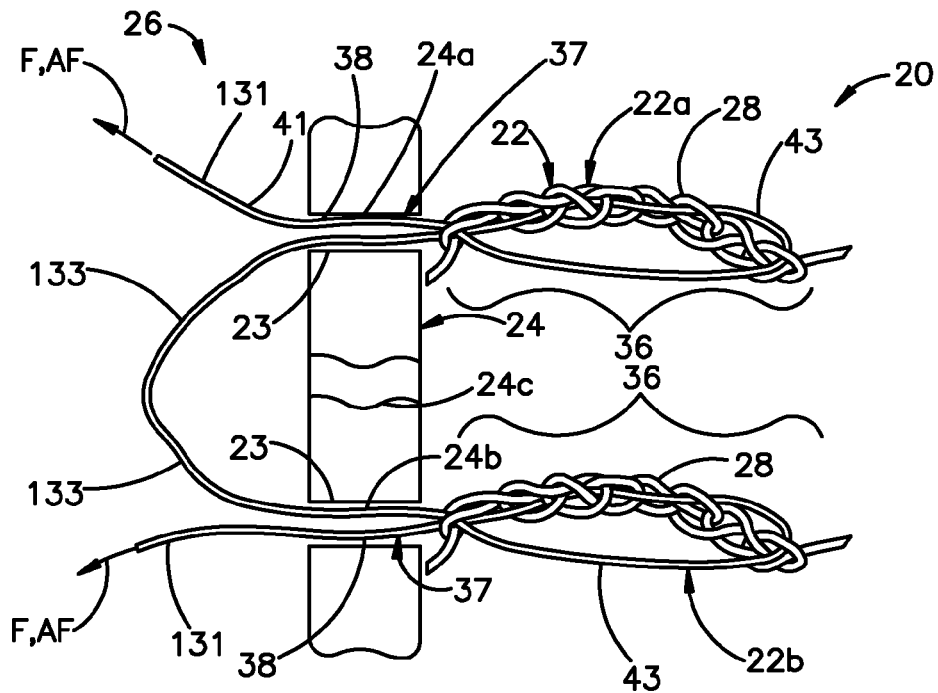
FIG. 1A is a schematic side elevation view of an anchor assembly including a pair of anchor bodies implanted across an anatomical defect and shown in a first configuration.
Figure 1B:
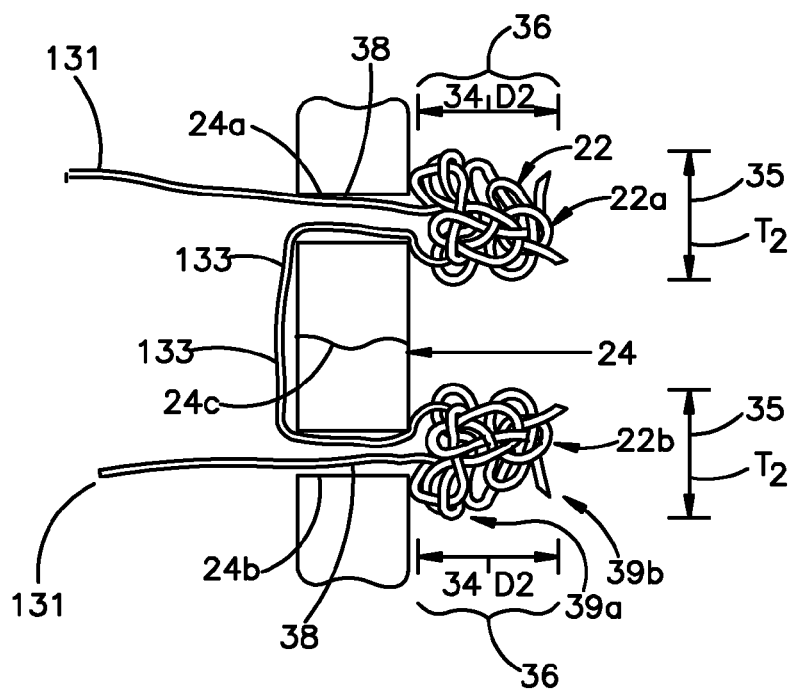
FIG. 1B is a schematic side elevation view of the anchor assembly illustrated in FIG. 1, showing the anchor bodies in an expanded configuration and in an approximated position.

Referring initially to FIGS. 1A-B, an anchor assembly 20 can include at least one expandable anchor 22 such as a plurality of expandable anchors 22 that, in turn, include respective anchor bodies 28 configured to be secured to an anatomical location, which can be defined by at least one anatomical structure 24. In accordance with the illustrated embodiment, the anchor assembly 20 includes a first anchor 22a and a second anchor 22b each configured to be secured to the anatomical location, such as the anatomical structure 24. The anatomical structure 24 can be defined by, for instance, anatomy of a human or other animal, or an implant that is secured or configured to be secured to anatomy of a human or other animal. The anatomy can be defined by tissue that can include at least one of bone and soft tissue such as a tendon, a ligament, cartilage, the annulus of an intervertebral disc, or the like.

In accordance with one embodiment, the at least one anatomical structure 24 can define first and second target anatomical locations 24a and 24b on opposite sides of a gap, such as a gap 24c. Thus, the gap 24c can be disposed in an anatomical structure, and can for instance define an anatomical defect, or can be disposed between different anatomical structure. First and second anchors 22a and 22b can be injected or otherwise driven or inserted into the respective first and second target anatomical locations 24a and 24b on opposite sides of the gap 24c, and subsequently drawn toward each other so as to approximate the gap 24c. Alternatively or additionally still, as described in more detail below with respect to FIGS. 1C-D, the anchor assembly 20 is configured to secure an auxiliary structure 25 to the anatomical structure 24. In this regard, it should be further appreciated that the anchor assembly 20 can include any number of anchors 22 as desired.

Each anchor body 28 can include an expandable portion 36 and an actuation member 37, such as an actuation strand 38, that is configured to actuate the expandable portion 36, and thus the anchor body 28, from a first configuration illustrated in FIG. 1A, whereby the anchor body 28 is initially placed at the target anatomical location, to an expanded configuration illustrated in FIG. 1B, whereby the anchor body 28 can be secured to the anatomical structure 24. Thus, the anchor bodies 28 of the anchors 22a and 22b can be inserted through an opening 23 at the respective target anatomical locations 24a and 24b that can be created, for example, when injecting the anchor bodies 28 to the target anatomical locations 24a and 24b.

Each of the actuation strands 38 of the first and second anchors 22a and 22b can be attached to each other. For instance, the actuation strand 38 of the first anchor 22a can be integral with the actuation strand 38 of the second anchor 22b. Alternatively, as will be described in more detail below, the actuation strand 38 of the first anchor 22a can be separate from the actuation strand 38 of the second anchor 22a, such that the actuation strands 38 of the first and second anchors 22a and 22b are subsequently attached, directly or indirectly, using any suitable connector member 63 (see e.g., FIG. 18C). The connector member 63 can be integral with either or both of the actuation strands 38 (see e.g., FIG. 19A) or can be separately attached to each of the actuation strands 38 (see e.g., FIG. 20A). In accordance with one embodiment, the actuation strands 38 of the each of the first and second anchors 22a and 22b defines at least one actuation portion 131 and can further include at least one attachment portion 133. The actuation portions 131 are each configured to receive an actuation force that causes the respective anchor 22a and 22b to actuate from the first configuration to the expanded configuration.

In accordance with the illustrated embodiment, the attachment portions 133 of the actuation strands 38 of the first and second anchors are configured to be attached to each other. The attachment portions 133 can be integral with each other, or attached to each other using any suitable connector member. Furthermore, in accordance with the illustrated embodiment, the actuation portions 131 can also define attachment portions that are configured to be attached to each other in any suitable manner, either before or after the actuation force F is applied to the actuation portions 131. Thus, the attachment portion 133 of a respective anchor is configured to attach the respective anchor to another anchor, such as an attachment portion 133 of the other anchor. Furthermore, the actuation portion 131 of a respective anchor is configured to attach the respective anchor to another anchor. In accordance with the illustrated embodiment, the attachment portion 133 of the actuation strand 38 of the first anchor 22a is integral with the attachment portion 133 of the actuation strand 38 of the second anchor 22b, though it should be appreciated that the attachment portions 133 of the first and second anchors 22a and 22b can be separate from each other and attached to each other, as described in more detail below.

With continuing reference to FIGS. 1A-B, once the expandable portions 36 of the anchors 22a and 22b have actuated to the expanded configuration, the actuation strands 38 can be placed in tension. For instance, in accordance with one embodiment, an approximation Force AF can be applied to either or both of the actuation portion 131 of the actuation strands 38 of the first and second anchors 22a and 22b, thereby inducing a tension in the actuation strands 38 of the first and second anchors 22a and 22b so as to apply a biasing force that draws the first and second anchors 22a and 22b toward each other. Accordingly, if a gap 24c is disposed between the first and second anchors 22a and 22b, movement of the anchors 22a and 22b toward each other in response to the biasing force approximates the gap 24c which, in certain embodiments, can be an anatomical defect, such as a tissue defect as described above.

Figure 1C:
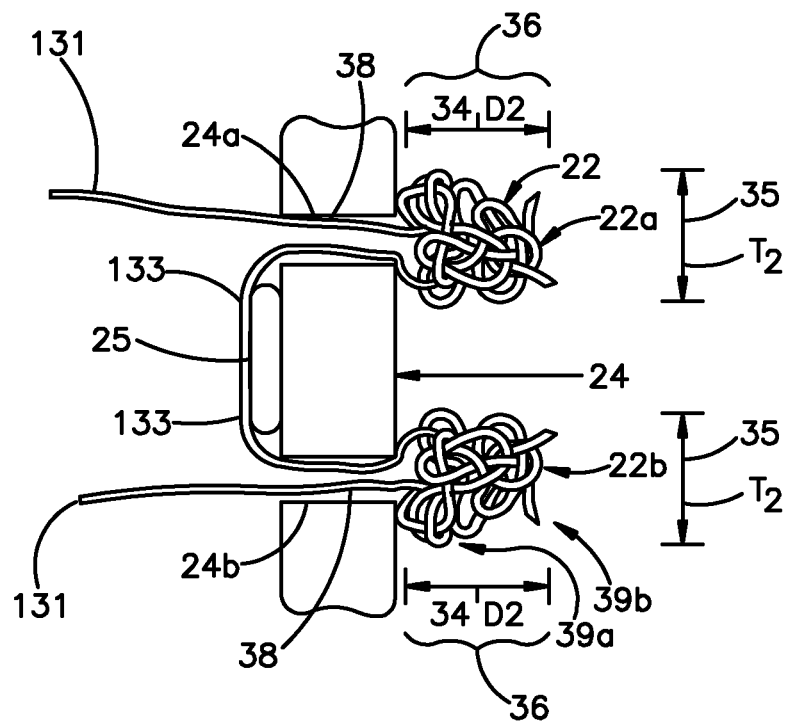
FIG. 1C is a schematic side elevation view of the an anchor assembly illustrated in FIG. 1A, shown secured to an auxiliary structure in accordance with one embodiment.

Alternatively or additionally, as illustrated in FIG. 1C, the anchor assembly 20 is configured to secure an auxiliary structure 25 to the anatomical structure 24 that can define the respective target anatomical locations 24a and 24b. The auxiliary structure 25 can be configured as an anatomical structure, such as tissue as described above or an implant that can be configured as a graft, a mesh, a clay, hardware, a bone plate, or any alternative structure as desired. In this regard, it should be further appreciated that the anchor assembly 20 can include any number of anchors 22 as desired. For instance, the auxiliary structure 25 can be positioned between one or both of the actuation strands 38, and in particular between one or both of the attachment portions 133, and the at least one anatomical structure 24. Accordingly, when tension is induced in the actuation strand 38, and in particular in the attachment portions 33, the auxiliary structure 25 (such as soft tissue) can be drawn toward and secured to the anatomical structure 24 (such as bone), for instance between the actuation strand 38 and the anatomical structure 24 at a location between the first and second target anatomical locations 24a and 24b. In this regard, it should be appreciated that a gap is reduced between the auxiliary structure 25 and the anatomical structure 24. Furthermore, if a gap is disposed between the anchors 22a and 22b, as illustrated in FIGS. 1A-B, tension in the actuation strand 38 can further approximate the gap 24c in addition to securing the auxiliary structure 25 to the anatomical structure 24. Accordingly, unless otherwise indicated, descriptions below of tension in the actuation strand 38 that are configured to approximate the gap 24c is also configured to secure an auxiliary structure between the actuation strand 38 and the at least one anatomical structure 24 that defines the first and second target anatomical locations 24a and 24b.

Figure 1D:
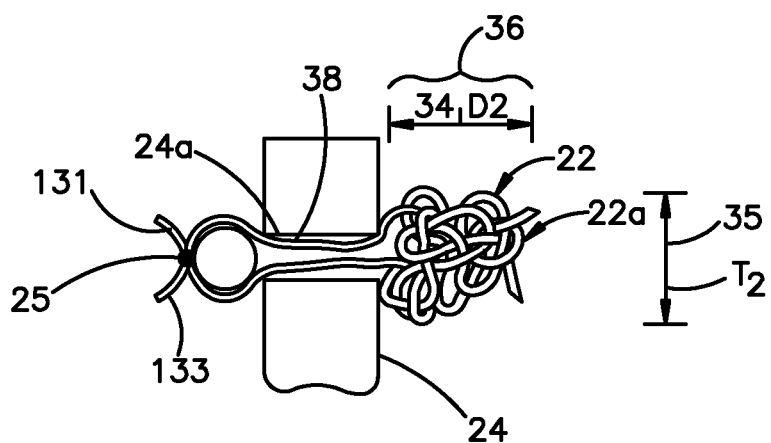
FIG. 1D is a schematic side elevation view of the anchor assembly as illustrated in FIG. 1C, but shown secured to an auxiliary structure in accordance with another embodiment
Figure 8A:
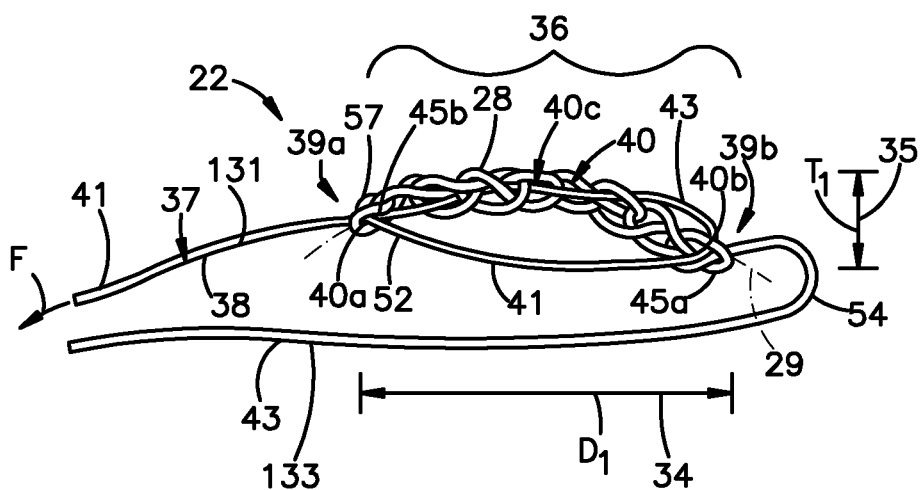
FIG. 8A is a perspective view of an anchor including an actuation strand integral with an anchor body woven through a plurality of openings defined by an expandable portion of the anchor body in accordance with an alternative embodiment, showing the anchor body in a first configuration.

Alternatively or additionally still, as illustrated in FIG. 1D, the anchor assembly 20 can include at least one anchor 22 that is configured to secure the auxiliary structure 25 between the actuation strand 38 and the anatomical structure 24. For instance, the anchor 22 can be fixed to a target anatomical location 24a of an anatomical structure 24 in the manner described above. The actuation strand 38, such as opposed first and second ends (which can be defined by the actuation portion 131 and the attachment portion 133, respectively) can be tied, stitched, or otherwise secured to another anatomical structure 27, thereby inducing tension in the actuation strand 38 and drawing and securing the auxiliary structure 25 (such as soft tissue) to the anatomical structure 24 (such as bone), for instance between the actuation strand 38 and the anatomical structure 24. In this regard, it should be appreciated that a gap is reduced between the auxiliary structure 25 and the anatomical structure 24. The actuation strand 38 can be separate from and woven through the anchor body 28, for instance as illustrated in FIGS. 2A-B, or can be integral with the anchor body 28, for instance as illustrated in FIG. 8A.

Furthermore, when the actuation strands 38 are maintained in tension after the defect 24 has been approximated, the anchor bodies 28 are prevented from backing out from the anatomy which could allow the anatomical defect to open. Thus, once the gap 24c has been approximated, the actuation strand 38 of the first anchor 22a can be attached to the actuation strand 38 of the second anchor 22b so as to maintain tension between the first and second anchors 22a and 22b and prevent the first and second anchors 22a and 22b from separating.

While the first and second anchors 22a and 22b illustrated in FIGS. 1A-B are constructed as described below with reference to FIGS. 2A and 2B, respectively, it should be appreciated that the anchors 22a and 22b can be constructed in accordance with any embodiment described herein or any alternative embodiment as desired. Furthermore, it should be appreciated that while the anchor assembly 20 includes first and second anchors 22a and 22b that are configured to be implanted on opposed sides of the gap 24c, the anchor assembly 20 can include as many anchors 22 as desired that can be attached in a plurality of (e.g., at least two) anchors 22, which can be arranged in individual pairs or otherwise arranged as desired, for instance across the same gap, or anatomical defect, across more than one gap, or disposed on the same side of a gap as desired. Alternatively still, the plurality of anchors 22 can all be attached together, such that select ones of the anchors 22 can be disposed on one side of the anatomical defect and select others of the anchors 22 can be disposed on another side of the anatomical defect, or alternatively disposed across different anatomical defects.

Figure 2A:
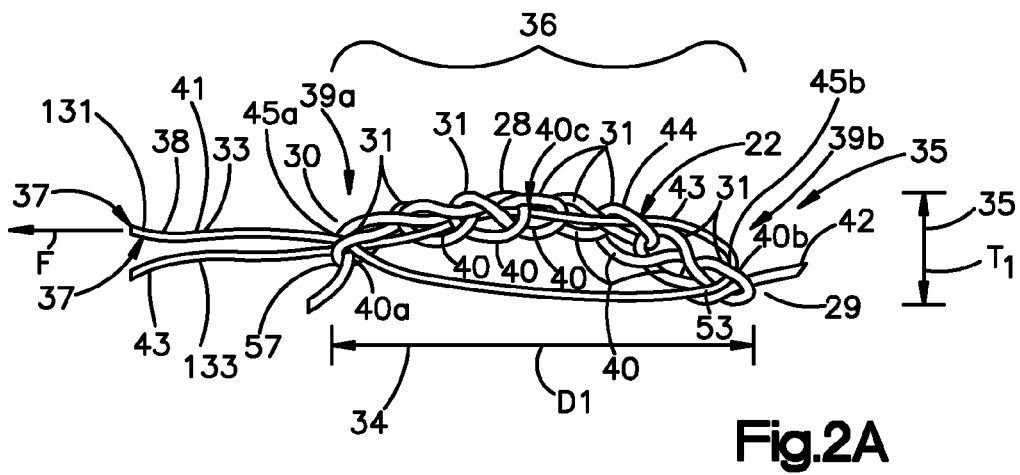
FIG. 2A is a perspective view of an anchor constructed in accordance with one embodiment.
Figure 2B:
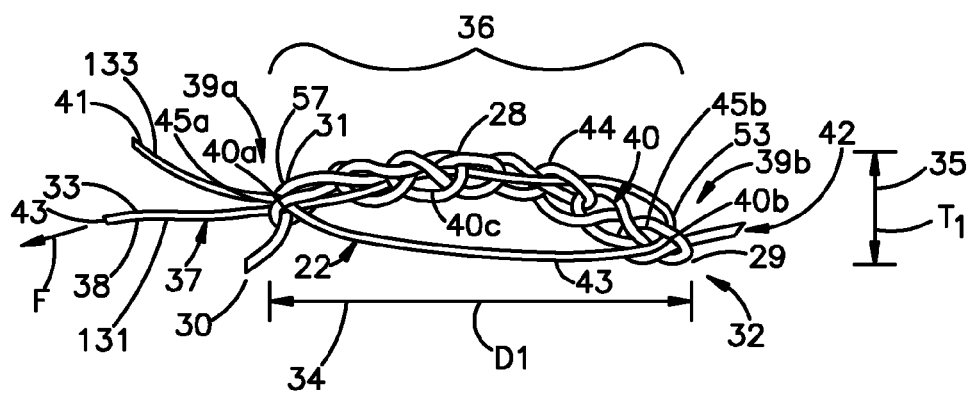
FIG. 2B is a perspective view of an anchor constructed in accordance with another embodiment.

With continuing reference to FIGS. 2A-B, the anchor body 28, and also the expandable portion 36, is elongate along a central axis 29, and defines a first or proximal end 30 and a second or distal end 32 that is spaced from the proximal end 30 substantially along the central axis 29. The central axis 29 can define any shape, or portions having any shape as desired. For instance, the central axis 29, or portions of the central axis 29, can be linear, substantially linear, nonlinear, including regularly, irregularly, otherwise curved, or can be otherwise shaped as desired. Accordingly, the anchor body 28 can define a direction of elongation 34 that extends linearly between the first and second ends 30 and 32. It should be appreciated, for instance when the central axis 29 is substantially straight, that the direction of elongation 34 can be substantially coincident with the central axis 29. It should be further appreciated, for instance when the central axis 29 is nonlinear that the direction of elongation 34 at least partially or substantially entirely spaced from the central axis 29. The anchor body 28 further defines an expandable portion 36 that has a first or proximal end 39a and a second or distal end 39b. The proximal end 39a of the expandable portion 36 can be coincident with or different than (for instance recessed with respect to) the proximal end 30 of the anchor body 28, and the distal end 39b of the expandable portion 36 can be coincident or different than (for instance recessed with respect to) the distal end 32 of the anchor body 28.

The anchor 22 further includes an actuation member 37 that can be configured as an actuation strand 38 that can actuate the expandable portion 36, and thus the anchor body 28, from the first configuration illustrated in FIG. 1A to the expanded configuration illustrated in FIG. 1B. The actuation strand 38 can be provided as a suture or any alternatively constructed strand as desired. The expandable portion 36 of the anchor body 28 extends along the direction of elongation 34 so as to define an initial distance D1 as measured from the proximal end 39a to the distal end 39b along the direction of elongation 34 when in the first configuration. The initial distance D1 can be any length as desired, such within a range having a lower end that can be defined by approximately 5 mm, alternatively approximately 10 mm, alternatively still approximately 20 mm, and alternatively still approximately 24.5 mm, and having an upper end that can be defined by approximately 50 mm, alternatively approximately 40 mm, alternatively still approximately 30 mm, and alternatively still approximately 25.5 mm.

Furthermore, when in the first configuration, the expandable portion 36 defines an initial maximum thickness T1 that extends in a second direction 35 that is substantially perpendicular, with respect to the direction of elongation 34. The initial maximum thickness T1 can be sized as desired. As illustrated in FIG. 1B, when the expandable portion 36 in the expanded configuration, the expandable portion 36 is collapsed, for instance compressed or tangled, along the direction of elongation 34 to a second distance D2 as measured from the proximal end 39a to the distal end 39b along the direction of elongation 34. The second distance D2 can be less than the initial distance D1. As the expandable portion 36 collapses along the direction of elongation, for instance as it is actuated from the first configuration to the expanded configuration, the expandable portion 36 expands along the second direction 35 to a second maximum thickness T2 that is greater than the initial maximum thickness T1. The second maximum thickness T2 extends along the second direction 35 which is substantially perpendicular to the direction of elongation 34.

The maximum thicknesses T1 and T2 in the second direction 35 can be defined such the anchor body 28 does not define a thickness in the second direction 35 that is greater than the maximum thicknesses T1 and T2, respectively. It should be appreciated that the proximal and distal ends 39a and 39b can change locations on the expandable portion 36 as the expandable portion 36 actuates to the expanded configuration, for instance due to configuration of the expandable portion 36 when in the expanded configuration. However, when the expandable portion 36 is in the expanded configuration, the proximal and distal ends 39a and 39b continue to define the proximal-most and distal-most ends of the expandable portion 36, such that the distance D2 along the direction of elongation 34 is defined linearly between the proximal and distal ends 39a and 39b of the expandable portion 36 when the expandable portion 36 is in the expanded configuration.

Figure 3A:
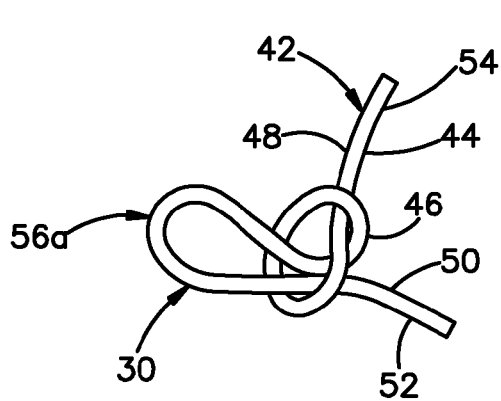
FIGS. 3A-C illustrate method steps for creating an anchor body of an anchor.
Figure 3B:
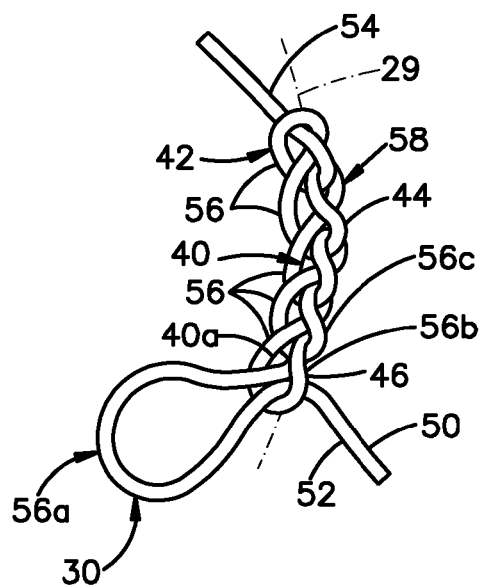
Figure 3C:
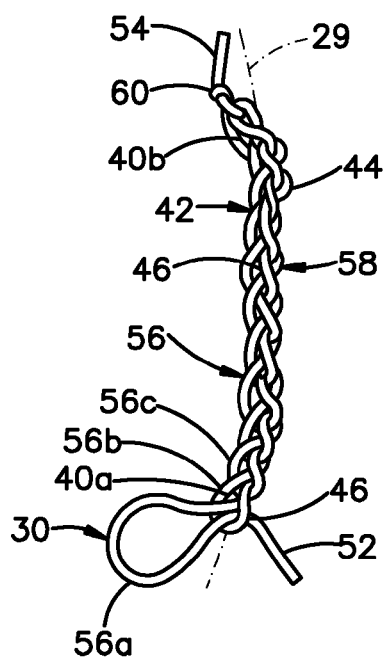

The expandable portion 36 can define a plurality of loops 31 that define respective openings 40 (such as at least two openings 40) that extend through the expandable portion 36 along the second direction 35. For instance, the loops 31 can be constructed as described below with respect to the loops 56 as illustrated in FIGS. 3A-C, the loops 99 illustrated in FIGS. 11A-H, or any suitable alternatively constructed loops. The expandable portion 36 can include any number of loops 31, for instance eight loops, more than eight loops, or less than eight loops. The openings 40 are spaced substantially along the central axis 29, and thus are also spaced substantially along the direction of elongation 34. For instance, the openings 40 are spaced along a direction having a component along the direction of elongation 34. Thus, the openings 40 can be spaced both along the direction of elongation 34 and along the second direction 35.

The openings 40 can define a proximal-most opening 40a, and distal-most opening 40b, and at least one intermediate opening 40c such as a plurality of intermediate openings 40c disposed between the proximal-most opening 40a and the distal-most opening 40b. The expandable portion 36 can be disposed between and including the loops 31 that define the proximal and distal openings 40a and 40b. The actuation strand 38 is configured to be woven through at least one of the openings 40, including a plurality of the openings 40 (for instance at least two up to all of the openings 40). Accordingly, when an actuation force F is applied to the actuation strand 38 substantially along the direction of elongation 34, the actuation strand 38 can bias the expandable portion 36, and thus the anchor body 28, to collapse along the direction of elongation 34 and expand along the second direction 35, thereby expanding the anchor from the first configuration to the expanded configuration. The force F can be a tensile force, including a pure tensile force or a force that can be offset from a pure tensile force but has a component that is a pure tensile force. It should thus be appreciated that the force F can be applied to the respective actuation strand 38 substantially along the direction of elongation 24, such that the force F can have a directional component that is parallel to or coincident with the direction of elongation 24, or can be entirely parallel to or coincident with the direction of elongation 24.

It should be appreciated that when the expandable portion 36 is in the first configuration, at least one of the openings 40 up to all of the openings 40 can define a first maximum dimension between the proximal and distal ends of the respective loops 31, and a second maximum dimension between opposed sides of the respective loops 31 that extend between the proximal and distal ends of the respective loops 31. The ratio of the second dimension to the first dimension of at least one of the loops 40 up to all of the loops 40 can increase when the expandable portion 36 expands from the first configuration to the expanded configuration. Furthermore, when the expandable portion is in the expanded configuration, a plurality of the loops 31, such as the opposed sides of the loops 31, can overlap along the second direction 35 an amount greater than when the expandable portion 36 is in the first configuration. In accordance with one embodiment, the opposed sides of the loops 31 do not overlap along the second direction 35, or can overlap slightly along the second direction 35 depending on the amount of tension induced in the expandable portion 36.

Referring now to FIGS. 3A-C, the anchor body 22 can be in the form of a substrate 42, which in one embodiment can be a strand, such as a suture strand or any alternatively constructed strand, that defines an anchor body strand 44. The anchor body strand 44, along with the other components of the anchor assembly 20, can be resorbable as desired. The anchor body strand 44 can have any suitable USP (United States Pharmacopia) size (or diameter) as desired, for instance between and including USP 7-0 and USP 5, such as between and including USP 2-0 and USP 5, for instance USP 2. The anchor body strand 44 can be woven and porous so as to defining openings, or can be nonwoven and devoid of openings as desired. Whether the anchor body strand 44 is woven or nonwoven, the anchor body strand 44 can be braided as desired so as to define the openings 40. One method of constructing the anchor body 22, and thus the expandable portion 36, from the anchor body strand 44 includes the step of tying a first stopper knot 46, which can define a proximal stopper knot 46 of the anchor body 28, having a post end 48 and a free end 50.

The anchor body strand 44 defines a first end portion 52, such as a proximal end portion, that defines the free end 50 of the first stopper knot 46, and a second end portion 54, such as a distal end portion, that defines the post end 48 of the proximal stopper knot 46. The method further includes the step of looping the first end portion 52 at a location adjacent the first stopper knot 46 so as to form a first proximal loop 56a, which can be a terminal loop disposed at the proximal end 30. The first proximal loop 56a is passed through the stopper knot 46 such that the first end portion 52 extends from the first proximal loop 56a through the stopper knot 46. The first end portion 52 can be further drawn through the first proximal loop 56a and tightened so as to define a proximal-most loop 57 of the loops 31 of the anchor body 28 as illustrated in FIGS. 2A-B. The first end portion 52 of the anchor body strand 44 can be cut or tied in a simple knot if desired at a location proximate to the proximal-most loop 57 of the loops 31, and thus proximate to the proximal ends 30 and 39a, and singed as desired so as to maintain structural integrity of the anchor strand 44 during use. Thus, the first end portion 52 can define the free end of the proximal-most loop 57 of the loops 31 of the anchor body 28.

The method further includes the step of braiding the second end portion 54 distally so as to define a plurality of similarly constructed loops 56 of the expandable portion 36 that are spaced substantially along the central axis 29. The loops 56 define respective ones of the plurality of openings 40. For instance, the method can further include the step of looping the second end portion 54 so as to form a new loop, such as a second distal loop 56b, adjacent a prior loop, such as the first proximal loop 56a, and passing the second distal loop 56b through the first proximal loop 56a. The step of braiding can further include additional steps of creating a new loop, which can be a third distal loop 56c, from the second end portion 54 such that a prior loop, such as the second loop 56b, is disposed proximal with respect to the additional distal loop 56c. The additional distal loop 56c is disposed immediately adjacent the prior loop 56b, and the method further includes the step of passing the additional distal loop 56c through the immediately proximal loop 56b.

The method further includes the steps of creating additional distal loops from the second end portion 54 as desired, and passing each of the additional new distal loops 56 through the respective prior loop to creating another new distal loop. Additional new distal loops 56 can be created as desired until a braid 58 of a desired length and a desired number of loops 56 has been created. Once the braid 58 has reached the desired length, the second end portion 54 can be knotted or otherwise terminated at a location distal of the distal-most loop 56 so as to define a second stopper knot 60, which can define the distal stopper knot of the anchor body 28. The second end portion 54 can be cut or tied into a simple knot if desired at a location proximate to the second stopper knot 60, and singed so as to maintain structural integrity during use. Thus, the second end portion 54 defines the free end of the second stopper knot 60.

It should be appreciated that while the loops 56 of the expandable portion 36 can be constructed from the same anchor body strand 44 as illustrated in FIGS. 3A-C, and thus are integral with each other in accordance with the illustrated embodiment, the expandable portion 36 can alternatively include two or more anchor strands 55 that alone and/or in combination define braided segments or loops 56 that can be joined, for instance welded (as described in more detail below with respect to FIG. 5C), stitched (as described in more detail below with respect to FIG. 5D), tied, spliced, or otherwise attached. It should be further appreciated that the anchor body strand 44 can alternatively be braided in any alternative manner as desired so as to define the anchor body 28 having an expandable portion 36 that is configured to be actuated from the first configuration to the expanded configuration as described herein.

The actuation strand 38 can be separate or non-integral from the expandable portion 36, and thus anchor body 28, and attached to the expandable portion 36 as illustrated in FIGS. 1A-B and 2A-B in any manner as desired such that the actuation force F applied to the actuation strand 38 causes the anchor body 28 to actuate from the first configuration to the expanded configuration. The actuation strand can have any suitable USP (United States Pharmacopia) size (or diameter) as desired, for instance between and including USP 7-0 and USP 5, such as between and including USP 2-0 and USP 5. For instance, as illustrated in FIG. 2A, the anchor 22 can include an auxiliary strand 33 that is separate or non-integral from the substrate 42 of the actuation body 28, and attached to the substrate 42. The auxiliary strand 33 can be woven, and thus extend, through a pair of the openings 40, such as a first or proximal select opening 45a and a second or distal select opening 45b that is disposed distal with respect to the first select opening 45a. In accordance with the illustrated embodiment, the first select opening 45a is the proximal-most opening 40a and the second select opening 45b is the distal-most opening 40b, though it should be appreciated that either or both of the first and select openings 45a and 45b can be selected from the intermediate openings 40c. The actuation strand 38 can define a first portion 41 that can define an actuation portion that extends out, for instance proximally out, from the anchor body 28 at a location proximal with respect to the openings 40 that receive the actuation strand 38. The first portion 41 can further extend and out the anatomical location 24, and is configured to receive the actuation force F. In accordance with some embodiments, the first portion 41 can furthermore define a terminal end of the actuation strand 38. The actuation strand 38 can extend distally from the first portion 41.

Several embodiments are described herein with reference to first and second select openings 45a and 45b. It should be appreciated that the reference "45a" and "45b" are used to conceptually identify first and select openings with respect to the various embodiments that identify first and second select openings. The particular ones of the openings 40 that define the particular first and select openings 45a and 45b do not necessarily coincide from embodiment to embodiment, and can in fact vary from embodiment to embodiment as desired.

The actuation strand 38 can be further looped through the second select opening 45b so as to define first and second portions that define the first portion 41 and a second portion 43 that can define a looped portion that extends proximally out the anatomical structure 24 and is opposite the first portion 41. As will be described in more detail below, in accordance with certain embodiments, the actuation force F can be applied to the actuation strand 38, for instance to at least one or both of the first portion 41 and the second portion 43, so as to actuate the expandable portion 36 from the first configuration to the expanded configuration. In accordance with the illustrated embodiment, the second portion 43 can be woven through, and thus extend through, at least one of the openings 40 such as a plurality of select openings 40 that can be disposed between the first and second select openings 45a and 45b, such that the actuation strand 38 defines a loop 53. For instance, the second portion 43 of the actuation strand 38 can be woven through a plurality of the intermediate openings 40c, and further woven through the first select opening 45a, which can be the proximal-most opening 40a. The first and second portions 41 and 43 can extend proximally from the anchor body and out the anatomy, such that the actuation force F can be applied to the first portion 41, the second portion 43 can attach to the actuation strand of a second anchor. Thus, in accordance with the illustrated embodiment, the first portion 41 defines an actuation portion 131 of the actuation strand 38, and the second portion 43 defines an attachment portion 133 of the actuation strand 38. Alternatively, as illustrated in FIG. 2B, the second portion 43 can receive the actuation force F and the first portion 41 can attach to the actuation strand of a second anchor. Thus, the second portion 43 can define the actuation portion 131 of the actuation strand 38 and the first portion 41 can define the attachment portion 133 of the actuation strand 38.

As described above with respect to FIGS. 1A-B, the actuation strand 38 can be integral with the actuation strand of the second anchor. Alternatively, the actuation strand 38 can be attached in any manner as desired, for instance via any suitable connector member such as an adhesive, a knot, a weldment (see, e.g., FIG. 5C), stitching (see e.g., FIG. 5D), a splice (see, e.g., FIGS. 19D-H), a knot (see, e.g., FIG. 4A), an auxiliary connector member (see, e.g., FIG. 20A), or any alternative suitable connector member as desired.

During operation, with continuing reference to FIG. 2A, when the actuation force F is applied to the actuation strand 38 and in particular to the first portion 41 of the actuation strand 38 when the proximal end 39a of the expandable portion 36 is braced and the second portion 43 of the actuation strand 38 is in tension, the distal end 39b of the expandable portion 36 is drawn toward the proximal end 39a of the expandable portion 36 as the size of the loop 53 decreases. The proximal end 39 can be braced for instance by the anatomical structure 24 or a bracing tool, or can alternatively be braced when the proximal end 30 of the anchor body 28 is braced, for instance by the anatomical structure 24 or a bracing tool. Accordingly, the expandable portion 36 expands from the first configuration to the expanded configuration. In accordance with the illustrated embodiment, as the distal end 39b is drawn toward the proximal end 39a, the expandable portion 36 can define a substantial u-shape.

Referring also to FIGS. 1A-B, as the actuation force F continues to be applied to the first portion 41, the auxiliary strand 38 is translated through the anchor body 28, thereby reducing slack in the second portion 43 and eventually inducing tension in the second portion 43. Once the second portion 43 is under tension, further application of the actuation force F to the first portion 41 causes the loop 53 to decrease in size, which thereby causes the expandable portion 36 to slide along the second portion 43 of the actuation strand 38, thereby drawing the distal end 39b further toward the proximal end 39a along the actuation strand 38, and causing the expandable portion 36 to become tangled or otherwise collapsed as it remains in the expanded configuration. It should be appreciated that additional tension induced in the second portion 43 of the actuation strand, or the end of the actuation strand 38 that is attached to the second anchor, can bias the anchor 22 toward the second anchor, thereby approximating the gap 24c as described above.

When the anchor 22 illustrated in FIG. 2A defines the first anchor 22a illustrated in FIGS. 1A-B and the anchor 22 illustrated in FIG. 2B defines the second anchor 22b illustrated in FIGS. 1A-B, first portion 41 of the actuation strand 38 of the first anchor 22a receives the actuation force F, and the second portion 43 of the actuation strand 38 of the second anchor 22b can receive the actuation force F. The second portion 43 of the actuation strand 38 of the first anchor 22a can be attached to the first portion 41 of the actuation strand 38 of the second anchor 22b. Thus, tension induced in the actuation strands 38 of the first and second anchors 22a and 22b due to the application of the actuation force to the actuation strands 38 causes the first and second anchors 22a and 22b to actuate from the first configuration to the expanded configuration. As described in more detail below, it should be appreciated that either or both of first and second portions 41 and 43 of the actuation strand 38 of the first anchor 22a can receive the actuation force F, either or both of the first and second portions 41 and 43 of the actuation strand 38 of the first anchor 22a can be attached to the actuation strand 38 of the second anchor 22b (either integrally or separately attached), either or both of first and second portions 41 and 43 of the actuation strand 38 of the second anchor 22b can receive the actuation force F, and either or both of the first and second portions 41 and 43 of the actuation strand 38 of the second anchor 22b can be attached to the actuation strand 38 of the first anchor 22a (either integrally or separately attached).

It should further be appreciated that actuation of the first and second anchors 22a and 22b can occur independent of tension that is induced in the actuation strands 38 across the gap 24c. For instance, one of the anchors 22a and 22b can be actuated to its expanded configuration, and the other of the anchors 22a and 22b can be actuated to its expanded configuration. Continued application of force to the actuation portion 131 of either or both of the actuation strands 38 can induce tension in the attachment portion 133 of the actuation strands 38 when the attached portions 133 of the actuation strands 38 are attached to each other.

Figure 2C:
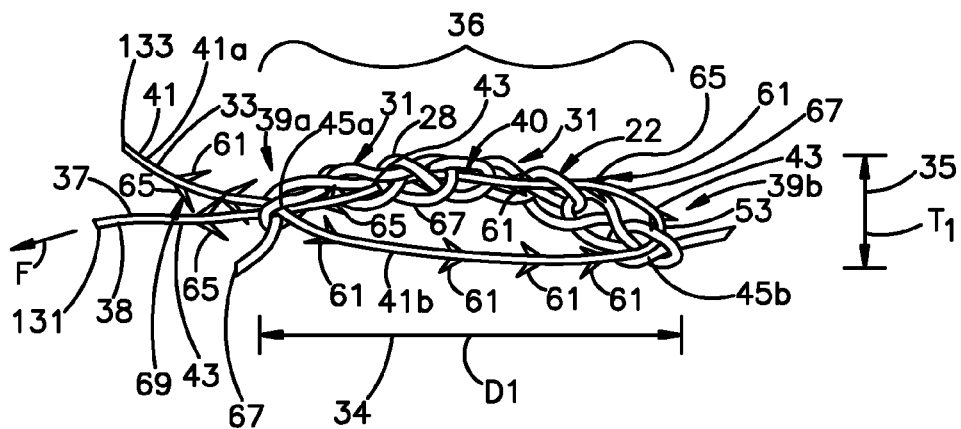
FIG. 2C is a perspective view of an anchor constructed in accordance with another embodiment.

Referring now to FIG. 2C, it should be appreciated that the actuation strand 38 can be barbed so as to facilitate movement of the actuation strand 38 through the openings 40 along an actuation direction that causes the expandable portion 36 to actuate from the first configuration to the expanded configuration. Thus, the actuation strand 38 can define a ratchet that allows for unidirectional movement of the actuation strand through the expandable portion 36 along the actuation direction, but prevents or limits movement of the actuation strand 38 along a direction that is opposite the actuation direction.

The actuation strand 38 can comprise a monofilament, and in one embodiment can be a quill suture. The actuation portion 131 of the actuation strand 38, which can be the second portion 43 as illustrated, can include a first at least one barb 61, such as a first plurality of barbs 61, that each define a leading end 65 that defines a cam so as to facilitate movement of the actuation strand 38 in the direction of the leading ends 65 (e.g., the actuation direction). Each of the barbs 61 can further define a trailing end 67 that defines a catch so as to prevent movement of the actuation strand 38 through the openings 40 along a direction opposite the actuation direction.

The attachment portion 133 of the actuation strand 38, which can be the first portion 41 as illustrated, includes first portion 41a that is configured to remain external to the expandable portion 36 both prior to and during actuation of the expandable portion 36 from the first configuration to the expanded configuration. The first portion 41a of the first portion 43 can include a second at least one barb 69, such as a second plurality of barbs 69, that each defines a leading end 65 that is oriented opposite the leading end 65 of each of the first plurality of barbs 61. Each of the second plurality of barbs 69 can further define a trailing end 67 that are oriented opposite the trailing ends 67 of the first plurality of barbs 61. Accordingly, the trailing ends 67 of the first and second barbs 61 and 69, respectively, face each other. The trailing end 67 of each of the second barbs 69 can define an engagement member that is configured to catch the anchor body strand 44 so as to prevent movement of the actuation strand 38 through the openings 40 as the actuation strand 38 travels along the actuation direction. The attachment portion 133 of the actuation strand 38, which can be the first portion 41 as illustrated, further includes a second portion that is disposed distal of the first select opening 45a and can also carry a plurality of the first barbs 61.

Accordingly, during operation, when the actuation force F is applied to the actuation portion 131 of the actuation strand 38, such as the second portion 43, the actuation strand 38 travels through the openings 40. Each of the first plurality of barbs 61 is oriented so as to define a ratchet that permits movement of the actuation strand 38 through the openings 40 along a direction that actuates the expandable portion 36 from the first configuration to the expanded configuration. The actuation strand 38 translates through the openings 40 until the trailing end 67 of one of the second barbs 69 catches the anchor body strand 44 at a location proximate to the first select opening 45a, which can be the loop 31 that defines the proximal-most opening 40. As the actuation force F is further applied to the actuation strand 38 while the proximal end 39a of the expandable portion 36 is braced, the mated second barb 69 causes the actuation strand 38 to move the expandable portion from the second select opening 45b toward the first select opening 45a, thereby entangling or otherwise collapsing the expandable portion 36 and actuating the expandable portion 36 from the first configuration to the expanded configuration.

Figure 2D:
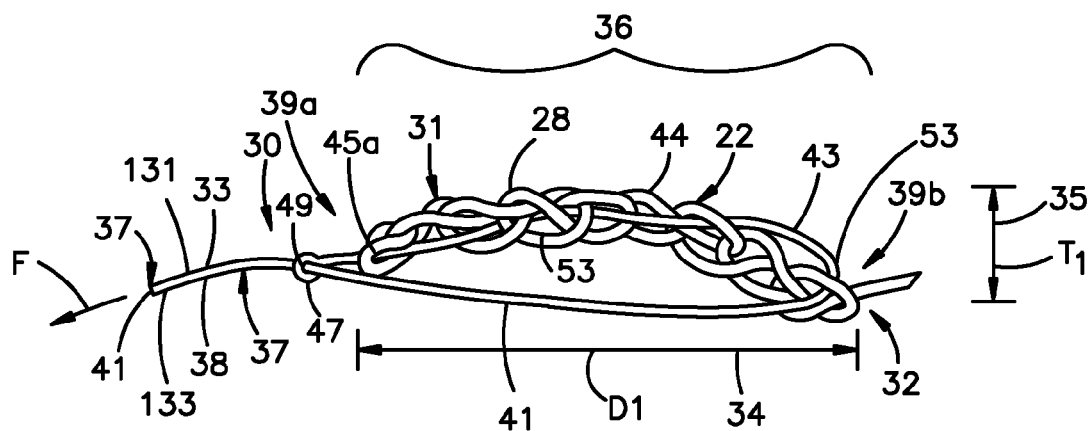
FIG. 2D is a perspective view of an anchor constructed in accordance with another embodiment.

Alternatively still, referring to FIG. 2D, the auxiliary strand 33 can define or carry a sliding member 47 which can define an opening 49 disposed proximally with respect to the expandable portion 36. In particular, the second portion 43 can be woven through a plurality of the openings 40 and can further define the sliding member 47. In accordance with the illustrated embodiment, the second portion 43 can terminate at the sliding member 47. The first portion 41 can be woven through at least one of the openings 40, for instance through a plurality of the openings 40, and can extend proximally through the opening 49 of the sliding member 47 so as to define the loop 53. Accordingly, the first and second portions 41 and 43 are slidably coupled to each other. In accordance with one embodiment, the actuation strand 38 can be configured as a woven strand that defines a plurality of openings including the opening 49. Alternatively, the opening 49 can be cut, for instance laser cut, through the second portion 43. During operation, the actuation force F can be applied to the first portion 41 when at least one of the sliding member 47 and the expandable portion 36 is braced (for instance by the anatomical structure 24 or a bracing tool) which decreases the size of the loop 53 and causes the expandable portion 36 to ride along the actuation strand 38, for instance the second portion 43, as the expandable portion 36 actuates from the first configuration to the expanded configuration. The first portion 41 can further be attached to the actuation strand 38 of a second anchor. Thus, the first portion 41 can define both the actuation portion 131 and the attachment portion 133. Otherwise stated, the actuation strand can define an end, such as the portion 41 or the portion 43, that can both receive the actuation force F and be attached to the actuation strand 38 of a second anchor. In this regard, it should be appreciated that the first portion 41 can define or carry the sliding member 47 and the second portion 43 can define the actuation portion 131 and the attachment portion 133.

Figure 2E:
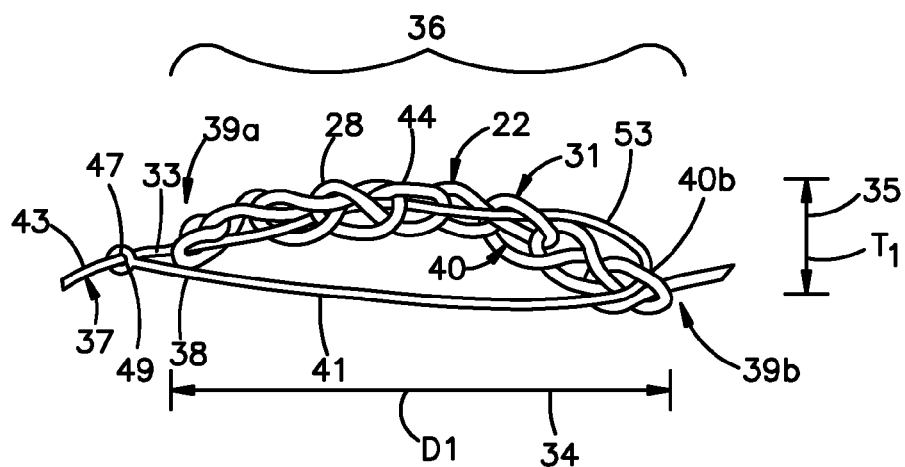
FIG. 2E is a perspective view of an anchor constructed in accordance with another embodiment.

For instance, referring to FIG. 2E, the first portion 41 can define or carry the sliding member 47 as described above with respect to FIG. 2D. In accordance with the illustrated embodiment, the first portion 41 can terminate at the sliding member 47. In particular, the second portion 43 can be woven through a plurality of the openings 40 and extend proximally from the anchor body 28 through sliding member 47. Accordingly, the first and second portions 41 and 43 are slidably coupled to each other.

It should thus be appreciated that the sliding member 47 can slidably couple the actuation portion 131 of the actuation strand 38 (for instance the first portion 41 or the second portion 43) with respect to the attachment portion 133 of the actuation strand 38 (for instance the other of the first portion 41 and the second portion 43). During operation, the actuation force F can be applied to the actuation portion 131 when the sliding member 47 or the expandable portion 36 is braced (for instance by the anatomical structure 24 or a bracing tool) which decreases the size of the loop 53 and causes the expandable portion 36 to ride along the actuation strand 38 as the expandable portion 36 actuates from the first configuration to the expanded configuration.

Figure 2F:
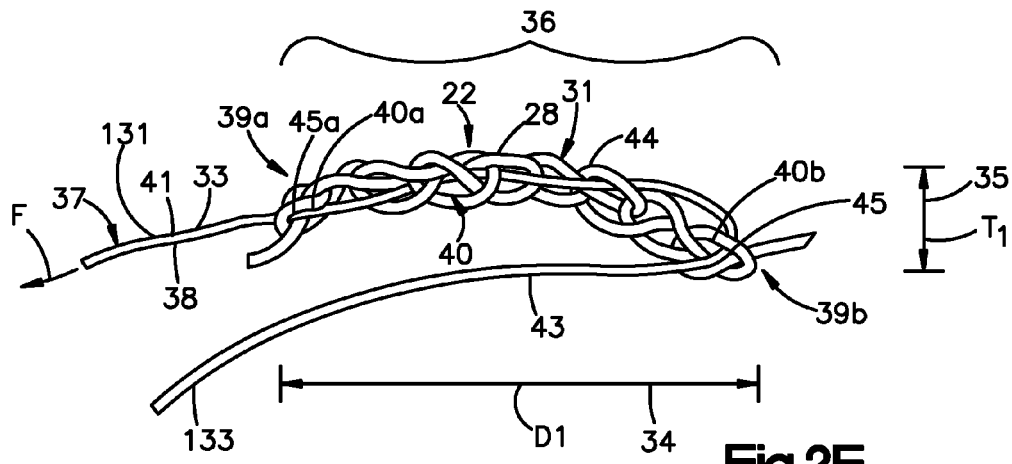
FIG. 2F is a perspective view of an anchor constructed in accordance with another embodiment.

Alternatively still, referring to FIG. 2F, the first portion 41 can extend through a plurality of the openings 40 as described above and proximally out of the anchor body 28 so as to define the actuation portion 131, and the second portion 43 can extend from the distal-most one of the openings 40 that the second portion 43 extends through, and proximally out the anatomical structure 24 without passing through any of the openings 40 or anywhere else in the anchor body 28. The second portion 43 can define the attachment portion 133 that can attach to an actuation strand 38 of the anchor 22 and is configured to attach to another anchor 22. During operation, when the actuation force F is applied to the actuation portion 131 of the actuation strand 38, such as the first portion 41 in accordance with the illustrated embodiment, when the proximal end 39*a* of the expandable portion 36 is braced (for instance by the anatomical structure 24 or a bracing tool), the distal end 39*b* of the expandable portion 36 is drawn toward the proximal end 39*a* along the portion of the actuation strand 38 that is woven through the openings 40, thereby causing the expandable portion 36 to become tangled as it is actuated from the first configuration to the expanded configuration.

Figure 2G:
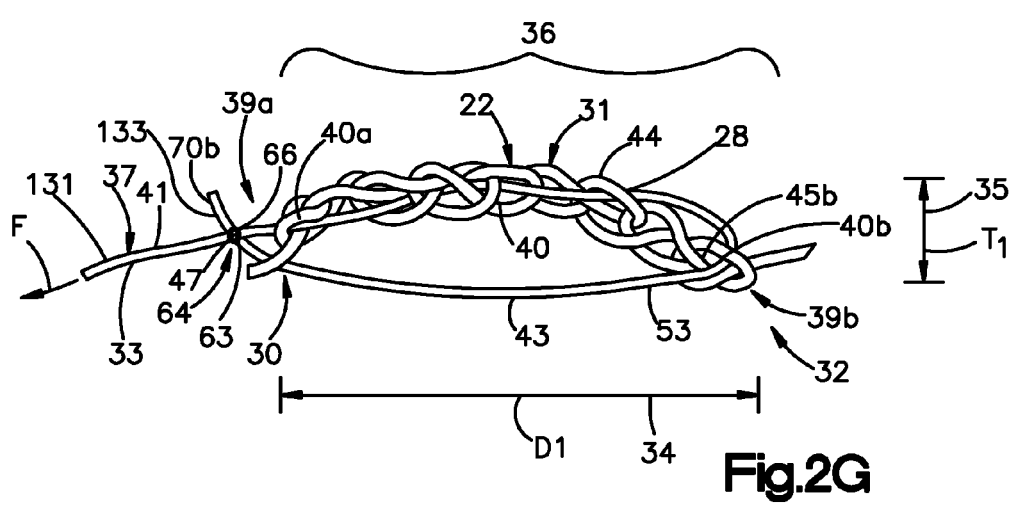
FIG. 2G is a perspective view of an anchor constructed in accordance with another embodiment.
Figure 4A:
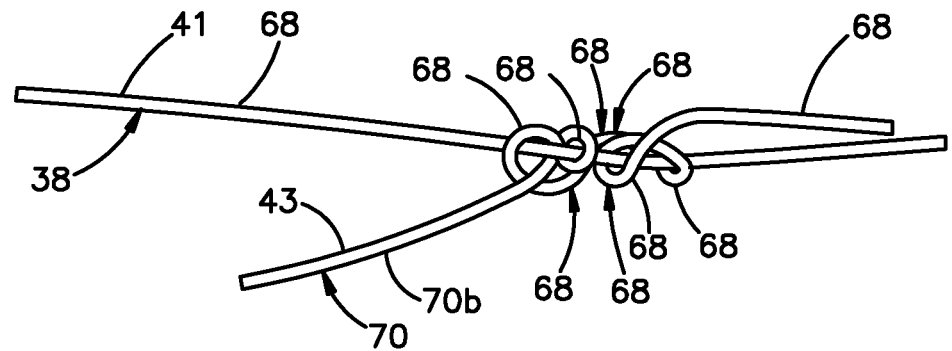
FIGS. 4A-F illustrate method steps for creating a sliding knot of the anchor illustrated in FIG. 2G in accordance with one embodiment.

Referring now to FIGS. 2G and 4A, the anchor 22 can further include a any suitable connector member 63 that can define a locking member 64 configured to selectively fix the relative position of the slidable portions (e.g., the actuation portion 131 and the attachment portion 133) of the actuation strand 38. The connector member 63 can be configured as a knot 66 or as any suitable alternatively constructed connector member 63 of the type described herein or any suitable alternative connector member. The knot 66 can be defined by the actuation strand 38 and can be disposed proximal with respect to the proximal end 30 of the anchor body 28. The actuation strand 38 can define a post end 68 of the knot 66 and a free end 70 of the knot 66 that is looped and knotted around the post end 68 such that the post end 68 is slidable with respect to the free end 70 before the free end 70 is tightened about the post end 68 at the knot 66. In accordance with the illustrated embodiment, the free end 70 can define a plurality of loops, such as four loops 71A-D about the post end 68, though it should be appreciated that the free end 70 can define as many loops about the post end 68 as desired. The free end 70 of the actuation strand 38 includes a static portion 70*a* that extends distally from the knot 66 and into the anchor body 28, and a free portion 70*b* that extends from the knot 66 and does not extend into the anchor body 28.

The post end 68 can be defined by one of the first portion 41 and the second portion 43, and the free end 70 can be defined by the other of the first portion 41 and the second portion 43. In accordance with the illustrated embodiment, the post end 68 is defined by the actuation portion 131, illustrated as the first portion 41, and the free end 70 is defined by the second portion 43. Accordingly, the first portion 41 and the second 43 are slidably coupled to each other such that the first portion 41 slides relative to the second portion 43. Thus, it should be appreciated that the locking member 64 can further define the sliding member 47, and the knot 66 can further be referred to as a sliding locking knot.

During operation, when the actuation force F is applied to the first portion 41, the first portion 41 slides proximally with respect to the second portion 43 thereby reducing the size of the loop 53 and actuating the anchor body 28 from the first configuration to the expanded configuration. The free end 70, which can be defined by the second portion 43, can be tightened so as to tighten the free end 70 about the post end 68, thereby locking the post end 68, defined by the first portion 41, with respect to translation relative to the free end 70. When the free end 70 is tightened about the post end 68, thereby fixing the knot 66 about the post end 68, the free end 70 can define the attachment 133 of the actuation strand 38. Alternatively or additionally, once the anchor body 28 has been expanded to the expanded configuration, the knot 66 can translate distally along the post end 68, thereby decreasing the size of the loop 53 and actuating the expandable portion 36 to the expanded configuration, and the knot 66 can subsequently be tightened about the post end 68 so as to fix the decreased size of the loop 53 and in some instances assist in retaining the anchor body 28 in the expanded configuration.

Figure 4B:
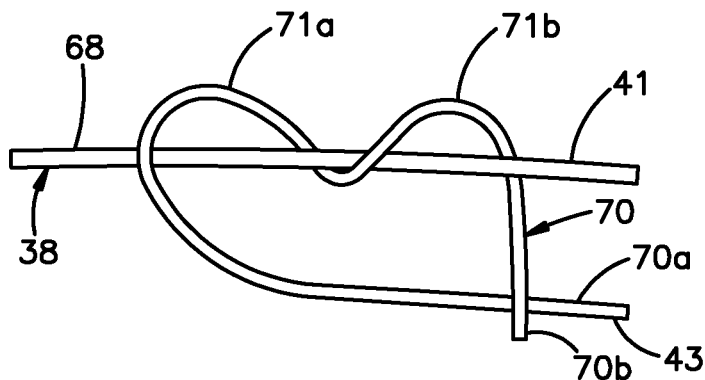

The construction of the knot 66 in accordance with one embodiment will now be described with reference to FIGS. 4A-E. As illustrated in FIG. 4A, the free end 70 defines a plurality of sliding loops 71A-D about the post end 68 that are configured to slide along the post end 68. At least one of the loops 71A-D, for instance the distal-most loops 71A and 71B as illustrated, can further define locking loops that are configured to be tightened when a tightening force F1 is applied to the free portion 70b, thereby tightening the free end 70 about the post end 68 in the manner described above. As illustrated in FIG. 4B, the knot 66 is created by looping the free end 70 about the post end 68 any of at least once such as twice along the same direction, thereby creating at least one sliding loop 71A such as a pair of loops, for instance a first sliding loop 71A and a second sliding loop 71B, about the post end 68. It should be appreciated that the free end 70 can be looped about the post end 68 as many times as desired so as to create as many sliding loops 71 as desired. In accordance with the illustrated embodiment, the free end 70 is translated distally as it is looped about the post end 68 such that the first loop 71A is disposed proximally with respect to the second loop 71B. The free end 70 thus defines a free portion 70b that extends proximally from the loops 71 and a static portion 70a that extends distally from the loops 71, and can also define the second portion 43 of the actuation strand 38.

Figure 4C:
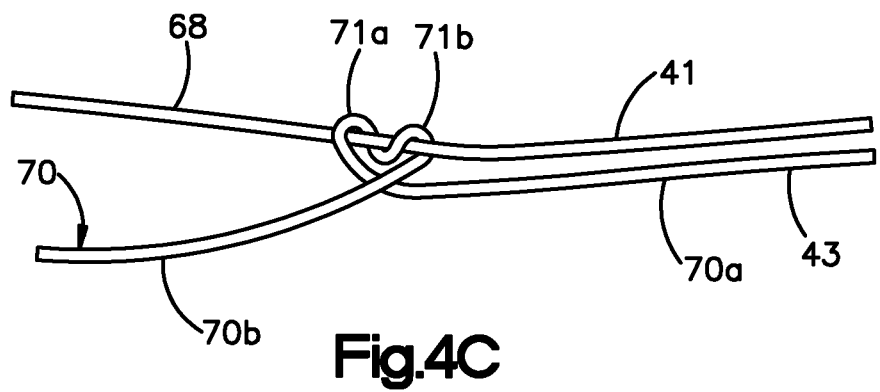
Figure 4D:
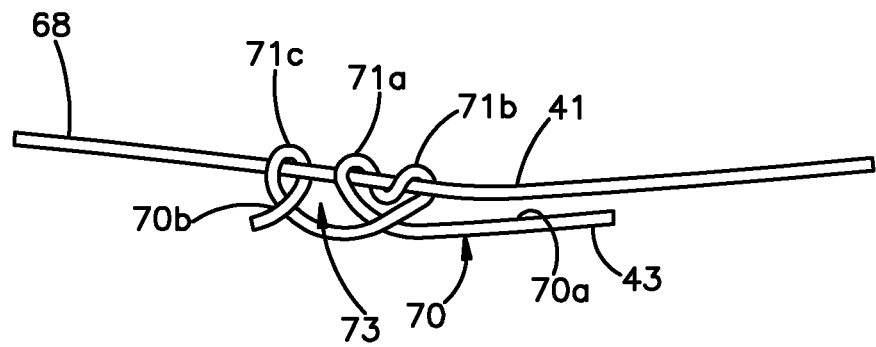
Figure 4E:
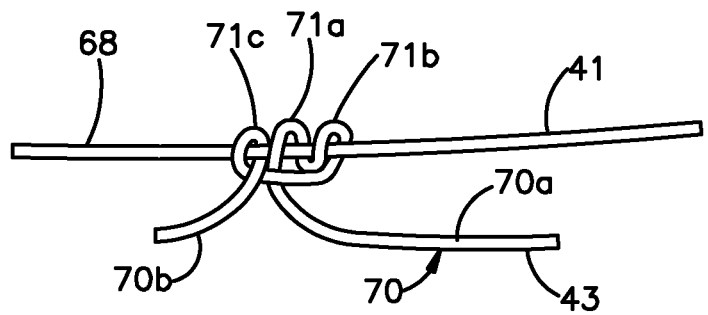

Next, referring to FIG. 4C, the free portion 70b of the free end 70 is tightened while maintaining the post end 68 and the free strand 70a in tension so as to bring the sliding loops 71A and 71B against each other. For instance, a distal tightening force can be applied to the free portion 70b, thereby bringing the second loop 71B against the first loop 71A. Next, as illustrated in FIG. 4D, the free portion 70b is again looped around the post end 68 in the same direction as the sliding loops 71A and 71B, at a location proximal of the first sliding loop 71A, so as to define a third sliding loop 71C. As the free portion 70b is looped the post end 68, a gap 73 is defined between the free portion 70b and the post end 68. The free portion 70b can then be fed through the gap 73 such that the sliding loop 71C further defines a locking loop, and the free portion 70b extends out from the sliding loop 71C. Next, referring to FIG. 4E, the free portion 70b can be tightened so as to bring the third sliding loop 71C against the immediately adjacent and proximally spaced first sliding loop 71A, such that the free portion 70b extends out from the gap 73.

Figure 4F:
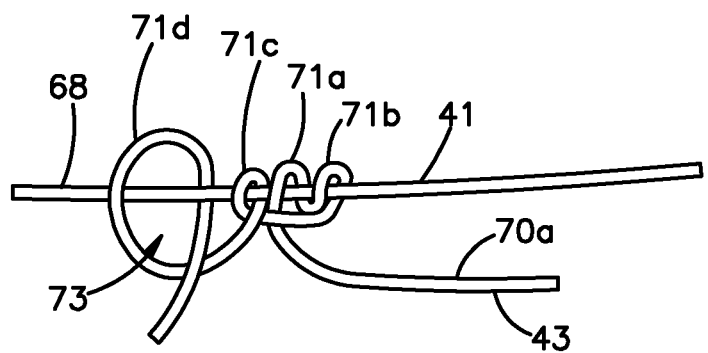

As illustrated in FIG. 4F, the free portion 70b is again looped the post end 68 in the same direction as the sliding loops 71A-C, at a location proximal of the third sliding loop 71C, so as to define a fourth sliding loop 71D. As the free portion 70b is looped the post end 68, a gap 73a is defined between the free portion 70b and the post end 68. The free portion 70b can then be fed through the gap 73 such that the fourth sliding loop 71D further defines a locking loop, and the free portion 70b extends out from the fourth sliding loop 71D. Next, the free portion 70b can be tightened so as to bring the fourth sliding loop 71D against the immediately adjacent and proximally spaced third sliding loop 71C, as illustrated in FIG. 4A.

It be appreciated that the knot 66 can define any number of sliding loops 71, such as at least one sliding loop 71 or a plurality of sliding loops 71. It should be further appreciated that at least one up to all of the sliding loops 71 can further define locking loops 71 as desired. During operation, once the knot 66 has been created, the actuation force F can be applied to the post end 68, which can define the actuation portion 131, illustrated as the first portion 41, such that the expandable portion 36 of the anchor body 28 expands from the first configuration to the expanded configuration. It should be further appreciated that the knot 66 can be disposed in an unlocked configuration whereby the post end 68 can translate through to the knot 66 relative to the loops 71 as the anchor body 28 expands. A locking force, which can be a tensile force, can be applied to the free portion 70b so as to actuate the knot 66 to a locked configuration. In particular, the locking loops 71 are tightened about the post end 68, preventing the actuation portion 131 from translating through the knot 66. The free portion 70b of the free end 70 can extend from the knot 66 as illustrated in FIG. 2G and define the attachment portion 133 of the actuation strand 38 that attaches the anchor body 28 to another anchor.

Figure 2H:
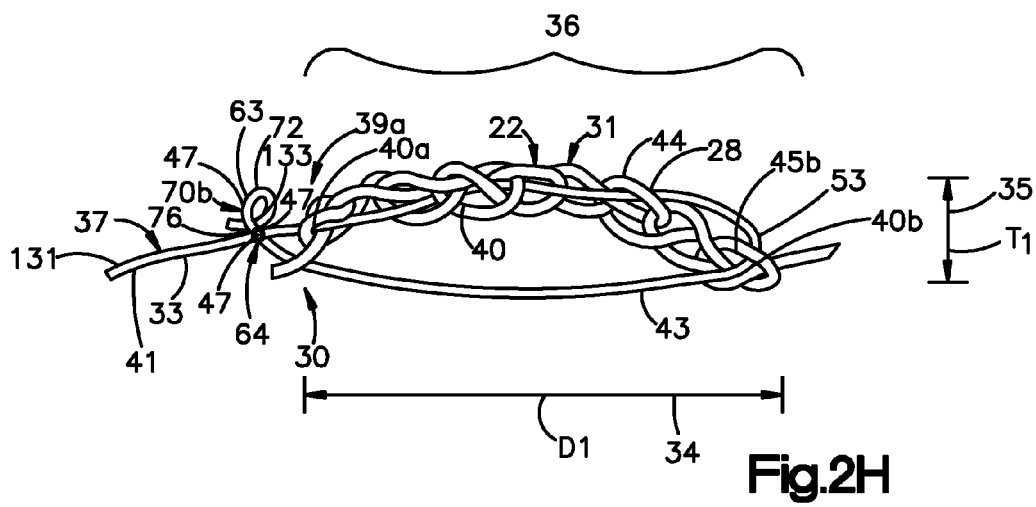
FIG. 2H is a perspective view of an anchor constructed in accordance with another embodiment.

As illustrated in FIG. 2H, the free portion 70b, and thus the attachment portion 133, can define a connector member 63 that is configured to attach to an actuation strand of another anchor, either directly or indirectly. In accordance with the illustrated embodiment, the connector member 63 is configured as an eyelet 72 that is integral with the actuation strand 38.

Accordingly, because the actuation strand 38 extends from the expandable portion 36 of the anchor body 28, it can also be said that the eyelet 72 likewise extends from the expandable portion 36. Alternatively or additionally, the anchor body 28 can include an eyelet 84b (see FIGS. 6A-B) that extends from the expandable portion 36, an eyelet 90 (see FIGS. 9A-C) that also extends from the expandable portion 36, or any alternatively constructed eyelet that extends, directly or indirectly, from the expandable portion 36.

A complementary strand, such as an attachment portion of an actuation strand, or an auxiliary connector member such as a connector strand (see, e.g. FIGS. 33A-C) can be fed through the eyelet 72 or so as to attach the anchor 22 to a second anchor. The complementary strand can translate through the eyelet 72, thus it should be appreciated that the eyelet 72, along with the eyelets 84b and 90, can define a sliding member 47. For instance, the attachment portion 133 defined by the free portion 70b of the actuation strand 48 as illustrated in FIG. 2G can be fed through an eyelet of a second anchor body, configured as the eyelet 72, the eyelet 84b, the eyelet 90, or any suitable alternatively constructed eyelet that is attached, directly or indirectly, to the expandable portion of an anchor body so as to attach the anchor body 28 to the second anchor body. In that regard, it should be appreciated that the anchor assembly 20 can include at least one connector member 63 that is configured to join more than one anchor together. The connector member 63 can be integral with at least one of the actuation strands 38, or can be separate and attached to at least one of the actuation strands 38.

Figure 5A:
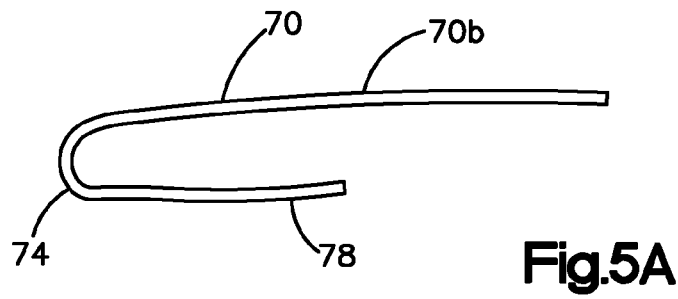
FIGS. 5A-B illustrate method steps for creating an eyelet of the anchor illustrated in FIG. 2H in accordance with one embodiment.
Figure 5B:
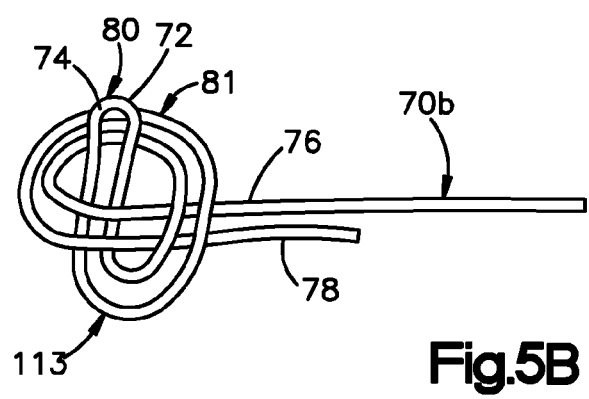

Referring to FIGS. 5A-B, the eyelet 72 can be constructed by first folding the free portion 70b over itself so as to define a folded portion 74 that extends from a first end, such as a stem 76. The stem 76 thus extends between the knot 66 (see FIG. 2H) and the folded portion 74. The free portion 70b defines a second end, such as a terminal end 78, that extends from the folded portion 74. The free portion 70b can be oriented such that the terminal end 78 can be disposed adjacent the stem 76. The folded portion 74 can be looped over the stem 76 and the terminal end 78 so as to define a loop 81, and can subsequently be fed under the stem 76 and the terminal end 78, and through the loop 81 so as to define an eyelet knot 80 at a closure location 111 that closes the folded portion 78 and defines the eyelet 72. A tensile force can then be applied to the folded portion 78 so as to tighten the knot 80 and close the folded portion 74, such that the stem 76 and the terminal end 78 extend from the knot 80, and the folded portion 74 also extends from the knot and defines the eyelet 72. Thus, the eyelet 72 has a base that is defined, for instance, by the knot 80, or can be defined by any alternative closure member.

Figure 5C:
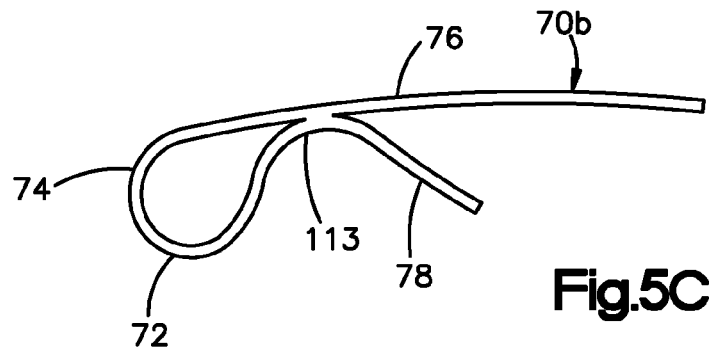
FIG. 5C illustrates method steps for creating an eyelet of the anchor illustrated in FIG. 2H in accordance with an alternative embodiment.
Figure 5D:
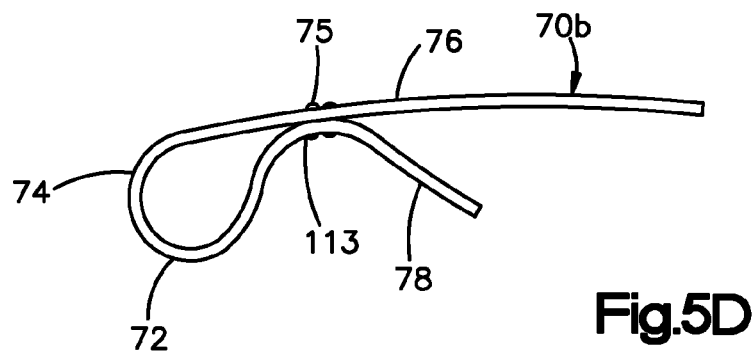
FIG. 5D illustrate method steps for creating an eyelet of the anchor illustrated in FIG. 2H in accordance with an alternative embodiment.

For instance, referring to FIG. 5C, the terminal end 78 can be welded, for instance heated or via an adhesive, to the stem 76 at the closure location 113 so as to close the folded portion 74 and define the eyelet 72. The closure location 113 can define the base of the eyelet 72. Alternatively still, referring to FIG. 5D, the terminal end 78 can be stitched to the stem 76 at the closure location 113 so as to close the folded portion 74 and define the base of the eyelet 72. For instance, a strand, such as at least one suture strand 75, can be stitched through the terminal end 78 and the stem 76 so as to join the terminal end 78 to the stem 76. Thus, it should be appreciated that the terminal end 78 can be attached to the stem 76 in any known manner so as to define the eyelet 72, such that a strand, such as an actuation strand, of another anchor 22 or a connection strand can be fed through the eyelet 72 and apply a force, for instance an approximation force, to the eyelet 72 as described above with respect to FIGS. 1A-B. The approximation force can be sufficient so as to approximate a gap 24c that is disposed between the anchor bodies 28 as illustrated in FIGS. 1A-B.

Figure 6A:
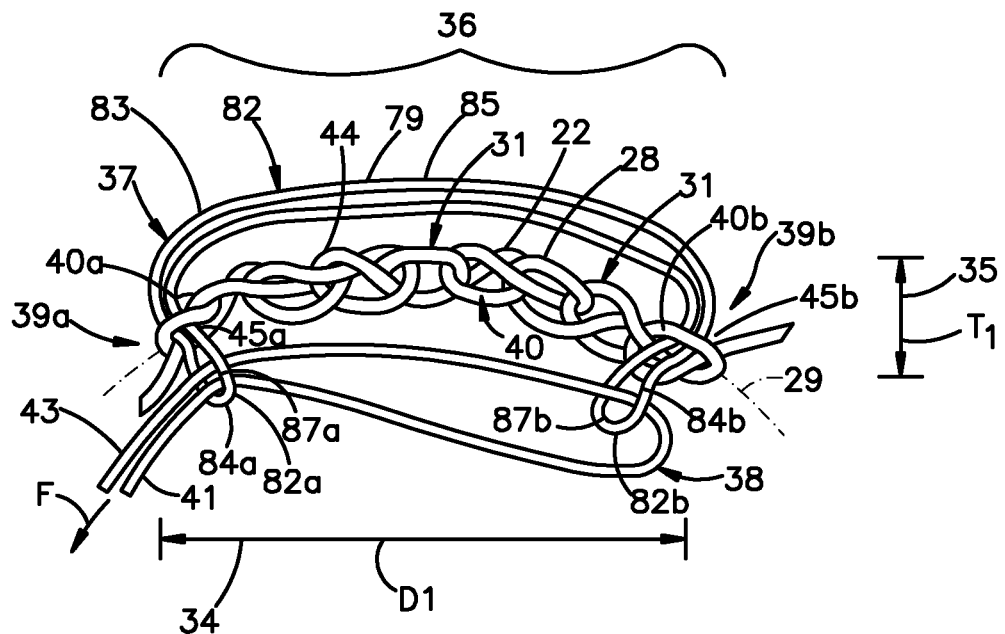
FIG. 6A is a perspective view of an anchor constructed in accordance with another embodiment, showing the anchor in a first configuration.
Figure 6B:
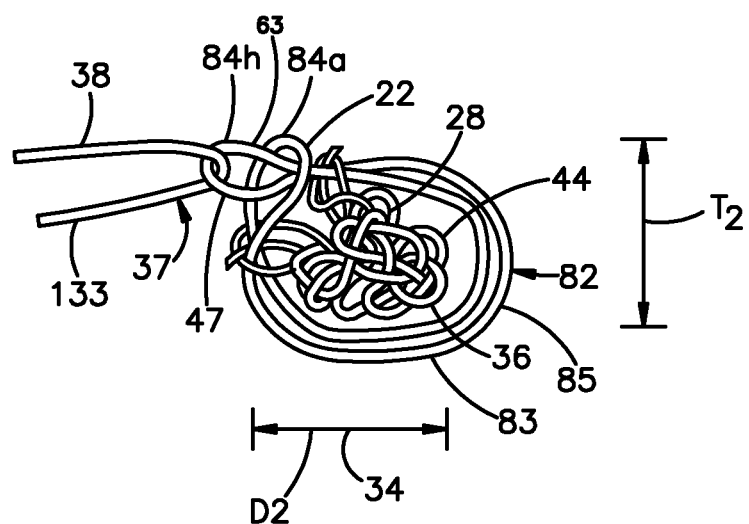
FIG. 6B is a perspective view of the anchor illustrated in FIG. 6A, showing the anchor in an expanded configuration.

Referring now to FIGS. 6A-B, the anchor 22 can further include an attachment member 82 that can attach to both the anchor body 28, such as the expandable portion 36, and the actuation strand 38 so as to operably couple the actuation strand 38 to the expandable portion 36. The attachment member 82 can be auxiliary to the anchor body 28, and separate or non-integral with respect to both the anchor body strand 44 and the actuation strand 38. The attachment member 82 can define a looped strand 79 that defines at least one fixation region such as an eyelet, for instance a first eyelet 84a and a second eyelet 84b at opposed first and second ends 82a and 82b, respectively of the looped strand 79. The attachment member 82 can further include a body portion 85 that is attached between the eyelets 84a and 84b, such that the attachment member 82 can define a continuous loop 83.

The first and second eyelets 84a and 84b can extend substantially along the second direction 35 from the body portion 85 through at least one respective opening 40 of the anchor body 28. In accordance with the illustrated embodiment, the first and second eyelets 84a and 84b extend through respective first and second select openings 45a and 45b which can be located as desired such that the first eyelet 84a is disposed proximal with respect to the second eyelet 84b. The body portion 85 can extend outside the expandable portion 36 between the first and second eyelets 84a and 84b as illustrated, or the body portion 85 can alternatively extend through at least one of the openings 40 between the first and second select openings 45a and 45b, including a plurality of openings 40. In accordance with one embodiment, the first select opening 45a can be the proximal-most opening 40a, such that the first eyelet 84a can extend through the proximal-most opening 40a, and the second select opening 45b can be the distal-most opening 40b such that the second eyelet 84b can extend through the distal-most opening 40b. It should be appreciated that once the attachment member 82 is attached to the anchor body 28, the first and second eyelets 84a and 84b define respective openings 87a and 87b of the anchor 22.

The actuation strand 38 can be attached to the second eyelet 84b, for example fed through the opening 87b of the second eyelet 84, so as to define the first and second portions 41 and 43 that extend from the second eyelet 84b. The actuation force F can be applied to the both the first and second portions 41 and 43 such that the actuation strand 38 biases the second eyelet 84b toward the first eyelet, thereby moving the expandable portion 36 proximally from the loop 31 that defines the second select opening 45b toward the loop 31 that defines the first select opening 45a, thereby actuating the expandable portion 36 from the first configuration to the expanded configuration. In accordance with the illustrated embodiment, the actuation strand 38 is folded so as to define a connection location such as a fold 86 that is configured to attach to the second eyelet 84b. The first and second portions 41 and 43 extend proximally from opposite sides of the fold 86. The fold 86 can extend through the second eyelet 84b, and the first and second portions 41 and 43 can extend proximally from the fold 86 and through the opening 87a of the first eyelet 84a. Accordingly, both the first and second portions 41 and 43 extend through the first opening 87a of the first eyelet 84a, and the fold is looped through the opening 87b of the second eyelet 84b so as to attach the actuation strand 38 to the second eyelet 84b. It should be appreciated that the actuation strand 38 thus defines a travel path for the second eyelet 84b through the first eyelet 82a when the expandable portion 36 is actuated from the first configuration to the expanded configuration.

For instance, during operation, the actuation force F can be applied to both the first and second portions 41 and 43, which extend proximally from the first eyelet 84a. Thus, both the first and second portions 41 and 43 can define actuation portions 131 of the actuation strand 38. Alternatively, the actuation force F can be applied to either of the first and second portions 41 and 43 while the other of the first and second ends is braced so as to induce tension in the actuation strand during application of the actuation force F. Thus, it can be said that at least one of the first and second portions 41 and 43 can define an actuation portion 131 that receives the actuation force F so as to actuate the expandable portion 36 from the first configuration to the expanded configuration. The actuation force F causes the fold 86, and thus the actuation strand 38, to bias the second eyelet 84b proximally toward and through the first eyelet 84a along the path defined by the actuation strand 38. As the second eyelet 84b moves proximally, the attachment member 82 actuates the expandable portion 36 to actuate from the first configuration to the expanded configuration.

Figure 28A:
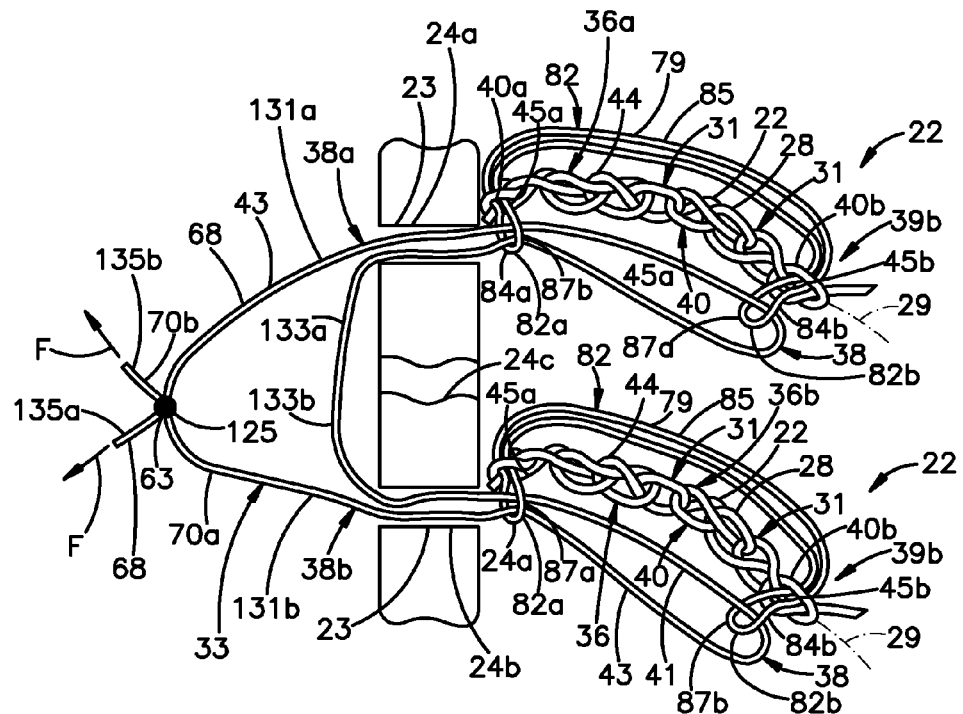
FIG. 28A is a side elevation view of an anchor assembly constructed in accordance with another embodiment, including first and second anchors shown in respective first configurations and implanted in an anatomical structure.

It should be further appreciated that at least one or both of the first and second portions 41 and 43 can define attachment portions 133 that attach to a second anchor (see e.g., FIG. 28A). Alternatively, the second eyelet 84b can extend out from the first eyelet 84a and further out the anatomical structure 24 if desired, the actuation strand 38 can be removed from the eyelet 84b, and a connector member, such as a connector strand, can subsequently be fed through the second eyelet 84b and attached to a second anchor, directly or indirectly, so as to attach the anchor 22 to the second anchor as desired.

Figure 6C:
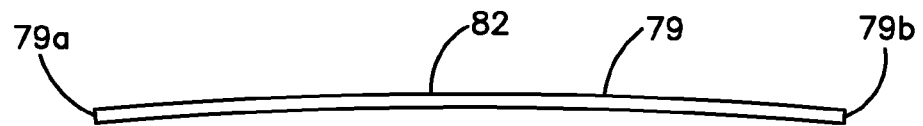
FIGS. 6C-E are perspective views showing method steps for creating the anchor illustrated in FIG. 6A.
Figure 6D:
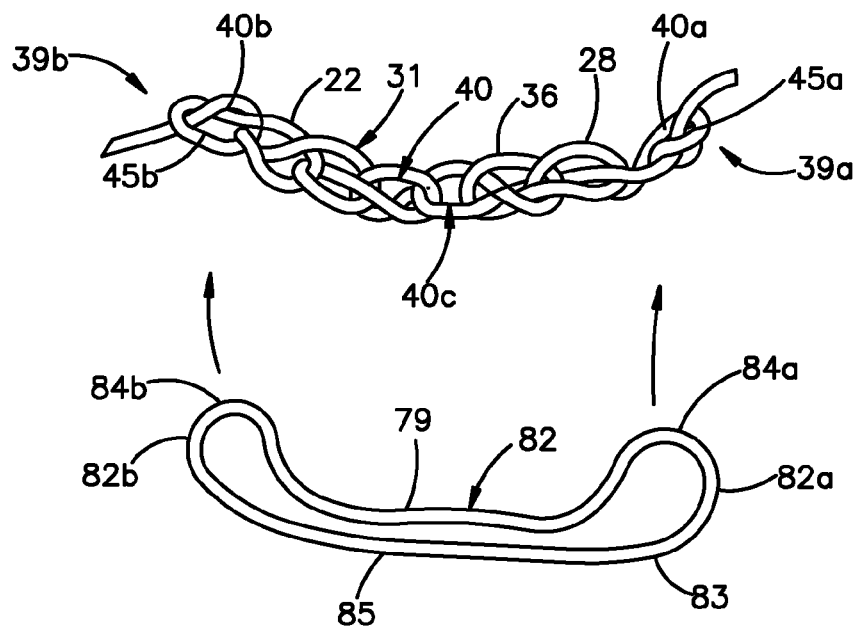
Figure 6E:
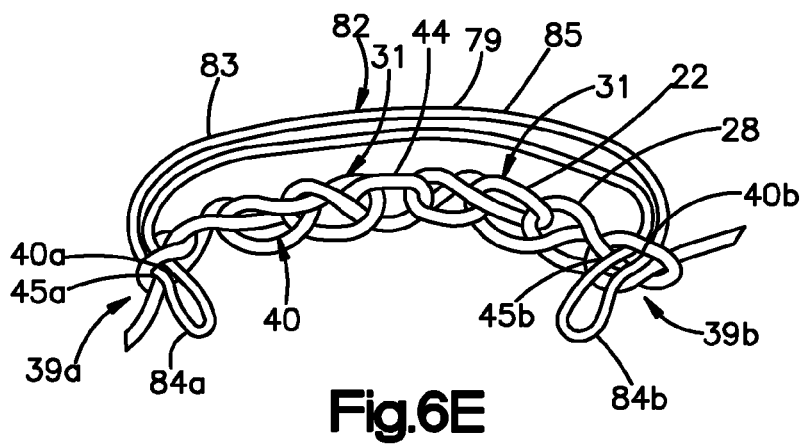

As illustrated in FIG. 6C, the attachment member 82 can be in the form of a substrate, which in one embodiment can be a strand, such as a suture strand or any alternatively constructed strand 79 having first and second opposed ends 79a and 79b. The opposed ends 79a and 79b can be attached as desired such that the attachment member 82 defines the continuous loop 83 as illustrated in FIG. 6D. The loop 83 can be configured so as to define the first and second eyelets 84a and 84b, for instance at opposed ends of the loop 83, that can be aligned with the first and second select openings 45a and 45b. The first and second eyelets 84a and 84b can be inserted into the respective select openings 45a and 45b as illustrated in FIG. 6E. It should be appreciated that the body portion 85 can be further woven through at least one of the openings 40 disposed between the first and second select openings 45a and 45b, such as a plurality of the intermediate openings 40c, as desired.

While the actuation strand 38 can be separate or non-integral from the substrate 42 of the anchor body 28 and attached to the anchor body 28 as described above, it should be appreciated that the actuation member 37 can alternatively be integral with the anchor body 28. Thus, the actuation strand 38 can alternatively be integral with the substrate 42, such as the anchor body strand 44, and thus also therefore integral with the expandable portion 36.

Figure 7A:
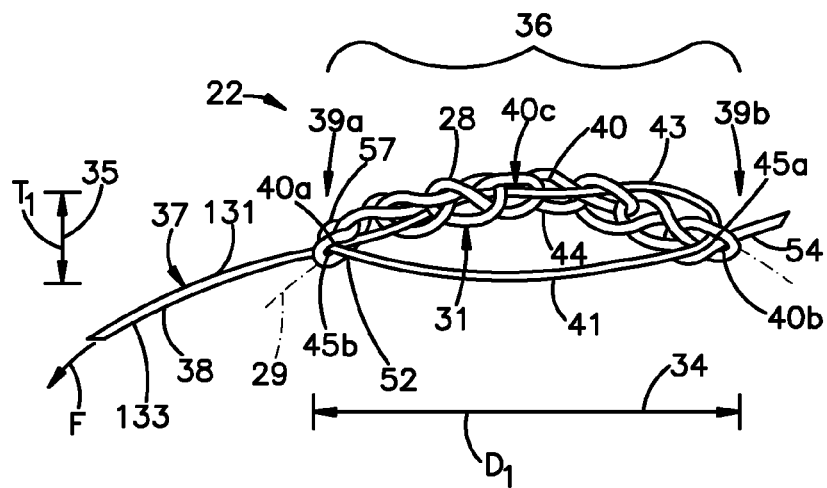
FIG. 7A is a perspective view of an anchor including an actuation strand integral with an anchor body woven through a plurality of openings defined by an expandable portion of the anchor body, showing the anchor body in a first configuration.
Figure 7B:
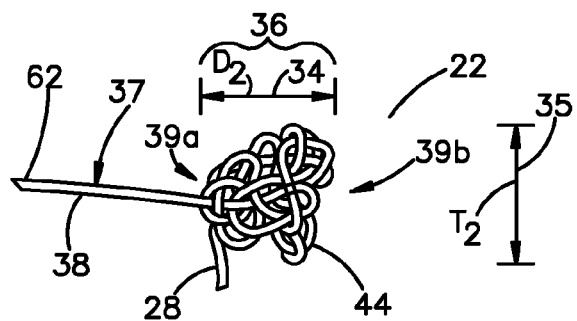
FIG. 7B is a perspective view of the anchor illustrated in FIG. 7A, showing the anchor body in an expanded configuration.
Figure 7C:
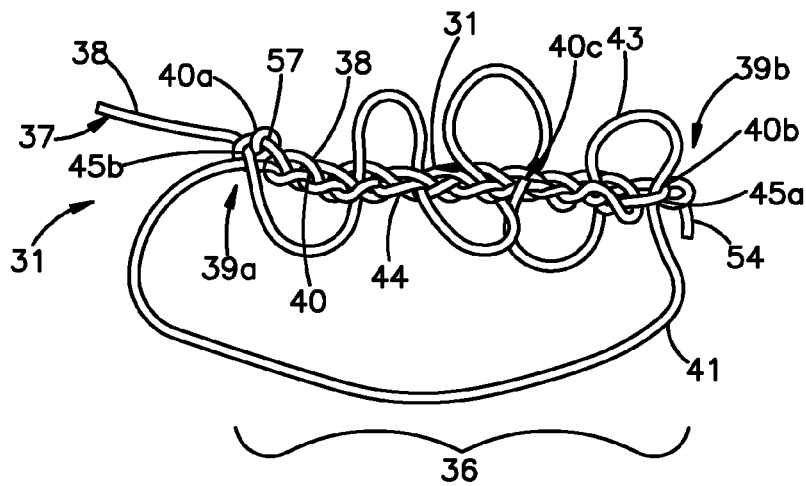
FIG. 7C is a perspective view illustrating the insertion of the actuation strand through the openings when the anchor body is in the first configuration as illustrated in FIG. 7A.

For instance, Referring now to FIGS. 7A-C, the actuation strand 38 can be defined by one of the first and second end portions 52 and 54 of the anchor body strand 44, which can be configured as described above with respect to FIGS. 3A-C, or otherwise configured. In accordance with the illustrated embodiment, the first end portion 52 that extends proximally from the anchor body 28 defines the actuation strand 38, and the second end portion 54 that extends distally from the anchor body 28 can be terminated at a location proximate to the anchor body 28, for instance proximate to corresponding distal end 39b of the expandable portion 36, such that the second end portion 54 has a length insufficient to attach the anchor body 28 to an anchor body of a second anchor.

While the first end portion 52 of the anchor body strand 44 can be terminated at a location proximate to the proximal-most loop 57 of the loops 31 as described above with reference to FIGS. 3A-C, the first end portion 52 can alternatively define the actuation strand 38 that extends distally from the proximal end 39a of the expandable portion 36, and can be woven through, and thus extend through, at least one select opening 45a of the openings 40 that is spaced distally from the proximal end 39a of the expandable portion 36. The select opening 45a can be the distal-most opening 40b as illustrated, or can alternatively be one of the intermediate openings 40c. The actuation strand 38 can be extended through the select opening 45a so as to define a loop 53, including first and second portions 41 and 43. For instance, the first portion 41 can extend from the first portion 52 distally to the first select opening 45a. The second portion 43 can extend from the first select opening 45a proximally out the anchor body 28 and out the anatomical structure 24. For instance, in accordance with the illustrated embodiment, the second portion 43 can be woven through, and thus extend through, at least one of the openings 40 such as a plurality of select openings 40 that can be disposed between the proximal end 39a and the select opening 45a. For instance, the second portion 43 of the actuation strand 38 can be woven through at least one of the intermediate openings such as a plurality of the intermediate openings 40c. The second portion 43 can extend out the expandable portion 36 of the anchor body 28 through the second select opening 45b of the openings 40, which can be the proximal-most opening 40a, for instance of the proximal-most stopper knot 46.

Thus, a tensile force F, which can be a proximally directed force, applied to the actuation strand 38, for instance at the first portion 41, when the expandable portion 36, such as the proximal end 39a, is braced, causes the expandable portion 36 to move from the first configuration to the expanded configuration. The first portion 41 can thus define the actuation portion 131 of the integral actuation strand 38. In particular, the expandable portion 36 slides along the actuation strand 38, for instance along the second portion 43, as it collapses along the direction of elongation 35 from the first distance D1 to the second distance D2 along the direction of elongation 34. As the expandable portion 36 collapses along the actuation strand 38, the expandable portion 36 can become entangled or otherwise deformed in the second direction as it travels along the second portion 43, thereby causing the expandable portion 36 to expand in the second direction 35 from the initial maximum thickness T1 to the expanded maximum thickness T2 that is greater than the initial maximum thickness T1. The first portion 41 can then be terminated, for instance cut and singed at a location proximate to the anchor body 28, or can alternatively define an attachment portion 133 that can be attached to a second anchor, for instance joined to a complementary connector member of the second anchor in any desired manner as described herein. Thus, it should be appreciated that the first portion 41 that extends out the anatomical structure 24 from the anchor body 28 can define at least one of or both of the actuation portion 131 and the attachment portion 133.

Figure 8B:
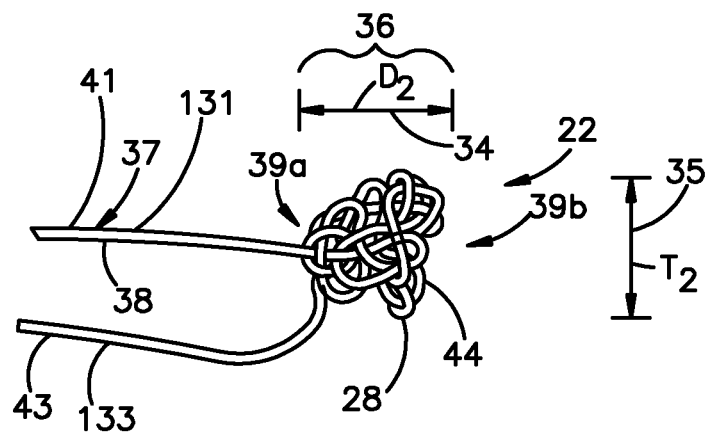
FIG. 8B is a perspective view of the anchor illustrated in FIG. 8A, showing the anchor body in an expanded configuration.

Alternatively, as illustrated in FIGS. 8A-B, the anchor 22 can be constructed as described above with respect to FIGS. 7A-C, however the second end portion 54 of the anchor body strand 44 can extend from the distal end 39b of the expandable portion 36 a sufficient distance so as to define the attachment portion 133 that is configured to attach to a second anchor so as to attach the anchor 22 to the second anchor. For instance, the attachment portion 133 can attach to an anchor strand of the second anchor. The attachment portion 133 can be integral with the anchor strand of the second anchor, or the anchor assembly 20 can include a connector that attaches the attachment portion 133 to the second anchor, such as the actuation strand of the second anchor. The connector can be integral with at least one or both of the actuation strand 38 and the actuation strand of the second anchor, or can be separate and attached to at least one or both of the actuation strand 38 and the actuation strand of the second anchor. During operation, the actuation force F can be applied to the first portion 41, which can define the actuation portion 131 as described above. It should be appreciated that the actuation force F can be at least partially counterbalanced by the attachment portion 133, which defined by the second portion 43 in the illustrated embodiment. Furthermore, as described above with respect to FIG. 1D, the opposed first and second ends of the actuation strand 38 (which can be defined by the actuation portion 131 and the attachment portion 133, respectively) can be tied, stitched, or otherwise secured to another anatomical structure 27, thereby inducing tension in the actuation strand 38 and securing the auxiliary structure 25 between the actuation strand 38 and the anatomical structure 24.

Figure 9A:
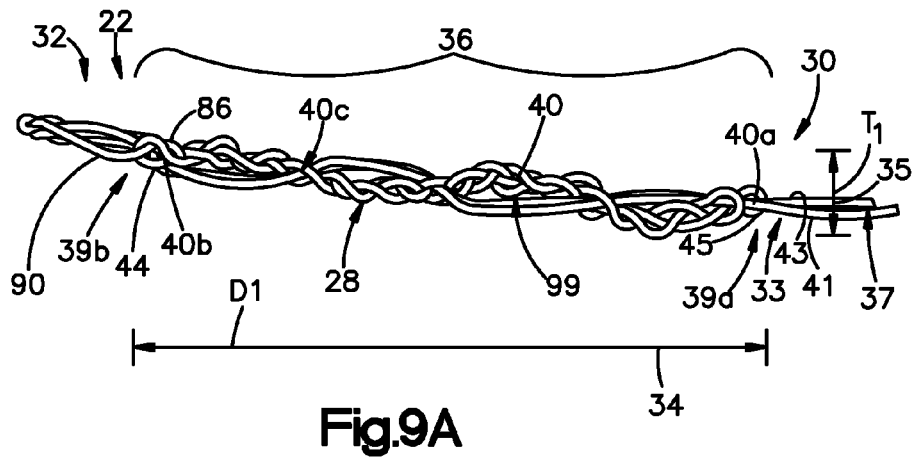
FIG. 9A is a perspective view of an anchor including an anchor body and an eyelet extending from the anchor body, and an actuation strand attached to the eyelet and woven through an expandable portion the anchor body, showing the expandable portion in a first configuration.

Referring now to FIG. 9A, and as described above, the anchor body 28 can include an eyelet 90 that extends from the expandable portion 36. In accordance with the illustrated embodiment, the eyelet 90 can be disposed at the distal end 32 of the anchor body 28 when the expandable portion 36 is in the first configuration. The eyelet 90 can be constructed as described herein, or can alternatively comprise a select one of the loops of the anchor body 28, for instance a loop that might be larger than one or more of the other loops defined by the anchor body 28. The anchor 22 can include an auxiliary strand 33 that can define an actuation strand configured to actuate the anchor 22 between the first configuration and the expanded configuration in the manner described above when the anchor is implanted at the target anatomical structure 24. Alternatively or additionally, the auxiliary strand 33 can define a deployment strand that is configured to facilitate attachment of the anchor 22 to another anchor, as described in more detail below, for instance with reference to FIGS. 37A-D.

The auxiliary strand 33 can define first and second portions 41 and 43, and a connection location such as a fold 86 that is disposed between and integrally attached between the first and second portions 41 and 43. The fold 86 can extend through the eyelet 90, so as to attach the auxiliary strand 33 to the eyelet 90, such that the first and second portions 41 and 43 extend proximally from the eyelet 90 through at least a select opening 45 such as a plurality of select openings 45 of the openings 40 when the expandable portion 36 is in the first configuration. The select openings 45 can include at least one intermediate opening 40c, and can further include the proximal-most opening 40a. The auxiliary strand 33 can further be tied or otherwise attached to the eyelet 90 if desired. In accordance with the illustrated embodiment, the first and second portions 41 and 43 extend through a plurality of select openings 45 of the openings 40, and further extend through the same openings 40. For instance, the first and second portions 41 and 43 can extend through every other opening 40 along the proximal direction from the eyelet 90, every third opening 40 along the proximal direction from the eyelet 90, every opening 40 along the proximal direction from the eyelet 90, or can extend through the eyelets 40 in any regular repeating pattern or any irregular nonrepeating pattern as desired.

Figure 9B:
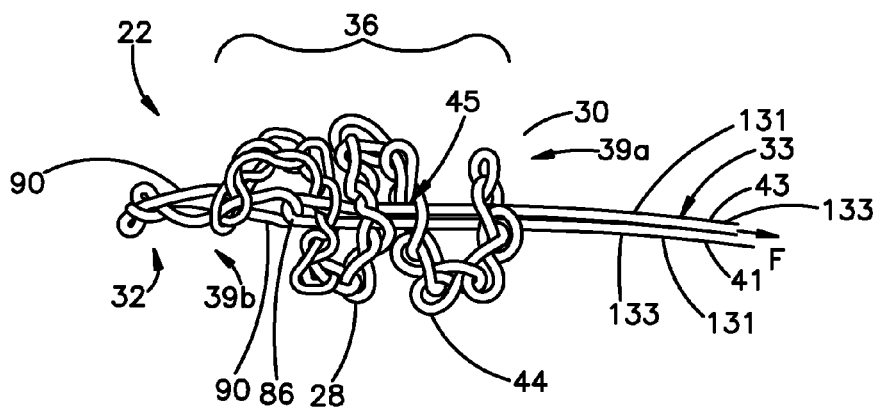
FIG. 9B is a perspective view of the anchor illustrated in FIG. 9A, showing the expandable portion being actuated from the first configuration to an expanded configuration.
Figure 9C:
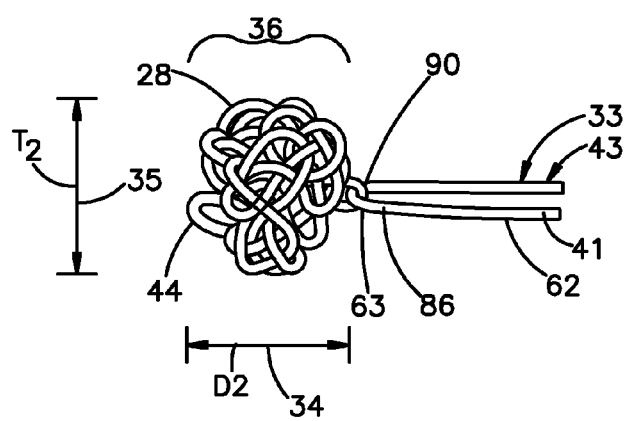
FIG. 9C is a perspective view of the anchor illustrated in FIG. 9A, showing the expandable portion in the expanded configuration.

Referring to FIG. 9B, because the first and second portions 41 and 43 extend through the same select openings 45 along the proximal direction from the eyelet 90, the first and second portions 41 and 43 define a travel path for the eyelet 90 through the select openings 45 when the actuation force F is applied to the first and second portions 41 and 43. Accordingly, as the first and second portions 41 and 43 of the auxiliary strand 33 travel proximally through the select openings 45 of the anchor body 28 in response to the applied actuation force F, the eyelet 90 travels with the actuation member 38 through the select openings 45 as the expandable portion actuates from the first configuration to the expanded configuration. As a result, as illustrated in FIG. 9C, the auxiliary strand 38 can travel a sufficient distance in response to the applied actuation force F such that the loop 86 is disposed proximally with respect to the expandable portion 36 when the expandable portion 36 is in the expanded configuration. Accordingly, the eyelet 90 also extends proximally from the expandable portion 36 when the expandable portion 36 is in the expanded configuration.

The eyelet 90 can thus define a connector member 63 of the anchor body 28, and thus the anchor 22, that is configured to attach to a second anchor, either directly (for instance via a connector member that is integral with the second anchor), or indirectly (for instance via at least one connector member that is separate or non-integral from and attached to the second anchor). In accordance with one embodiment, the eyelet 90 can receive a strand that attaches the anchor 22 to the second anchor. For instance, the received strand can be the actuation strand of the second anchor, or a connector strand that attaches, directly or indirectly, the actuation strand of the second anchor to the eyelet 90.

The anchor body 28 can be constructed in any manner as desired, for instance by creating the eyelet 90 and further by creating the expandable portion 36 in any suitable manner as desired. Thus, the anchor body strand 44 can be tied in a knot so as to define the eyelet 90, or welded, stitched, or otherwise attached to itself so as to define the eyelet 90.

Figure 10A:
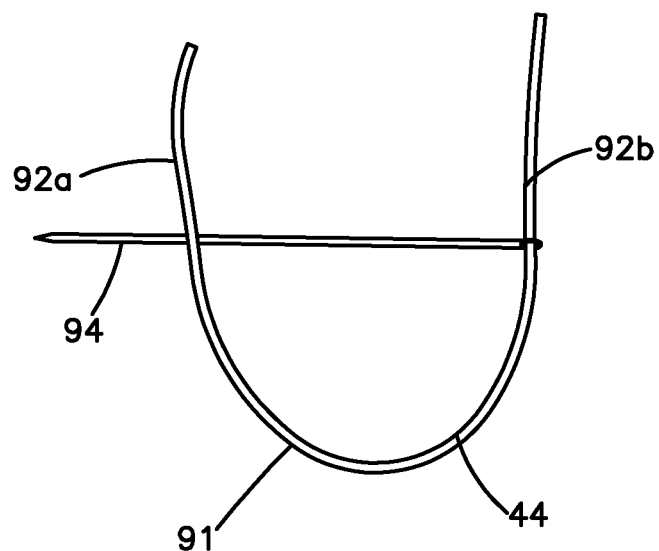
FIGS. 10A-G illustrate method steps of creating the eyelet illustrated in FIG. 9A in accordance with one embodiment.
Figure 10B:
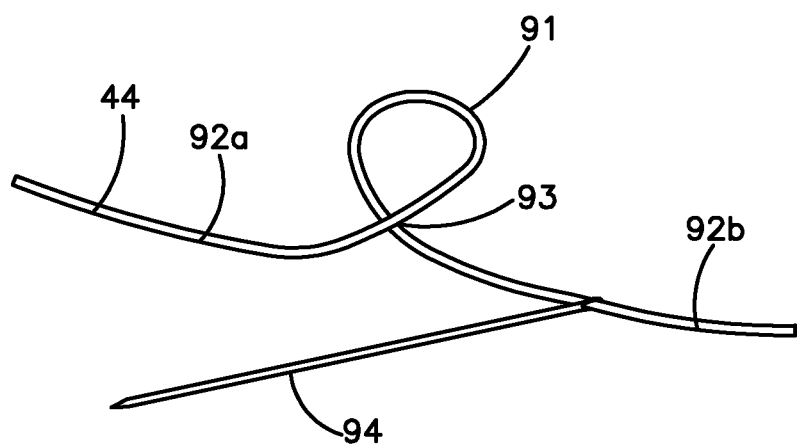
Figure 10C:
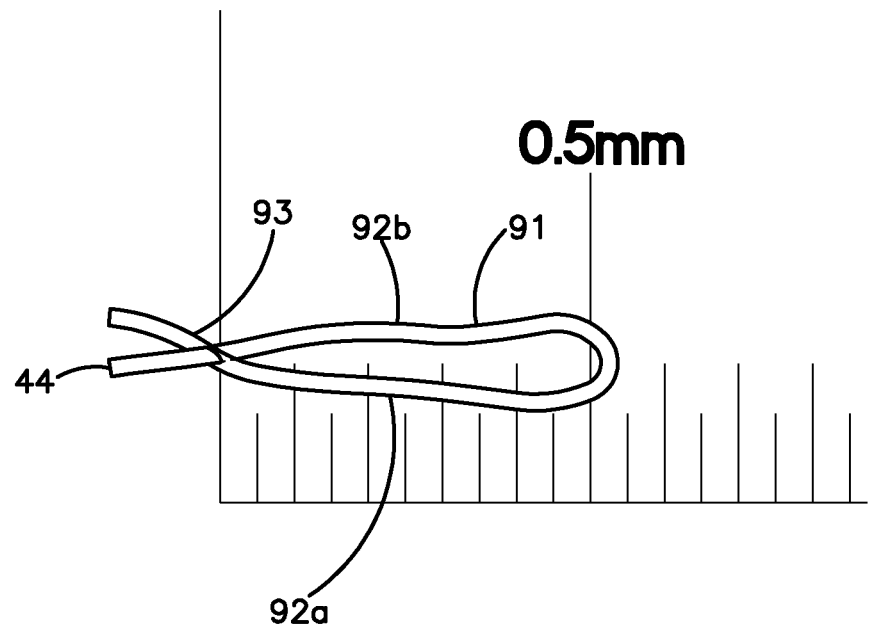

In accordance with one embodiment, referring to FIGS. 10A-B generally, the anchor body strand 44 can be folded and stitched through itself so as to define a loop 91, and first and second segments 92a and 92b, respectively, that extend from opposed sides of the loop 91. The tip of a needle 94 can be inserted through the first segment 92a so as to define a first channel that extends through the first segment 92a. The second segment 92b can be fed through the eyelet of the needle 94 at the trailing end of the needle 94. The needle 94 can then be translated forward through the first segment 92a such that the second segment 92b is drawn through the channel in the first segment 92a as created by the needle 94, thereby closing the loop 91 as illustrated in FIG. 10B and defining a first stitch 93. The loop 91 extends distally from the first stitch 93. As illustrated in FIG. 10C, the second segment 92b can be translated in opposite directions through the first segment 92a so as to adjust the size of the loop 91 as desired. In accordance with one embodiment, the loop 91 can be adjusted to a length of approximately 5 mm when pulled taught as illustrated in FIG. 10C.

Figure 10D:
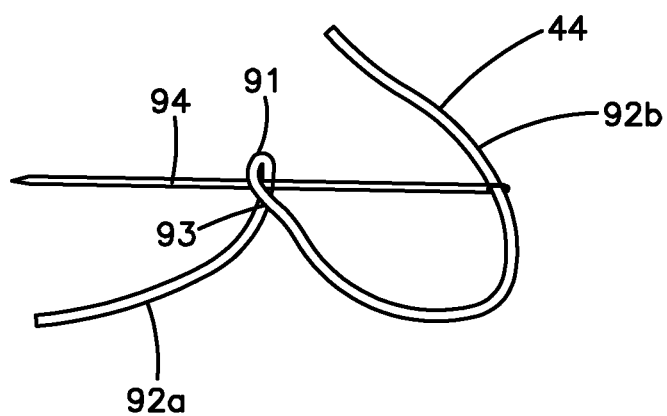
Figure 10E:
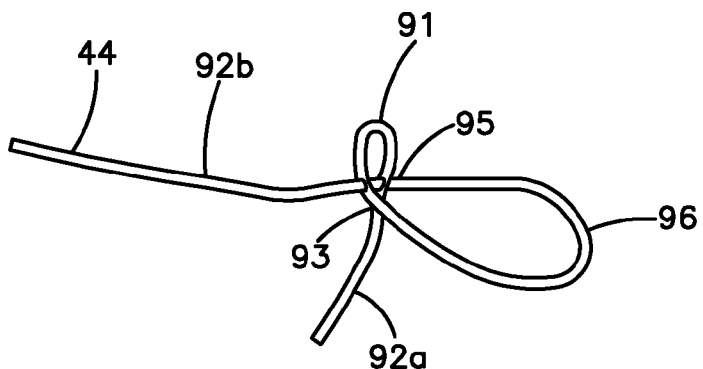

Next, referring to FIGS. 10D-E, the anchor body strand 44 can be stitched through itself a second time. For instance, the tip of the needle 94 can be driven through both segments 92a and 92b of the anchor body strand 44 at a location distal of the first stitch 93, thereby creating second and third channels that extend through the first and second segments 92a and 92b, respectively, at a location distal of the first stitch 93. As illustrated in FIG. 10E, the second segment 92b can be fed through the eyelet of the needle 94, and the needle 94 can then be translated forward through the second and third channels such that the second segment 92b is drawn through itself at one side of the loop 91, and further drawn through the first segment 92a at the opposite side of the loop 91 so as to define a second stitch 95 at a location distal of the first stitch 93. The first and second stitches 93 and 95 can define a base of the loop 91. The second segment 92b further defines a loop 96 that extends from the first and second stitches 93 and 95. It is appreciated that the size of the loop 91 is therefore decreased, for instance by approximately 1 mm, after the second stitch 95 is created.

Figure 10F:
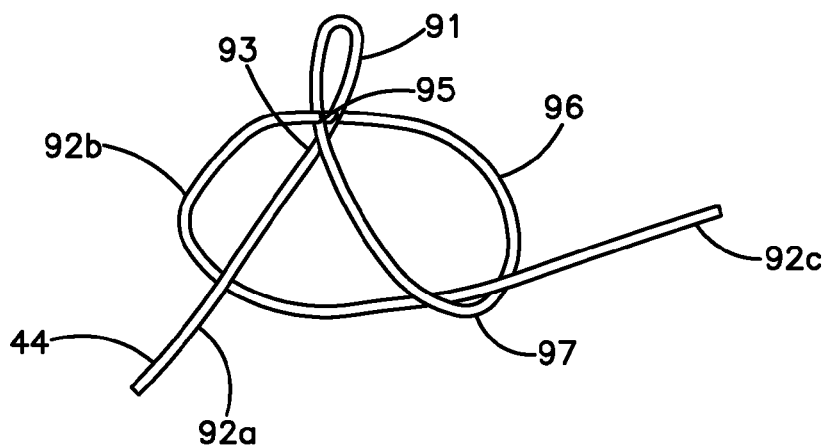
Figure 10G:
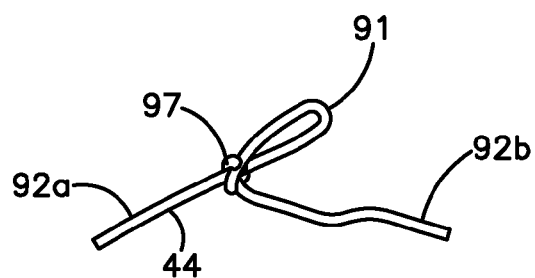

Referring to FIGS. 10E-G, the anchor body strand 44 can be tied in a knot 97 at the first and second stitches 93 and 95 to fix the size of the loop 91, which defines the eyelet 90. For instance, the second segment 92b can define a free end 92c that extends from the third channel of the second segment 92b through the loop 96, and is subsequently tightened so as to define the knot 97. Thus, the knot 97 is disposed at the base of the loop. It should be appreciated that the second segment 92b can be stitched through the loop 91 as many times as desired prior to creating the knot 97 so as to fix the loop 91. Thus, it should be appreciated that the eyelet 90 can be created by stitching the anchor body strand 44 through itself so as to create at least one stitch, for instance two stitches, thereby define a loop, and subsequently tying a knot 97 about the base of the loop so as to fix the eyelet 90.

Figure 11A:
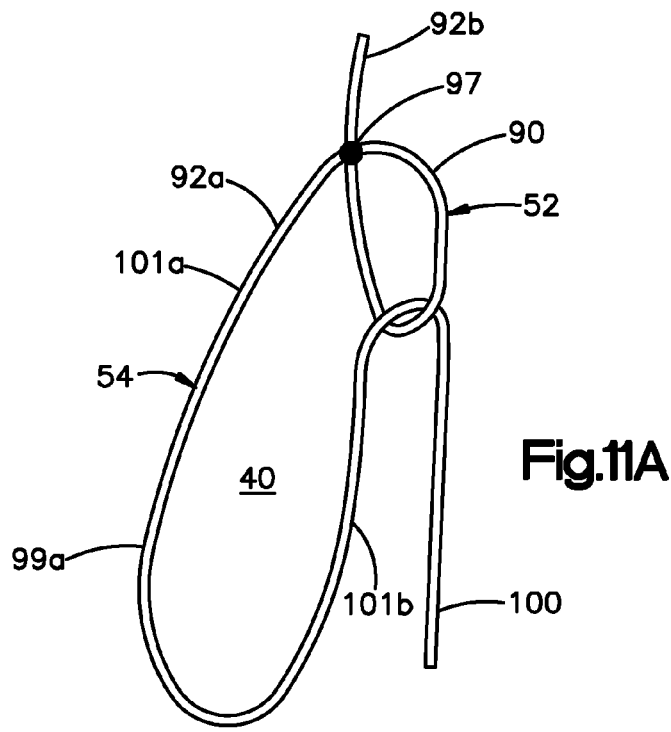
FIGS. 11A-H illustrate method steps of creating the expandable portion illustrated in FIG. 9A in accordance with one embodiment.

One method of constructing the expandable portion includes braiding the actuation strand 44 as will now be described with reference to FIGS. 11A-H. For instance as illustrated in FIG. 11A, one end of the anchor body strand 44 includes the eyelet 90 having a base that is defined, for instance, by the knot 97 or any alternative closure member, such as the closure members illustrated in FIGS. 5A-D. The anchor body strand 44 thus defines a first or proximal end portion 52 that defines the eyelet 90 and the second segment 92b, and a second or distal end portion 54 that extends from the eyelet 90 and can include the first segment 92a.

The method of constructing the expandable portion 36 of the anchor body 28 generally includes the step of braiding the second end portion 54 distally so as to define a plurality of similarly constructed loops 99 defining respective openings 40 that are spaced substantially along the direction of elongation 34 as illustrated in FIG. 9A. It should be appreciated that if the loops 99 and respective openings 40 are spaced along a direction that has a directional component along the direction of elongation 34, the loops 99 and openings 40 can be said to be spaced substantially along the direction of elongation 34. Each of the loops 99 can define respective ones of the plurality of openings 40 as described above. For instance, as illustrated in FIG. 11A, the method can further include the step of looping the second end portion 54 through a first prior loop, such as the eyelet 90, so that the second end portion 54 defines a first new loop, such as a first loop 99a that extends between the knot 86 and the eyelet 90. The first loop 99a defines a respective opening 40, and includes a first segment 101*a* and a second segment 101*b*. The first segment 101*a* of the first loop 99*a* extends from the knot 97, and the second segment 101*b* extends distally from the first segment 101*a* so as to define the first loop 99*a*. The second end portion 54 can define a free end 100 that extends distally from the second segment 101*b*, such that the free end 100 of the second end portion 54 and the first loop 99*a* are on opposite sides of the eyelet 90.

Figure 11B:
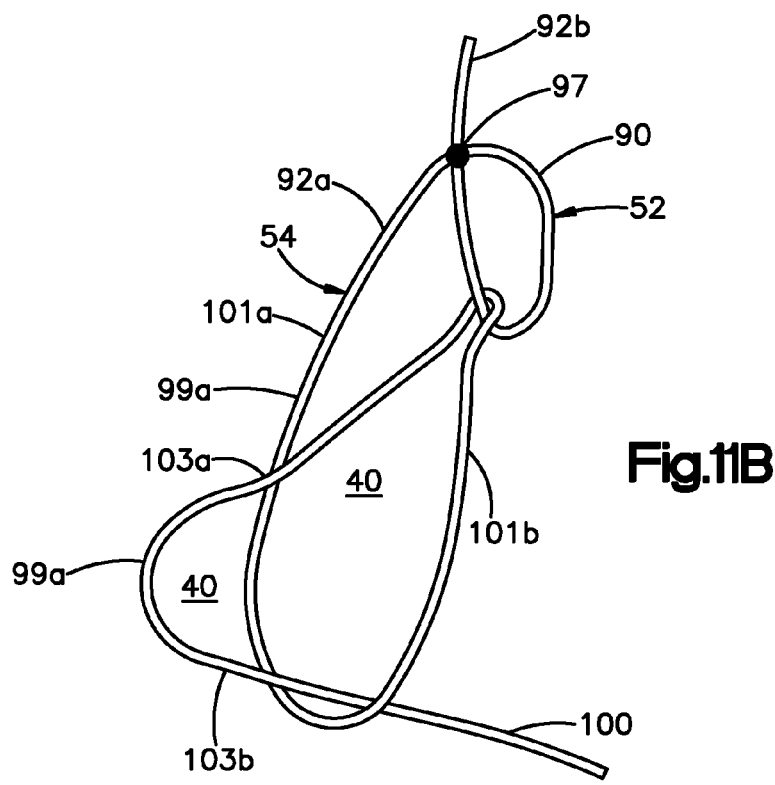
Figure 11C:
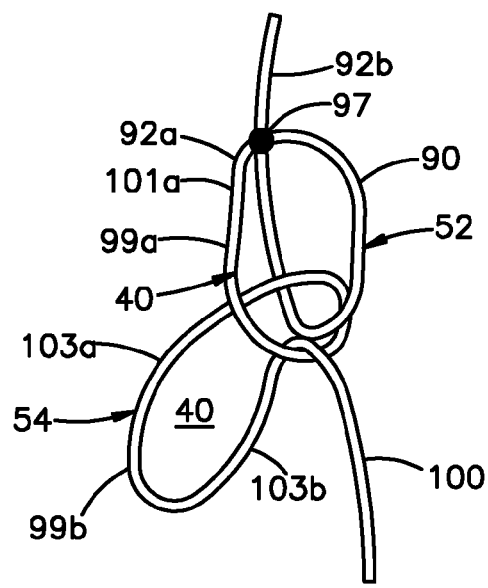

Next, as illustrated in FIG. 11B, the second end portion 54 can be folded so as to define a second new loop, such as a second loop 99*b* that defines a respective opening 40 and includes a first segment 103*a* and a second segment 103*b*. The second loop 99*b* can be pulled through a second prior loop, which can be defined by the first loop 99*a*, such that the first segment 103*a* is disposed proximally with respect to the second segment 103*b*. Alternatively, the free end 100 can be fed through the first loop 99*a* in a first direction, folded so as to define the second loop 99*b*, and fed back through the first loop 99*a* in a second direction that is opposite the first direction. Accordingly, the first segment 103*a* extends from the eyelet 90, and the second segment 103*b* extends from the first segment 103*a* so as to define the second loop 99*b*. The free end 100 of the second end portion 54 extends distally from the second segment 103*b*, such that the free end 100 of the second end portion 54 and the second loop 99*b* are on opposite sides of the first loop 99*a*. As illustrated in FIG. 11C, tension can be applied to the first segment 103*a* of the second loop 99*b*, which causes the size of the first loop 99*a* to decrease and tighten about the second loop 99*b*.

Figure 11D:
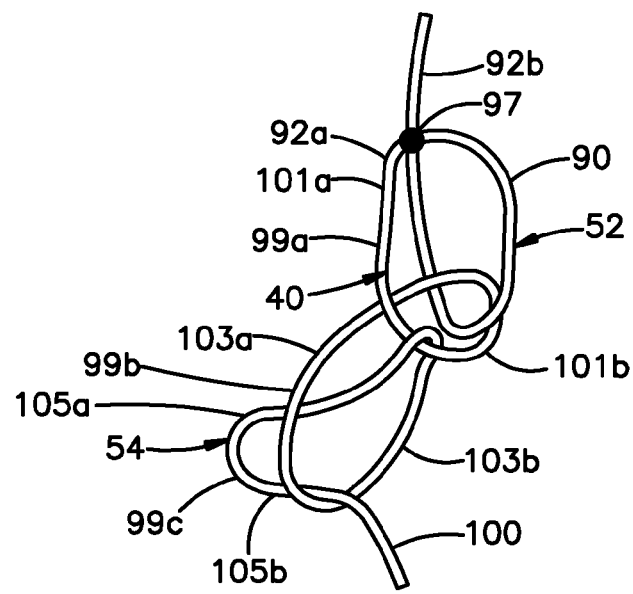
Figure 11E:
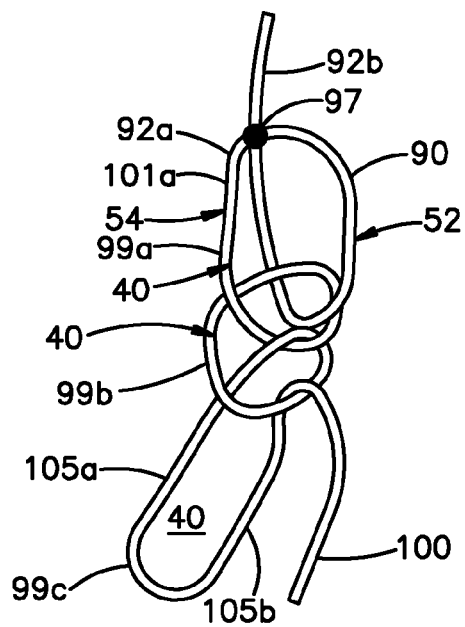

Next, as illustrated in FIG. 11D, the second end portion 54 is again folded so as to define a new loop, such as a third loop 99*c*, that defines an opening 40 and includes a first segment 105*a* and a second segment 105*b*. The third loop 99*c* can be pulled through the opening 40 of a prior loop, such as the second loop 99*b*, such that the first segment 105*a* is disposed proximal with respect to the second segment 105*b*. Alternatively, the free end 100 can be fed through the second loop 99*b* in a first direction, folded so as to define the third loop 99*c*, and fed back through the second loop 99*b* in a second direction that is opposite the first direction. Accordingly, the first segment 105*a* extends from the first loop 99*a*, and the second segment 105*b* extends from the first segment 105*a* so as to define the third loop 99*c*. The free end 100 of the second end portion 54 extends distally from the second segment 105*b*, such that the free end 100 of the second end portion 54 and the third loop 99*c* are on opposite sides of the second loop 99*b*. Referring to FIG. 11E, the first segment 105*a* is tightened, which causes the size of the second loop 99*b* to decrease and tighten about the third loop 99*c*.

Figure 11F:
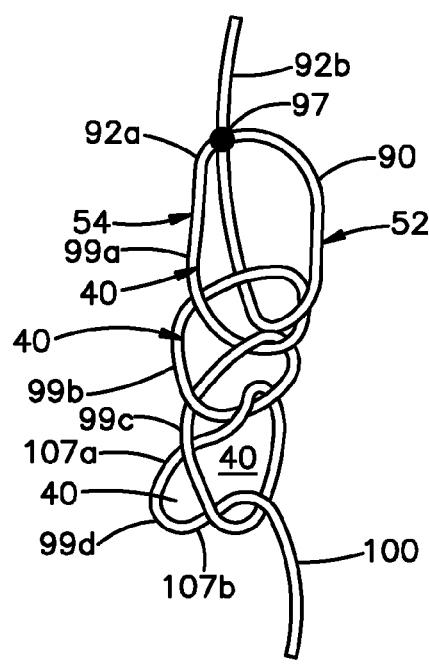
Figure 11G:
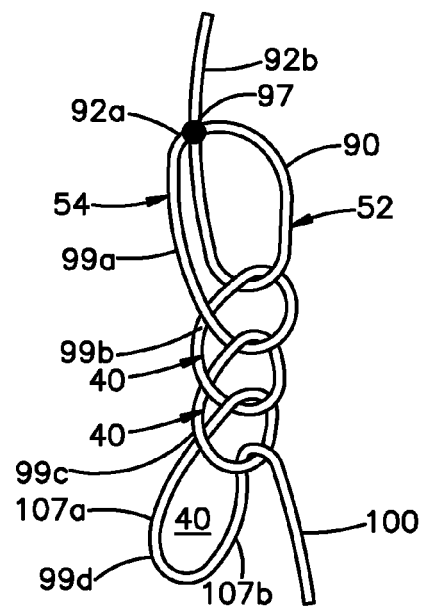

Next, as illustrated in FIG. 11F, the second end portion 54 can again be folded so as to define a new loop, such as a fourth loop 99*d*, that defines a respective opening 40 and includes a first segment 107*a* and a second segment 107*b*. The fourth loop 99*d* can be pulled through the opening 40 of a prior loop, such as the third loop 99*c*, such that the first segment 107*a* is disposed proximally with respect to the second segment 107*b*. Alternatively, the free end 100 can be fed through the third loop 99*c* in a first direction, folded so as to define the fourth loop 99*d*, and fed back through the third loop 99*c* in a second direction that is opposite the first direction. Accordingly, the first segment 107*a* extends from the second loop 99*b*, and the second segment 107*b* extends from the first segment 107*a* so as to define the fourth loop 99*d*. The free end 100 of the second end portion 54 extends distally from the second segment 107*b*, such that the free end 100 of the second end portion and the fourth loop 99*d* are on opposite sides of the third loop 99*c*. Referring to FIG. 11G, the first segment 107*a* is tightened, thereby causing the size of the third loop 99*c* to decrease and tighten about the fourth loop 99*d*.

Figure 11H:
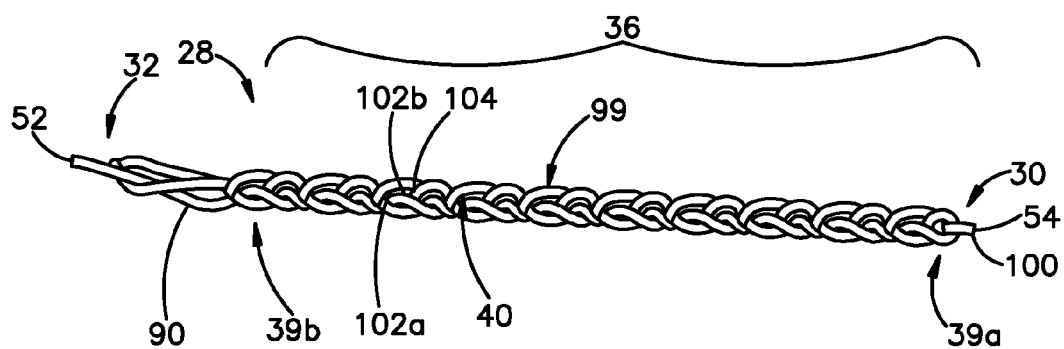

Thus, the method of creating the expandable portion 36, and thus the anchor body 28, can include repeated method steps of creating a prior loop, folding the second end portion 54 such that a subsequent loop 99 is disposed on one side of the prior loop and an end portion extends from the subsequent loop 99 on an opposite side of the prior loop, and applying tension to the first segment of the subsequent loop 99 so as to reduce the size of the prior loop. The method steps can be repeated so as to create as many loops 99 as desired, depending for instance on the desired length and expandability of the resulting anchor body 28 as illustrated in FIG. 11H. Once the final loop 99 has been created, the free end 100 of the second end portion 54 can be fed through the final loop and tightened so as to define a knot that closes the distal end 39*b* of the expandable portion 36. The remainder of the second end portion 54 can then be terminated at a location proximate to the distal end 39*b* of the expandable portion 36, or can extend proximally from the expandable portion so as to define an actuation strand 38 that is integral with the anchor body 28 and can be woven through select openings 40 as described above with respect to FIGS. 7A-8B, or can alternatively define an integral connector strand that is configured to attach the anchor 22 to another anchor as described below with respect to FIGS. 42A-C. It should be appreciated that the final loop 99 can be devoid of an opening 40 in accordance with the illustrated embodiment. In one embodiment, the expandable portion 36 can include fifteen loops 99 each having an opening 40. In another embodiment, the expandable portion 36 can include eighteen loops 99 each having an opening 40. In still another embodiment, the expandable portion 36 can define eight openings 40.

While the anchor body 22 includes the expandable portion 36 and the eyelet 90 that can be constructed as described above, it should be appreciated that the expandable portion 36 and the eyelet 90 can be created using any suitable alternative method. For instance, the anchor body strand 44 can alternatively be braided in any alternative manner as desired so as to define the anchor body 28 having an expandable portion 36 that is configured to be actuated from the first configuration to the expanded configuration as described herein. Additionally, the expandable portion 36 can be created from the anchor body strand 44, the eyelet 90 can be fabricated from a strand that is separate or non-integral from the anchor body strand 44, and the eyelet 90 can be attached to the expandable portion 36, for instance using an adhesive, a splice, a knot, or any suitable alternative attachment. Thus, the eyelet 90 can be integral with the anchor body strand 44, and thus integral with the expandable portion 36, or can be separate or non-integral from and attached to the actuation portion 36. Furthermore, while the loops 56 of the expandable portion 36 can be constructed from the same anchor body strand 44, and thus are integral with each other in accordance with the illustrated embodiment, the expandable portion 36 can be include two or more anchor body strands that alone and/or in combination define braided segments or loops 56 that can be joined, for instance stitched (see FIG. 5C), welded (see FIG. 5D), tied, spliced, or otherwise attached together.

Figure 12A:
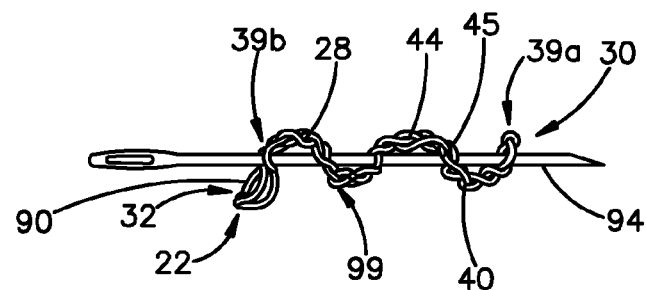
FIGS. 12A-B illustrate method steps of removably attaching of the actuation strand into the anchor body as illustrated in FIG. 9A.
Figure 12B:
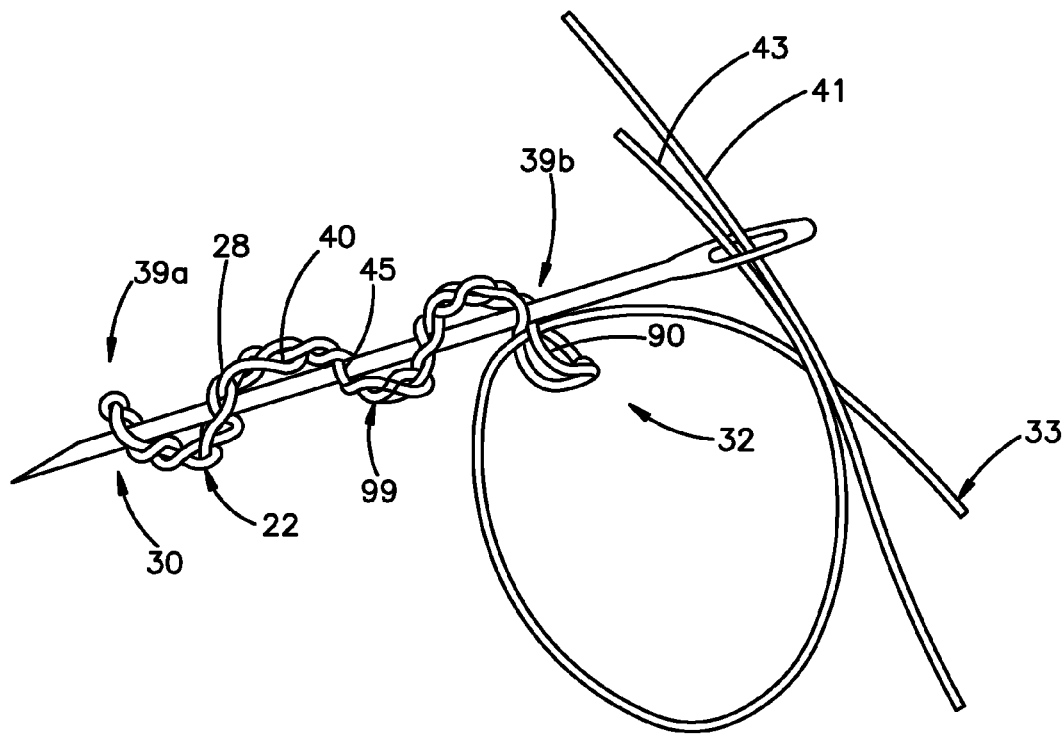

Referring now to FIGS. 12A-B, the auxiliary strand 33 can extend through the eyelet 90, and can further extend through at least a select opening 45 of the openings 40, such as a plurality of select openings 40, when the expandable portion 36 is in the first configuration. For instance, one of the first and second portions 41 and 43 of the auxiliary strand 33 can be fed through the eyelet 90. A needle, such as the needle 94 can be fed through the select openings 40 that have been identified as openings 40 that the auxiliary strand 33 is to extend through. The select openings 40 can be defined by any one or more, up to all, of the openings 40 of the expandable portion 36. For instance, the needle 94 can extend distally through the opening 40 of the second loop 99, and every fourth subsequent loop 99. The first and second portions 41 and 43 can be fed through the eye of the needle 94, and the needle 94 can be translated proximally through the expandable portion 36, thereby weaving the first and second portions 41 and 43 proximally from the eyelet 90 through at least one of the openings 40, such as each of the select openings 45. Once the eye of the needle 94 has passed through the expandable portion 36, the first and second portions 41 and 43 can be subsequently removed from the needle 94 as illustrated in FIG. 9A.

Referring now to FIGS. 11H and 12A-B, each of at least a plurality of the openings 40 up to all of the openings 40 is divided so as to define a first portion 102*a* and a second portion 102*b* adjacent the first portion 102*a* substantially along the second direction and separated by a strand 104 that extends through the opening 40 and is integral with the anchor body strand 44. In accordance with one embodiment, the first and second portions 41 and 43 extend alternatingly through a select one of the first and second portions 102*a* and 102*b* through the select openings 45 sequentially. Furthermore, the first and second portions 41 and 43 extend through the same portions 102*a* and 102*b*. For instance, the first and second portions 41 and 43 extend through a the same first one of the first and second portions 102*a* and 102*b* of the first select opening 45, through the same second one of the first and second openings 102*a* and 102*b* of the second select opening, and continue to alternate between the first and second portions 102*a* and 102*b* of the sequentially subsequent select openings.

Referring again to FIGS. 9A-C, it should be appreciated that the first and second portions 41 and 43 of the auxiliary strand 33 are attached to the eyelet 90, extend from the eyelet 90 through the same openings 40, extend through the same portions 102*a* and 102*b* of the openings 40, and extend out the anchor body 28, for instance proximally out the anchor body 28, and out the target anatomical location. Accordingly, the auxiliary strand 33, and in particular the first and second portions 41 and 43, define a travel path for the eyelet 90 when an actuation force F is applied to the auxiliary strand 33, and in particular to at least one of the first and second portions 41 and 43. Thus, at least one or both of the first and second portions 41 and 43 can define the actuation portion 131, and at least one or both of the first and second portions 41 and 43 can define the attachment portion 133. Accordingly, when the actuation force F is applied to at least one of the first and second portions 41 and 43 while the proximal end 39*a* of the expandable portion 36 is braced with respect to the actuation force F, the eyelet 90 travels proximally through the expandable portion 36, which causes the expandable portion 36 to actuate from the first configuration to the expanded configuration. The actuation force F can be applied to the auxiliary strand 33 until the eyelet 90 extends proximally from the expanded actuation body 36.

As will be described in more detail below, the eyelet 90 can define a connector member 63 that is configured to attach the anchor 22, directly or indirectly, to an to a second anchor. For instance, the auxiliary strand 33 of the anchor 22 can be attached, to the second anchor. For instance, the auxiliary strand 33 can be integral or separate from and attached to the actuation strand of the second anchor, directly or indirectly, or can alternatively be attached directly to the anchor body of the second anchor, for instance if the actuation strand is removed from the second anchor after the second anchor has been actuated from the first configuration to the expanded configuration. Alternatively, the auxiliary strand 33 can be removed from the anchor 22 and another strand, for instance an auxiliary strand of another anchor, can be inserted into the eyelet 90 so as to attach the anchor 22 to the other anchor and provide an actuation strand when the anchor 22 is implanted in the anatomical structure as described in more detail below.

Figure 13A:
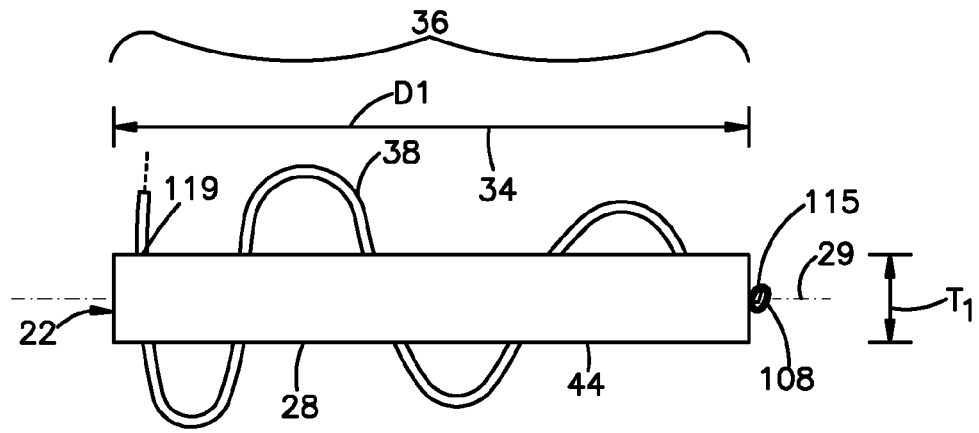
FIG. 13A is a side elevation view of an anchor including an anchor body and an actuation member woven through the anchor body in accordance with an alternative embodiment, showing the anchor body in a first configuration.
Figure 13B:
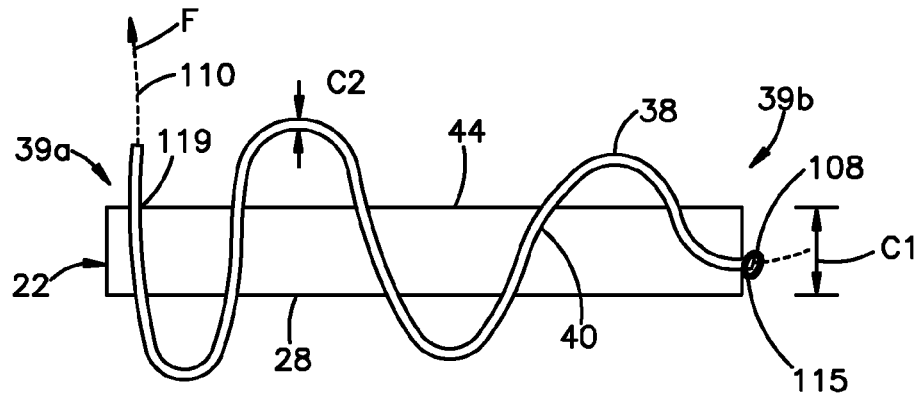
FIG. 13B is a sectional side elevation view of the anchor illustrated in FIG. 13A.

Referring now to FIGS. 13A-B, and as described above, the anchor body strand 44 can be porous so as to defining openings 40, or nonporous such that the openings 40 are created in the anchor body strand 44. For instance, the openings can be laser-cut, created by insertion of a needle through the anchor body strand 44, or otherwise created as desired. The central axis 29 of the anchor body can also define the central axis of the anchor body strand 44. The anchor body strand 44 can define a cross-sectional dimension C1 that extends substantially perpendicularly to the central axis 29. In accordance with one embodiment, the cross-sectional dimension C1 can be a diameter of the anchor body strand 44. The actuation strand 38 can likewise define a cross-sectional dimension C2 that is perpendicular to its central axis 110. The cross-sectional dimension C2 is less than the cross-sectional dimension C1 of the anchor body strand 44. Otherwise stated, the actuation strand 38 is thinner than the anchor body strand 44. In accordance with one embodiment, the cross-sectional dimension C2 of the actuation strand 38 can be a diameter of the actuation strand 38.

Accordingly, the anchor body strand 38 can be inserted through, and thus extends through, at least one of the openings 40, such as a plurality of the openings 40. The actuation strand 38 can be fixed to the anchor body strand 44 at a connection 108 at a fixation location 115. The connection 108 can be defined by the actuation strand 38 or can be defined by an auxiliary strand that is attached to the actuation strand. In accordance with the illustrated embodiment, the connection 108 can be a knot, a singe, or the like. The connection 108 can be disposed external to the anchor body strand 44 and sized greater than the adjacent opening 40, such that the connection abuts the outer surface of the actuation strand 44 without traveling through the opening 40 when a tensile force applied to the actuation strand 38. Alternatively the connection 108 can be welded, stitched, spliced, or otherwise fixed to the anchor body strand 44, externally of the anchor body strand 44 or inside the anchor body strand 44. In this regard, it should be appreciated that the anchor body strand 38 can be attached, e.g., tied, welded, stitched, spliced, or otherwise attached, to any of the anchor bodies 28 described above at a location distal with respect to a location along the anchor body 28 where the actuation strand 38 exits the anchor body 28.

Figure 13C:
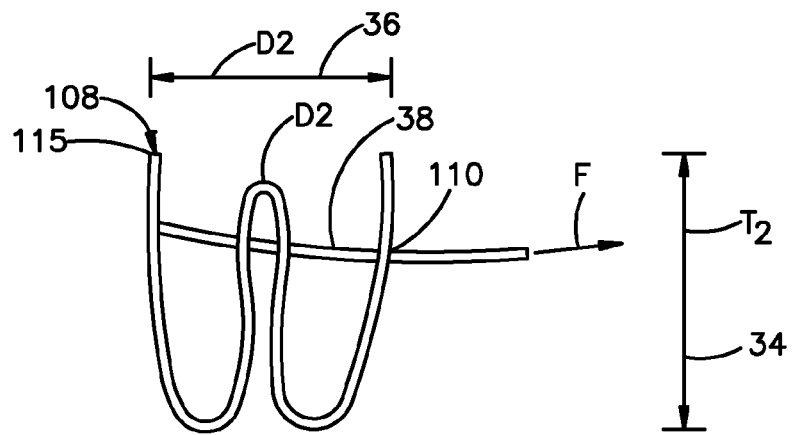
FIG. 13C is a side elevation view of the anchor illustrated in FIG. 13A, showing the anchor body in an expanded configuration.

The actuation strand 38 extends through the anchor body strand 44 and exits the anchor body strand 44 at an exit location 119 that is disposed proximal with respect to the connection 108. Referring to FIG. 13C, during operation, when the actuation force F is applied to the actuation strand while the proximal end 39*a* of the expandable portion 36 is braced, the fixation location 115 of the expandable portion 36 translates proximally toward the exit location 119, thereby actuating the expandable portion 36 from the first configuration to the expanded configuration. For instance, the expandable portion 36 can fold into a substantially accordion-shaped structure.

Figure 14A:
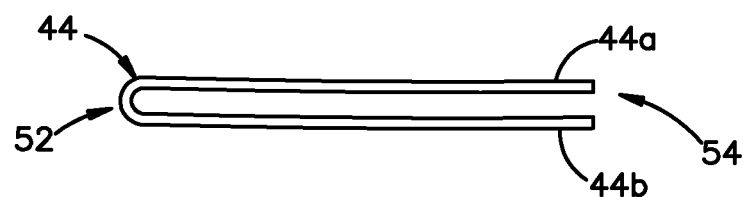
FIG. 14A is a side elevation view of a double-segmented anchor body strand constructed in accordance with one embodiment.
Figure 14B:
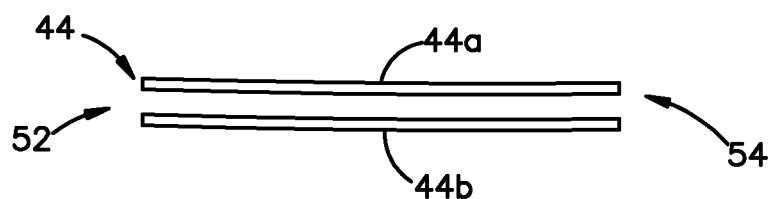
FIG. 14B is a side elevation view of a double-segmented anchor body strand including a pair of separate strands in accordance with another embodiment.

Referring now to FIG. 14A, it should be appreciated that the anchors 22 described above can be constructed by a double-segmented anchor strand 44. For instance, the anchor strand 44 can be folded so as to define first and second anchor strand segments 44*a* and 44*b* that can together define the opposed end portions 52 and 54. For instance, as illustrated, the folded end of the anchor strand 44 can define the first end portion 52 and the free ends of the anchor strand segments 44a and 44b can define the second end portion 54. Alternatively, the folded end of the anchor strand 44 can define the second end portion 54 and the free ends of the anchor strand segments 44a and 44b can define the first end portion 52. The anchor strand segments 44a and 44b can be manipulated together as described above with respect to the anchor strand 44 so as to construct the anchors 22 in accordance with the various embodiments. It should be appreciated that the anchor strand 44 can be folded as many times as desired so as to create a desired number of anchor strands that can be manipulated together as described above. Alternatively and additionally, as illustrated in FIG. 14B, the anchor strands segments 44a and 44b, or as many anchor strands as desired, can be defined by separate non-integral anchor strands 44. Accordingly, it should be appreciated that the anchor body 28 can be double-segmented, or otherwise define multiple segments of strand.

Referring now to FIGS. 15A-D, and as described above, the substrate 42 of the anchor body 28 can be woven and can thus define the openings 40 as-manufactured. For instance, as illustrated in FIG. 15A, the substrate 42 of the anchor body 28, including the expandable portion 36, can define a plurality of anchor body fibers 109 that are interwoven so as to define a mesh 111. It should be appreciated that the fibers 109 can alternatively define a woven structure, such as a braid, a weave, a mesh, or a knit. The substrate 42 defines a plurality of openings 40 that extend through the mesh 111 and can be spaced both substantially along the direction of elongation 34 and substantially along the second direction 35.

In accordance with one embodiment, as illustrated in FIG. 15B, the actuation strand 36 can be integral with the mesh 111, and can be woven through select openings 45 of the openings 40 in the manner described above, for instance with respect to FIGS. 7A-C. For instance, the actuation strand 38 can extend proximally from the anchor body 28, for instance from the proximal end 30 of the anchor body 28, and can be woven through so as to extend through select ones of the openings 40. As the actuation strand 38 is woven through the openings 40, the anchor body fibers 109 of the mesh 111 can separate or fracture so as to enlarge the openings 40 that receive the actuation strand 38. In accordance with the illustrated embodiment, the anchor strand 38 can be looped through a first select opening 45, and subsequently woven proximally through at least one additional select opening 45 such as a plurality of select openings 45 that are spaced along the direction of elongation 34. The actuation strand 38 can extend, for instance, proximally, from the expandable portion 36, such that the actuation strand 38 actuates the expandable portion 36 from the first configuration to the expanded configuration when the actuation force F is applied to the actuation strand 38, as described above.

Referring now to FIG. 15C, the substrate 42 of the anchor body 28 can be woven or nonwoven as described above, and the openings 40 can be cut through the substrate 42 prior to weaving the actuation strand 38 through the substrate 42. For instance, the openings 40 can be laser-cut, mechanically cut, chemically cut, or cut using any suitable alternative method as desired. The openings 40 can be spaced substantially along the direction of elongation 34. The actuation strand 38 can be integral with the anchor body 28 and can be woven through the openings 40 such that the actuation strand 38 actuates the expandable portion 36 from the first configuration to the expanded configuration when the actuation force F is applied to the actuation strand 38, as described above.

Referring now to FIG. 15D, the substrate 42 of the anchor body 28 can define at least one anchor body strand such as a plurality of anchor body strands 44, that can be woven or nonwoven, and are braided so as to define a braided strand having a plurality of openings 40 as-manufactured. The openings 40 can be spaced substantially along the direction of elongation 34. The actuation strand 38 can be integral with the anchor body 28 and can be woven through the openings 40 such that the actuation strand 38 actuates the expandable portion 36 from the first configuration to the expanded configuration when the actuation force F is applied to the actuation strand 38, as described above.

Referring now to FIG. 16A, the substrate 42 of the anchor body 28, including the expandable portion 36, can define a plurality of anchor body fibers 109 that are interwoven so as to define a mesh 111 as described above with reference to FIG. 15A. The substrate 42 defines a plurality of openings 40 that extend through the mesh and can be spaced both substantially along the direction of elongation 34 and substantially along the second direction 35. The anchor body 28 can further define an eyelet 112 that extends from the expandable portion 36 when the expandable portion 36 is in the first configuration. For instance, the eyelet 112 can extend distally from the expandable portion 36, and can be drawn proximately through the expandable portion as described above with respect to the eyelet 90.

In accordance with one embodiment, as illustrated in FIG. 16B, the actuation strand 36 can be separate or non-integral from the anchor body 28, can extend through the eyelet 112, and can further extend through at least one of the openings 40, such as a plurality of the openings 40. For instance, the actuation strand 36 can define first and second portions 41 and 43, and a fold 86 disposed and integrally attached between the first and second portions 41 and 43 as described above with respect to FIGS. 9A-C. The first and second portions 41 and 43 can be woven through a plurality of the openings 40 along a direction proximally from the eyelet 112 so as to define a travel path for the eyelet 112 when the expandable portion 36 is actuated to the expanded configuration as described above with respect to FIGS. 9A-C. Accordingly, the eyelet 112 can extend proximally from the expandable portion 36 when the expandable portion is in the expanded configuration.

Alternatively, the eyelet 112, or the eyelet 90, can extend proximally from the respective expandable portion 36 when the expandable portion 36 is in the first configuration, and the actuation strand 38 can extend through a plurality of openings 40 of the expandable portion 36 so as to receive an actuation force to actuate the expandable portion 36 from the first configuration to the expanded configuration as described above. The eyelet 112 and 90 can thus extend proximally from the expandable portion 36 after the expandable portion has been actuated to the expanded configuration.

Referring to FIG. 16C, the substrate 42 of the anchor body 28 can be woven or nonwoven as described above, and the openings 40 can be cut through the substrate 42 prior to weaving the actuation strand 38 through the substrate 42, as described above with respect to FIG. 15C,. For instance, the openings 40 can be laser-cut, mechanically cut, chemically cut, or cut using any suitable alternative method as desired. The openings 40 can be spaced substantially along the direction of elongation 34. The anchor body 28 can further include an eyelet 112 that extends, for instance distally, from the expandable portion 36 when the expandable portion 36 is in the first configuration. In accordance with one embodiment, the actuation strand can be separate or non-integral from the anchor body 28, can extend through the eyelet 112, and can further extend through at least one of the openings 40, such as a plurality of the openings 40 as described above with respect to FIGS. 9A-C and 16A-B. Accordingly, the eyelet 112 can extend proximally from the expandable portion 36 when the expandable portion is in the expanded configuration.

Figure 17A:
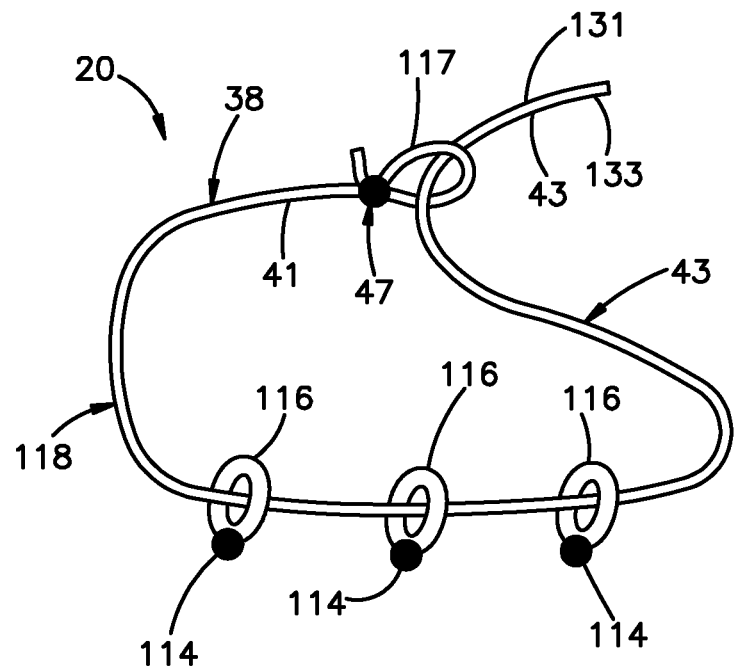
FIG. 17A is a perspective view of an anchor including a plurality of anchor members slidably coupled to a common strand, showing the anchor in a first configuration.
Figure 17B:
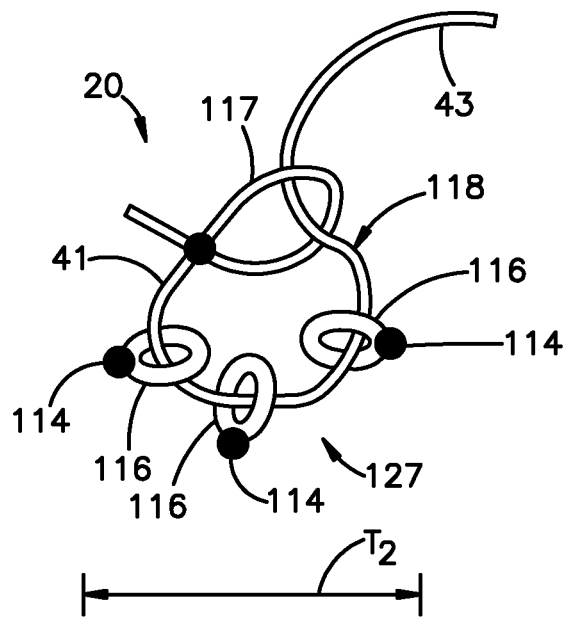
FIG. 17B is a perspective view of the anchor illustrated in FIG. 17B, showing the anchor in an expanded configuration.

Referring now to FIGS. 17A-B, the anchor assembly 20 can include an actuation member 37, such as a common actuation strand 38, that connects multiple anchor members 114 that are slidable with respect to each other along the common actuation strand 38. The anchor members 114 can be defined as pre-tied knots, and the respective eyelets 116 are configured to slidably couple each of the anchor members 114 to the common actuation strand 38. For instance, each of the anchor members 114 can be inserted to a common target anatomical location, for instance through an opening in the common target anatomical location that can be created, for example, when injecting the anchors members 114 in the common target anatomical location, or can be created due to a defect in the tissue as described above with respect to FIGS. 1A-B.

The first portion 41 of the common actuation strand 38 can define an eyelet 117 that defines a sliding member 47 such as a sliding knot that allows the second portion 43 to translate with respect to the first portion 41 through the eyelet 117 so that the actuation strand 38 defines a loop 118. Thus, the first and second portions 41 and 43 can be slidably attached to each other. As the actuation force F is applied to the second portion 43, which draws the second portion 43 through the eyelet 117, the size of the loop 118 decreases, which causes the anchor members 114 to slide along the common actuation strand 38 and bunch together so as to define a cluster 120 of bunched knots. Thus, the second portion 43 can define the actuation portion 131, and can also be attached to a second anchor so as to define the attachment portion 133. The cluster 120 is dimensioned so as to define a maximum thickness T2 that is greater than the maximum thickness T1 of each individual anchor member 114, and can be at least equal to or greater than that of the opening at the common target anatomical location.

Accordingly, the cluster 120 can define an anchor 22 that can be attached to another anchor across an gap 24c so as to approximate the gap 24c of the type described above with respect to FIGS. 1A-B. Alternatively, the anchor members 114 can define anchor bodies 28 constructed in accordance with any of the embodiments as described above, either in the first configuration or in the expanded configuration. The cluster 120 can be attached to a second anchor 22 in any manner described herein. For instance, the common actuation strand 38 can be attached, directly or indirectly, to a second anchor. For instance, the common actuation strand 38 can be attached to an actuation strand of the second anchor, directly or indirectly. In accordance with one embodiment, the common actuation strand is integral with the actuation strand of the second anchor.

Figure 18A:
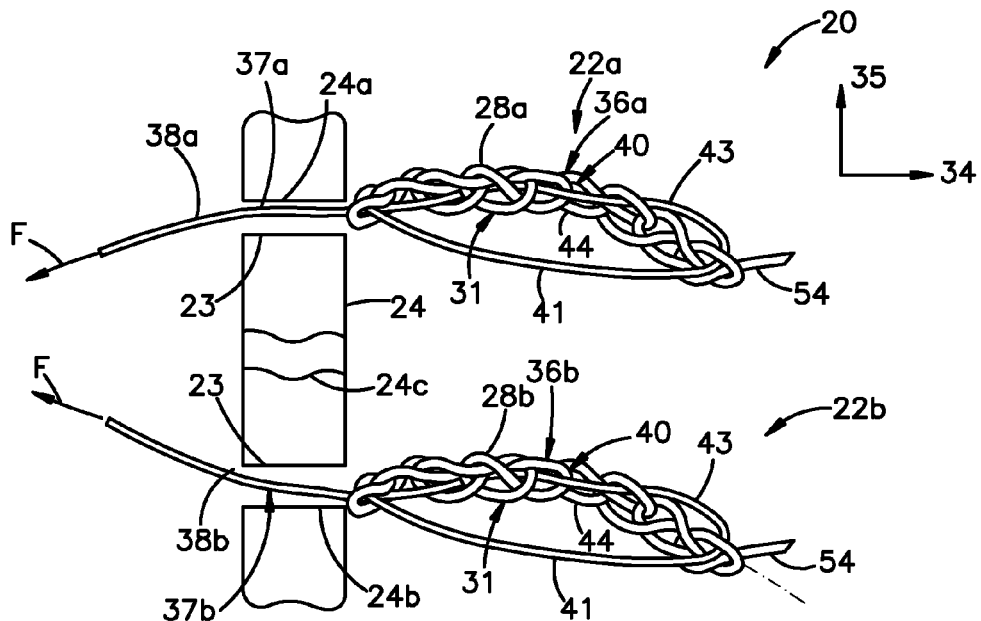
FIG. 18A is a side elevation view of an anchor assembly including first and second anchors shown in respective first configurations and implanted in an anatomical structure
Figure 18B:
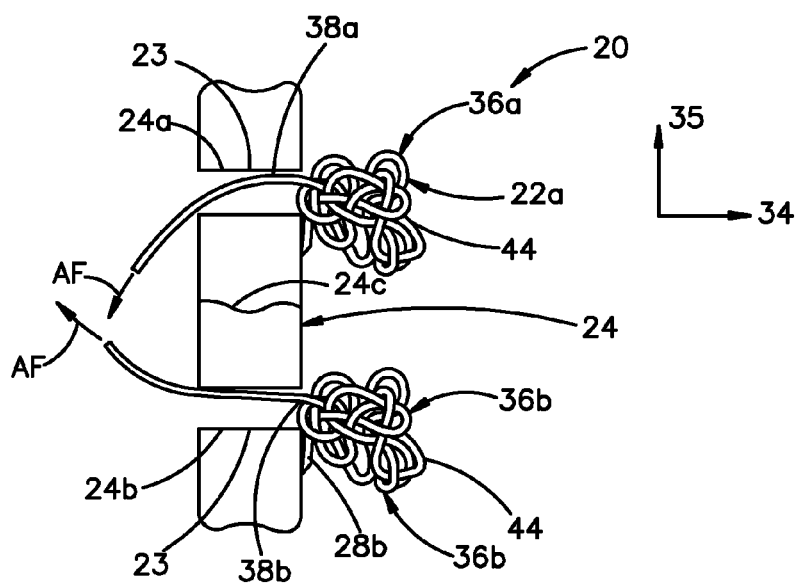
FIG. 18B is a side elevation view of the anchor assembly illustrated in FIG. 18A, showing the first and second anchors in respective expanded configurations.
Figure 18C:
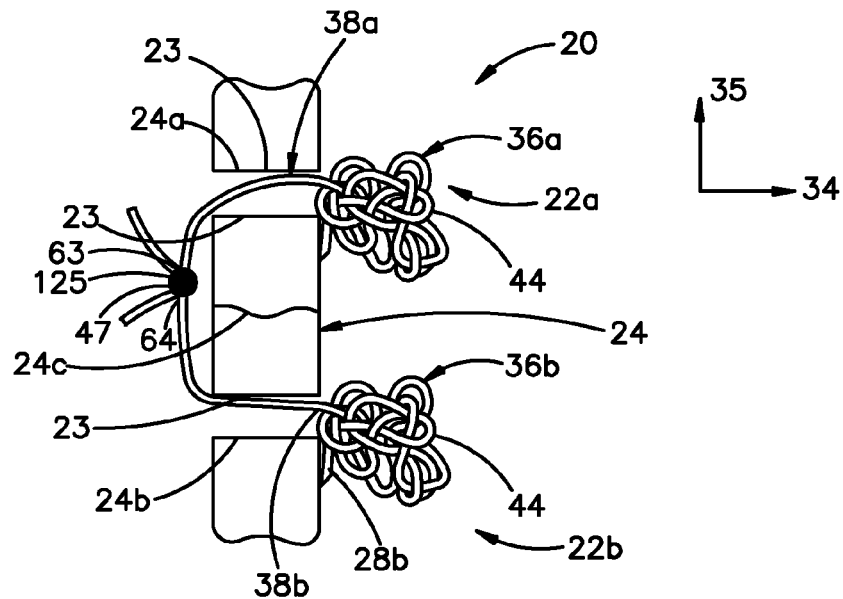
FIG. 18C is a side elevation view of the anchor assembly illustrated in FIG. 18B, including a connector member that attaches the first anchor to the second anchor.

Referring now to FIGS. 18A-C, and as generally described above with respect to FIGS. 1A-B, the anchor assembly 20 can include first and second anchors 22a and 22b. The first anchor 22a includes a first anchor body 28a that extends substantially along the direction of elongation 34 and defines a first plurality of openings 40a that extend through the first anchor body 28a. The first anchor 22a further includes a first actuation strand 38a that extends through at least one of the openings 40a, such as a plurality of the openings, and is configured to receive an actuation force F that causes the first anchor body 28a to actuate from the first configuration to the expanded configuration in the manner described above. The first actuation strand 38a can be separate from and attached to, for instance woven through, the first anchor body 28a as described, for instance, with respect to FIGS. 2A-H, or can be integral with the first anchor body 28a as described above with respect to FIGS. 7A-C.

The second anchor 22b includes a second anchor body 28b that extends substantially along the direction of elongation 34 and defines a second plurality of openings 40b that extend through the second anchor body 28b. The second anchor 22b further includes a second actuation strand 38b that extends through at least one of the openings 40b, such as a plurality of the openings, and is configured to receive an actuation force F that causes the second anchor body 28b to actuate from the first configuration to the expanded configuration in the manner described above. The second actuation strand 38b can be separate from and attached to, for instance woven through, the second anchor body 28b as described above with respect to FIGS. 2A-H, or can be integral with the second anchor body 28b as described above with respect to FIGS. 7A-C.

Both the first anchor 22a and the second anchor 22b can include respective first and second anchor bodies 28a and 28b and first and second actuation members 37a and 37b, such as actuation strands 38a and 38b that are integral with the first and second anchor bodies 28a and 28b. Each of the first and second anchor bodies 28a and 28b include respective first and second expandable portions 36a and 36b that are configured to actuate from a first configuration to a second expanded configuration as described above.

In accordance with the embodiment illustrated in FIGS. 18A-B, the first and second actuation strands 38a and 38b are integral with the respective first and second anchor bodies 28a and 28b. In accordance with other embodiments, the first and second actuation strands 38a and 38b are illustrated as separate from and attached to the respective first and second anchor bodies 28a and 28b. In accordance with still other embodiments, one of the first and second actuation strands 38a and 38b is integral with the respective anchor body and the other of the first and second actuation strands 38a and 38b is separate from and attached to the respective anchor body. In accordance with embodiments whereby the first and second actuation strands 38a and 38b are illustrated and described as integral with the respective first and second anchor bodies 28a and 28b, it should be appreciated that the first and second actuation strands 38a and 38b can alternatively be separate from and attached to the respective first and second anchor bodies 28a and 28b, unless otherwise indicated. Furthermore, in accordance with embodiments whereby the first and second actuation strands 38a and 38b are illustrated and described as separate from and attached to the respective first and second anchor bodies 28a and 28b, it should be appreciated that the first and second actuation strands 38a and 38b can alternatively be integral with the respective first and second anchor bodies 28a and 28b, unless otherwise indicated.

With continuing reference to FIG. 18C, the anchor assembly 20 can include at least one connector member 63 that is configured to join the anchors 22 and allow a biasing force to be applied to at least one of the anchors 22a and 22b that draws the anchors 22a and 22b together, thereby approximating the anatomical defect 24. The connector member 63 can be integral with one or both of the first and second anchors 22a and 22b, for instance integral with one or both of the first and second actuation strands 38a and 38b, can be integral with one or both of the first and second anchor bodies, or can be separate from and attached (directly or indirectly) to one or both of the first and second anchors 22a and 22b. For instance, the connector member 63 can be separate from and attached between the first and second anchors 22a and 22b, as will be described in more detail below. While connector members 63 are described herein in accordance with various embodiments, it should be appreciated that the anchor assembly 20 can alternatively include any suitable connector member configured to attach the first anchor 22a to the second anchor 22b. At least one or both of the actuation strands, or a connector strand that can be attached to, for instance, the eyelet 90 or any suitable alternative eyelet after the actuation strand 38 has been removed from the eyelet 90, is configured to receive an approximation force AF that biases at least one of the first and second anchors 22a and 22b toward the other so as to approximate the gap 24c.

The anchor assembly 20 can include a connector member 63 that is integral with the corresponding actuation strands 38a and 38b. As described above, each of the first and second anchor bodies 28a and 28b can be implanted at respective first and target anatomical locations 24a and 24b that are disposed on opposite sides of an gap 24c as illustrated in FIG. 18A. Each of the first and second actuation strands 38a and 38b can receive an actuation force F substantially along the direction of elongation 34 that causes the respective first and second anchor bodies 28a and 28b, and in particular the respective expandable portions 36a and 36b, to actuate from the first configuration to the expanded configuration so as to fix the first and second anchor bodies 28a and 28b at the respective first and second target anatomical locations 24a and 24b. The actuation force F applied to each of the actuation strands 38a and 38b can be in the form of different actuation forces, or, as is described in more detail below, can be the same actuation force.

Referring now to FIG. 18B, once the first and second anchor bodies 28a and 28b are secured to the respective first and second target anatomical locations 24a and 24b, an approximation force AF can be applied to at least one or both of the first and second actuation segments 38a and 38b substantially along a direction toward the other of the respective first and second anchor bodies 28a and 28b, which can also be toward the respective gap 24c. Thus the approximation force AF can have a directional component that is toward the other of the respective first and second anchor bodies 28a and 28b, for instance can be directed purely toward the other of the first and second anchor bodies 28a and 28b. Likewise, the approximation force AF can have a directional component that is directed toward the gap 24c, for instance directed purely toward the gap 24c. Accordingly, the approximation force AF biases at least one or both of the anchor bodies 28a and 28b toward the other of the anchor bodies 28a and 28b to respective biased positions that to approximate the gap 24c.

Referring again to FIG. 18C, the connector member 63 that can define at least one of a sliding member 47 and a locking member 64 that attaches the first and second connector actuation strands 38a and 38b together, for instance at a junction 125. Thus, it should be appreciated that the at least one of the sliding member 47 and locking member 64 can likewise attach the first actuation strand 38a to the second actuation strand 38b. In accordance with one embodiment, the connector member 63 can attach the first and second actuation strands 38a and 38b after the first and second actuation strands 38a and 38b have been put under tension so as to maintain the gap 24c in an approximated state. The member 63 can be actuated to the locked configuration so as to prevent or resist separation of the first and second anchors 22a and 22b that would cause the gap 24c to open from the approximated state. Alternatively or additionally, the connector member 63 can attach the first and second actuation strands 38a and 38b to each other prior to applying the approximation force AF to the actuation strands 38a and 38b, and placing the actuation strands 38a and 38b under tension, and therefore prior to approximating the gap 24c.

In accordance with certain embodiments, the connector member 63 is defined by, and integral with, the first and second actuation strands 38a and 38b. The connector member 63 defines the at least one of the sliding member 47 and the locking member 64 at the junction 125. In accordance with certain embodiments described below, the connector member 63 can be configured as an auxiliary connector member 77 (See, e.g., FIG. 20A) that is attached between the first and second actuation strands 38a and 38b, and is configured to receive two or more strands, such as either or both of the first and second actuation strands 38a and 38b along with additional strands that can connect to other anchors or other anatomical structure. Thus, it can be said that the connector member 63 can directly or indirectly attach the first and second actuation strands 38a and 38b together.

Figure 18D:
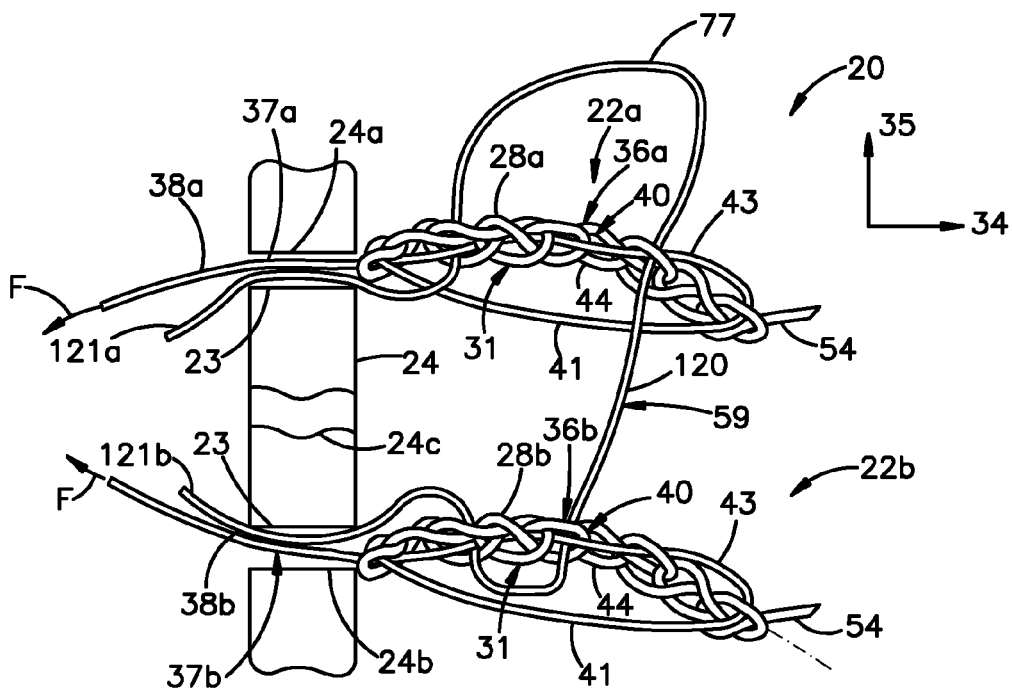
FIG. 18D is a side elevation view of the anchor assembly as illustrated in FIG. 18A, but including an auxiliary connector strand attached between the first and second anchor bodies in accordance with one embodiment.
Figure 32A:
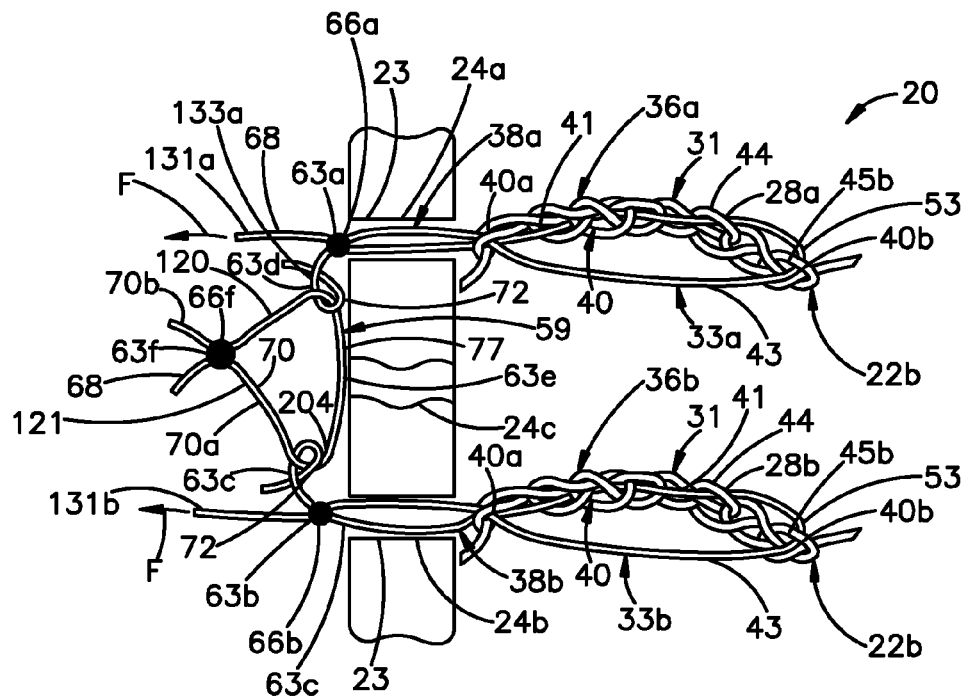
FIG. 32A is a side elevation view of an anchor assembly constructed in accordance with another embodiment, including first and second anchors shown in respective first configurations and implanted in an anatomical structure.
Figure 32B:
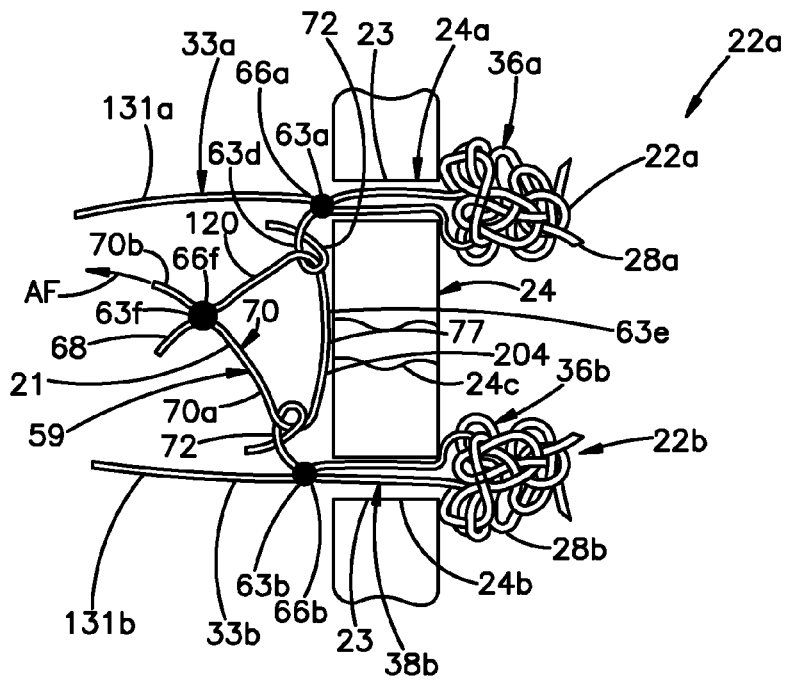
FIG. 32B is a side elevation view of the anchor assembly illustrated in FIG. 32A, showing the first and second anchors in respective expanded configurations.
Figure 32C:
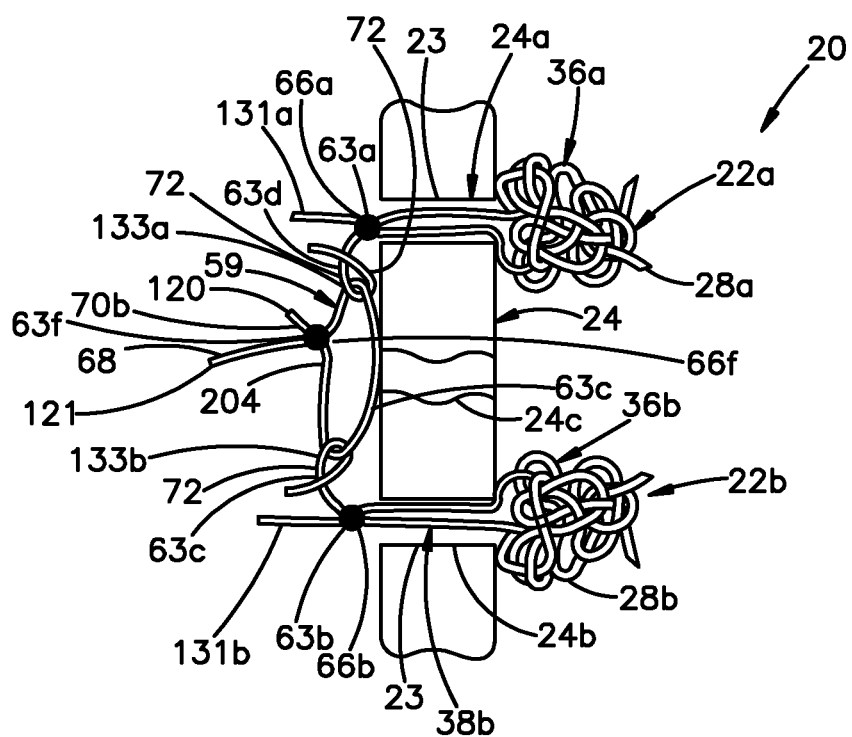
FIG. 32C is a side elevation view of the anchor assembly illustrated in FIG. 32B, showing the first and second anchors in an approximated configuration.

In certain embodiments, for instance as illustrated in FIG. 18D, the auxiliary connector member 77 can be configured as a connector strand 59, such that the connector member 63 can attach the connector strand 59 to itself so as to attach the first and second actuation strands 38a and 38b to each other (see, e.g., also FIGS. 32A-C). For instance, the connector strand 59 can extend through a first of the openings 40 of the first anchor body 28a along a direction away from the second anchor body 28b, can be folded back through a second one of the openings 40 of the first anchor body 28a along a direction toward the second anchor body 28b and through a first one of the openings 40 of the second anchor body 28b, and folded back through a second one of the openings 40 of the second anchor body 28b. The connector strand 59 can thus define a first portion 120 that extends between the first and second anchor bodies 28a and 28b, a second portion 121a that extends from the second one of the openings 40 of the first anchor body 28a and out the anatomical structure 24, and a third portion 121b that extends from the second one of the openings 40 of the second anchor body 28b and out the anatomical structure 24. It should be appreciated that the anchor assembly 20 can include any suitable connector as described herein that attaches the second portion 121a to the third portion 121b so as to attach the first and second anchors 22a and 22b to each other. It should be further appreciated that the connector strand 59 can extend through as many openings of the first and second anchor bodies 28a and 28b as desired.

Alternatively, the connector strand can be attached between the first and second actuation strands 38a and 38b, such that the connector member 63 can attach the connector strand 59 to one or both of the first and second actuation strands 38a and 38b. Thus, the anchor assembly 20 can include at least one connector member 63 that attaches the first and second actuation strands 38a and 38b together, thereby attaching the first and second anchors 22a and 22b and the corresponding anchor bodies 28a and 28b together.

Figure 19A:
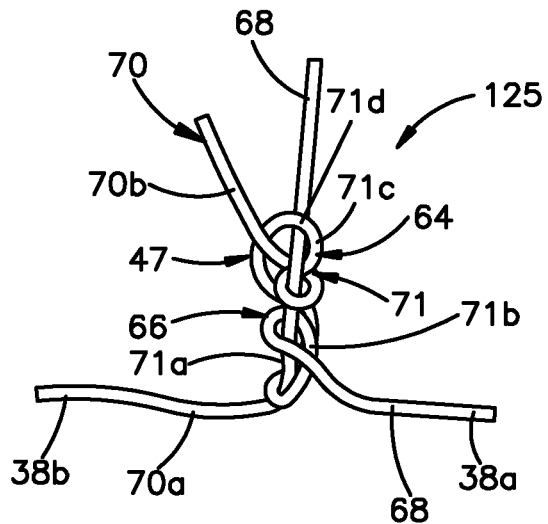
FIG. 19A is a perspective view of the connector member illustrated in FIG. 18C, configured as a knot.

Referring also to FIG. 19A, the connector member 63 can define a sliding member 47 and a locking member 64 that attach and secure the two anchors 22a and 22b together. The sliding member 47 can allow at least one of the first and second actuation strands 38a and 38b to slide relative to the other so as to induce tension in the actuation strands 38a and 38b, and bias at least one or both of the anchors 22a and 22b toward the other of the anchors 22a and 22b to respective biased positions, thereby approximating the anatomical defect. The locking member 64 is configured to be actuated so as to prevent translation of the actuation strands 38a and 38b relative to the other through the connector member, thereby securing the at least one or both of the anchors 22a and 22b in their respective biased positions.

For instance, the connector member 63 can define a knot 66 that can be constructed as described above with respect to FIGS. 4A-F and can be defined by the first and second actuation strands 38a and 38b. In accordance with the illustrated embodiment, the first and second actuation strands 38a and 38b define the knot 66, though it should be appreciated that the knot 66 can be defined by a select one of the first and second actuation strands 38a and 38b, and a connector strand that is attached to the select actuation strand. Thus, at least a portion of the connector member 63 can be integral with at least one or both of the actuation strands 38a and 38b.

One of the first and second actuation strands 38a and 38b can define the post end 68 and the other of the first and second actuation strands 38a and 38b can define the free end 70. In accordance with the illustrated embodiment, the first actuation strand 38a defines the post end 68 and the second actuation strand 38b defines the free end 70. The first and second actuation strands 38a and 38b can be tied into the knot 66 prior to applying tension to the actuation strands 38a and 38b that biases the first and second anchors 22a and 22b toward each other. Once the knot 66 is formed, and when the knot 66 is in an unlocked configuration, the approximation force AF can be applied to the post strand 68, which causes the post end 68 to slide through the loops 71a-d, and draws the respective anchor, such as the first anchor 22a, toward the other anchor, such as the second anchor 22b. Once the gap 24c has been approximated, the free strand 70b of the free end 70, for instance defined by the second actuation strand 38b, can be placed in tension so as to lock the loops 71a-d about the post strand 68, or first actuation strand 38a, thereby actuating the knot 66 to the locked configuration and fixing the actuation strands 38a and 38b in tension.

Figure 19B:
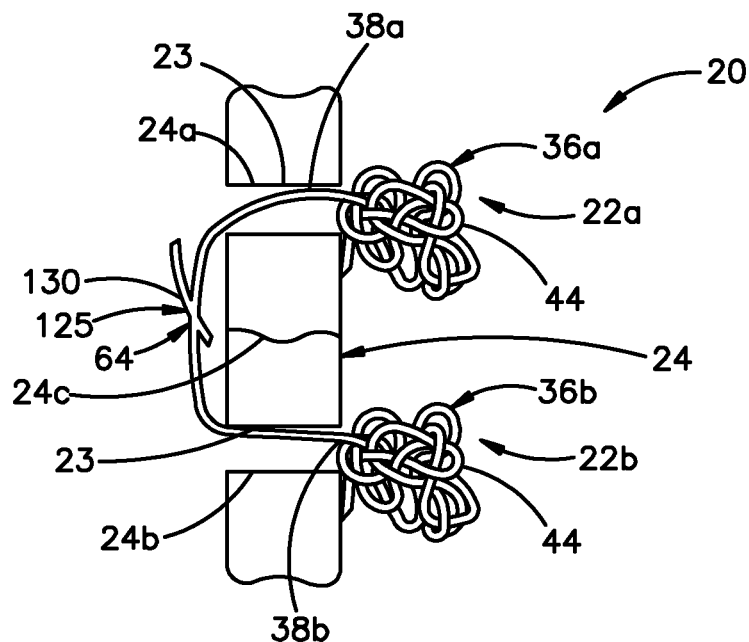
FIG. 19B is a side elevation view of an anchor assembly including first and second anchors and a connector member constructed in accordance with another embodiment that attaches the first anchor to the second anchor.

While the connector member 63 can define the locking member 64 configured as a knot, it should be appreciated that the connector member 63 can be alternatively constructed so as to define locking member 64 as desired. For instance, referring to FIG. 19B, the connector member 63 can be configured as a weldment 130 that defines the locking member 64. For instance, the actuation strands 38a and 38b can be welded together, for instance heated to each other or glued to each other via an adhesive, so as to define the weldment 130 that secures the first and second actuation strands 38a and 38b to each other, for example with respect to relative movement that would allow the anchor bodies 28a and 28b to separate. At least one or both of the first and second actuation strands 38a and 38b can thus receive a respective approximation force AF that biases at least one or both of the anchor bodies 28a and 28b toward the other of the anchor bodies 28a and 28b to a biased position so as to approximate the gap 24c. The first and second actuation strands 38a and 38b can then be welded to each other so as to define the weldment 130 that secures the first and second anchor bodies 28a and 28b in their biased positions.

Figure 19C:
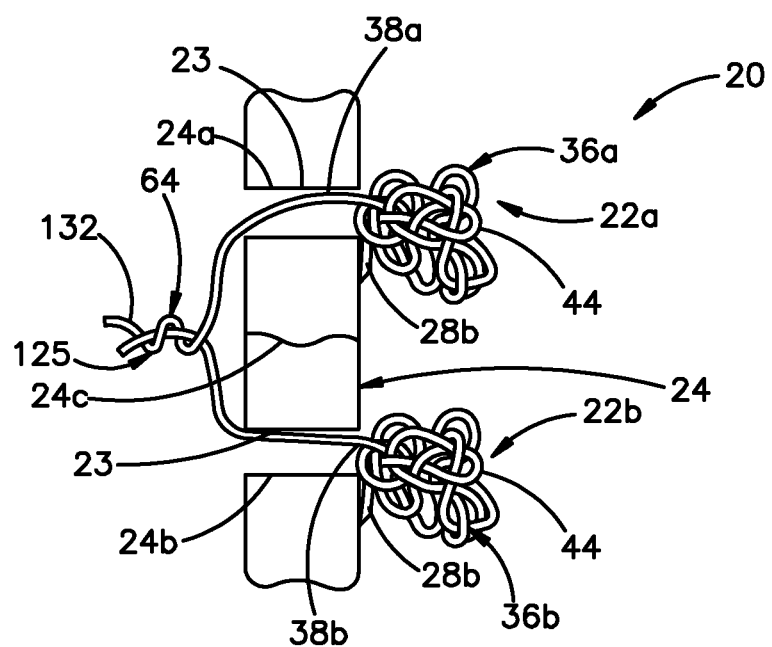
FIG. 19C is a side elevation view of an anchor assembly including first and second anchors and a connector member constructed in accordance with another embodiment that attaches the first anchor to the second anchor.
Figure 19D:
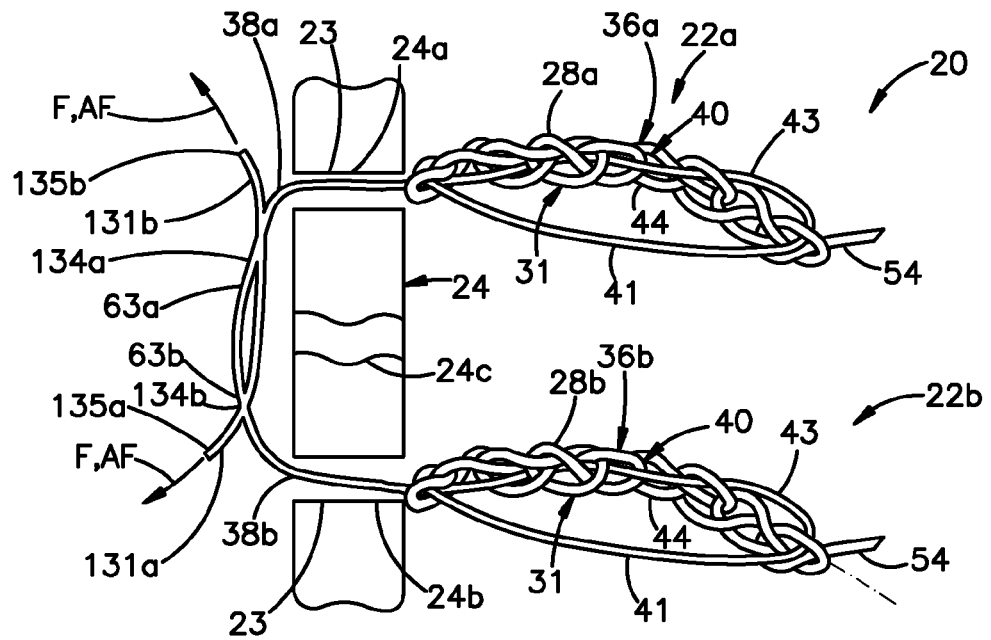
FIG. 19D is a side elevation view of an anchor assembly constructed in accordance with another embodiment, including first and second anchors shown in respective first configurations and implanted in an anatomical structure.
Figure 19E:
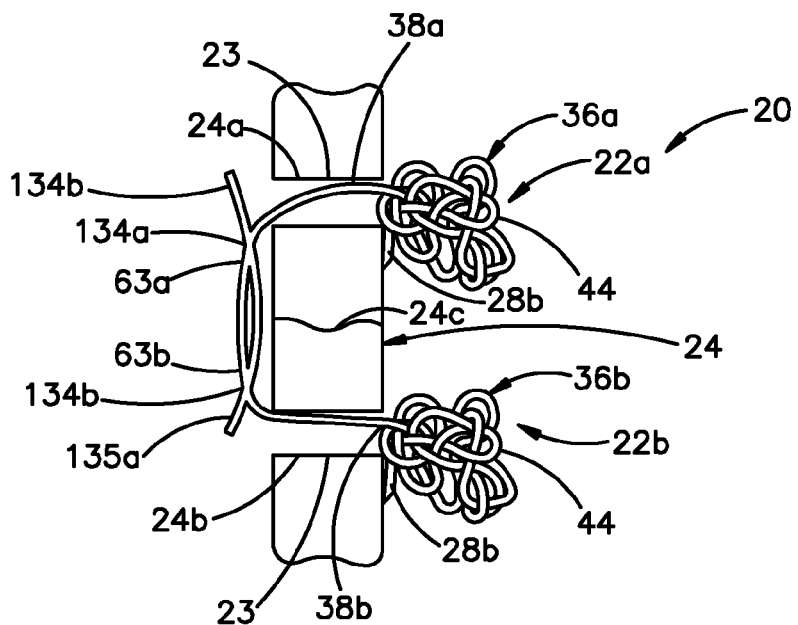
FIG. 19E is a side elevation view of the anchor assembly illustrated in FIG. 19D, showing the first and second anchors in respective expanded configurations.
Figure 19F:
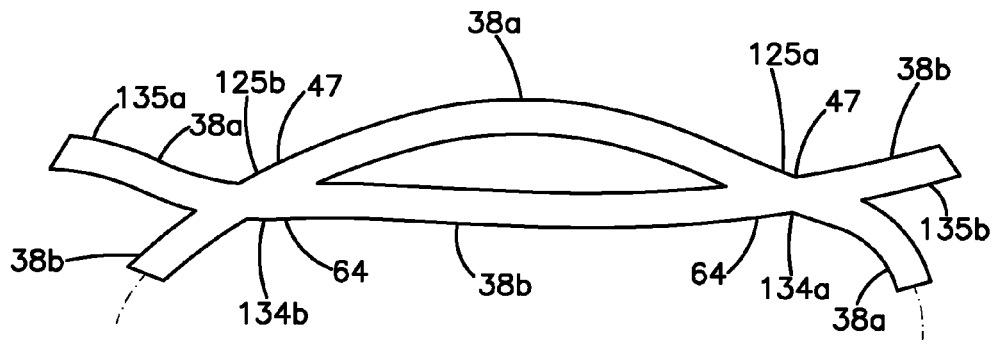
FIG. 19F is an enlarged side elevation view of a portion of the anchor assembly as illustrated in FIG. 19E, including first and second connector members.
Figure 19G:
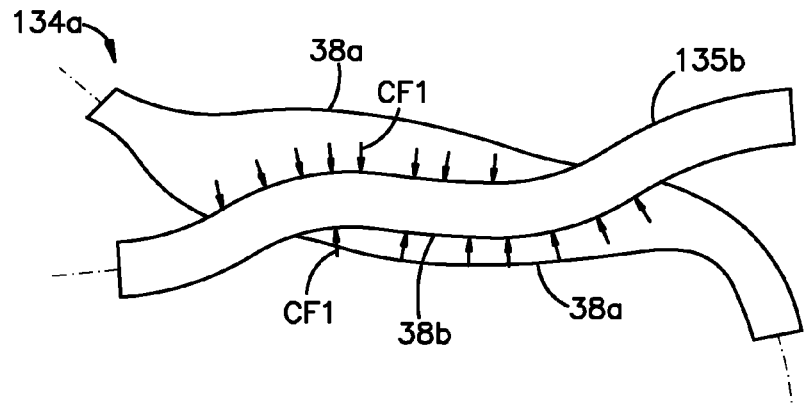
FIG. 19G is an enlarged sectional side elevation view of the first connector member illustrated in FIG. 19F.
Figure 19H:
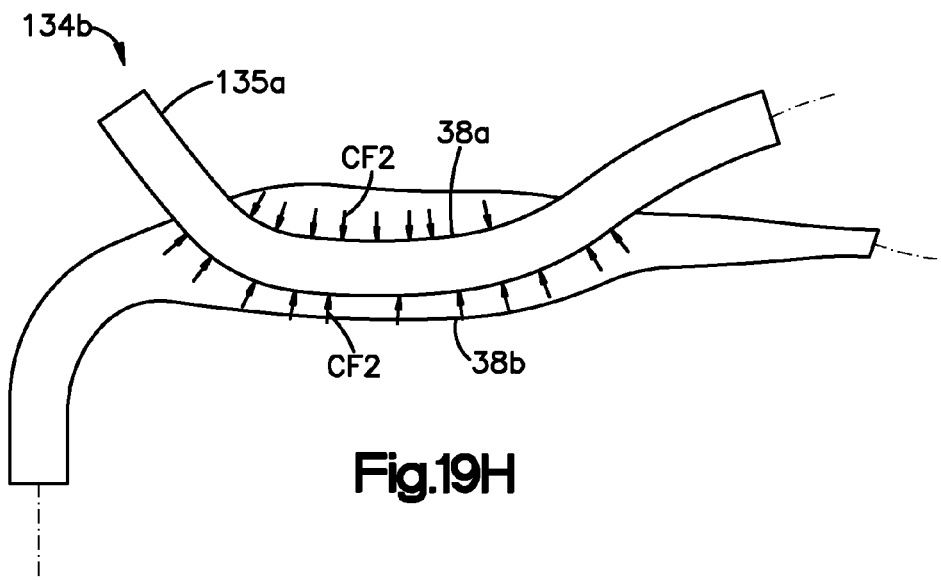
FIG. 19H is an enlarged sectional side elevation view of the second connector member illustrated in FIG. 19F.

Referring now to FIG. 19C, the connector member 63 can be configured as a twist tie 132 that defines the locking member 64 that attaches the first anchor 22a to the second anchor 22b. The twist tie 132, and thus the connector member 63, can be defined, for instance, by the first and second actuation strands 38a and 38b. Thus, at least one or both of the actuation strands 38a and 38b can me made from a pliable deformable material, such that the first and second actuation strands 38a and 38b can be twisted together at the junction 125 so as to define the twist tie 132. Thus, during operation, at least one or both of the first and second actuation strands 38a and 38b can receive a respective approximation force AF that biases at least one or both of the anchor bodies 28a and 28b toward the other of the anchor bodies 28a and 28b to a biased position so as to approximate the gap 24c. The first and second actuation strands 38a and 38b can then be twisted together so as to define the twist tie 132 that secures the first and second anchor bodies 28a and 28b in their biased positions. Alternatively or additionally, the approximation force AF can be applied to one or both of the first and second actuation strands 38a and 38b as the first and second actuation strands 38a and 38b are twisted into the twist tie 132 so as to approximate, or further approximate, the gap 24c.

Referring now to FIGS. 19D-H, the anchor assembly 20 can include at least one connector member 63, such as a pair of connector members 63a and 63b that join the first actuation strand 38a to the second actuation strand 38b at a pair of respective junctions 125a and 125b. For instance, each of the connector members 63a and 63b can be configured as a respective splice 134a and 134b that is defined by the first and second actuation strands 38a and 38b. In one example, one of the first and second actuation strands 38a and 38b can be woven or otherwise spliced through the other of the actuation strands 38a and 38b. In accordance with the illustrated embodiment, the second actuation strand 38a can be woven or otherwise spliced through the first actuation strand 28a so as to define the first splice 134a, and the first actuation strand 38a can be woven or otherwise spliced through the second actuation strand 38b so as to define the second splice 134b. The first and second splices 134a and 134b can be spaced, such that the first splice 134a is disposed closer to the first anchor 22a than the second splice 134b, and the second splice 134b is disposed closer to the second anchor 22b than the first splice 134a.

In particular, the second actuation strand 38b can enter the first actuation strand 38a and can extend along the first actuation strand 38a inside the first actuation strand 38a along a direction away from the corresponding second anchor body 28b so as to define the first splice 134a prior to exiting the first actuation strand 38a. Thus, the first actuation strand 38a can circumscribe the second actuation strand 38b along a portion of the length of second actuation strand 38b. The second actuation strand 38b defines a terminal portion 135b that exits the first actuation strand 38a and can define an actuation portion 131a of the first actuation strand 38a. The second actuation strand 38b can exit the first actuation strand 38a from the opposite side of the first actuation strand 38a that the second actuation strand 38b entered. For instance, the second actuation strand 38b can be disposed inboard of the first actuation strand 38a with respect to the anatomical structure 24 before entering the first actuation strand 38a, and can be disposed outboard of the first actuation strand 38a with respect to the anatomical structure 24 after exiting the first actuation strand 38a.

The first actuation strand 38a can enter the second actuation strand 38b and extend along the second actuation strand 38b inside the second actuation strand 38b along a direction away from the first anchor body 28a so as to define the second splice 134b prior to exiting the second actuation strand 38b. Thus, the second actuation strand 38b can circumscribe the first actuation strand 38a along a portion of the length of the first actuation strand 38a. The first actuation strand 38a defines a terminal portion 135a that exits the second actuation strand 38b, and can define the actuation portion 131a of the first actuation strand 38a. The first actuation strand 38a can exit the second actuation strand 38b from the same side of the second actuation strand 38b that the first actuation strand 38a entered. For instance, the first actuation strand 38a can be disposed outboard of the second actuation strand 38b with respect to the anatomical structure 24 both before entering and after exiting the second actuation strand 38b.

During operation, the first and second actuation strands 38a and 38b can each receive a respective actuation force F that causes the anchor bodies 28a and 28b to actuate from their respective first configurations to their respective expanded configurations. The actuation force F can be applied directly to the first and second actuation strands 38a and 38b at the respective first and second terminal portions 135a and 135b as illustrated, or can be applied to the first and second actuation strand 38a and 38b at a location upstream of the respective splices 134b and 134a. Next, each of the first and second terminal portions 135a and 135b of the first and second actuation strands 38a and 38b, respectively, can each receive an approximation force AF that biases at least one or both of the anchor bodies 28a and 28b toward the other of the anchor bodies 28a and 28b to a biased position so as to approximate the gap 24c. The approximation force AF can be a continuation of the actuation force F if, for instance, the actuation force F is applied to the terminal portions 135a and 135b. It should be appreciated that once both the first and second actuation strands 38a and 38b are placed under tension, the first actuation strand 38a applies a compressive force CF1 to the second actuation strand 38b at the first splice 134a, and the second actuation strand 38b applies a compressive force CF2 to the first actuation strand 38a at the second splice 134b. The first compressive force CF1 is sufficient to prevent the second actuation strand 38b from backing out of the first splice 134a along a direction toward the second anchor body 28b, and the second compressive force CF2 is sufficient to prevent the first actuation strand 38a from backing out of the second splice 134b along a direction toward the first anchor body 28a.

Accordingly, the first and second splices 134a and 134b each define a sliding member 47 that allows one of the first and second actuation strands 38a and 38b to slide with respect to the other of the first and second actuation strands 38a and 38b so as to approximate the gap 24c, and further define a locking member 64 that secures the first and second actuation strands 38a and 38b to each other, for example with respect to relative movement that would allow the first and second anchor bodies 28a and 28b to separate.

While certain connector members 63 have been described as being integral with at least one or both of the actuation strands 38a and 38b such that the actuation strands 38a and 38b attach directly to each other, it should be appreciated that the anchor assembly 20 can alternatively or additionally include a connector member 63 configured as an auxiliary connector member 77 that is attached to one or both of the first and second actuation strands 38a and 38b so as to attach the first and second anchors 22 and 22b to each other. The auxiliary connector member 77 can alternatively or additionally attach at least one of the first and second actuation strands 38a and 38b to a connector strand, which can also define an auxiliary connector member 77, or can attach portions of the connector strand to itself so as to attach the first actuation strand 38a to the second actuation strand 38b, for instance when the actuation strands 38a and 38b define eyelets and the connector strand extends through the eyelets. The auxiliary connector member 77 can be made of metal, plastic, suture, or any suitable alternative material as will be described from the description below.

Figure 20A:
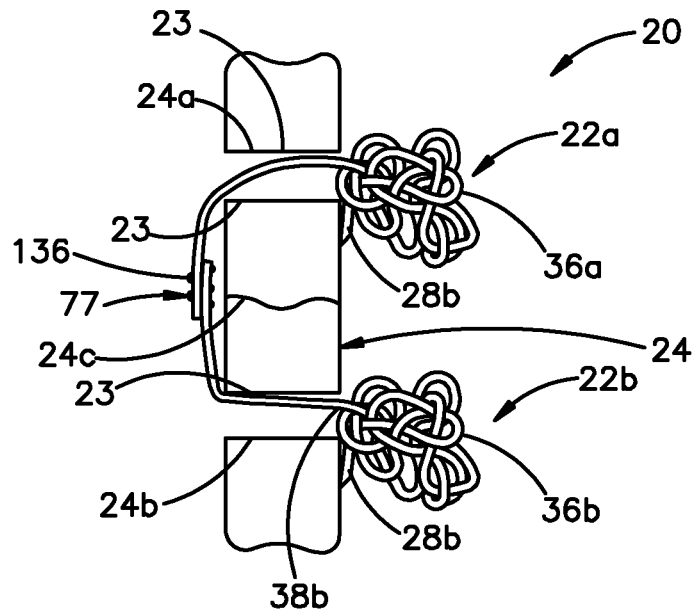
FIG. 20A is a side elevation view of an anchor assembly constructed in accordance with another embodiment.

For instance, referring now to FIG. 20A, the auxiliary connector member 77 can be configured as a strand 136 that is stitched through the first and second actuation strands 38a and 38b so as to attach the first and second actuation strands 38a and 38b to each other, for instance after the gap 24c has been approximated in the manner described above. The strand 136 can be stitched through the first and second actuation strands 38a and 38b at a location between the anchors 22a and 22b, which can be constructed in any manner desired, for instance as illustrated in FIGS. 7A-C.

Figure 20B:
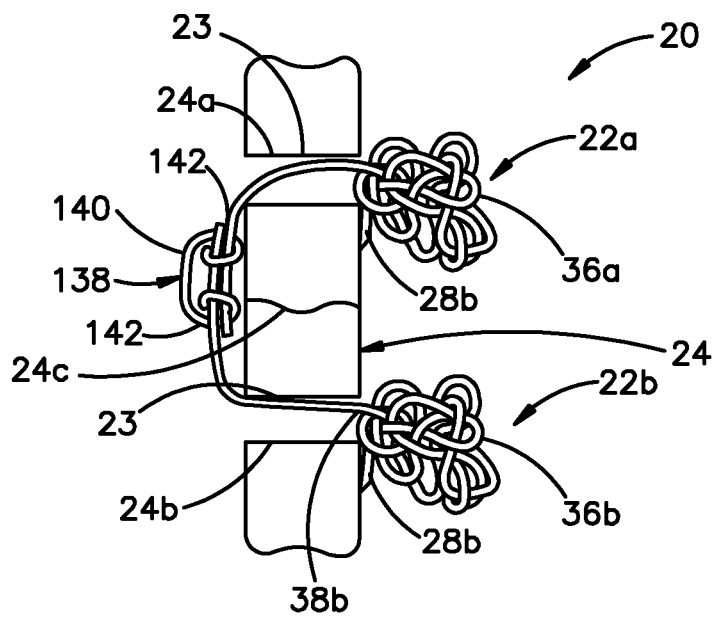
FIG. 20B is a side elevation view of an anchor assembly constructed in accordance with another embodiment.
Figure 20C:
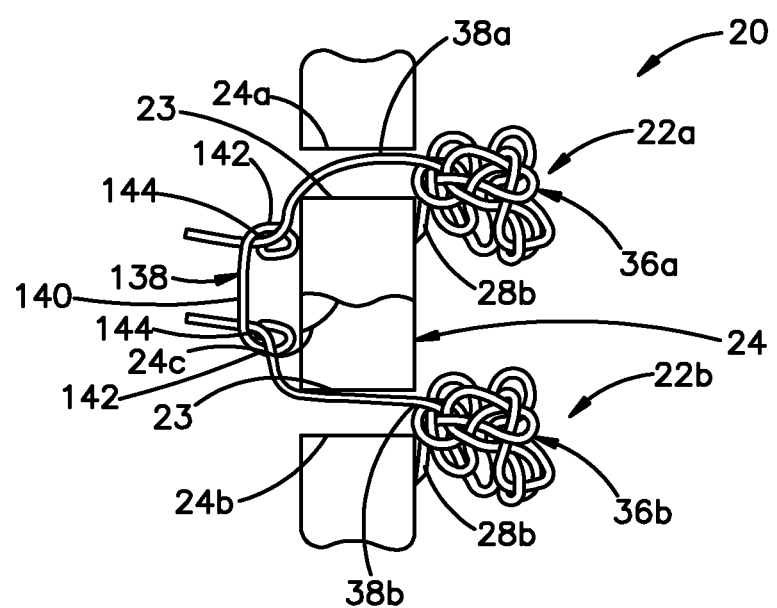
FIG. 20C is a side elevation view of an anchor assembly constructed in accordance with another embodiment.

Alternatively or additionally, as illustrated in FIG. 20B, the auxiliary connector member 77 can be configured as a staple 138 having a crossbar 140 and a pair of spaced legs 142 that extend from the crossbar 140. At least one or both of the legs 142 can extend through the first and second actuation strands 38a and 38b so as to attach the actuation strands 38a and 38b to the staple 138, and thus to each other, after the gap 24c has been approximated in the manner described above. Alternatively or additionally, as illustrated in FIG. 20C, the legs 142 can be curved towards the crossbar 140 so as to define respective openings 144, and at least one or both of the openings 140 can receive a respective one or both of the first and second actuation strands 38a and 38b so as to attach the actuation strands 38a and 38b to the staple 138, and thus to each other. For instance, the legs 142 can be deformed toward the crossbar 140 so as to pinch the respective one or both of the actuation strands 38a and 38b between the respective leg 142 and the crossbar 140. The staple 138 can be attached to the first and second actuation strands 38a and 38b at a location between the anchors 22a and 22b.

Figure 21A:
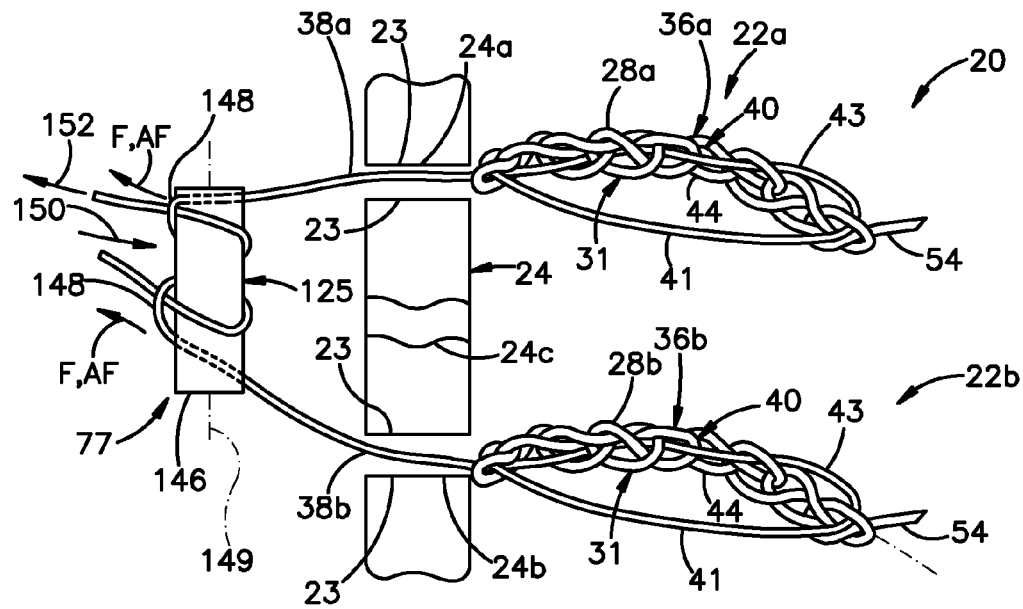
FIG. 21A is a side elevation view of an anchor assembly constructed in accordance with another embodiment, including first and second anchors shown in respective first configurations and implanted in an anatomical structure.
Figure 21B:
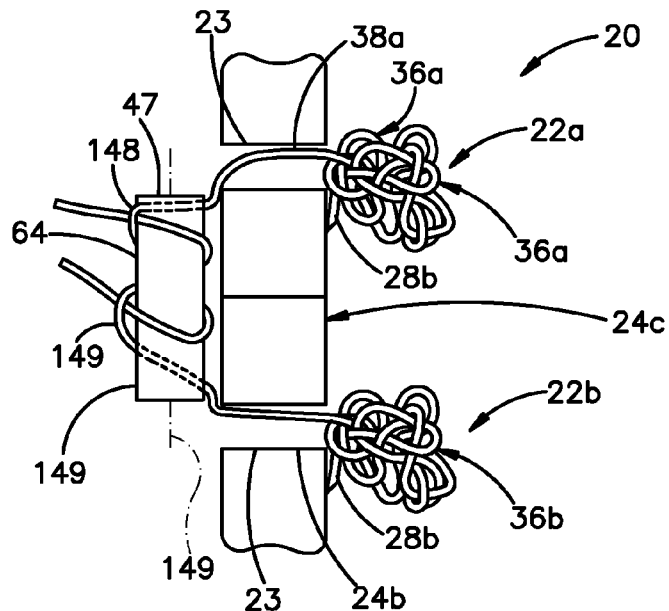
FIG. 21B is a side elevation view of the anchor assembly illustrated in FIG. 21A, showing the first and second anchors in respective expanded configurations.

Referring to FIGS. 21A-B, the auxiliary connector member 77 can be made from any suitable metal, plastic, or any alternative biocompatible material, and can be configured as a body 146, which can be flexible or rigid, that is configured to attach to either or both of the first actuation strands 38a and 38b at a location between the anchors 22a and 22b. For instance, each of the first and second actuation strands 38a and 38b can be stitched through the body 146 and tied about the body 146 so as to define a knot 148 that can be actuated from an unlocked configuration to a locked configuration. The first and second actuation strands 38a and 38b are slidable with respect to the body 146 when the knots 148 are in the unlocked configuration, and fixed with respect to sliding movement relative to the body 146 when the knots 148 are in the locked configuration. The body 146 can define any shape as desired, such as substantially cylindrical, and can be flexible or substantially rigid as desired.

During operation, the actuation strands 38a and 38b can be stitched through the body 146 along a direction away from the anatomical structure 24 and tied about the body 146 such that the respective knots 148 are in the unlocked configuration. The body 146 can be oriented such that its long axis 149 is oriented substantially parallel to the anatomical structure 24. The body 146 can be translated along the first and second actuation strands 38a and 38b along the direction of Arrow 150 toward the anatomical structure 24 while the actuation strands 38a and 38b are under tension, which causes the actuation strands 38a and 38b to translate relative to the body 146 along an opposite direction indicated by Arrow 152. As the body 146 translates along the actuation strands 38a and 38b toward the gap 24c, the body 146 applies the actuation force F to the actuation strands 38a and 38b, thereby causing the anchors 22a and 22b to actuate from the first configuration to the expanded configuration.

As the body 146 further translates toward the gap 24c after the anchors 22a and 22b have been actuated to their expanded configuration, the body 146 applies the approximation force AF to at least one or both of the actuation strands 38a and 38b that draws at least one or both of the anchors 22a and 22b inward toward the other, thereby approximating the gap 24c. In this regard, it should be appreciated that the approximation force AF can be a continuation of the actuation force F. Alternatively, the actuation force F can be applied to the actuation strands 38a and 38b at a location upstream of the body 146, or prior to attaching the actuation strands 38a and 38*b* to the body 146. The knot 148 can then be tightened so as to secure the first and second actuation strands 38*a* and 38*b* to the body 146, and therefore also to each other so as to prevent separation of the first and second anchors 22*a* and 22*b*. Once the gap 24*c* has been approximated, the body 146, and thus the knots 148, can be disposed along the outer surface of the anatomical structure 24. Alternatively, the body 146 can be sized such that a portion of the body 146, and thus the knots 148, is disposed in the opening 23 that receives the anchor bodies 28*a* and 28*b* once the gap 24*c* has been approximated. Accordingly, the knots 148 can be disposed behind the anatomical structure 24, or can be embedded in the anatomical structure 24.

The body 146 can thus define a sliding member 47 that allows one of the first and second actuation strands 38*a* and 38*b* to slide with respect to the other of the first and second actuation strands 38*a* and 38*b* so as to approximate the gap 24*c*, and can further define a locking member 64 that secures the first and second actuation strands 38*a* and 38*b* to each other, for example with respect with respect to relative movement that would allow the first and second anchor bodies 28*a* and 28*b* to separate.

Figure 21C:
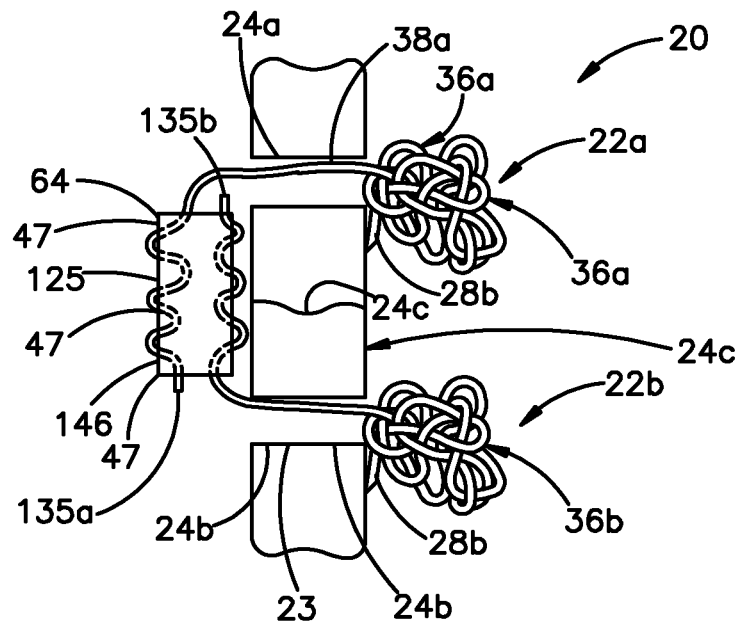
FIG. 21C is a side elevation view of an anchor assembly similar to FIG. 22B, but including a connector member constructed in accordance with an alternative embodiment.

Alternatively, referring to FIG. 21C, at least one or both of the first and second actuation strands 38*a* and 38*b* can be woven into the body 146, for instance in opposite directions substantially along the long axis 149. The body 146 can be configured as a suture that defines a core, such that the actuation strands 38*a* and 38*b* are woven into the core, or as a braided body such as tube, such that the actuation strands 38*a* and 38*b* are woven into select braids of the body. Thus, the actuation force F and the approximation force AF can be applied to the terminal portions 135*a* and 135*b* of the actuation strands 38*a* and 38*b* that extend out from the body 146, which the actuation strands 38*a* and 38*b* to translate through the body 146. Thus, the body 146 can define a sliding member 47. The actuation force F causes each of the anchors 22*a* and 22*b* to actuate from the first configuration to the expanded configuration, and further causes the anchors 22*a* and 22*b* to be drawn together so as to approximate the gap 24*c*. The actuation strands 38*a* and 38*b* can frictionally engage the body 146 so as to prevent the actuation strands 38*a* and 38*b* from backing out of the body 146 along a direction toward the respective anchor bodies 28*a* and 28*b*, which would allow the anchors 22*a* and 22*b* to separate. Thus, the body 146 can define a locking member 64. Alternatively or additionally, the actuation strands 38*a* and 38*b* can be tied into a knot at the respective first and second terminal portions. The knots can be sized sufficient so as to prevent the first and second actuation strands 38*a* and 38*b* from backing out of the body 146.

It should be appreciated that connector members 63 that are configured to allow the actuation strands 38*a* and 38*b*, or a connector strand that is attached, directly or indirectly, to one or both of the actuation strands 38*a* and 38*b*, to translate therein can be said to define a sliding member. Furthermore, connector members 63 that are configured to subsequently prevent the actuation strands 38*a* and 38*b*, or the connector strand that is attached, directly or indirectly, to one or both of the actuation strands 38*a* and 38*b*, from translate therein can be said to define a locking member 64.

Figure 22A:
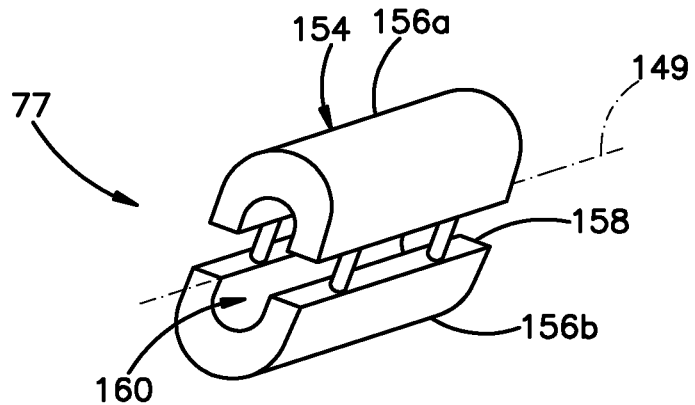
FIG. 22A is a perspective view of a connector member constructed in accordance with one embodiment.
Figure 22B:
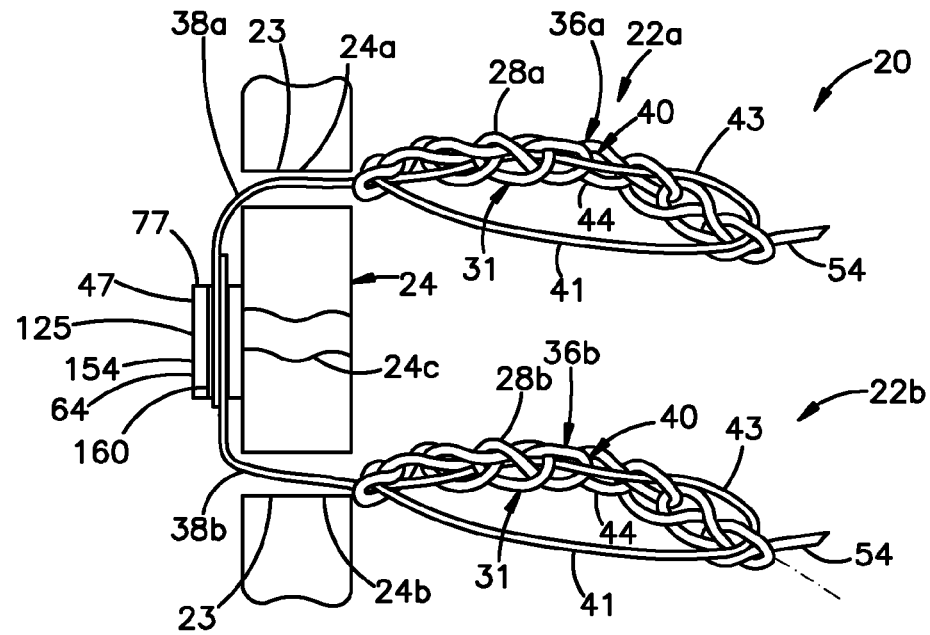
FIG. 22B is a side elevation view of an anchor assembly including first and second anchors shown in respective first configurations and implanted in an anatomical structure and attached via the connector member illustrated in FIG. 22A.
Figure 22C:
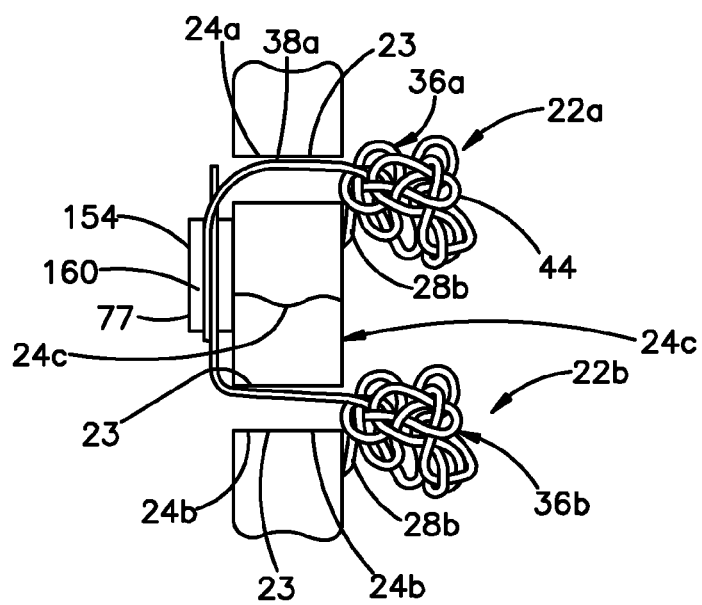
FIG. 22C is a side elevation view of the anchor assembly illustrated in FIG. 22B, showing the first and second anchors in respective expanded configurations.

Referring now to FIGS. 22A-C, the auxiliary connector member 77 can be configured as a clip 154 that is configured to attach to the first and second actuation strands 38*a* and 38*b* so as to attach the first and second actuation strands 38*a* and 38*b* to each other after the gap 24*c* has been approximated in the manner described above. The clip 154 can be attached to the first and second actuation strands 38*a* and 38*b* at a location between the anchors 22*a* and 22*b*. For instance, the clip 154 can include a pair of body portions 156*a* and 156*b* that can be attached to each other. In accordance with one embodiment, at least one or both of the body portions 156*a* and 156*b* can include legs 158 that lock into respective openings of the other body portion so as to fasten the body portions 156*a* and 156*b* together.

When the body portions 156*a* and 156*b* are attached to each other, the clip 154 defines a channel 160 that can receive the actuation strands 38*a* and 38*b*. The body portions 156*a* and 156*b* can be attached to each other in a first configuration and subsequently tightened toward each other to a second configuration whereby the size of the channel is reduced. Accordingly, the clip 154 is movable from an unlocked configuration (FIG. 22B) whereby the channel 160 is sized such that the actuation strands 38*a* and 38*b* can move freely within the channel 160 and to a locked configuration (FIG. 22C) whereby the channel 160 is sized such that the clip 154 secures the actuation strands 38*a* and 38*b* and prevents the actuation strands 38*a* and 38*b* from moving relative to each other and the clip 154.

The actuation strands 38*a* and 38*b* can be fed through the channel 160 in opposite directions substantially along the long axis 149 when the clip 154 is positioned between the first and second anchors 22*a* and 22*b*, and the clip 154 is in the unlocked configuration. The actuation force F can be applied to the actuation strands 38*a* and 38*b*, thereby causing the anchors 22*a* and 22*b* to actuate from the first configuration to the expanded configuration. Once the anchors 22*a* and 22*b* have actuated, an approximation force AF is applied to at least one or both of the actuation strands 38*a* and 38*b* that draws at least one or both of the anchors 22*a* and 22*b* inward toward the other, thereby approximating the gap 24*c*. In this regard, it should be appreciated that the approximation force AF can be a continuation of the actuation force F. Alternatively, the actuation force F can be applied directly to the actuation strands 38*a* and 38*b* at a location upstream of the clip 154 or prior to attaching the actuation strands 38*a* and 38*b* to the clip 154. Once the gap 24*c* has been approximated, the clip 154 can be actuated to its locked configuration, thereby securing the first and second actuation strands 38*a* and 38*b* with respect to translation through the clip 154, and therefore also securing the actuation strands 38*a* and 38*b* to each other, so as to prevent separation of the first and second anchors 22*a* and 22*b*.

The clip 154 can thus define a sliding member 47 that allows one of the first and second actuation strands 38*a* and 38*b* to slide with respect to the other of the first and second actuation strands 38*a* and 38*b* so as to approximate the gap 24*c*, and can further define a locking member 64 that secures the first and second actuation strands 38*a* and 38*b* to each other, for example with respect with respect to relative movement that would allow the first and second anchor bodies 28*a* and 28*b* to separate.

Figure 22D:
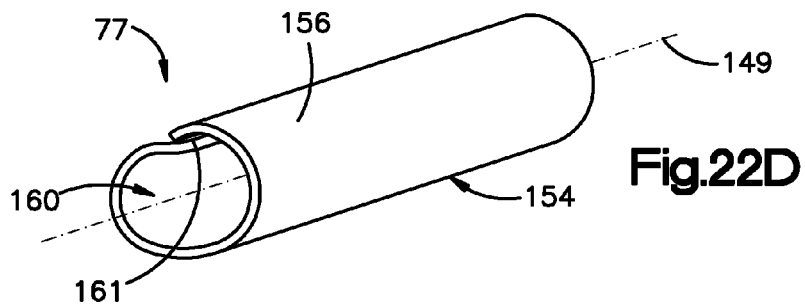
FIG. 22D is a perspective view of a connector member constructed in accordance with another embodiment.
Figure 22E:
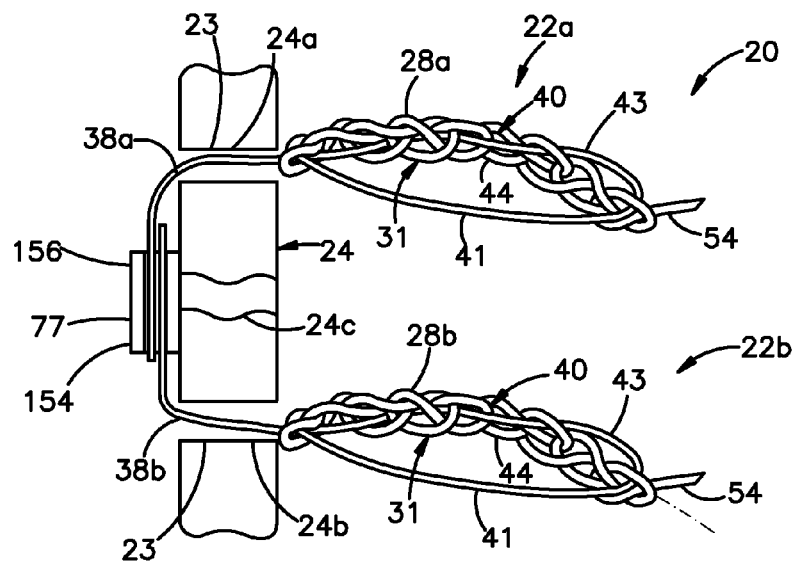
FIG. 22E is a side elevation view of an anchor assembly including first and second anchors shown in respective first configurations and implanted in an anatomical structure and attached via the connector member illustrated in FIG. 22D.
Figure 22F:
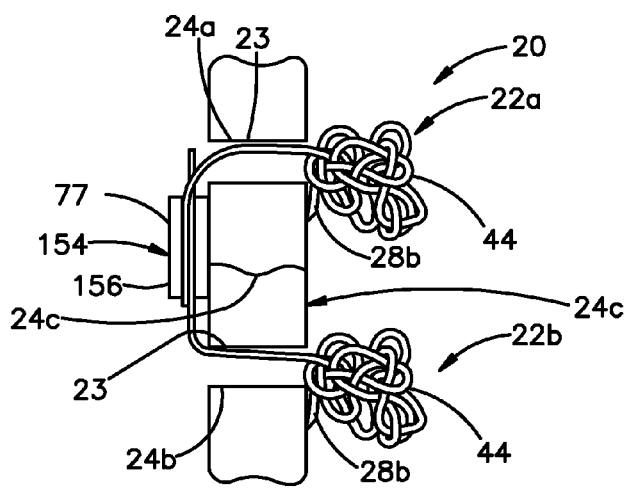
FIG. 22F is a side elevation view of the anchor assembly illustrated in FIG. 22E, showing the first and second anchors in respective expanded configurations.

Referring to FIGS. 22D-F, the clip 154 can include a unitary housing 156, and can be configured to be crimped onto the first and second actuation strands 38*a* and 38*b* so as to attach the first and second actuation strands 38*a* and 38*b* to the clip 154, and therefore also to each other after the gap 24*c* has been approximated in the manner described above. For instance, the first and second actuation strands 38*a* and 38*b* can be inserted into or through the channel 160 in opposite directions substantially along the long axis 149. Alternatively, or additionally, the clip 154 can define an opening 161 that extends through the housing 156 and into the channel 160, and is configured to receive the actuation strands 38*a* and 38*b* along a direction angularly offset, for instance substantially perpendicular, with respect to the long axis 149.

The clip 154 can receive the actuation strands 38a and 38b when the clip 154 is in the unlocked configuration such that the actuation strands 38a and 38b are slidable in the channel 160 (FIG. 2E). The actuation force F can be applied to the actuation strands 38a and 38b, thereby causing the anchors 22a and 22b to actuate from the first configuration to the expanded configuration. Once the anchors 22a and 22b have actuated, an approximation force AF is applied to at least one or both of the actuation strands 38a and 38b that draws at least one or both of the anchors 22a and 22b inward toward the other, thereby approximating the gap 24c. In this regard, it should be appreciated that the approximation force AF can be a continuation of the actuation force F. Alternatively, the actuation force F can be applied to the actuation strands 38a and 38b at a location upstream of the clip 154 or prior to or attaching the actuation strands 38a and 38b to the clip 154. Once the gap 24c has been approximated, the clip 154 can be actuated to its locked configuration as illustrated in FIG. 2F, whereby the clip 154 is crimped onto the first and second actuation strands 38a and 38b, thereby preventing translation of the first and second actuation strands 38a and 38b through the clip 154, securing the actuation strands 38a and 38b to each other, and preventing separation of the first and second anchors 22a and 22b.

Referring to FIGS. 23A-D, the auxiliary connector member 77 can be configured as a shrink wrap material 162 that is wrapped about the first and second actuation strands 38a and 38b. For instance, as illustrated in FIGS. 23A-B, the shrink wrap material 162 can define a channel 164 that receives the first and second actuation strands 38a and 38b while the shrink wrap material 162 is in an unlocked configuration, such that the first and second actuation strands 38a and 38b are slidable within the channel 164. It should be appreciated that the shrink wrap material 162 can be substantially tubular in shape so as to define the channel 164 that receives the first and second actuation strands 38a and 38b, or can alternatively be wrapped around the first and second actuation strands 38a and 38b so as to define the channel 164.

The actuation force F can be applied to the actuation strands 38a and 38b, so as to actuate the anchors 22a and 22b from the first configuration to the expanded configuration. Once the anchors 22a and 22b have actuated, an approximation force AF is applied to at least one or both of the actuation strands 38a and 38b that draws at least one or both of the anchors 22a and 22b inward toward the other, thereby approximating the gap 24c. In this regard, it should be appreciated that the approximation force AF can be a continuation of the actuation force F. Once the gap 24c has been approximated, the shrink wrap material 162 can be activated, for instance heated, which causes the shrink wrap material 162 to actuate to a locked configuration and tighten about the first and second actuation strands 38a and 38b as illustrated in FIGS. 23C-D, thereby applying a compressive force to the first and second actuation strands 38a and 38b, and attaching the first and second actuation strands 38a and 38b to each other so as to prevent separation of the first and second anchors 22a and 22b.

The shrink wrap material 162 can thus define a sliding member 47 that allows one of the first and second actuation strands 38a and 38b to slide through the shrink warp material 162 with respect to the other of the first and second actuation strands 38a and 38b so as to approximate the gap 24c. The shrink wrap material 162 can further define a locking member 64 that secures the first and second actuation strands 38a and 38b with respect to translation therethrough that would allow the first and second anchor bodies 28a and 28b to separate.

Figure 24A:
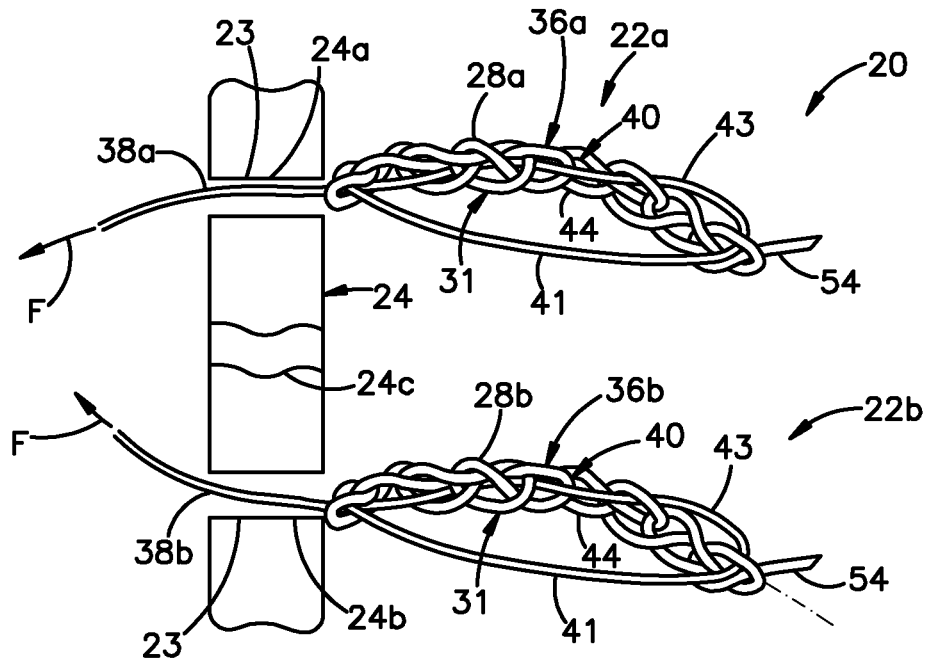
FIG. 24A is a side elevation view of an anchor assembly constructed in accordance with another embodiment, including first and second anchors shown in respective first configurations and implanted in an anatomical structure.
Figure 24B:
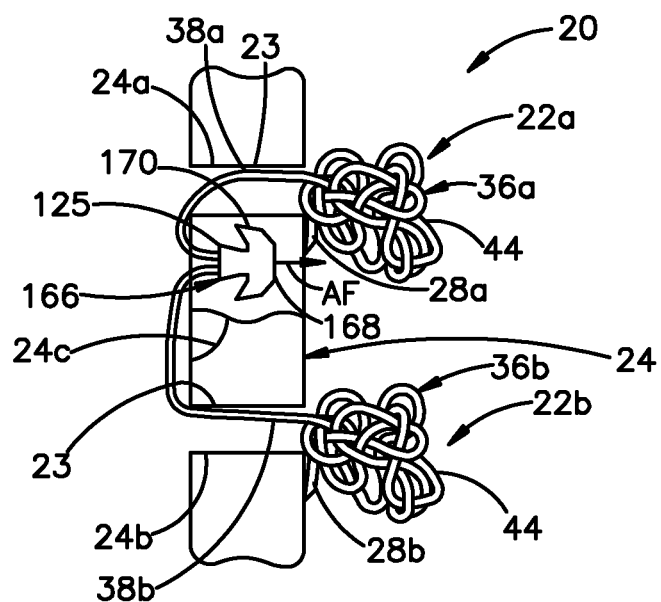
FIG. 24B is a side elevation view of the anchor assembly illustrated in FIG. 24A, showing the first and second anchors in respective expanded configurations.

Referring to FIGS. 24A-B, the auxiliary connector member 77 can be configured as a suture cleat 166 that includes a body 168 and at least one barb 170, such as a pair of barbs 170, that extend out from the body 168 and are configured to anchor the suture cleat 166 in the anatomical structure 24. In accordance with one embodiment, the suture cleat 166 can be configured as a ligating clip configured to attach to the anatomy when, for instance, the anatomical structure 24 is a bone. Thus, as illustrated in FIG. 24A, the actuation strands 32a and 32b are configured to receive the actuation force F so as to actuate each of the first and second anchors 22a and 22b from the first position to the expanded position. Next, the first and second actuation strands 38a and 38b can be fixed in the suture cleat body 168, and the suture cleat 166 can be implanted and embedded in the underlying anatomy 22 at a location adjacent to the gap 24c and between the anchors 22a and 22b. For instance, the first and second actuation strands 38a and 38b can be crimped in the suture cleat body 168 or otherwise secured to the suture cleat body as desired.

The length of the first and second actuation strands 38a and 38b between the respective anchor bodies 28a and 28b and the suture cleat 166 can be sized such that as the suture cleat 166 is implanted in the anatomy, the suture cleat 166 induces a tension in the first and second actuation strands 38a and 38b, such that the approximation force AF is applied to the first and second actuation strands 38a and 38b that biases the first and second anchors 22a and 22b to move toward each other and approximate the gap 24c. The barbs 170 assist in retaining the suture cleat 166 in the anatomical structure 24, and prevent the suture cleat 166 from backing out of the anatomical structure 24.

Figure 25A:
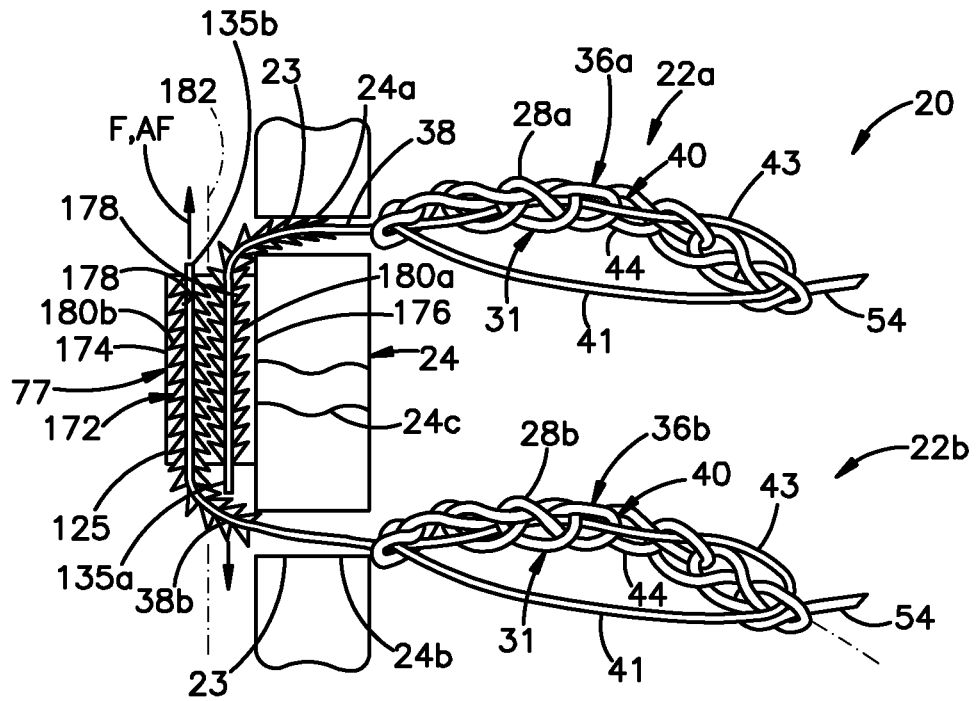
FIG. 25A is a side elevation view of an anchor assembly constructed in accordance with another embodiment, including first and second anchors shown in respective first configurations and implanted in an anatomical structure.
Figure 25B:
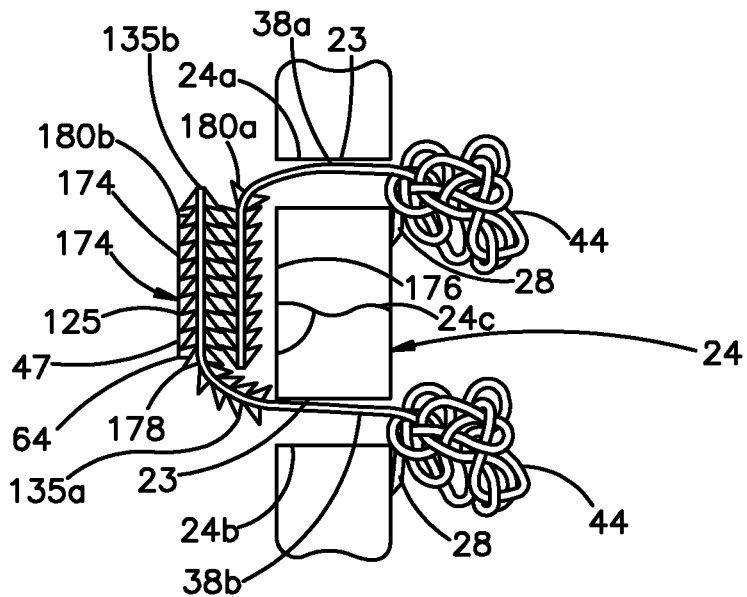
FIG. 25B is a side elevation view of the anchor assembly illustrated in FIG. 25A, showing the first and second anchors in respective expanded configurations.

Referring now to FIGS. 25A-B, the auxiliary connector member 77 can be configured as a collar 172 that is configured to attach to the first and second actuation strands 38a and 38b so as to attach the first and second actuation strands 38a and 38b to each other in the manner described above. The collar 172 can be attached to the first and second actuation strands 38a and 38b at a location between the anchors 22a and 22b. For instance, the collar 172 can define a pair of channels 174 and 176 configured to receive a select one of the first and second actuation strands 38a and 38b. The channels 174 and 176 can extend along respective axes that are oriented substantially parallel to the long axis 182 of the collar 172. Furthermore, the collar 172 defines at least one internal ratchet tooth 178, such as a plurality of ratchet teeth 178, and each of the first and second actuation strands 38a and 38b can define respective ratchet teeth 180a and 180b that are complementary with respect to the ratchet teeth 178 of the collar 172.

In accordance with the illustrated embodiment, the ratchet teeth 178 mate with the ratchet teeth 180a and 180b so as to allow the first and second actuation strands 38a and 38b to slide through the collar along a direction away from the respective first and second anchors 22a and 22b, and interlock so as to prevent the first and second actuation strands 38a and 38b from sliding in the 172 collar along a direction toward the respective first and second anchors 22a and 22b. Thus, the actuation strands 38a and 38b can be fed through the respective channels 174 and 176 in opposite directions substantially along a long axis 182 of the collar 176, for instance when the collar 172 is oriented substantially parallel to the underlying anatomical structure 24, and the collar 172 is positioned between the first and second anchors 22a and 22b.

The actuation force F can be applied to the actuation strands 38a and 38b, which in turn causes the anchors 22a and 22b to actuate from the first configuration to the expanded configuration. For instance, the actuation force F can be applied to the actuation strands 38a and 38b prior to inserting the actuation strands 38a and 38b into the collar. Alternatively, the actuation force F can be applied to the actuation strands 38a and 38b after the actuation strands 38a and 38b have been inserted into the collar, such that the ratchet teeth 180a and 180b slide past the complementary ratchet teeth 178 of the collar 172. Once the anchors 22a and 22b have actuated, an approximation force AF is applied to at least one or both of the actuation strands 38a and 38b, for instance to the respective terminal portions 135a and 135b, that causes the ratchet teeth 180a and 180b to slide past the complementary ratchet teeth 178 of the collar 172 as the first and second actuation strands 38a and 38b translate away from the respective anchors 22a and 22b, thereby drawing at least one or both of the anchors 22a and 22b inward toward the other and approximating the gap 24c. In this regard, it should be appreciated that the approximation force AF can be a continuation of the actuation force F. The ratchet teeth 178 of the collar 172 interlock with the ratchet teeth 180a and 180b of the first and second actuation strands 38a and 38b so as to prevent the actuation strands 38a and 38b from translating along a direction toward the respective anchor bodies 28a and 28b, which would allow the first and second anchors 22a and 22b to separate.

The collar 172 can thus define a sliding member 47 that allows one of the first and second actuation strands 38a and 38b to slide with respect to the other of the first and second actuation strands 38a and 38b so as to approximate the gap 24c, and can further define a locking member 64 that secures the actuation strands 38a and 38b to each other, for example with respect with respect to relative movement that would allow the first and second anchor bodies 28a and 28b to separate.

While the connectors 63 have been illustrated in FIGS. 18A-25B as attached between first and second actuation strands 38a and 38b that are integral with the respective anchor bodies 28a and 28b, it should be appreciated as described above that the connectors 63 can alternatively attach the first and second actuation strands 38a and 38b, whereby at least one or both of the actuation strands 38a and 38b are defined by an auxiliary strand 33 that is separate from and attached to, for instance interwoven in, the respective anchor bodies 28a and 28b. Furthermore, as described above with respect to FIGS. 1A-B, each of the first and second actuation strand 38a and 38b can define a respective first or actuation portion 131a and 131b that is configured to receive the actuation force F, and can be further configured to receive the approximation force AF, and a respective second or attachment portion 133a and 133b.

The attachment portion 133a and 133b of each of the actuation strands 38a and 38b is configured to attach to the attachment portion 133a and 133b of the other of the actuation strands 38a and 38b so as to attach the respective anchors 22a and 22b to each other. For instance, the attachment portions 133a and 133b of the actuation strands 38a and 38b can be integral with each other. Alternatively, the attachment portions 133a and 133b can be attached via any suitable connector 63, which can be integral with either or both of the actuation strands 38a and 38b, or separate from and attached to either or both of the actuation strands 38a and 38b, either directly or indirectly.

It should be further appreciated that the actuation portions 131a and 131b of the actuation strands 38a and 38b can further attach to each other so as to attach the anchors 22a and 22b to each other. Thus, regardless of whether the attachment portions 133a and 133b are attached, it can be said that attachment of the actuation portions 131a and 131b attaches the respective first and second anchors to each other. Thus, regardless of whether the attachment portions 133a and 133b are attached, it can be said that attachment of the actuation portions 131a and 131b attaches the respective first and second anchors 22a and 22b to each other. Likewise, regardless of whether the actuation portions 131a and 131b are attached, it can be said that attachment of the attachment portions 133a and 133b attaches the respective first and second anchors 22a and 22b to each other.

It should thus be appreciated that description herein of a connector member 63 that attaches the actuation strands 38a and 38b can, unless otherwise indicated, can apply to connecting portions of the actuation strands 38a and 38b even though other portions of the actuation strands 38a and 38b are already attached, for instance integrally or via another connector member 63, which can include a connector strand. For instance a connector member 63 can attach the connector strand to either or both of the actuation strands 38a and 38b. Alternatively, a connector member 63 can attach the connector strand to itself so as to attach the first and second actuation strands 38a and 38b, or anchor bodies 28a and 28b, to each other.

Figure 26A:
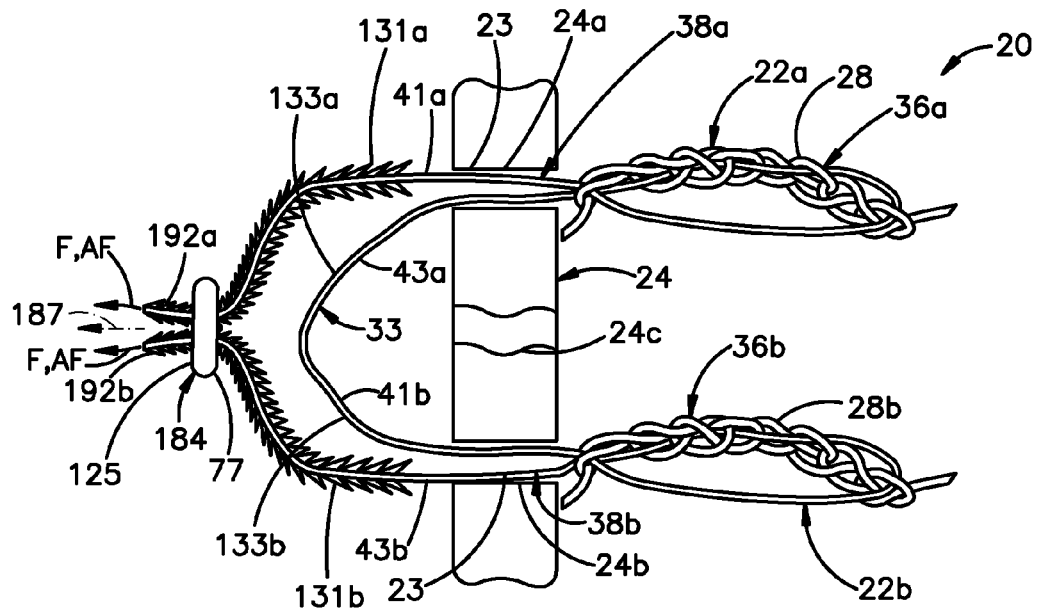
FIG. 26A is a side elevation view of an anchor assembly constructed in accordance with another embodiment, including first and second anchors shown in respective first configurations and implanted in an anatomical structure.
Figure 26B:
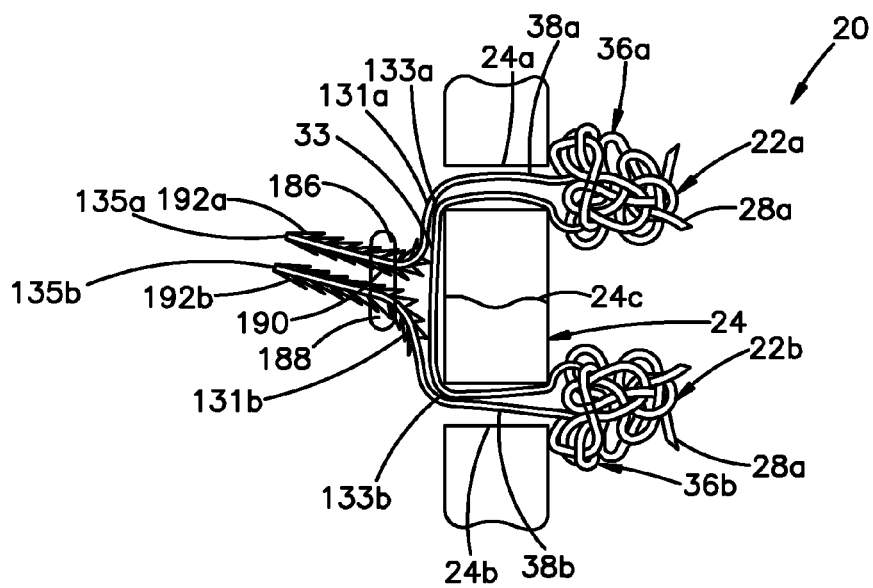
FIG. 26B is a side elevation view of the anchor assembly illustrated in FIG. 26A, showing the first and second anchors in respective expanded configurations.

Referring now to FIGS. 26A-B, and as generally described above with respect to FIGS. 1A-B, the anchor assembly 20 includes an auxiliary strand 33 that can be woven through the anchor bodies 28a and 28b so as to define respective actuation strands 38a and 38b. The first attachment portion 133a can be integral with the second attachment portion 133b so as to attach the actuation strands 38a and 38b, and thus the anchors 22 and 22b, across the gap 24c. The actuation strands 38a and 38b further define the first and second actuation portions 131a and 131b that are each configured to receive the actuation force F so as to actuate the anchors 22a and 22b from their first configurations to their expanded configurations, and the approximation force AF so as to bias the anchors 22a and 22b toward each other, thereby approximating the gap 24c. Furthermore, the first and second actuation portions 131a and 133b are configured to attach to each other.

Referring now in particular to FIGS. 26A-B, the auxiliary connector member 77 can be configured as a ratchet housing 184 that is configured to attach to the first and second actuation portions 131a and 131b, thereby attaching the first and second actuation strands 38a and 38b to each other, and also attaching the anchors 22a and 22b to each other. The ratchet housing 184 can be attached to the first and second actuation strands 38a and 38b at a location between the anchors 22a and 22b. For instance, the ratchet housing 184 can define a pair of channels 186 and 188 configured to receive a select one of the first and second actuation strands 38a and 38b. The first and second actuation strands 38a and 38b can be inserted into the channels 186 and 188 along substantially the same direction away from the underlying anatomical structure 24, and away from the corresponding anchors 22a and 22b. The ratchet housing 184 can be oriented such that the channels 186 and 188 extend along respective axes that can be substantially parallel to the central axis 187 of the ratchet housing 184. Thus, the ratchet housing 184 can be oriented such that the central axis 187 extends substantially perpendicular to the underlying anatomical structure 24.

Furthermore, the ratchet housing 184 defines at least one internal ratchet tooth 190, such as a plurality of ratchet teeth 190, and each of the first and second actuation strands 38a and 38b can define respective ratchet teeth 192a and 192b that are complementary with respect to the ratchet teeth 190 of the ratchet housing 184. In accordance with the illustrated embodiment, the ratchet teeth 190 mate with the ratchet teeth 192a and 192b so as to allow the ratchet housing 184 to slide along the first and second actuation strands 38a and 38b in a direction toward the underlying anatomical structure 24, and thus toward the gap 24c. The ratchet teeth 190 further interlock with the ratchet teeth 192a and 192b so as to prevent the ratchet housing 184 from sliding along the first and second actuation strands 38a and 38b in a direction away from the underlying anatomical structure 24. Thus, during operation, the actuation strands 38a and 38b can be fed through the respective channels 184 and 186 in a direction away from the anatomical structure 24, such that the ratchet teeth 192a and 192b mate with the ratchet teeth 190 of the ratchet housing 184.

The actuation force F can be applied to the actuation strands 38a and 38b, thereby causing the anchors 22a and 22b to actuate from the first configuration to the expanded configuration as the ratchet teeth 192a and 192b slide past the complementary ratchet teeth 190 of the ratchet housing 184. Once the anchors 22a and 22b have actuated, an approximation force AF is applied to at least one or both of the actuation strands 38a and 38b that causes the ratchet teeth 192a and 192b to slide past the complementary ratchet teeth 190 of the ratchet housing 184 as the ratchet housing 184 translates toward the anatomical structure 24, thereby applying the approximation force AF to the first and second actuation strands 38a and 38b, thereby inducing tension in the first and second actuation strands 38a and 38b, including both the actuation portions 131a-b and the attachment portions 133a-b. Otherwise stated, the first and second actuation strands 38a and 38b, and in particular the terminal portions 135a and 135b of the actuation portions 131a and 131b, respectively, translate away from the anatomical structure 24, and the respective anchors 22a and 22b, with respect to the ratchet housing 184.

In this regard, it should be appreciated that the approximation force AF can be a continuation of the actuation force F. Alternatively, the actuation force F can be applied to the actuation strands 38a and 38b at a location upstream of the ratchet housing 184, or to the attachment strands 133a-b, or to the actuation strands 38a and 38b prior to attaching the actuation strands 38a and 38b to the ratchet housing 184. The ratchet teeth 190 of the ratchet housing 184 interlock with the ratchet teeth 192a and 192b of the first and second actuation strands 38a and 38b so as to prevent the ratchet housing 184 from translating along a direction away from the anchors 22a and 22b which could allow the first and second anchors 22a and 22b to separate.

The ratchet housing 184 can thus define a sliding member 47 that allows one of the first and second actuation strands 38a and 38b to slide with respect to the other of the first and second actuation strands 38a and 38b so as to approximate the gap 24c, and can further define a locking member 64 that secures the actuation strands 38a and 38b to each other, for example with respect with respect to relative movement to each other and the housing ratchet housing 184 that would allow the first and second anchor bodies 28a and 28b to separate.

Figure 27A:
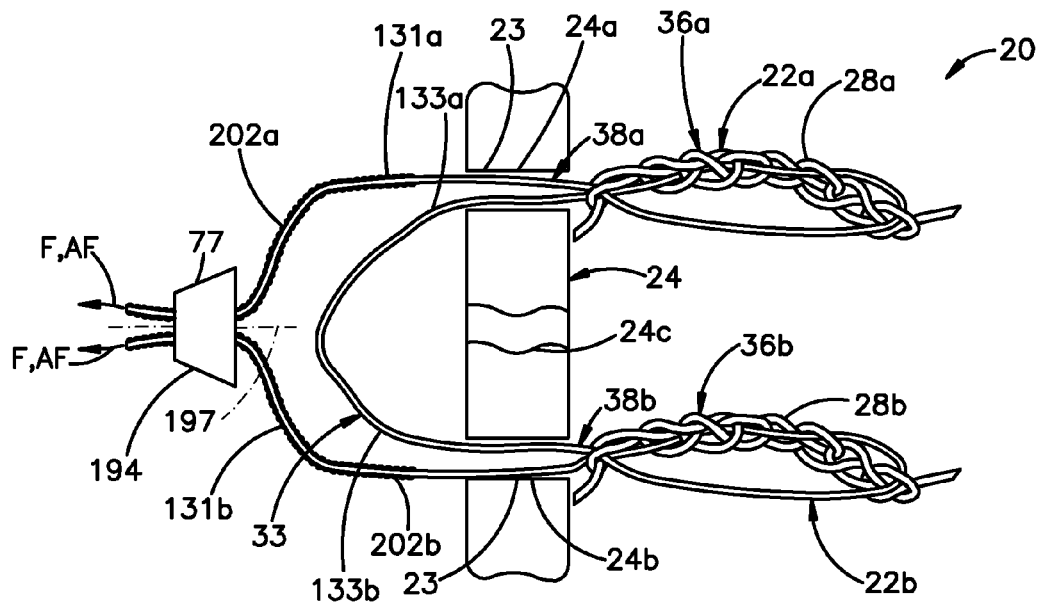
FIG. 27A is a side elevation view of an anchor assembly constructed in accordance with another embodiment, including first and second anchors shown in respective first configurations and implanted in an anatomical structure.
Figure 27B:
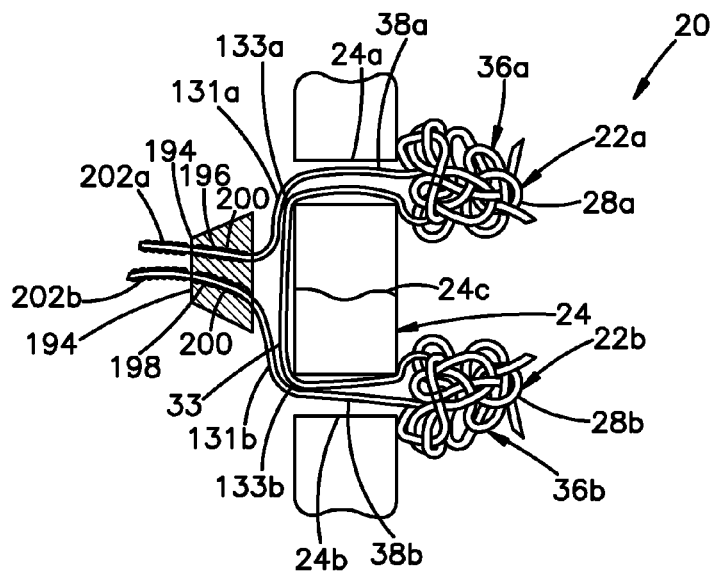
FIG. 27B is a side elevation view of the anchor assembly illustrated in FIG. 27A, showing the first and second anchors in respective expanded configurations.

Referring to FIGS. 27A-B, the auxiliary connector member 77 can be configured zip tie housing 194 that is configured to attach to the first and second actuation strands 38a and 38b to each other. The zip tie hosing 194 can be attached to the first and second actuation strands 38a and 38b, and in particular to the actuation portions 131a-b, at a location between the anchors 22a and 22b. For instance, the zip tie hosing 194 can define a pair of channels 196 and 198 configured to receive a select one of the first and second actuation strands 38a and 38b. The zip tie hosing 194 can be oriented such that the channels 196 and 198 extend along respective axes that can be substantially parallel to the central axis 197 of the zip tie hosing 194. Thus, the zip tie hosing 194 can be oriented such that the central axis 197 extends substantially perpendicular to the underlying anatomical structure 24.

Furthermore, the zip tie hosing 194 defines at least one internal tooth 200, such as a plurality of teeth 200, and each of the first and second actuation strands 38a and 38b can define respective racks of teeth 202a and 202b that are complementary with respect to the teeth 200 of the zip tie hosing 194. The teeth 200 and 202a-b can be shallower than the teeth 190 and 192a-b as described above, and the teeth 202a-b can be spaced more closely together with respect to the ratchet teeth 192a-b described above. Alternatively still, at least one or both of the actuation strands 38a and 38b can be substantially smooth and mate with the teeth 200 of the zip tie housing 194 in the manner described herein.

In accordance with the illustrated embodiment, the teeth 200 mate with the complementary teeth 202a-b so as to allow the zip tie hosing 194 to slide along the first and second actuation strands 38a and 38b in a direction toward the underlying anatomical structure 24, and thus toward the gap 24c. The teeth 200 further interlock with the teeth 202a and 202b so as to prevent the zip tie hosing 194 from sliding along the first and second actuation strands 38a and 38b in a direction away from the underlying anatomical structure 24, and away from the anchor bodies 28a and 28b. Thus, during operation, the actuation strands 38a and 38b can be fed through the respective channels 196 and 198 in a direction away from the respective anchor bodies 28a and 28b, such that the teeth 202a and 202b mate with the ratchet teeth 200 of the zip tie hosing 194.

The actuation force F can be applied to the actuation strands 38a and 38b, and in particular to the actuation portions 131a-b, thereby causing the anchor bodies 28a and 28b to actuate from the first configuration to the expanded configuration as the teeth 202a and 202b slide past the complementary teeth 200 of the zip tie hosing 194. Once the anchors 22a and 22b have actuated, an approximation force AF can be applied to at least one or both of the actuation strands 38a and 38b that causes the teeth 202a and 202b to slide past the complementary teeth 200 of the zip tie hosing 194 as the zip tie hosing 194 translates toward the anatomical structure 24, thereby inducing tension in the actuation strands 38a and 38b, including both the actuation portions 131a-b and the attachment portions 133a-b. Otherwise stated, the first and second actuation strands 38a and 38b translate away from the anatomy, and the respective anchor bodies 28a and 28b, with respect to the zip tie hosing 194.

In this regard, it should be appreciated that the approximation force AF can be a continuation of the actuation force F. Alternatively, the actuation force F can be applied directly to the actuation strands 38a and 38b, including either or both of the actuation portions 131a-b and the attachment portions 133a-b, prior to or after attaching the actuation portions 131a-b to the zip tie hosing 194. The teeth 200 of the zip tie hosing 194 interlock with the teeth 202a and 202b of the first and second actuation strands 38a and 38b so as to prevent the zip tie hosing 194 from translating along a direction that would allow the first and second anchors 22a and 22b to separate.

The zip tie hosing 194 thus define a sliding member 47 that allows one of the first and second actuation strands 38a and 38b to slide with respect to the other of the first and second actuation strands 38a and 38b so as to approximate the gap 24c, and can further define a locking member 64 that secures the first and second actuation strands 38a and 38b with respect to translation relative to each other, and the zip tie housing 194, that would allow the first and second anchor bodies 28a and 28b to separate.

Figure 28B:
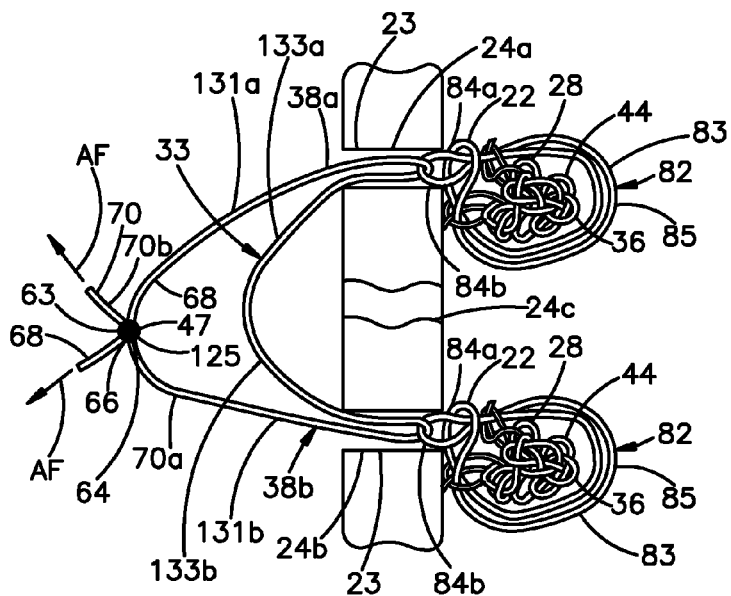
FIG. 28B is a side elevation view of the anchor assembly illustrated in FIG. 28A, showing the first and second anchors in respective expanded configurations.
Figure 28C:
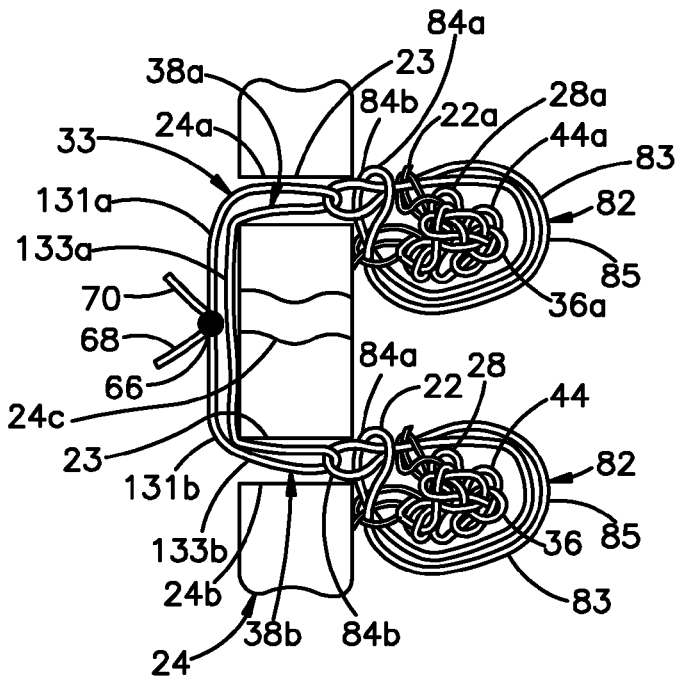
FIG. 28C is a side elevation view of the anchor assembly illustrated in FIG. 28B, showing the first and second anchors in an approximated configuration.

Referring now to FIGS. 28A-C, the first and second anchors 22a-b can include respective first and second attachment members 82a-b of the type described above with respect to FIGS. 6A-E. Thus, the first and second attachment members 82a-b include respective looped strands 79 that define respective eyelets 84a and 84b that, in turn, define respective openings 87a and 87b. The auxiliary strand 33 can define actuation strands 38a and 38b that extend through the respective eyelets 84a and through the respective eyelets 84b, respectively, so as to operably couple the actuation strands 38a and 38b to the respective expandable portions 36 of the anchor bodies 28a and 28b. It should be appreciated that the eyelet 84b can further extend out from the anatomical structure 24.

The anchor assembly 20 includes a connector member 63 that can be configured to attach to the first and second actuation portions 131a and 131b, thereby attaching the first and second actuation strands 38a and 38b to each other, and also attaching the anchors 22a and 22b to each other. The attachment portions 133a-b of the auxiliary strand 33 can be attached, for instance integrally in accordance with the illustrated embodiment, across the gap 24c.

As described above, the connector member 63 that can define at least one of a sliding member 47 and a locking member 64 that attaches the first and second actuation strands 38a and 38b together, for instance at a junction 125 as described above with respect to FIG. 18C. Furthermore, in accordance with the illustrated embodiment, the connector member 63 can be defined by the auxiliary strand 33, and thus by the actuation strands 38a and 38b. Thus, in accordance with one embodiment, the connector member 63 can attach the first actuation strand 38a to the second actuation strand 38b while the actuation strands 38a and 38b are under tension, so as to maintain the gap 24c in an approximated state. Alternatively or additionally, it should be appreciated that the connector member 63 can attach the first and second actuation strands 38a and 38b to each other prior to placing the actuation strands 38a and 38b under tension and therefore prior to approximating the gap 24c.

In accordance with the illustrated embodiment, the connector member 63 is defined by and integral with the first and second actuation strands 38a and 38b. Thus, the actuation strands 38a and 38b are attached directly to each other. The connector member 63 can define the sliding member 47 and the locking member 64 at the junction 125. For instance, the connector member 63 can define a knot 66 that can be constructed as described above with respect to FIGS. 4A-F and can be defined by one or more, up to all of, the actuation strands 38a and 38b, though it should be appreciated that the knot can alternatively be defined by at least one of actuation strands 38a and 38b and a connector strand. Alternatively still the knot 66 can attach portions of a connector strand to each other so as to attach the actuation strands 38a and 38b, for instance when the connector strand is attached to the actuation strands 38a and 38b. In accordance with the illustrated embodiment, the first and second actuation strands 38a and 38b define the knot 66. Thus, at least a portion of the connector member 63 can be integral with at least one or both of the actuation strands 38a and 38b.

One of the first and second actuation strands 38a and 38b can define the post end 68 and the other of the first and second actuation strands 38a and 38b can define the free end 70. In accordance with the illustrated embodiment, the first actuation strand, such as the first actuation portion 131a, defines the post end 68 and the second actuation strand 38b, such as the second actuation portion 131b, defines the free end 70. The free portion 70b of the free and can be defined by the terminal portion 135b of the second actuation strand 135b. Likewise, the terminal portion 135a of the first actuation strand 38a extends out from the knot 66 as the post end 68.

The first and second actuation strands 38a and 38b can be tied into the knot 66 prior to applying tension to the actuation strands 38a and 38b that biases the first and second anchors 22a and 22b toward each other and approximates the gap 24c. Once the knot 66 is formed, and when the knot 66 is in an unlocked configuration, the actuation force F can be applied to the actuation strands 38a and 38b, and in particular to the actuation portions 131a-b, so as to actuate the respective expandable portions 36 from the first configuration to the expanded configuration. Next, the approximation force AF can be applied to the terminal portion 135a of the first actuation strand 38a, which defines the post strand 68, thereby causing the post end 68 to slide through the knot 66 and draw the respective anchor, such as the first anchor 22a, toward the other anchor, such as the second anchor 22b. Once the gap 24c has been approximated, the free strand 70b of the free end 70, for instance defined by the terminal portion 135b of the second actuation strand 38b, can be placed in tension so as to lock knot 66 and prevent the first actuation strand 38a from translating through the knot 66, thereby fixing the actuation strands 38a and 38b in tension.

Figure 28D:
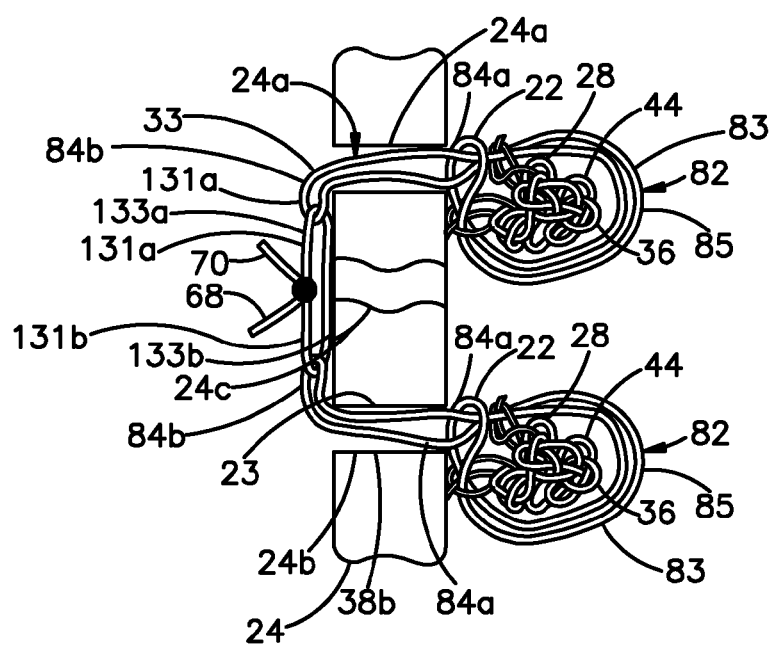
FIG. 28D is a side elevation view of the anchor assembly similar to that illustrated in FIG. 28C, but showing eyelets extending out from anatomical structure.

While the connector member 63 can be configured as the knot 66, it should be appreciated that the connector member 63 can alternatively be configured in accordance with any embodiment described herein or any suitable alternative connector as desired. Furthermore, while each of the anchors 22a and 22b is illustrated as including respective attachment members 82, it should be appreciated that one of the anchors can include the attachment member 82 while the other anchor is directly coupled to the respective actuation strand 38. It should be further appreciated, as illustrated in FIG. 28D, that the eyelets 84b of one or both of the anchors 22a and 22b can extend out the anatomical structure 24 as desired.

Figure 29A:
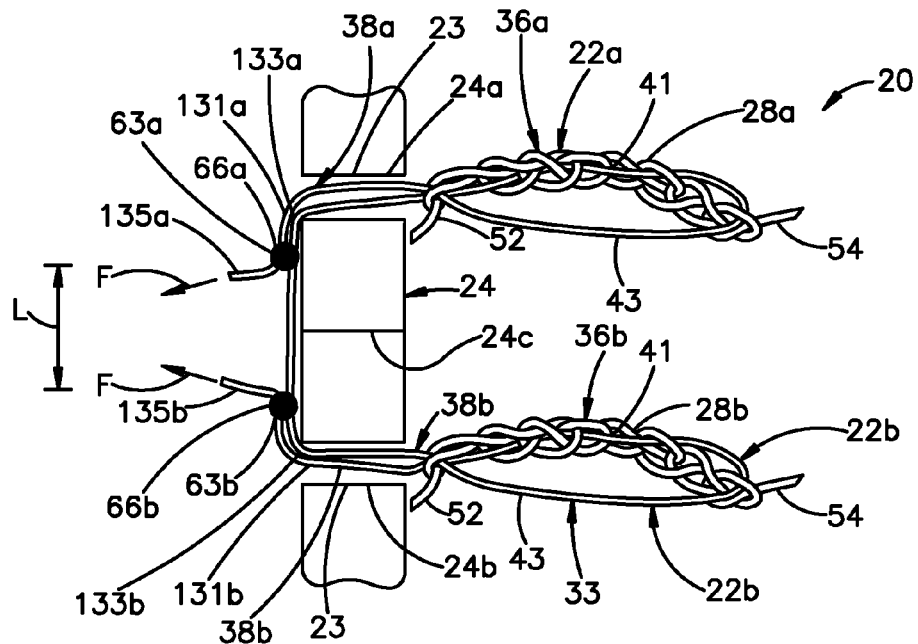
FIG. 29A is a side elevation view of an anchor assembly constructed in accordance with another embodiment, including first and second anchors shown in respective first configurations and implanted in an anatomical structure.
Figure 29B:
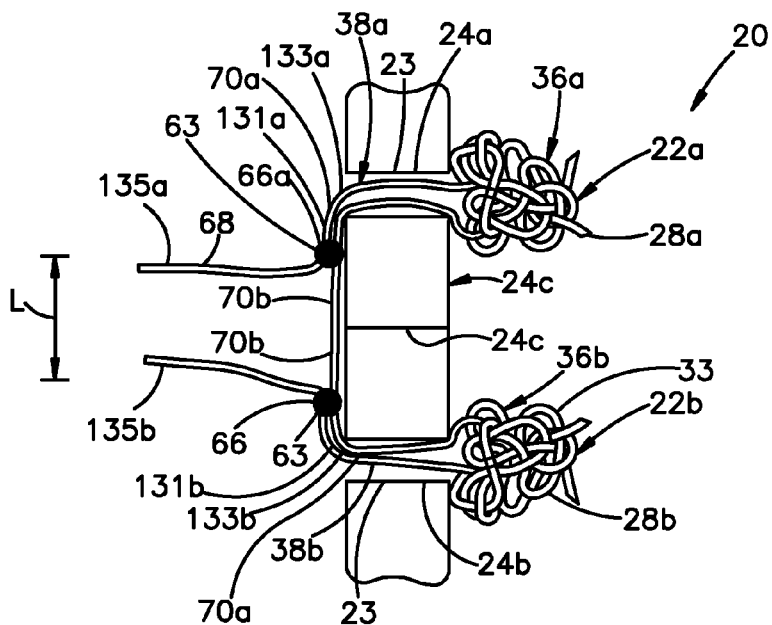
FIG. 29B is a side elevation view of the anchor assembly illustrated in FIG. 29A, showing the first and second anchors in respective expanded configurations.
Figure 29C:
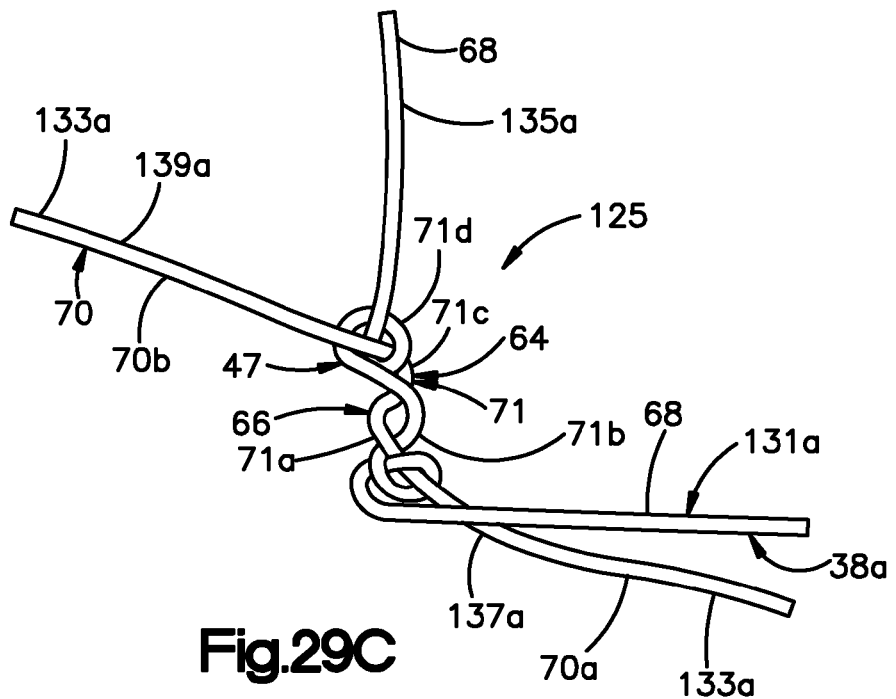
FIG. 29C is a perspective view of a connector member of the anchor assembly illustrated in FIG. 29B.
Figure 29D:
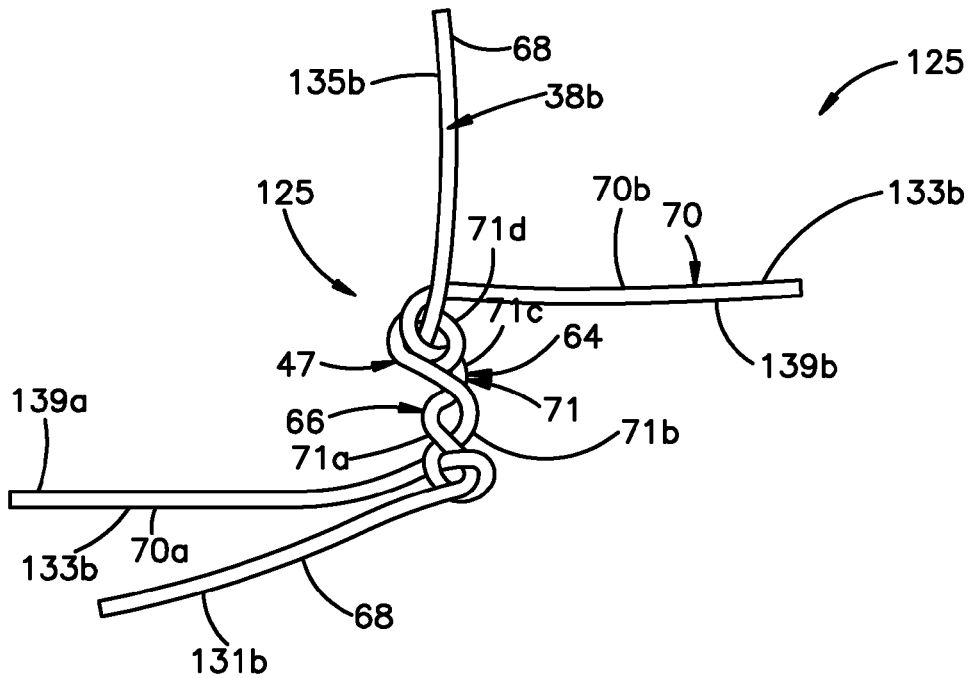
FIG. 29D is a perspective view of another connector member of the anchor assembly illustrated in FIG. 29B.

Referring now to FIGS. 29A-B, the anchor assembly 20 can include a plurality of connector members 63 that are configured to attach at least one or both of the actuation strands 38a and 38b. In accordance with the illustrated embodiment, the actuation strands 38a and 38b are defined by a common strand, such as the auxiliary strand 33, such that the respective attachment portions 133a and 133b are integral with each other. Thus, in accordance with the illustrated embodiment, the first and second actuation strands 38a and 38b are integral with each other. The anchor assembly 20 can include first and second connector members 63a and 63b that are configured to attach the actuation portions 131a and 131b to other locations of the common strand, and thus to each other. In accordance with the illustrated embodiment, the first and connector member 63a can attach the corresponding first actuation portion 131a to another location of the auxiliary strand 33 that is spaced from the first actuation portion 131a. Likewise, the second and connector member 63b can attach the corresponding second first actuation portion 131b to another location of the auxiliary strand 33 that is spaced from the second first actuation portion 131b. For instance, in accordance with the illustrated embodiment, the first connector member 63a attaches the first actuation portion 131a to the first attachment portion 133a, and the second connector member 63b attaches the second actuation portion 131b to the second attachment portion 133b.

Thus, it can be said that at least one connector member, such as the first and second connector members 63a and 63b, can attach the first and second actuation portions 131a and 131b to respective other locations of the auxiliary strand 33 so as to attach the first and second actuation portions 131a and 131b to each other, for instance indirectly through at least one or both of the attachment portions 133a and 133b. It can further be said that the first connector member 63a operably attaches one portion of the first actuation strand 38a to another location of the actuation strand 38a, and the second connector member 63b operably attaches one portion of the second actuation strand 38b to another location of the second actuation strand 38b. Alternatively, it should be appreciated that the first and second connector members 63a and 63b can attach the respective first and second actuation portions 131a and 131b to the anchor body 28, such as the first and second end portions 52 and 54. While the actuation strands 38a and 38b are illustrated as separate from each other, the actuation strands 38a and 38b can alternatively be attached to each other, for instance via any suitable connector member 63 of the type described herein, so as to define an outer connector strand.

In accordance the illustrated embodiment, each of the first and second connector members 63a and 63b can be configured as respective knot 66a and 66b that are defined by the auxiliary strand 33. The knots 66a and 66b can be constructed as described above with respect to FIGS. 4A-F, or can be alternatively constructed as desired. In accordance with the illustrated embodiment, the first knot 66a includes a post end 68, which can be defined by the actuation portion 131a of the first actuation strand 38a, and a free end 70, which can include a static portion 70a that is defined by a first end 137a of the first attachment portion 133a and a free portion 70b that is defined by a second end 139a of the first attachment portion 133a. The first end 137a can be disposed between the knot 66a and the first anchor body 28a, and the second end 139a can be disposed between the knot 66a and the second connector member 63b. Alternatively, the free portion 70b can be defined by the attachment portion 133b of the second actuation strand 38b.

In accordance with one embodiment, the second knot 66a includes a post end 68, which can be defined by the actuation portion 131b of the second actuation strand 38b, and a free end 70, which can include a static portion 70a that is defined by a first end 137b of the second attachment portion 133b and a free portion 70b that is defined by a second end 139b of the second attachment portion 133b. The first end 137b can be disposed between the knot 66b and the second anchor body 28b, and the second end 139b can be disposed between the knot 66b and the first connector member 63a. Alternatively, the free portion 70b can be defined by the attachment portion 133a of the first actuation strand 38a. The attachment portions 133a and 133b are illustrated as being integral with each other, though it should be appreciated that the attachment portions 133a and 133b be separate and attached to each other, for instance when the anchor assembly 20 defines first and second auxiliary strands 33a and 33b operably coupled to the first and second anchors 22a and 22b, respectively (see, e.g., FIGS. 30A-D).

Each of the first and second knots 66a and 66b can define respective sliding members 47 that allow the respective post ends 68 to translate therethrough relative to the free ends 70. Thus, the sliding members 47 allow the first and second actuation portions 131a and 131b to translate relative to the first and second attachment portions 133a and 133b, for instance in response to the applied actuation force F when the knots 66a and 66b are in unlocked configurations, thereby actuating the respective anchor body 28a and 28b from the first configuration to the expanded configuration. Each knot 66 further defines a locking member 64 that can be actuated to a locked configuration so as to secure the at least one or both of the anchors 22a and 22b in their respective biased positions. For instance, a tensile locking force can be applied to the free portions 70b of the free ends of the knots 66a and 66b so as to prevent the actuation portions 131a and 131b from translating through the knots 66a and 66b relative to the attachment portions 133a and 133b.

The first and second knots 66a and 66b can be spaced apart a fixed distance L along the auxiliary strand 33, such that the gap 24c is maintained approximated when the anchor bodies 22a and 22b are inserted into the respective target anatomical locations 24a and 24b. For instance, the gap 24c can be approximated prior to injecting the knots 66a and 66b into the respective target anatomical locations 24a and 24b. During operation, once the first and second anchors 22a and 22b are implanted at the respective first and second target anatomical locations 24a and 24b, the knots 66a-b can be in an unlocked configuration such that application of the actuation force F to the respective actuation strands 38a-b, for instance the actuation portions 131a-b, causes the respective anchor bodies 28a-b to actuate from the first configuration to the expanded configuration. Next, a tensile locking force can be applied to the respective attachment portions 133a-b against the corresponding knots 66a-b, so as to actuate the knots 66a-b to their locked configurations and maintain the anchor 22a-b in their expanded configurations.

The distance L between the first and second knots 66a and 66b can be substantially equal to or less than the distance between the target anatomical locations 24a and 24b, such that the gap 24c is approximated when the first and second anchors 22a and 22b are expanded behind the anatomy and joined by the auxiliary strand 33, such that tension induced in the actuation strands 38a and 38b maintains the approximation of the gap 24c. While the first and second connector members 63a-b can be configured as respective knots 66, it should be appreciated that either or both of the first and second connector members 63a and 63b can be alternatively configured as any suitable locking member 63 of any type described herein or any suitable alternatively constructed locking member. For instance, at least one or both of the connector members 63a-b can define a splice, whereby the respective actuation strands 38a-b can be spliced through the other of the actuation strands 38a-b or itself, and the connector strand is placed in tension after actuation of the anchors 22a and 22b so as to apply a compressive force that prevents translation of the anchor strands 38a-b. One example of such a splice is described above with respect to FIGS. 19D-H.

Figure 30A:
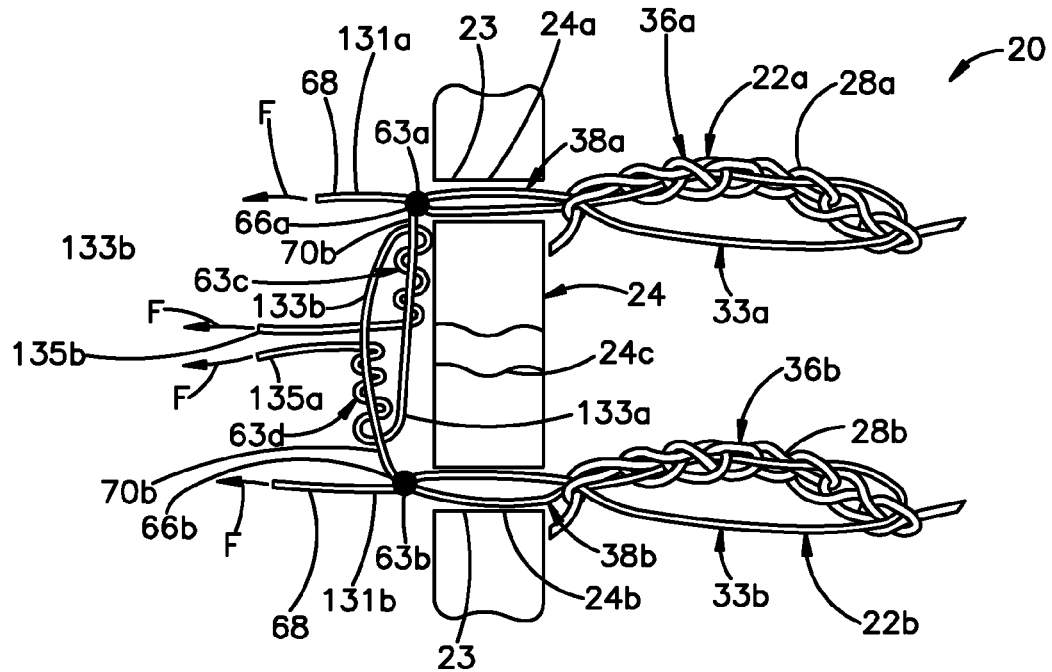
FIG. 30A is a side elevation view of an anchor assembly constructed in accordance with another embodiment, including first and second anchors shown in respective first configurations and implanted in an anatomical structure.
Figure 30B:
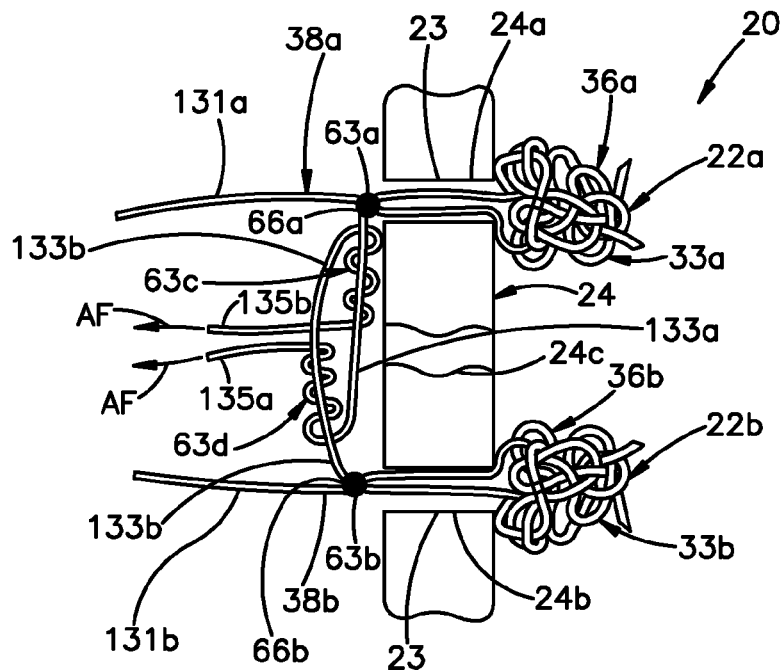
FIG. 30B is a side elevation view of the anchor assembly illustrated in FIG. 30A, showing the first and second anchors in respective expanded configurations.
Figure 30C:
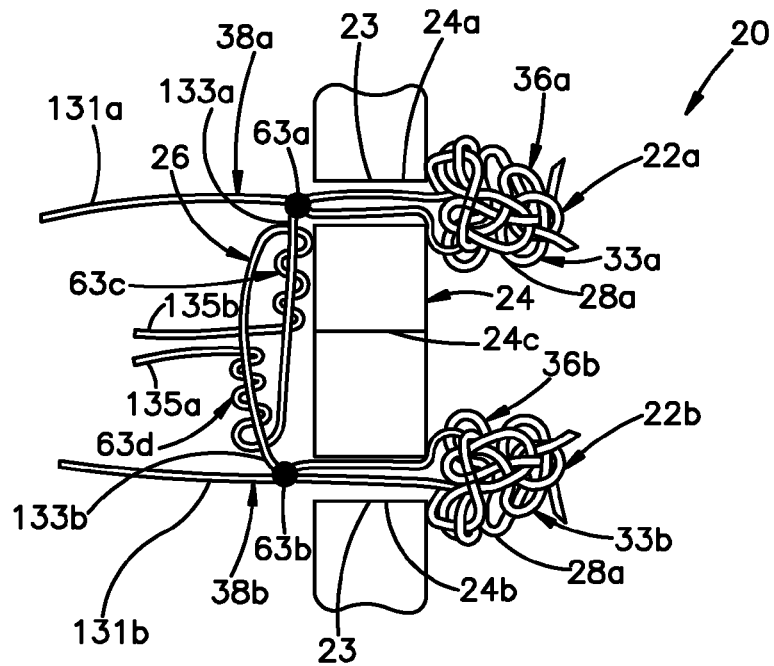
FIG. 30C is a side elevation view of the anchor assembly illustrated in FIG. 30B, showing the first and second anchors in an approximated configuration.
Figure 30D:
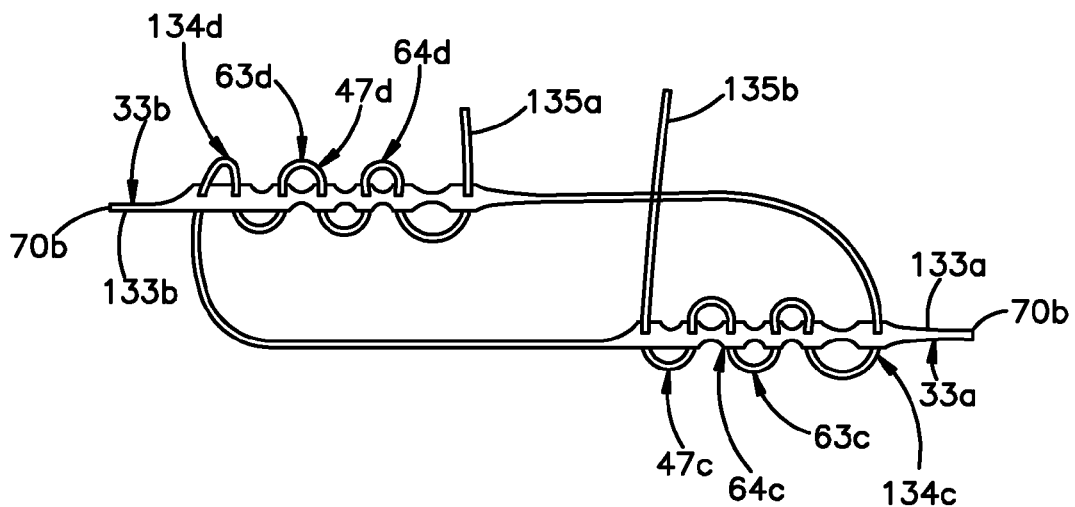
FIG. 30D is an enlarged portion of the anchor assembly illustrated in FIG. 30A.

As described above with respect to FIGS. 29A-D, the first and second attachment portions 133a and 133b can be integral with each other so as to attach the first and second actuation strands 38a and 38b that are both integral with a common auxiliary strand 33. Alternatively, as illustrated in FIGS. 30A-B, the anchor assembly 20 can include a first auxiliary strand 33a that defines the first actuation strand 38a, and a second auxiliary strand 33b that defines the second actuation strand 38b and is separate from the first auxiliary strand 33a. Accordingly, the first and second attachment portions 133a and 133b can be separate from each other. The anchor assembly 20 can include first and second connector members 63a-b that can attach the actuation portions 131a and 131b to the respective attachment portions 133a and 133b in the manner described above with respect to FIGS. 29A-D. The anchor assembly 20 can further include at least one connector member, such as a pair of third and fourth connector members 63c-d, that are configured to attach the actuation strands 38a and 38b, such as the attachment portions 133a and 133b, and thus the first and second anchors 22a and 22b, to each other.

In accordance the illustrated embodiment, each of the third and fourth connector members 63c and 63d can be defined by the first and second auxiliary strands 33a. For instance, the first attachment portion 133a extends from the first connector member 63a toward the second connector member 36b, and thus also extends toward the second attachment portion 133b. Likewise, the second attachment portion 133b extends from the second connector member 63b toward the first connector member 36a, and thus also extends toward the first attachment portion 133a.

In accordance with the illustrated embodiment, the second actuation strand 38b, and in particular the second attachment portion 133b, is woven or otherwise spliced through the first actuation strand 38a, and in particular the first attachment portion 133a, so as to define the third connector member 63c that attaches the first actuation strand 38a to the second actuation strand 38b. Thus, the third connector member 63c can be configured as a splice 134c. The second attachment portion 133b can be woven or otherwise spliced through the attachment portion 133a as many times as desired so as to define the third connector member 63c at a first location that attaches the first anchor 22a to the second anchor 22b. In accordance with the illustrated embodiment, the attachment portion 133b is woven through the first attachment portion 133a along a direction from the first connector member 63a toward the second connector member, and thus also along a direction from the first anchor body 28a toward the second anchor body 28b. It should be appreciated, however, that the second attachment portion 133b can be woven through the first attachment portion 133a along a direction from the second connector 63b toward the first connector 63a, and thus along a direction from the second anchor body 28b toward the first anchor body 38a. The second attachment portion 133b can exit the first attachment portion 133a so as to define the second terminal portion 135b.

In accordance with the illustrated embodiment, the first actuation strand 38a, and in particular the first attachment portion 133a, is woven or otherwise spliced through the second actuation strand 38b, and in particular the second attachment portion 133b, so as to define the fourth connector member 63d that attaches the first actuation strand 38a to the second actuation strand 38b. Thus, the fourth connector member 63c can be configured as a splice 134d. The first attachment portion 133a can be woven or otherwise spliced through the second attachment portion 133b as many times as desired so as to define the fourth connector 63d at a first location that attaches the first anchor 22a to the second anchor 22b. In accordance with the illustrated embodiment, the first attachment portion 133a is woven through the second attachment portion 133b along a direction from the second connector member 63b toward the first connector member 63a, and thus also along a direction from the second anchor body 28b toward the first anchor body 28a. It should be appreciated, however, that the first attachment portion 133a can be woven through the second attachment portion 133b along a direction from the first connector 63a toward the second connector 63b, and thus along a direction from the first anchor body 28a toward the second anchor body 38b. The first attachment portion 133a can exit the second attachment portion 133b so as to define the first terminal portion 135a.

The first terminal portion 135a is spaced from the second terminal portion 135b. For instance, the second terminal portion 135b can be disposed closer to the first anchor body 28a than the first terminal portion 135a, and the first terminal portion 135a can be spaced closer to the second anchor body 28b than the second terminal portion 135b, though it should be appreciated that the first and second terminal portions 135a and 135b can be spaced in so as to define any suitable spatial relationship with respect to each other and the first and second anchor bodies 28a and 28b as desired. For instance, the anchor assembly 20 can further include a connector member that attaches the first and second terminal portions 135a and 135b together. For instance, the first and second terminal portions 135a and 135b could be tied so as to define a suitable knot such as the knot 66 (for instance, as illustrated with respect to first and second connector strands 59a and 59b in FIGS. 33A-C).

During operation, the first and second knots 66a-b can be in respective unlocked configurations such that application of the actuation force F to each of the first and second actuation portions 131a-b causes the respective first and second anchor bodies 28a-b to actuate from the first configuration to the expanded configuration. Next, a tensile locking force can be applied to the first and second attachment portions 133a-b so as to lock the first and second knots 66a-b in the manner described above with respect to FIGS. 29A-D.

In accordance with the illustrated embodiment, the approximation force AF is applied to the first and second terminal portions 135a-b of the first and second actuation strands 38a and 38b. When the approximation force AF is applied to the second terminal portion 135b, the second attachment portion 133b of the second actuation strand 38b translates through the first attachment portion 133a of the first actuation strand 38a, for instance at the splice defined by third connector member 63c. When the approximation force AF is applied to the first terminal portion 135a, the first attachment portion 133a of the first actuation strand 38a through the second attachment portion 133b of the second actuation strand 38b, for instance at the splice defined by the fourth connector member 63d. It should thus be appreciated that the third and fourth connector members 63c and 63d can define sliding members 47 and 47 that permit the first and second attachment portion 133a and 133b, and thus the first and second actuation strands 38a and 38b, b to translate relative to each other. The approximation force AF induces tension in the actuation strands 38a and 38b that can apply the locking force to the free portion 70b of the knot 66, thereby actuating the knot 66 to the locked configuration. Thus, the approximation force AF can define the locking force for the knot 66. Furthermore, the tension induced in the first and second actuation strands 38a and 38b biases at least one or both of the first and second anchors 22a and 22b toward the other, thereby approximating the gap 24c.

It should be appreciated that the tension induced in the first attachment portion 133a in response to application of the approximation force AF to the respective first terminal portion 135a can cause the first attachment portion 133a to apply a compressive force to the second attachment portion 133b at the third connector member 63c. The compressive force prevents the second attachment portion 133b from translating with respect to the first attachment portion 133a at the splice that defines the third connector member 63c. Thus, it should be appreciated that the third connector member 63c can further define a respective third locking member 64c. Similarly, the tension induced in the second attachment portion 133b in response to application of the approximation force AF to the respective second terminal portion 135b can cause the second attachment portion 133b to apply a compressive force to the first attachment portion 133a at the fourth connector member 63d. The compressive force prevents the first attachment portion 133a from translating with respect to the second attachment portion 133b at the splice that defines the fourth connector member 63d. Thus, it should be appreciated that the fourth connector member 63d can further define a respective fourth locking member 64d.

While each of the third and fourth connector members 63c and 63d is configured as a splice, whereby one of the first and second actuation strands 38a-b is spliced through the other of the first and second actuation strands 38a-b, it should be appreciated that the third and fourth connector members 63c and 63d can be configured as any suitable connector member of the type described herein or any suitable alternative connector member that is configured to attach the first actuation strand 38a to the second actuation strand 38b. For instance, at least one or both of the third and fourth connector members 63c and 63d can be configured as respective knots, such as the knots 66 of the type described above, or any suitable alternative locking member.

Similarly, while each of the first and second connector members 63a and 63a is configured as a knot 66, whereby one of the first and second actuation strands 38a-b is tied to the other of the first and second actuation strands 38a-b, it should be appreciated that the first and second connector members 63a and 63b can be configured as any suitable connector member of the type described herein or any suitable alternative connector member that is configured to attach the first and second actuation portions 131a-b to the respective first and second attachment portions 133a-b. For instance, at least one or both of the first and second connector members 63a and 63b can be configured as respective splices, such as the splices 134c-d of the type described herein, or any suitable alternative locking member.

Figure 31A:
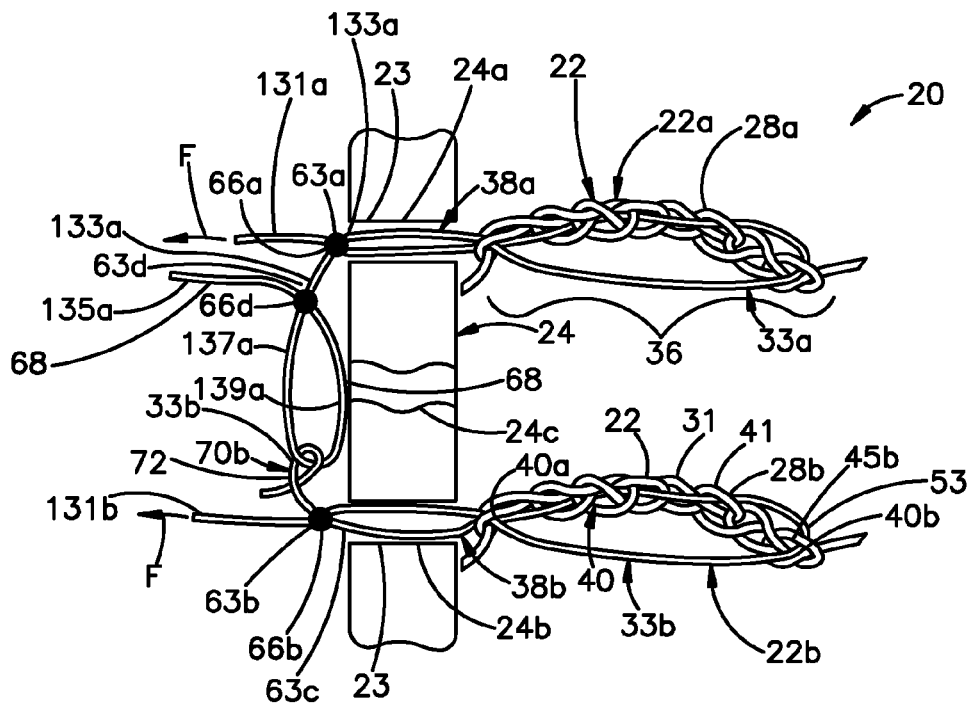
FIG. 31A is a side elevation view of an anchor assembly constructed in accordance with another embodiment, including first and second anchors shown in respective first configurations and implanted in an anatomical structure.
Figure 31B:
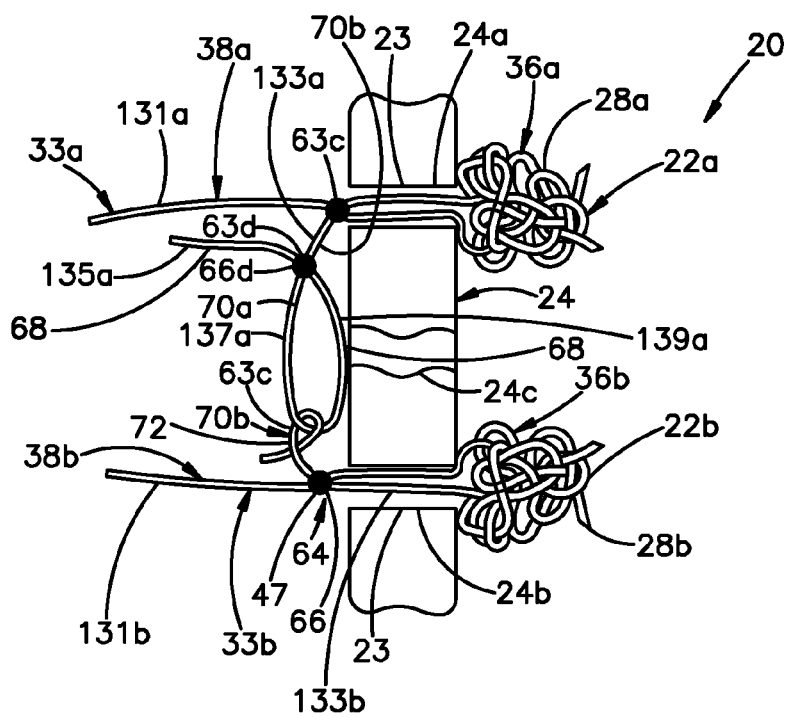
FIG. 31B is a side elevation view of the anchor assembly illustrated in FIG. 31A, showing the first and second anchors in respective expanded configurations.

Referring now to FIGS. 31A-B, the anchor assembly 20 can include the first and second connector members 63a and 63b configured as first and second knots 66a and 66b that attach the actuation portions 131a-b to the corresponding attachment portions 133a-b as described above with respect to FIGS. 30A-C. Furthermore, as described above with respect to FIGS. 30A-C, the third and fourth connector members 63c and 63d can be configured as any suitable connector of the type described herein or any suitable alternative connector. For instance, the third connector member 63c can be defined by the second actuation strand 38b, and can be configured as an eyelet, for instance the eyelet 72 of the type described above with respect to FIG. 2H, though it should be appreciated that the eyelet can be alternatively constructed in accordance with any embodiment described herein or any suitable alternative embodiment. Thus, the eyelet of the third connector member 63c can be defined by the actuation strand 38b, the anchor body 28b, or an attachment member such as the attachment member 82 that is configured to be attached to the anchor body 28b (see FIGS. 6A-B). In accordance with the illustrated embodiment, the second attachment portion 133b can extend from the second connector member 63b so as to define the free portion 70b of the second knot 66b in the manner described above. The second attachment portion 133b can further define the eyelet 72.

The third connector member 63c is thus configured to attach the second actuation strand 38b to the first actuation strand 38a. For instance, the first actuation strand 38a, and in particular the first end 137a of the first attachment portion 133a as illustrated, can extend from the first connector member 63a, and thus from the first anchor body 28a, in a first direction toward the third connector member 63c, and thus toward the second anchor 22b. The first attachment portion 133a can extend through the eyelet 72, such that the second end 139a of the first attachment portion 133a extends back toward the first connector member 63a, and thus toward the first anchor body 28a along a second direction that is substantially opposite the first direction so as to attach the first attachment portion 133a to the eyelet 72, and thus to the second attachment portion 133b. Because the first attachment portion 133a, and thus the first actuation strand 38a, is slidable with respect to the second attachment portion 133b, and thus the second actuation strand 38b, through the eyelet 72, the third connector member 63c can be said to define a sliding member 47.

The fourth connector member 63d can be configured as a knot, such as a knot 66d of the type described above that can be defined by the actuator strand 38a, such as the first attachment portion 133a, and in particular the first and second ends 137a and 137b of the first attachment portion 133a. Thus, the fourth connector member 63d can define both a sliding member 47 and a locking member 64 that attaches the actuation strand 38a to itself so as to attach the first and second actuation strands 38a and 38b. The knot 66d can include a post end 68 that can be defined by the second end 139a of the first attachment portion 133a, and a free end 70 including a static portion 70a that is defined by the first end 137a of the first attachment portion 133a, and a free portion 70b that is defined by the attachment portion 133a that is disposed between the first connector member 63a and the fourth connector member 63d. The first terminal portion 135a of the first actuation strand also therefore extends from the knot 66d and defines a portion of the post end 68.

Thus, during operation, the actuation force F can be applied to the actuation portions 131a and 131b of the first and second actuation strands 38a and 38b when the respective knots 66a and 66b are in their unlocked configurations, such that the actuation portions 131a and 131b are slidable through the knots 66a and 66b with respect to the attachment portions 133a and 133b, respectively. Accordingly, when the actuation force F is applied to the actuation portions 131a and 131b of the first and second actuation strands 38a and 38b, respectively, the corresponding anchor bodies 28a and 28b actuate from their first configurations to their expanded configurations in the manner described above.

Next, the locking forces can be applied to the free portions 70b of the knots 66a and 66b so as to actuate the knots 66a and 66b to their locking configurations and secure the anchor bodies 28a and 28b in their expanded configuration. For instance, the locking forces can be applied directly to the free portions 70b of the knots 66a and 66b. Alternatively, the approximation force AF can be applied to the first terminal portion 135a of the first actuation strand 38a so as to induce tension in the actuation strands 38a and 38b, thereby causing the locking forces to be applied to the free portions 70b of the first and second knots 66a and 66b.

For instance, the knot 66d can be configured in an unlocked configuration as described above, such that the second end 139a of the first attachment portion 133a is translatable through the knot 66d with respect to the first end 137a of the first attachment portion 133a. Thus, the approximation force AF can be applied to the first terminal portion 135a of the first actuation strand 38a so as to induce tension in the actuation strands 38a and 38b, which apply respective biasing forces to the first and second anchor bodies 28a and 28b that cause the anchor bodies 28a and 28b to translate toward each other, thereby approximating the gap 24c. Furthermore, once the gap 24c has approximated, continuing force applied to the terminal portion 135a can cause sufficient tension to accumulate in the actuation strands 38a and 38b such that the respective free portions 70b of the knots 66a, 66b, and 66d to apply locking forces to the knots 66a, 66b, and 66d, thereby actuating the knots 66a, 66b, and 66d to their locked configuration, thereby maintaining the gap 24c in the approximated state.

Figure 31C:
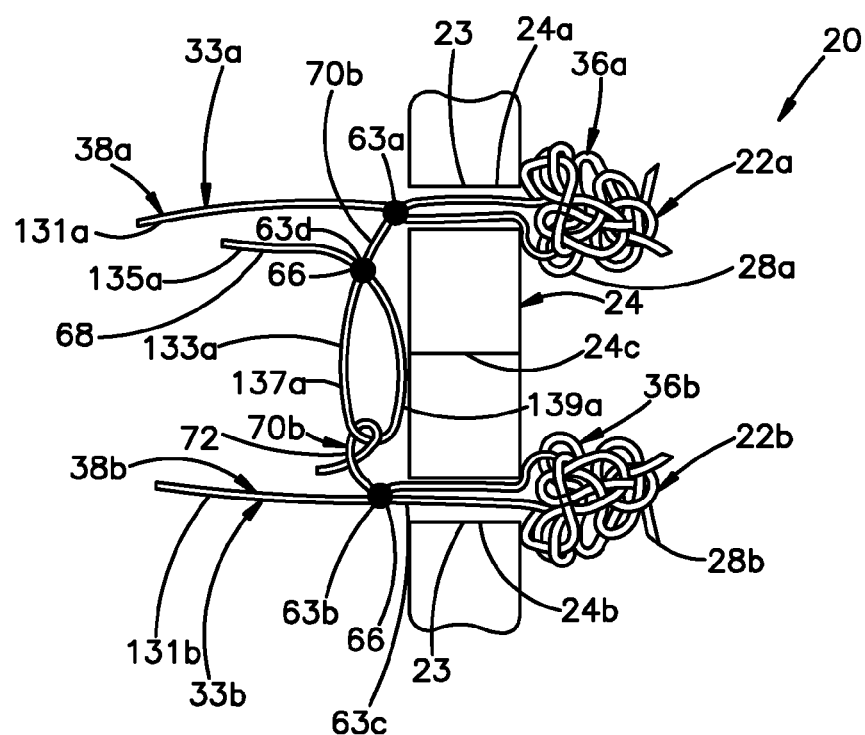
FIG. 31C is a side elevation view of the anchor assembly illustrated in FIG. 31B, showing the first and second anchors in an approximated configuration.

Referring now to FIGS. 32A-B, the anchor assembly 20 can include the first and second connector members 63a and 63b configured as first and second knots 66a and 66b that attach the actuation portions 131a-b to the corresponding attachment portions 133a-b as described above with respect to FIGS. 31A-C. Furthermore, as described above with respect to FIGS. 31A-C, the third and fourth connector members 63c and 63d can be configured as any suitable connector of the type described herein or any suitable alternative connector.

For instance, the third connector member 63c can be defined by the second actuation strand 38b, and can be configured as an eyelet, for instance the eyelet 72 of the type described above with respect to FIG. 2H, though it should be appreciated that the eyelet can be alternatively constructed in accordance with any embodiment described herein or any suitable alternative embodiment, as described above with respect to FIGS. 31A-C. Thus, the eyelet of the third connector member 63c can be defined by the actuation strand 38b, the anchor body 28b, or an attachment member such as the attachment member 82 that is configured to be attached to the anchor body 28b (see FIGS. 6A-B). In accordance with the illustrated embodiment, the second attachment portion 133b can extend from the second connector member 63b so as to define the free portion 70b of the second knot 66b in the manner described above. The second attachment portion 133b can further define the eyelet 72. The third connector member 63c is thus configured to attach the second actuation strand 38b to the first actuation strand 38a, directly as described above, or indirectly as illustrated in FIGS. 32A-C.

Furthermore, the fourth connector member 63d can be defined by the first actuation strand 38a, and can also be configured as an eyelet, for instance the eyelet 72 of the type described above with respect to FIG. 2H, though it should be appreciated that the eyelet can be alternatively constructed in accordance with any embodiment described herein or any suitable alternative embodiment, as described above with respect to FIGS. 31A-C. Thus, the eyelet of the fourth connector member 63d can be defined by the actuation strand 38a, the first anchor body 28a, or an attachment member such as the attachment member 82 (see FIGS. 28A-C) that is configured to be attached to the anchor body 28a. In accordance with the illustrated embodiment, the first attachment portion 133a can extend from the first connector member 63a so as to define the free portion 70b of the first knot 66a in the manner described above. The first attachment portion 133a can further define the eyelet 72. The fourth connector member 63d is thus configured to attach the second actuation strand 38b to the first actuation strand 38a, directly as described above, or indirectly as illustrated in FIGS. 32A-C.

In particular, the anchor assembly 20 can include at least one connector member, such as a fifth connector member 63e that is configured as an auxiliary connector member 77, such as a connector strand 59 that is attached between the first and second actuation strands 38a and 38b. The connector strand 59 can be provided as a suture or any alternatively constructed strand as desired. Thus, anchor assembly 20 can include at least one connector member, such as a sixth connector member 63f that can be configured to attach and secure the connector strand 59 to the first and second actuation strands 38a and 38b, thereby attaching and securing the first and second actuation strands 38a and 38b to each other. In accordance with the illustrated embodiment, the sixth connector member 63f attaches a first portion 120 of the connector strand 59 to a second portion 121 of the connector strand 59 so as to attach the first and second actuation strands 38a and 38b together, indirectly via the connector strand 59. Thus, unless otherwise indicated, it should be appreciated that any of the connector members 63 described herein that can attach the first actuation strand 38a to the second actuation strand 38b can also attach the first portion 120 of the connector strand 59 to the second portion 121 of the connector strand. Alternatively or additionally, the anchor assembly 20 can include a connector that attaches the first portion 120 of the connector strand 59 to the first anchor body 28a, and a second connector member that attaches the second portion 121 of the connector strand 59 to the second anchor body 28b. For instance the eyelet 72 of the first actuation strand 38a can attach the connector strand 59 to the first anchor body 28a, and the eyelet 72 of the second actuation strand 38b can attach the connector strand 59 to the second anchor body 28b.

In accordance with the illustrated embodiment, the first portion 120 of the connector strand 59 extends through the eyelet 72 of the first actuation strand 38a, and the second portion 121 of the connector strand extends through the eyelet 72 of the second actuation strand 38b, such that the first and second portions 120 and 121 are slidably attached to the respective eyelets 72, which thus define sliding members 47. The sixth connector 63e attaches first portion 120 of the connector strand 59 to the second portion 121 of the connector strand 59, thereby attaching the first actuation strand 38a to the second actuation strand, and thus attaching the first anchor 22a to the second anchor 22a.

It should be appreciated that the sixth connector member 63f can be configured as any suitable connector member of the type described herein or any suitable alternative connector member that is configured to attach the first portion 120 of the connector strand 59 to the second portion 121 of the connector strand 59. In accordance with the illustrated embodiment, the sixth connector member 63f includes a knot, such as a knot 66f of the type described above. In particular, one of the first and second portions of the connector strand 59, for instance the first portion 120, can define the post end 68 of the knot 66f, and the other of the first and second portions of the connector strand 59 can define the free end 70 of the knot 66f. Thus, the connector strand 59 and the connector 63f, which can be integral with the connector strand 59 or separate from and attached to the connector strand 59, can define a closed loop 204. The first portion first portion 120 is translatable through the knot 66f, relative to the second portion 121 so as to decrease the size of the loop 204 when the knot 66f is in the unlocked configuration.

Thus, during operation, the actuation force F can be applied to the actuation portions 131a and 131b of the first and second actuation strands 38a and 38b when the respective knots 66a and 66b are in their unlocked configurations, such that the actuation portions 131a and 131b are slidable through the knots 66a and 66b with respect to the attachment portions 133a and 133b, respectively. Accordingly, when the actuation force F is applied to the actuation portions 131a and 131b of the first and second actuation strands 38a and 38b, respectively, the corresponding anchor bodies 28a and 28b actuate from their first configurations to their expanded configurations in the manner described above.

Next, the locking forces can be applied to the free portions 70b of the knots 66a and 66b so as to actuate the knots 66a and 66b to their locking configurations and secure the anchor bodies 28a and 28b in their expanded configuration. For instance, the locking forces can be applied directly to the free portions 70b of the knots 66a and 66b. Alternatively, the approximation force AF can be applied to the actuation strands 38a and 38b, thereby causing the locking forces to be applied to the free portions 70b of the first and second knots 66a and 66b.

For instance, the knot 66f can be configured in an unlocked configuration as described above, such that the first portion 120 of the connector strand 59 is translatable through the knot 66f with respect to the second portion 121 of the connector strand, thereby decreasing the size of the loop 204 and inducing tension in the loop 204. Thus, the connector strand 59 applies the approximation force AF to the first and second actuation strands 38a-b, and in particular to the attachment portions 133a and 133b of the first and second actuation strands 38a-b. The approximation force AF can thus cause the first and second attachment portions 133a and 133b, which can define the free portions 70b of the knots 66a and 66b, to apply the tensile locking force to the knots 66a-b, thereby actuating the knots 66a-b to their respective locked configurations. The approximation force AF further biases the first and second actuation strands 38a-b, and thus the first and second anchor bodies 28a and 28b, to move toward each other, thereby approximating the gap 24c. Furthermore, once the gap 24c has approximated, continuing force applied to the first portion 120 of the connector strand 59 can cause sufficient tension in the loop 204 that causes the first and second anchor bodies 28a and 28b to apply a compressive force to the anatomical structure 24 at a location between the first and second anchor bodies 28a and 28b. Thus, the anchor bodies 28a and 28b apply a compressive force to the gap 24c, which maintains the gap 24c in its approximated state. The tensile locking force can be applied to the second portion 121 of the connector strand 59 so as to actuate the knot 66f to its locked configuration, thereby fixing the size of the loop 204 and maintaining the biasing force against the anchors 22a and 22b.

Figure 33A:
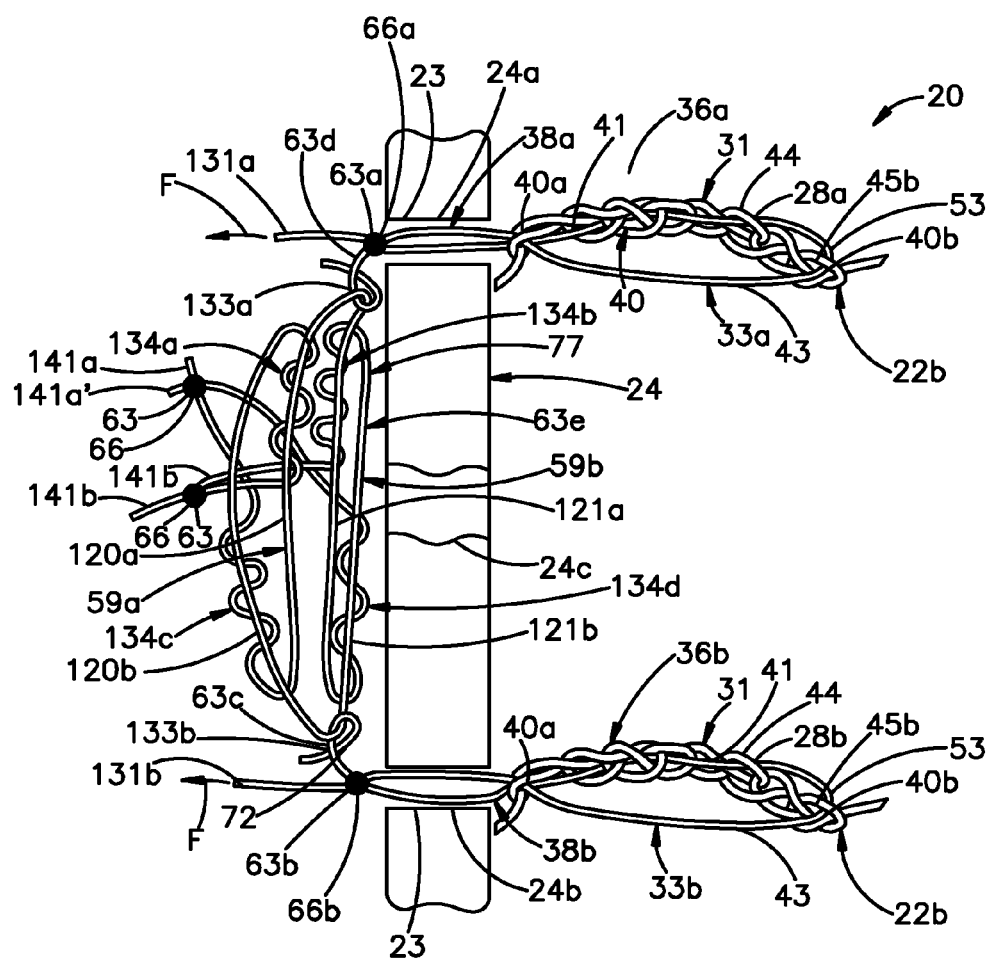
FIG. 33A is a side elevation view of an anchor assembly constructed in accordance with another embodiment, including first and second anchors shown in respective first configurations and implanted in an anatomical structure.
Figure 33B:
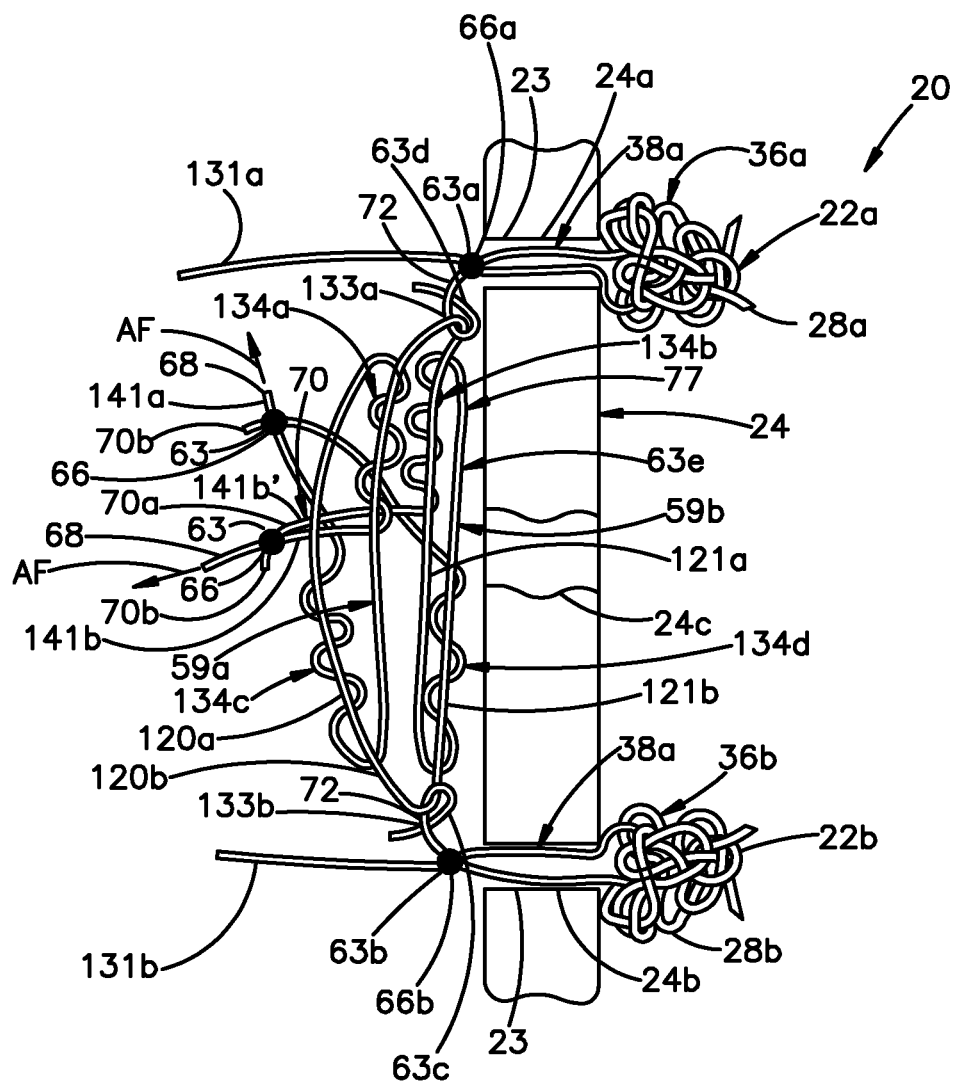
FIG. 33B is a side elevation view of the anchor assembly illustrated in FIG. 33A, showing the first and second anchors in respective expanded configurations.
Figure 33C:
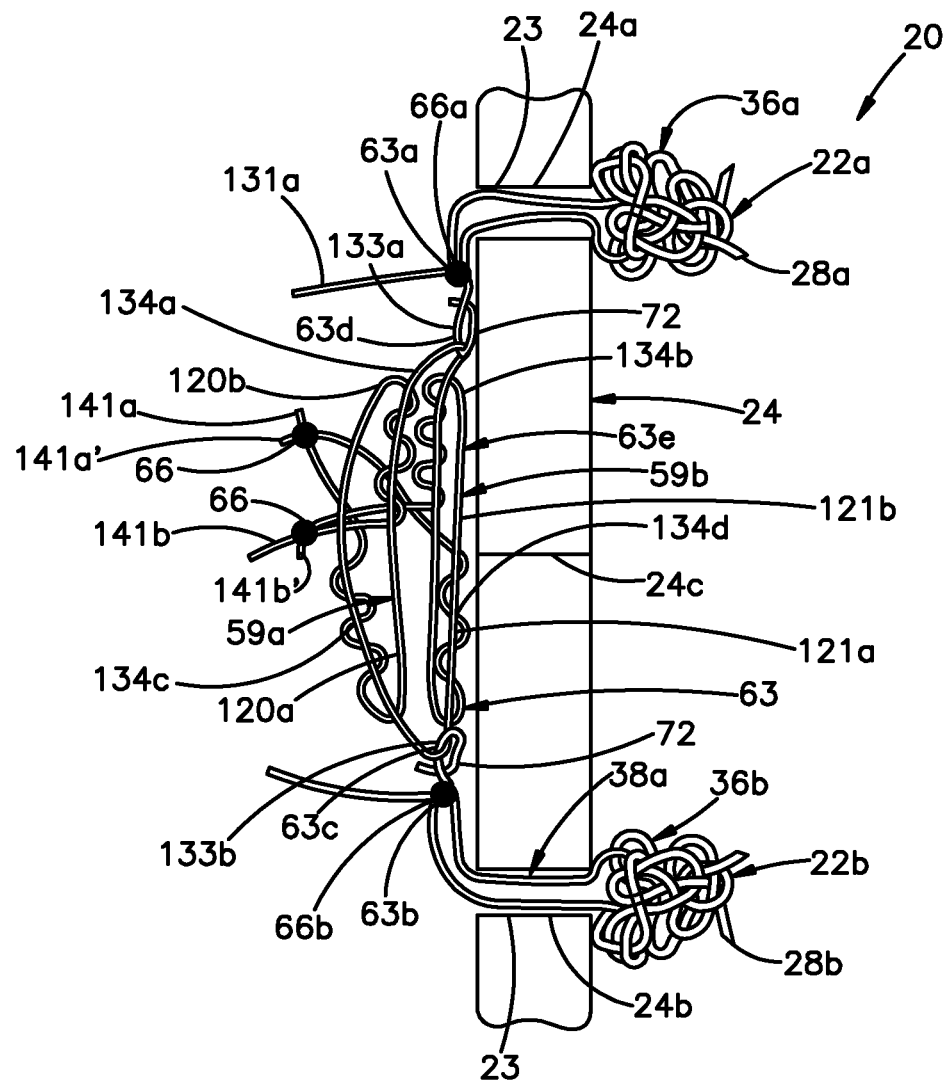
FIG. 33C is a side elevation view of the anchor assembly illustrated in FIG. 33B, showing the first and second anchors in an approximated configuration.

Referring now to FIGS. 33A-B, the anchor assembly 20 can include the first and second connector members 63a and 63b configured as first and second knots 66a and 66b that attach the actuation portions 131a-b to the corresponding attachment portions 133a-b as described above with respect to FIGS. 32A-C. Furthermore, as described above, the third and fourth connector members 63c-d can be defined by the second actuation strand 38b, and can be configured as an eyelet, for instance the eyelet 72 of the type described above with respect to FIG. 2H, though it should be appreciated that the eyelet can be alternatively constructed in accordance with any embodiment described herein or any suitable alternative embodiment In particular, the anchor assembly 20 can include at least one connector member that is attached between the first and second actuation strands 38a and 38b. For instance, the at least one connector can be configured as a fifth connector member 63e can include at least one connector strand, such as a first connector strand 59a and a second connector strand 59b that are attached to each other and further attached between the first and second actuation strands 38a and 38b. Thus, it can be said that the anchor assembly 20 can include at least one connector strand 59 that is configured to be attached, directly or indirectly, to at least one of or both of the first and second actuation strands. For instance, in accordance with the illustrated embodiment, the first connector strand 59a is directly attached to the first actuation strand 38a and the second connector strand 59b is directly attached to the second actuation strand 38b. In accordance with the illustrated embodiment, the first and second connector strands 59a-b are attached to the respective eyelets 72 of the first and second actuation strands 38a-b, which define sliding members 47 that allow the first and actuation strands 59a-b to slide relative to the respective actuation strands 38a-b as described above. Thus, the first connector strand 59a is indirectly attached to the second actuation strand 38b via the second connector strand 59b, and the second connector strand 59b is indirectly attached to the second actuation strand 38b via the second connector strand 59a. While the connector members 63c and 63d are integral with the respective actuation strands, it should be appreciated that the connector members 63c and 63d can alternatively or additionally be integral with the respective connector strands 59a and 59b. It should be further appreciated that the anchor assembly 20 can include an auxiliary connector member 77 that is separate from and attached between the first connector strand 59a and the first actuation strand 38a, and an auxiliary connector member 77 that is separate from and attached between the second connector strand 59b and the second actuation strand 38b.

Thus, the anchor assembly 20 can include at least strand that is configured to attach, directly or indirectly, the first and second anchors 22a and 22b, including the respective first and anchor bodies 28a and 28b, including the respective first and second expandable portions 36a and 36b, to each other across the gap 24c. The at least one strand can be the actuation strand of at least one or both of the anchors 22a and 22b, or can be a strand that is separate from the actuation strands 38a and 38b. For instance, it should be appreciated in some embodiments that the actuation strands 38a and 38b can be removed after the anchor bodies 28a and 28b have actuated from their first configurations to their expanded configurations, and at least one connector member can be attached, directly or indirectly, to at least one or both of the first and second anchor bodies 28a and 28b so as to attach the anchor bodies 28a and 28b across the gap 24c.

In accordance with the illustrated embodiment, the anchor assembly 20 can include at least one such as a plurality of connector members 63 that can attach portions of the first and second connector strands 59a and 59b to each other. In accordance with the illustrated embodiment, the first connector strand 59a defines a first portion 120a and a second portion 121a, and the second connector strand 59b defines a first portion 120b and a second portion 121b. The at least one connector member can attach at least one or both of the first and second portions 120a and 121a of the first connector strand 59a to at least one or both of the first and second portions 120b and 121b of the second connector strand 59b, thereby attaching the first and second actuation strands 38a and 38b together, indirectly via the connector strands 59a-b.

In accordance with the illustrated embodiment, the first connector strand 59a is folded through and thus extends through the eyelet 72 of the first actuation strand 38a so as to define the first and second portions 120a and 121a of the first connector strand 59a that are spaced from each other, such that the eyelet 72 of the first actuation strand 38a separates the first and second portions 120a and 121a. Likewise, the second connector strand 59b is folded through and thus extends through the eyelet 72 of the second actuation strand 38b so as to define the first and second portions 120b and 121b of the second connector strand 59b that are spaced from each other, such that the eyelet 72 of the second actuation strand 38b separates the first and second portions 120b and 121b. The first and second portions 120a and 121a of the first connector strand 59a extends toward the second anchor 22b, and the first and second portions 120b and 121b of the second actuation strand 38b extends toward the first anchor 22a. It should be appreciated that either or both of the connector strands 59a and 59b can be integral with the respective actuation strands 38a and 38b, and can extend through an eyelet of an anchor, such as the eyelet 90 or any alternatively constructed eyelet as described herein.

The first and second connector strands 59a-b can be attached to each other at one or more locations via any suitable connectors of the type described herein. For instance, the first connector strand 59b can be woven through an other strand, such as the second connector strand 59b, so as to attach the first anchor 22a to the second anchor 22b. It should be appreciated that, for instance in embodiments wherein the second actuation strand 38b does not define an eyelet, the first connector strand 59a can be woven through the second actuation strand 38b so as to attach the first and second anchors 22a-b. In accordance with the illustrated embodiment, the first portion 120b of the second connector strand 59b can be woven or otherwise spliced through the first portion 120a of the first connector strand 59a at two different locations so as to define respective first and second splices 134a-b, and the first portion 120a of the first connector strand 59a can be woven or otherwise spliced through the first portion 120b of the second connector strand 59b at two different locations so as to define respective third and fourth splices 134c-d. Thus, it should be appreciated that the anchor assembly 20 can include at least one such as a plurality of connector strands that can be attached to each other at one or more locations. For instance, each of the plurality of connector strands can be attached to each other at one or more splices, such as splices 134a-d.

In accordance with the illustrated embodiment, the first splice 134a can be defined by the first portion 120b of the second connector strand 59b and the first portion 120a of the first connector strand 59a. In particular, the first portion 120b of the second connector strand 59b can be woven through the first portion 120a of the first connector strand 59a as many times as desired along a direction, for instance away from the corresponding first anchor body 28a and toward the second anchor body 28b so as to define the first splice 134a that attaches the first and second connector strands 59a-b, and thus also attaches the first and second anchors 22a-b. While the first portion 120b of the second connector strand 59b can be woven through the first portion 120a of the first connector strand 59a as illustrated, it should be appreciated that the a section of the first portion 120b of the second connector strand 59b can extend within the first portion 120a of the first connector strand 59a along the direction of extension of the first portion 120a, such that the first portion 120a circumscribes the section of the first portion 120b along the length of the section, for instance as described above with respect to FIGS. 19G-H. The first portion 120b of the second connector strand 59b exits the first portion 120a of the first connector strand 59a so as to define a first terminal portion 141b of the second connector strand 59b.

The second splice 134b can be defined by the second portion 121b of the second connector strand 59b and the second portion 121a of the first connector strand 59a. For instance, the second portion 121b of the second connector strand 59b can be woven through the second portion 121a of the first connector strand 59a as many times as desired along a direction, for instance away from the corresponding first anchor body 28a and toward the second anchor body 28b so as to define the second splice 134b that attaches the first and second connector strands 59a-b, and thus also attaches the first and second anchors 22a-b. While the second portion 121b of the second connector strand 59b can be woven through the second portion 121a of the first connector strand 59a as illustrated, it should be appreciated that the a section of the second portion 121b of the second connector strand 59b can extend within the second portion 121a of the first connector strand 59a along the direction of extension of the second portion 121a, such that the second portion 121a circumscribes the section of the second portion 121b along the length of the section, for instance as described above with respect to FIGS. 19G-H. The second portion 121b of the second connector strand 59b exists the second portion 121a of the first connector strand 59a so as to define a second terminal portion 141b' of the second connector strand 59b.

The first and second terminal portions 141b and 141b' can define free ends that are separate and spaced from each other, that is detached from each other, or can alternatively be attached to each other, either directly or indirectly via any suitable connector member 63 of the type described herein or any suitable alternatively constructed connector member 63. For instance, in accordance with the illustrated embodiment, the anchor assembly 20 can define a knot, such as the knot 66 of the type described above, that is defined by the first and second terminal portions 141b and 141b'. For instance, one of the terminal portions such as the first terminal portion 141b can define the post end 68 of the knot 66, and the other of the ends such as the second terminal portion 141b' can define the free end of the knot 66. Thus, when the knot 66 is in the unlocked configuration, the first terminal portion 141b is translatable with respect to the second terminal portion 141b' through the knot 66. The locking force can be applied to the free portion 70b, defined by the second terminal portion 141b', in the manner described above so as to actuate the knot 66 to its locked configuration such that the first terminal portion 141b is translatably fixed with respect to the second terminal portion 141b' through the knot 66.

The third splice 134c can be defined by the first portion 120a of the first connector strand 59a and the first portion 120b of the second connector strand 59b. In particular, the first portion 120a of the first connector strand 59a can be woven through the first portion 120b of the second connector strand 59b as many times as desired along a direction, for instance away from the corresponding second anchor body 28b and toward the first anchor body 28a so as to define the third splice 134c that attaches the first and second connector strands 59a-b, and thus also attaches the first and second anchors 22a-b. While the first portion 120a of the first connector strand 59a can be woven through the first portion 120b of the second connector strand 59b as illustrated, it should be appreciated that the a section of the first portion 120a of the first connector strand 59a can extend within the first portion 120b of the second connector strand 59b along the direction of extension of the first portion 120b, such that the first portion 120b circumscribes the section of the first portion 120a along the length of the section, for instance as described above with respect to FIGS. 19G-H. The first portion 120a of the first connector strand 59a exits the first portion 120b of the second connector strand 59b so as to define a first terminal portion 141a of the first connector strand 59a.

The fourth splice 134d can be defined by the second portion 121a of the first connector strand 59a and the second portion 121b of the second connector strand 59b. For instance, the second portion 121a of the first connector strand 59a can be woven through the second portion 121b of the second connector strand 59b as many times as desired along a direction, for instance away from the corresponding second anchor body 28b and toward the first anchor body 28a so as to define the fourth splice 134d that attaches the first and second connector strands 59a-b, and thus also attaches the first and second anchors 22a-b. While the second portion 121a of the first connector strand 59a can be woven through the second portion 121b of the second connector strand 59b as illustrated, it should be appreciated that the a section of the second portion 121a of the first connector strand 59a can extend within the second portion 121b of the second connector strand 59b along the direction of extension of the second portion 121b, such that the second portion 121b circumscribes the section of the second portion 121a along the length of the section, for instance as described above with respect to FIGS. 19G-H. The second portion 121a of the first connector strand 59a exists the second portion 121b of the second connector strand 59b so as to define a second terminal portion 141a' of the first connector strand 59a.

The first and second terminal portions 141a and 141a' can define free ends that are spaced and separate from each other, that is detached from each other, or can alternatively be attached to each other, either directly or indirectly via any suitable connector member 63 of the type described herein or any suitable alternatively constructed connector member 63. For instance, in accordance with the illustrated embodiment, the anchor assembly 20 can define a knot, such as the knot 66 of the type described above, that is defined by the first and second terminal portions 141a and 141a'. For instance, one of the terminal portions such as the first terminal portion 141a can define the post end 68 of the knot 66, and the other of the ends such as the second terminal portion 141a' can define the free end 70 of the knot 66. Thus, when the knot 66 is in the unlocked configuration, the first terminal portion 141b is translatable with respect to the second terminal portion 141a' through the knot 66. The locking force can be applied to the free portion 70b, defined by the second terminal portion 141a', in the manner described above so as to actuate the knot 66 to its locked configuration such that the first terminal portion 141a is translatably fixed with respect to the second terminal portion 141a' through the knot 66.

During operation, the first and second actuation strands 38a and 38b can each receive a respective actuation force F that causes the anchor bodies 28a and 28b to actuate from their respective first configurations to their respective expanded configurations when the knots 66a and 66b are in their respective unlocked configurations. The actuation force F can be applied directly to the first and second actuation strands 38a and 38b at the respective first and second actuation portions 131a and 131b as illustrated, or can be applied to the first and second actuation strand 38a and 38b at a location upstream of the respective first and second connector members 63a and 63b, respectively. The knots 66a-b can then be locked by applying a tensile locking force to the respective attachment portions 133a-b of the actuation strands 38. Alternatively, the tensile locking force can be applied by the approximation force AF, as will now be described.

For instance, once the anchor bodies 28a and 28b have actuated to their respective expanded configurations, each of the first and second terminal portions 141a and 141b of the first and second connector strands 59a and 59b, respectively, can each receive an approximation force AF that induces tension in the connector strands 59a and 59b, thereby applying the approximation force AF to the actuation strands 38a and 38b and biasing at least one or both of the anchors 22a-b, and thus the respective anchor bodies 28a-b toward the other to a biased position so as to approximate the gap 24c. It should be appreciated that the tension induced in the connector strands 59a and 59b further places the eyelet 72 in tension. Because the eyelet 72 is defined by the respective attachment portions 133a-b, the tension induced in the eyelet 72 creates a tensile force against the respective knots 66a-b that actuate the knots 66a-b to their locking configurations.

Furthermore, because the first and second connector strands 59a-b are placed under tension in response to application of the approximation forces AF, the first connector strand 59a can apply a compressive force to the second connector strand 59b, for instance at the first and second splices 134a-b. In particular, the first portion 120a of the first connector strand 59a can apply a compressive force to the first portion 120b of the second connector strand 59b at the first splice 134a, and the second portion 121a of the first connector strand 59a can apply a compressive force to the second portion 121b of the second connector strand 59b at the second splice 134b. The compressive forces applied by the first connector strand 59a to the second connector strand 59b can reduce or prevent translation of the second connector strand 59b with respect to the first connector strand 59a at the respective splices 134a-b.

Additionally, the second connector strand 59b can apply a compressive force to the first connector strand 59a, for instance at the third and fourth splices 134c-d. In particular, the first portion 120b of the second connector strand 59b can apply a compressive force to the first portion 120a of the first connector strand 59a at the third splice 134c, and the second portion 121b of the second connector strand 59b can apply a compressive force to the second portion 121a of the first connector strand 59a at the fourth splice 134a. The compressive forces applied by the second connector strand 59b to the first connector strand 59a can reduce or prevent translation of the first connector strand 59a with respect to the second connector strand 59b at the respective splices 134c-d.

Once the gap 24c has been approximated, the knot 66 that attaches the respective first and second terminal portions 141a and 141a' of the first connector strand 59a can be actuated to its locked configuration, whereby the first and second portions 120a and 121a are prevented from translating relative to each other through the knot 66. Likewise, the knot 66 that attaches the respective first and second terminal portions 141b and 141b' of the second connector strand 59b can be actuated to its locked configuration, whereby the first and second portions 120b and 121b are prevented from translating relative to each other through the knot 66.

While the anchor assembly 20 has been described as including at least one anchor that can include an eyelet that attaches to a second anchor across a defect via at least one integral connector member, it should be appreciated that the anchor assembly can alternatively or additionally include an auxiliary connector member of any type described herein so as to attach the eyelet of one anchor to a second anchor across an anatomical defect.

Figure 34A:
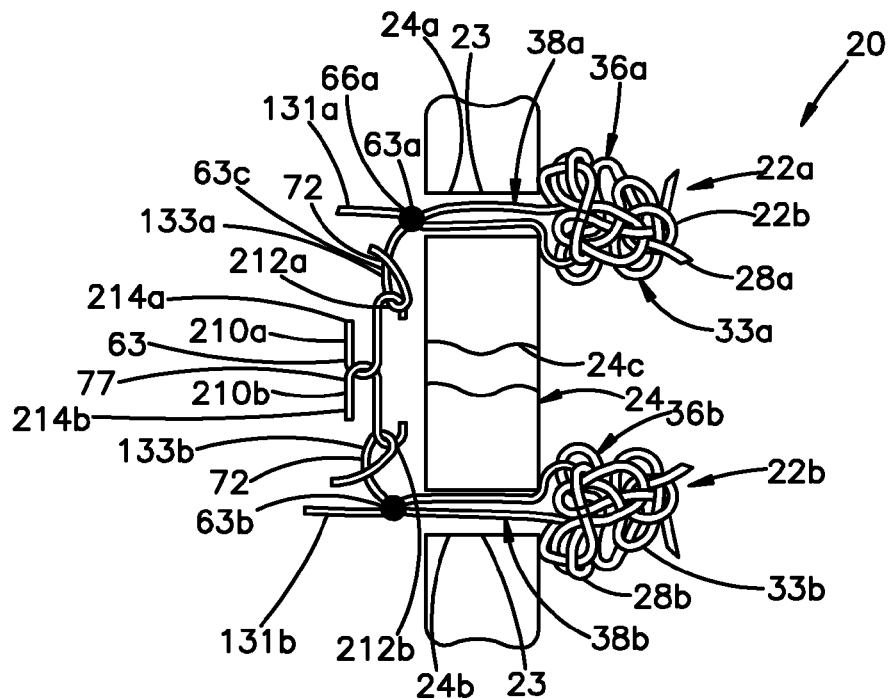
FIG. 34A is a side elevation view of an anchor assembly constructed in accordance with another embodiment, including first and second anchors shown in respective expanded configurations and implanted in an anatomical structure.
Figure 34B:
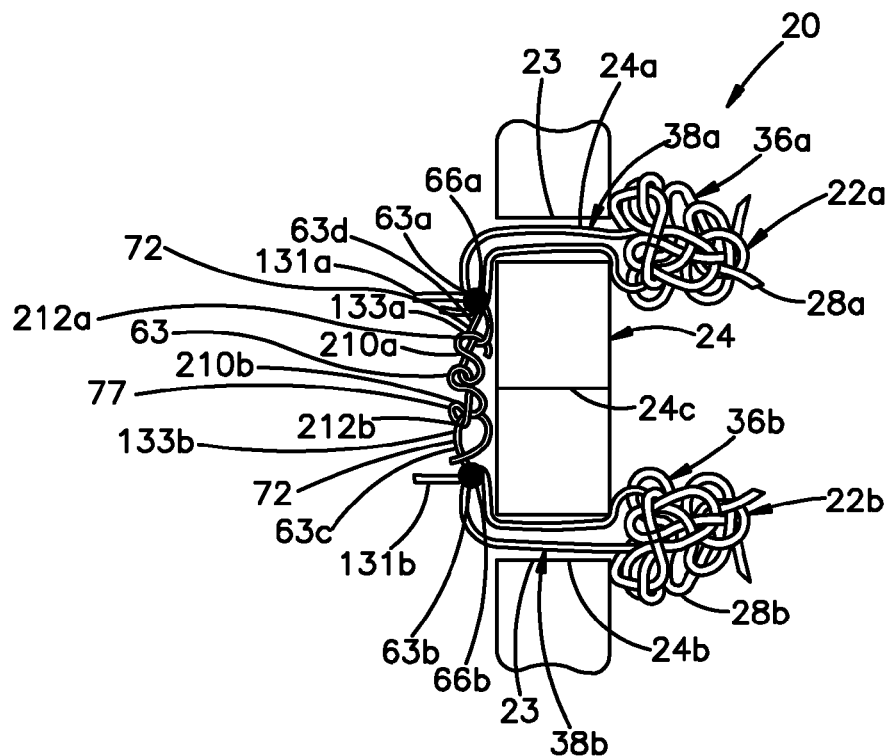
FIG. 34B is a side elevation view of the anchor assembly illustrated in FIG. 34A, showing the first and second anchors in an approximated configuration.

For instance, referring to FIGS. 34A-B, at least one or both of the first and second anchors 22a and 22b can include any suitable eyelet of the type described herein or any alternatively constructed eyelet, such as the eyelet 72 in accordance with the illustrated embodiment. The anchor assembly 10 can further include an auxiliary connector member 77 that attaches the first anchor 22a to the second anchor 22b. For instance, the auxiliary connector member 77 can be configured as at least one hook such as a pair of hooks 210a and 210b that attaches the first anchor 22a to the second anchor 22b. In accordance with one embodiment, the first hook 210a can define a corresponding first attachment end 212a and a second engagement end 214a, and the second hook 210b can define a second attachment end 212b and a second engagement end 214b. The first and second attachment ends 212a and 212b can be attached to the respective actuation strands 38a and 38b, such as the eyelets 72 defined by the first and second actuation strands 38a and 38b. In accordance with one embodiment, attachment ends 212a-b can define eyelets, and the respective actuation strands 38a-b, for instance the attachment portions 131a-b, can be fed through the first and second attachment ends 212a-b during construction of the respective eyelets 72. Alternatively, the first and second attachment ends 212a and 212b can be attached, for instance clipped onto, adhesively attached, or otherwise attached, to the preformed eyelets 72.

The engagement ends 214a-b are configured to mate with each other so as to attach the first hook 210a to the second hook 210b, thereby also attaching the first anchor 22a to the second anchor 22b, for instance after the anchors 22a and 22b have been actuated to their expanded configurations. In accordance with one embodiment, the hooks 210a and 210b can be made from a shape memory material, such as Nitinol, such that one the hooks 210a and 210b mate, the hooks 210a and 210b revert to a shape that is different than the shape of the hooks 210a and 210b when are mated. Thus, the hooks 210a-b can define a first shape when mated, and second shape that is different than the first shape after the hooks 210a-b are mated.

For instance, the hooks 210a and 210b can lay substantially flat across the anatomical structure 24. Alternatively, the hooks 210a and 210b can maintain their shape after they are mated with each other. The hooks 210a-b can define a sufficient length extending between the anchors 22a-b such that the hooks 210a-b apply approximation forces to the actuation strands 38a-b once they are mated that biases at least one or both of the anchor bodies 28a and 28b toward the other so as to approximate the gap 24c. Alternatively or additionally, for instance if the hooks 210a-b are made from a shape-memory material such as Nitinol, the length of the hooks 210a-b between the anchors 22a-b can decrease after they are mated so as to apply the approximation force to the actuation strands 38a-b. It should thus be appreciated that the auxiliary connector member 77 can define a locking member that can fixedly attach the first and second actuation strands 38 and 38b to each other, and can also apply the approximation forces that bias the anchors 22a and 22b toward each other so as to approximate the gap 24c, and maintain the gap 24c in its approximated state.

Figure 35A:
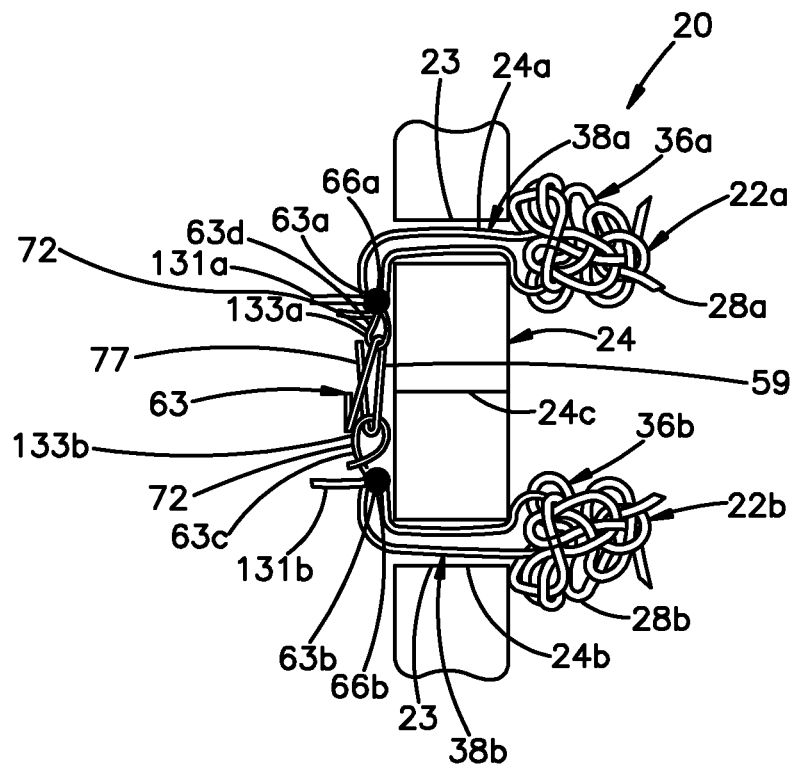
FIG. 35A is a side elevation view of an anchor assembly constructed in accordance with another embodiment, including first and second anchors shown in respective expanded configurations and implanted in target anatomical structure, showing the anchor assembly in an approximated configuration.
Figure 35B:
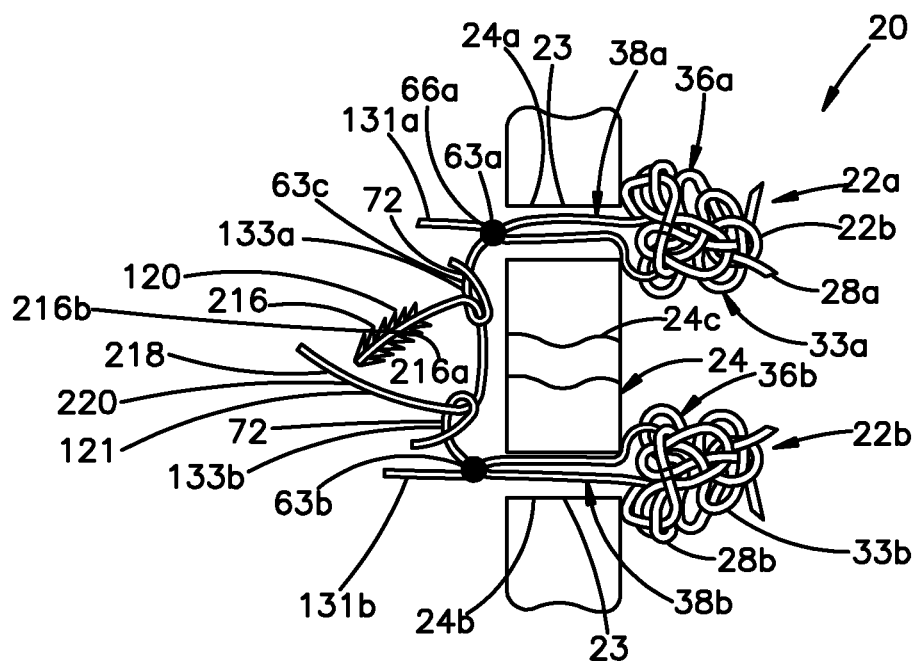
FIG. 35B is a side elevation view of the anchor assembly as illustrated in FIG. 35A, shown prior to actuating the anchor assembly to the approximated configuration.
Figure 35C:
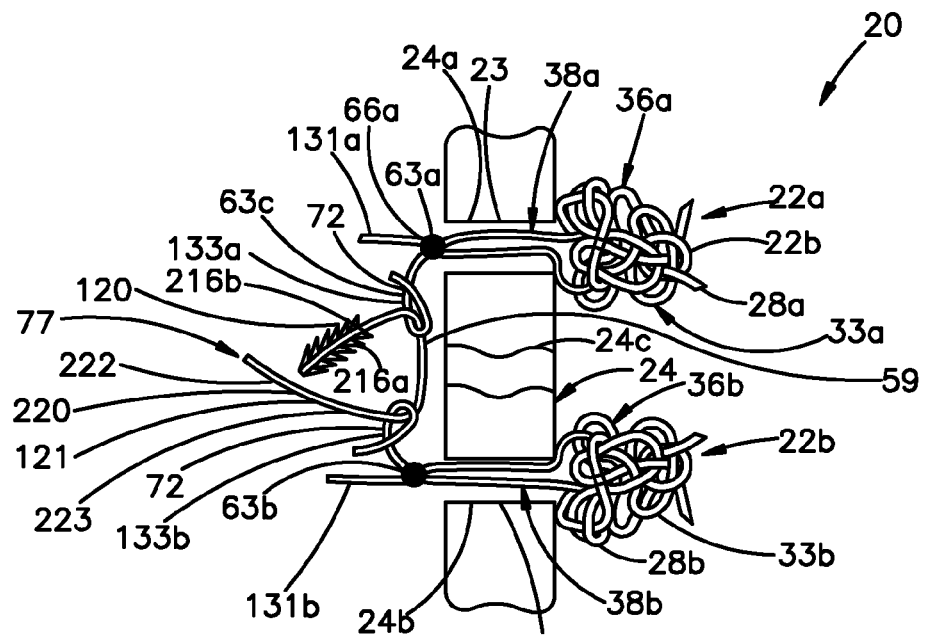
FIG. 35C is a side elevation view of an anchor assembly similar to the anchor assembly as illustrated in FIG. 35B, but including a connector member constructed in accordance with an alternative embodiment.

Referring now to FIGS. 35A-C, the auxiliary attachment member 77 can be configured as a connector strand 59 substantially as described above, that can define an connector member 63 integral with the first and second portions 120 and 121 of the connector strand. In accordance with the illustrated embodiment, the connector strand 59 can define an intermediate portion 123 that extends between the eyelets 72 of the first and second actuation strands 38a-b. The connector strand 59 is fed through or otherwise extends through the eyelets 72 such that the first and second portions 120 and 121 extend from the eyelets 72 and are configured to attach to each other. For instance, at least one of the first and second portions 120 and 121, such as the first portion 120 as illustrated, can be barbed, and thus define outwardly projecting ratchet teeth 216 having respective leading ends 216a and trailing ends 216b. The other of the first and second portions 120 and 121, such as the second portion 121 as illustrated, can define at least one catch member 218 that is configured to mate with the ratchet teeth 216 so as to attach the first portion 120 to the second portion 121. For instance, the catch member 218 can be configured as an aperture 220 defined by the respective one of the first and second portions 120 and 121. The aperture 220 can be cut through the second portion 121 as illustrated in FIG. 35B, can be defined by interstices 222 between fibers of the second portion 121, for instance when the second portion is a mesh 223 or a braided structure, or any alternatively structure that defines such interstices 222 suitable to receive the barbed first portion 120. It should be appreciated that the catch member 218 can alternatively be configured as desired.

During operation, the first and second anchors 22a-b can be actuated to their expanded configurations in the manner described above, and the connector strands 59 can be fed through the respective eyelets 72 either before or after the anchors 22a-b have been actuated. The ratchet teeth 216 of the first portion 120 can be mated with the catch member 218 of the second portion 210 such that the connector strand 59 defines an enclosed loop 204. For instance, barbed first portion 210 can be fed through the aperture 220 of the second portion 121 so as to attach the first portion 120 to the second portion 121, thereby also attaching the first actuation strand 38a to the second actuation strand 38b. The leading ends 216a and the trailing ends 216b of the ratchet teeth 216 can be configured so as to allow the first portion 120 to travel with respect to the second portion 121 substantially along a direction that causes the size of the loop 204 to decrease, and prevent the first portion 120 from traveling with respect to the second portion 121 substantially along an opposite direction that causes the size of the loop 204 to increase. As the size of the loop 204 decreases, the connector strand 59 applies approximation forces to the first and second actuation strands 38a and 38b that biases the first and second anchors toward each other so as to approximate the gap 24c. It should thus be appreciated that the connector member illustrated in FIGS. 34A-B can define both a sliding member and a locking member of the type described herein.

Figure 35D:
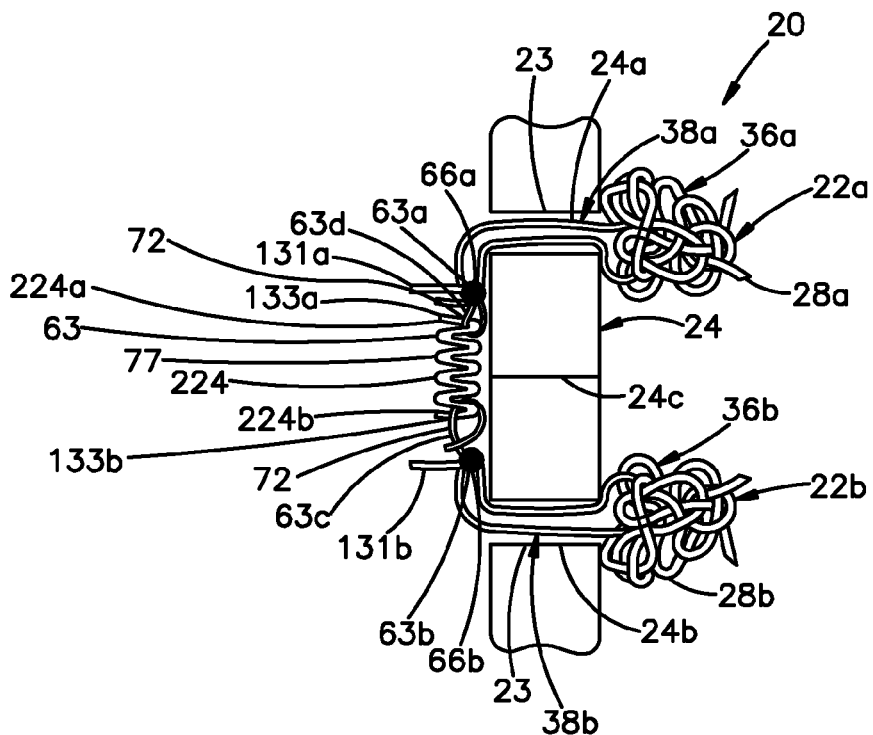
FIG. 35D is a side elevation view of an anchor assembly similar to the anchor assembly as illustrated in FIG. 35A, but including a connector member constructed in accordance with an alternative embodiment.

Referring now to FIG. 35D, the auxiliary attachment member 77 can be configured as a spring member 224 that is configured to be attached between the first and second actuation strands 38a and 38b, and thus between the first and second anchors 22a and 22b. The spring member 224 can be configured as a coil spring as illustrated, or any alternatively constructed spring member having a spring constant that biases the anchors 22a and 22b toward each other when attached between the anchors 22a and 22b. For instance, the spring member 224 can be configured as an elastic strand or any alternative suitably constructed spring member 224. The spring member 224 can define first and second attachment ends 224a and 224b that are configured to attach to the first and second actuation strands 38a and 38b, respectively. For instance, the attachment ends 224a-b can define eyelets, and the respective actuation strands 38a-b, for instance the attachment portions 131a-b, can be fed through the first and second attachment ends 212a-b during construction of the respective eyelets 72. Alternatively, the first and second attachment ends 212a and 212b can be attached, for instance clipped onto, adhesively attached, or otherwise attached, to the preformed eyelets 72. Alternatively still, the first and second attachment ends 214a-b can be integral with the actuation strands 38a and 38b, such that the spring member 224 is defined as an elastic portion of an auxiliary strand member 33 that defines both the first and second actuation strands 38a and 38b that can be integral with each other.

During operation, the first and second anchors 22a-b can be actuated to their expanded configurations in the manner described above, and the spring member 224 can be attached to the actuation strands 38a and 38b, and thus attached to the anchor bodies 28a-b, either before or after the anchors 22a-b have been actuated. The spring member 224 applies a spring force, which defines the approximation forces, to the first and second actuation strands 38a and 38b that bias the first and second anchors toward each other so as to approximate the gap 24c.

Figure 36A:
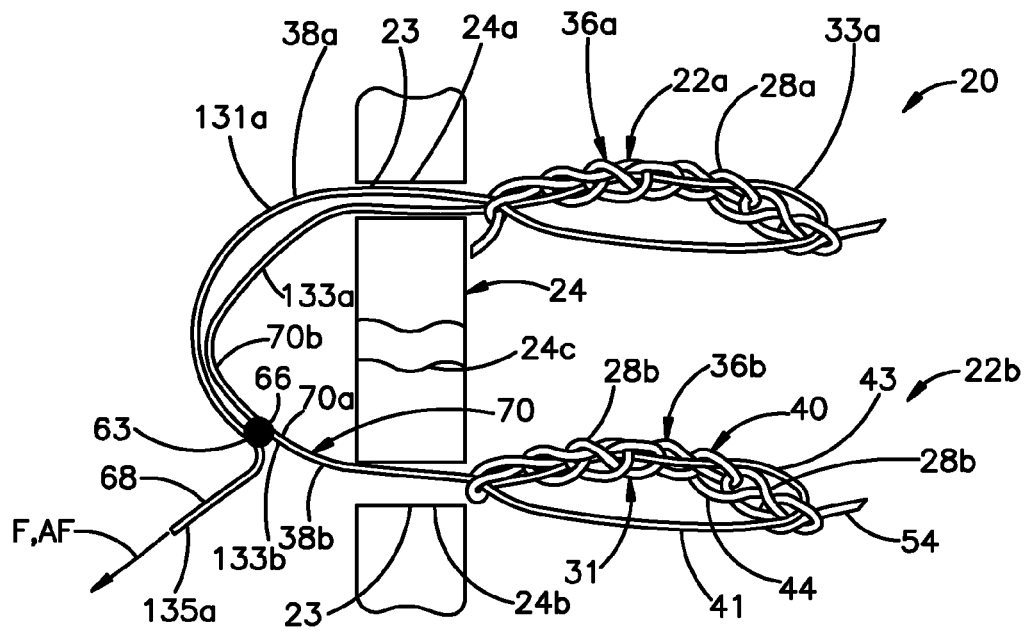
FIG. 36A is a side elevation view of an anchor assembly constructed in accordance with another embodiment, including first and second anchors shown in respective first configurations and implanted in an anatomical structure.
Figure 36B:
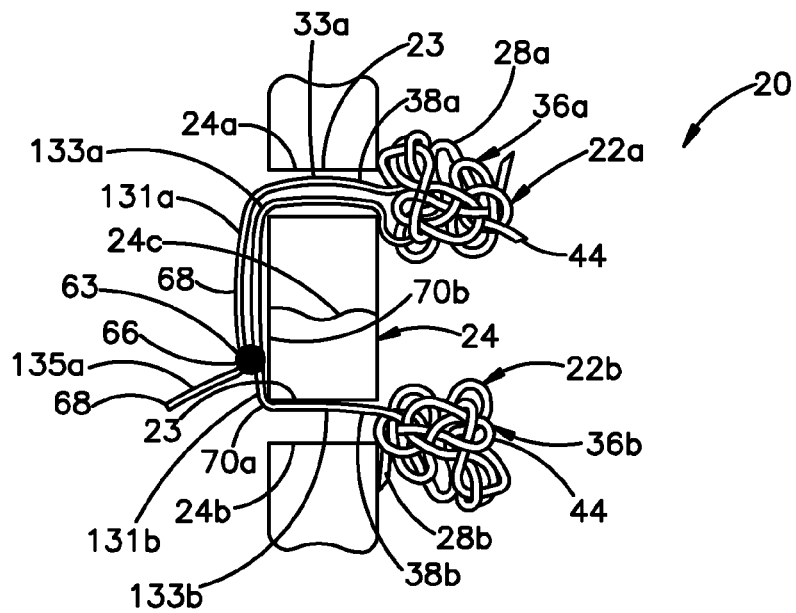
FIG. 36B is a side elevation view of the anchor assembly illustrated in FIG. 36A, showing the first and second anchors in respective expanded configurations.

It is appreciated that the connector members 63 of the type described herein are configured to attach first and second actuation strands 38a and 38b to each other, such that an approximation force can be applied to the anchors 22a and 22b that biases the anchors 22a and 22b toward each other so as to approximate the gap 24c. Referring to FIGS. 36A-B, it should further be appreciated that one of the actuation strands 38a and 38b can be integral with the respective anchor body 28a and 28b, and the other of the actuation strands 38b and 38b can be separate from and woven through the respective anchor body 28a and 28b so as to attach the actuation strand to the anchor body. In accordance with the illustrated embodiment, the second actuation strand 38b is integral with the anchor body 28b, and the first actuation strand 38a defines an auxiliary strand 33a with respect to the first anchor body 38a. Thus, the integral actuation strand 38b of the second anchor 22b can define the auxiliary actuation strand 38a of the first anchor. Thus, as described above with respect to FIGS. 7A-B, the first portion 41 of the second anchor body 22b can define both the respective actuation portion 131b and the attachment portion 133b. Furthermore, connector members 63 of the type described herein can attach directly to any eyelet of the type described herein, such as the eyelet 90 after the auxiliary strand 33 has been removed as described in more detail below with respect to FIGS. 37A-B.

The attachment portion 133b of the second actuation strand 38b can be integral with the attachment portion 133a of the first actuation strand 38a. The first actuation strand 38a can be woven through the anchor body in the manner described above, such that the first actuation portion 131a of the first anchor 22a extends out from the first anchor body 28a and is spaced from the first attachment portion 133a in the manner described above. The anchor assembly 20 can include a connector member 63 that attaches the first actuation portion 131a to another location of the auxiliary strand 33a, for instance to either or both of the first and second attachment portions 133a and 133b. In accordance with the illustrated embodiment, the connector member 63 attaches the first actuation portion 131a to the second attachment portion 133b. The connector member 63 can be configured in accordance with any of the embodiments described herein suitable to attach the first actuation portion 131a, directly or indirectly, to another target location of the auxiliary strand 33a, such as at least one or both of the first and second attachment portions 133a and 133b.

In accordance with the illustrated embodiment, the connector member 63 is configured as a knot 66 that is defined by the first actuation portion 131a and the target location of the auxiliary strand 33a, which can be the second attachment portion 133b as described above. The first actuation portion 131a can define the post end 68 of the knot 66, such that the terminal portion 135a extends out from the knot 66, and the second actuation strand 38b can define the free end 70 of the knot 66. For instance, the portion of the second actuation strand 38b that is disposed between the knot 66 and the anchor body 28b can define the static portion 70a of the free end 70, and the portion of the second actuation strand 38b that is disposed between the knot 66 and the first anchor body 28a can define the free portion 70b of the free end 70.

During operation, the knot can be disposed in its unlocked configuration such that the post end 68, or the first actuation portion 131a, is slidable through the knot 66 with respect to the free end 70, or the second actuation strand 38b. Thus, the actuation force F can be applied to the first actuation portion 131a, and in particular to the first terminal portion 135a, which induces tension in the first and second actuation strands 38a and 38b, thereby actuating the first and second anchors 22a and 22b, respectively, from their first configurations to their expanded configurations. Application of the approximation force AF to the first actuation portion 131a, and in particular to the first terminal portion 135a, further induces tension in the first and second actuation strands 38a and 38b, thereby biasing the first and second anchors 22a and 22b toward each other and approximating the gap 24c. Thus, the approximation force AF can be a continuation of the actuation force F.

As described above, the anchor assembly 20 can include a connector member 63 that is attached between a first eyelet of the first anchor 22a and a second eyelet of the second anchor 22b. At least one or both of the first and second eyelets can be constructed in accordance with any suitable embodiment described herein or any suitable alternative embodiment. Referring to FIGS. 37A-43C, at least one or both of the first and second eyelets can be configured as eyelets 90 as described above with reference to FIGS. 9A-12B.

For instance, referring to FIGS. 37A-D, and as described above with respect to FIGS. 9A-C, the auxiliary strand 33 can extend through the eyelet 90 and can be woven through the anchor body 28 so as to define a path for the eyelet 90 through the anchor body 28 when the anchor body 28 is actuated from the first configuration to the expanded configuration. Furthermore, the auxiliary strand 33 can be configured as a deployment strand that facilitates attachment of the anchor 22 to another anchor, or can alternatively or additionally be configured as an actuation strand that receives the actuation force causing the anchor to be actuated from the first configuration to the expanded configuration once implanted in the anatomical structure 24.

In accordance with the illustrated embodiment, the anchor assembly 20 can include a first and second anchor 22a and 22b each including respective eyelets 90a and 90b that are actuated to their expanded configuration as described above with respect to FIGS. 9A-C. Next, the auxiliary strand 33 of one of the anchors 22a-b can be removed from the respective eyelet 90a-b, and the auxiliary strand 33 of the other of the anchors 22a-b can be fed through the eyelet 90a-b of the anchor 22a-b from which the auxiliary strand was removed. Thus, the auxiliary strand 33 of one of the anchors can define the first actuation strand 38a and the second actuation strand 38b. Alternatively, the auxiliary strands 90a-b of both off the anchors 22a and 22b can be removed from the respective eyelets 90a-b, and a new auxiliary strand 33 can be fed through both eyelets 90a and 90b so as to attach the first anchors 22a and 22b to each other. Thus, FIG. 37A illustrates an auxiliary strand 33 that is separate from both anchor bodies 28a and 28b and extends through the respective eyelets 90a and 90b so as to define respective actuation strands 38a and 38b that are integral with each other.

As illustrated in FIG. 37B, the anchor bodies 28a and 28b can be urged along the respective actuation strands 38a and 38b from their respective expanded configurations to their respective first configurations. Accordingly, the actuation strands 38a and 38b extend through the same respective openings of the anchor bodies 28a and 28b as described above with respect to the auxiliary strand 33 as illustrated in FIGS. 9A-C. Thus, the actuation strands 38a and 38b define a first and second actuation portions 131a-b, respectively, and first and second attachment portions 133a-b. The first and second actuation portions 131a-b are configured to receive respective actuation forces F that actuate the anchor bodies 28a-b to their expanded configurations in the manner described above, and the second actuation portions 133a-b are configured to attach to each other. For instance, the first and second actuation portions 133a-b can be integral with each other, or can be attached via any suitable connector member of the type described herein.

With continuing reference to FIGS. 37A-D, the anchor assembly can include a connector member 63 that can be configured to attach to the first and second actuation portions 131a and 131b, thereby attaching the first and second actuation strands 38a and 38b to each other, and also attaching the anchors 22a and 22b to each other. The attachment portions 133a-b of the auxiliary strand 33 can be attached, for instance integrally in accordance with the illustrated embodiment, across the gap 24c.

As described above, the connector member 63 that can define at least one of a sliding member 47 and a locking member 64 that attaches the first and second actuation strands 38a and 38b together, for instance at a junction 125. Furthermore, in accordance with the illustrated embodiment, the connector member 63 can be defined by the auxiliary strand 33, and thus by the actuation strands 38a and 38b. Thus, in accordance with one embodiment, the connector member 63 can attach the first actuation strand 38a to the second actuation strand 38b while the actuation strands 38a and 38b are under tension, so as to maintain the gap 24c in an approximated state. Alternatively or additionally, it should be appreciated that the connector member 63 can attach the first and second actuation strands 38a and 38b to each other prior to placing the actuation strands 38a and 38b under tension and therefore prior to approximating the gap 24c.

In accordance with the illustrated embodiment, the connector member 63 is defined by and integral with the first and second actuation strands 38a and 38b. Thus, the actuation strands 38a and 38b are attached directly to each other. The connector member 63 can define the sliding member 47 and the locking member 64 at the junction 125. For instance, the connector member 63 can define a knot 66 that can be constructed as described above with respect to FIGS. 4A-F and can be defined by one or more, up to all of, the actuation strands 38a and 38b, though it should be appreciated that the knot can alternatively be defined by at least one of actuation strands 38a and 38b and a connector strand. Alternatively still the knot 66 can attach portions of a connector strand to each other so as to attach the actuation strands 38a and 38b, for instance when the connector strand is attached to the actuation strands 38a and 38b. In accordance with the illustrated embodiment, the first and second actuation strands 38a and 38b define the knot 66. Thus, at least a portion of the connector member 63 can be integral with at least one or both of the actuation strands 38a and 38b.

One of the first and second actuation strands 38a and 38b can define the post end 68 and the other of the first and second actuation strands 38a and 38b can define the free end 70. In accordance with the illustrated embodiment, the first actuation strand, such as the first actuation portion 131a, defines the post end 68 and the second actuation strand 38b, such as the second actuation portion 131b, defines the free end 70. The free portion 70b of the free and can be defined by the terminal portion 135b of the second actuation strand 135b. Likewise, the terminal portion 135a of the first actuation strand 38a extends out from the knot 66 as the post end 68.

The first and second actuation strands 38a and 38b can be tied into the knot 66 prior to applying tension to the actuation strands 38a and 38b that biases the first and second anchors 22a and 22b toward each other and approximates the gap 24c. Once the knot 66 is formed, and when the knot 66 is in an unlocked configuration, the actuation force F can be applied to the actuation strands 38a and 38b, and in particular to the actuation portions 131a-b, so as to actuate the respective expandable portions 36 from the first configuration to the expanded configuration. Next, the approximation force AF can be applied to the terminal portion 135a of the first actuation strand 38a, which defines the post strand 68, thereby causing the post end 68 to slide through the knot 66 and draw the respective anchor, such as the first anchor 22a, toward the other anchor, such as the second anchor 22b. Once the gap 24c has been approximated, the free strand 70b of the free end 70, for instance defined by the terminal portion 135b of the second actuation strand 38b, can be placed in tension so as to lock knot 66 and prevent the first actuation strand 38a from translating through the knot 66, thereby fixing the actuation strands 38a and 38b in tension.

While the connector member 63 can be configured as the knot 66, it should be appreciated that the connector member 63 can alternatively be configured in accordance with any embodiment described herein or any suitable alternative connector as desired. Furthermore, while each of the anchors 22a and 22b is illustrated as including respective attachment members 82, it should be appreciated that one of the anchors can include the attachment member 82 while the other anchor is directly coupled to the respective actuation strand 38.

Figure 37D:
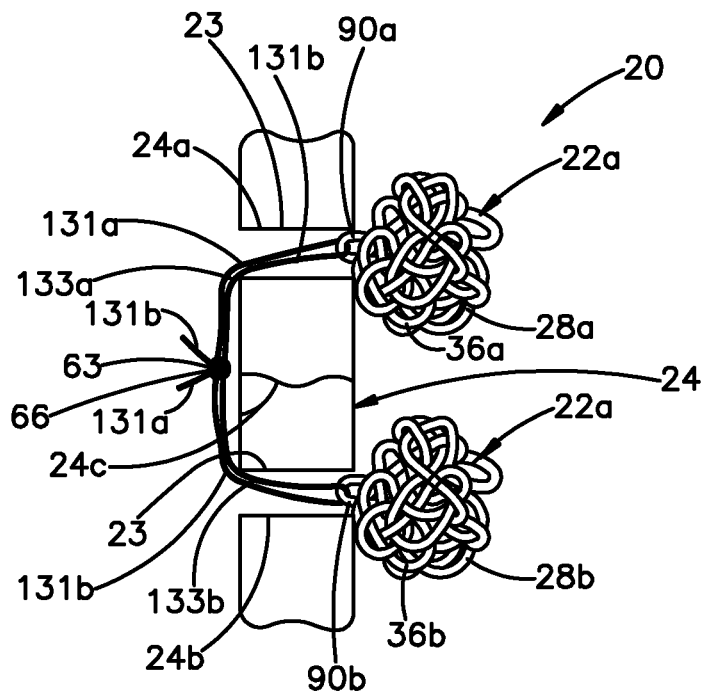
FIG. 37D is a side elevation view of the anchor assembly illustrated in FIG. 37A, showing the first and second anchors in respective expanded configurations.
Figure 37E:
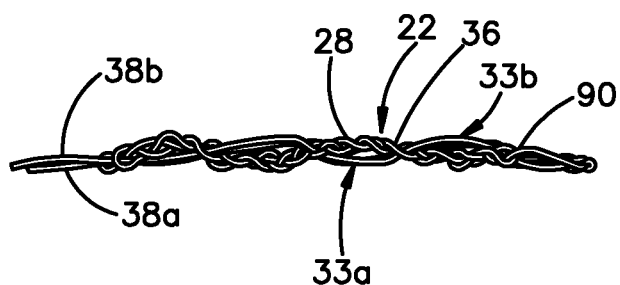
FIG. 37E is a side elevation view of an anchor having an eyelet, and a plurality of actuation strands that extend through the eyelet

Furthermore, referring now to FIG. 37E, it should be appreciated that at least one of the anchors 22 of the anchor assembly 20 can include a plurality of (for instance two or more) actuation strands 38a-b that extend through the eyelet 90 in the manner described above with respect to FIGS. 37A-B. For instance, once the anchor body 28 has been actuated to its expanded configuration such that the eyelet 90 projects proximally from the expandable portion 36, a plurality of auxiliary strands 33a-b can be inserted through the eyelet 90. The anchor body 28 can be urged along the respective actuation strands 38a-b from its expanded configurations to its respective first configurations. Accordingly, each of the plurality of actuation strands 38a-b extends through the same respective openings of the anchor body 28 as described above with respect to the auxiliary strand 33 as illustrated in FIGS. 9A-C. It should be appreciated that the actuation strands 38a-b can be configured to attach to other anchor bodies or anatomical locations as desired. In this regard, it should be appreciated that at least one of the plurality of actuation strands 38a-b can be further referred to as connector strands as desired.

Figure 38A:
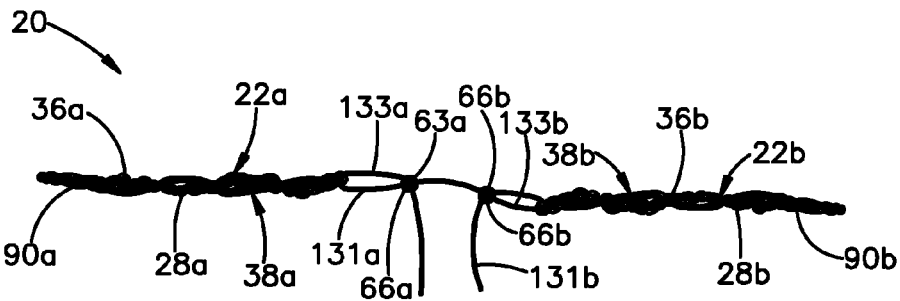
FIG. 38A is a side elevation view of an anchor assembly constructed in accordance with another embodiment, showing the first and second anchors in respective first configurations.
Figure 38B:
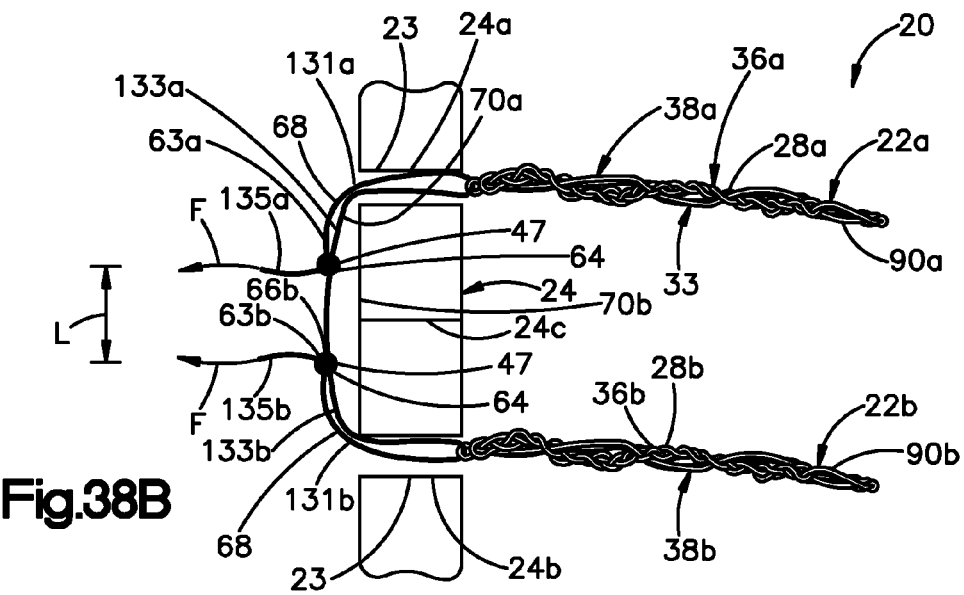
FIG. 38B is a side elevation view of an anchor assembly illustrated in FIG. 38A, shown implanted in a target anatomical structure.
Figure 38C:
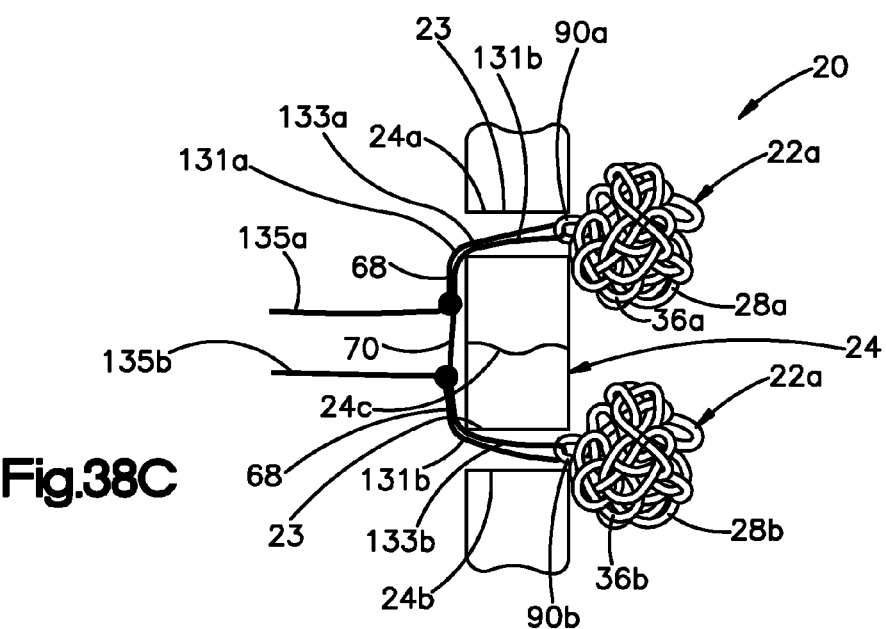
FIG. 38C is a side elevation view of the anchor assembly illustrated in FIG. 38B, showing the first and second anchors in respective expanded configurations.
Figure 39A:
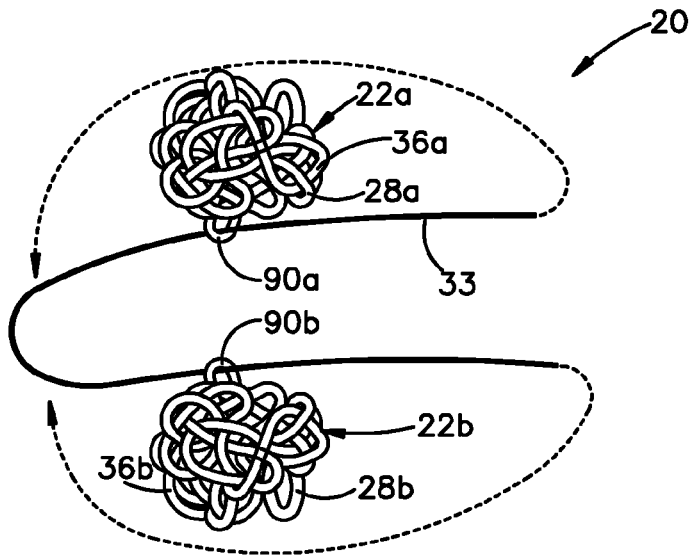
FIG. 39A is a side elevation view of an anchor assembly constructed in accordance with another embodiment, including first and second anchors.
Figure 39B:
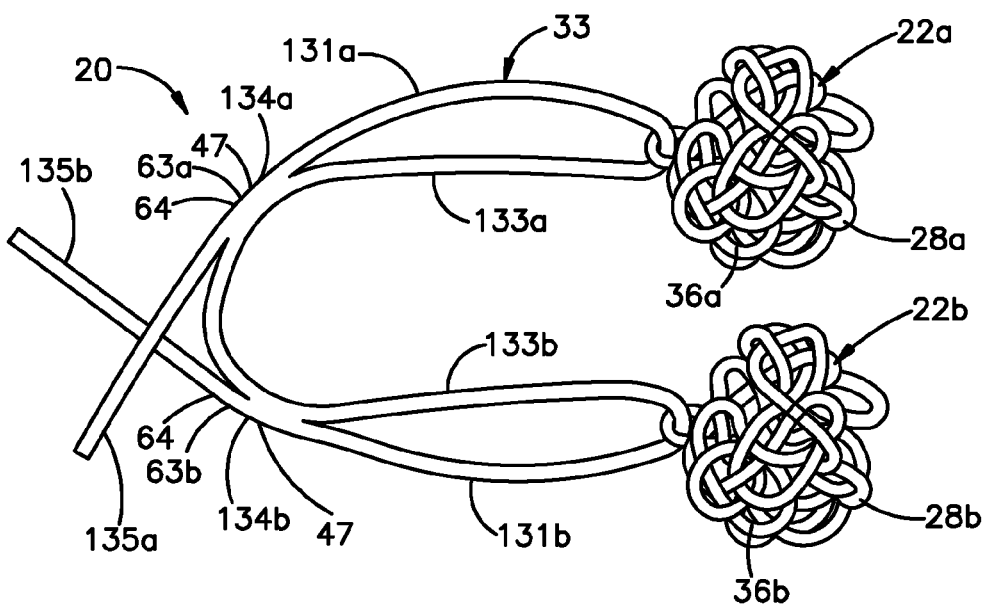
FIG. 39B is a side elevation view of an anchor assembly illustrated in FIG. 39A, showing the first anchor attached to the second anchor.
Figure 39C:
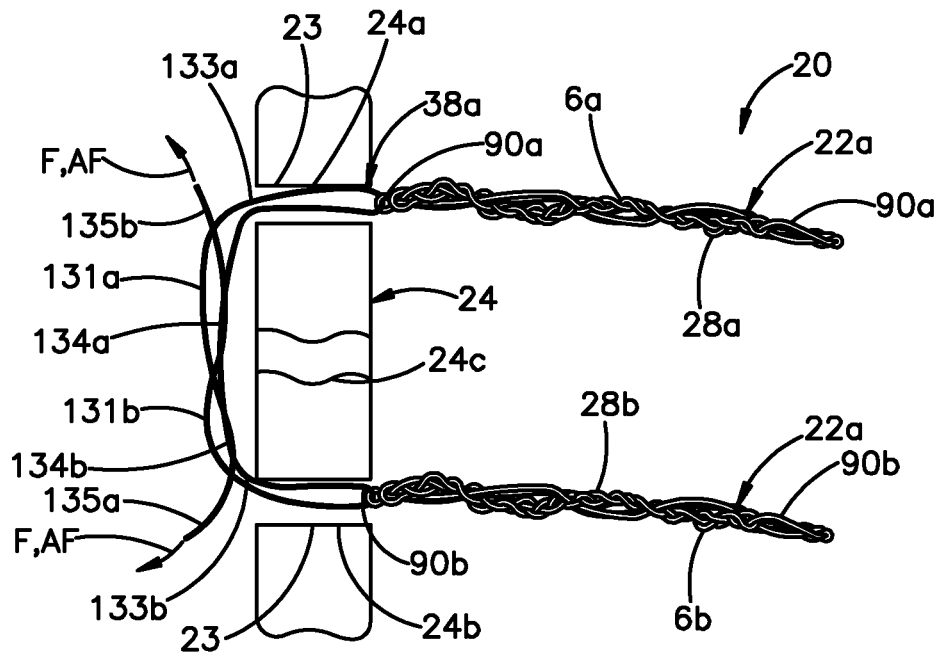
FIG. 39C is a side elevation view of the anchor assembly illustrated in FIG. 39B, showing the first and second anchors in respective first configurations and implanted in a target anatomical structure.
Figure 39D:
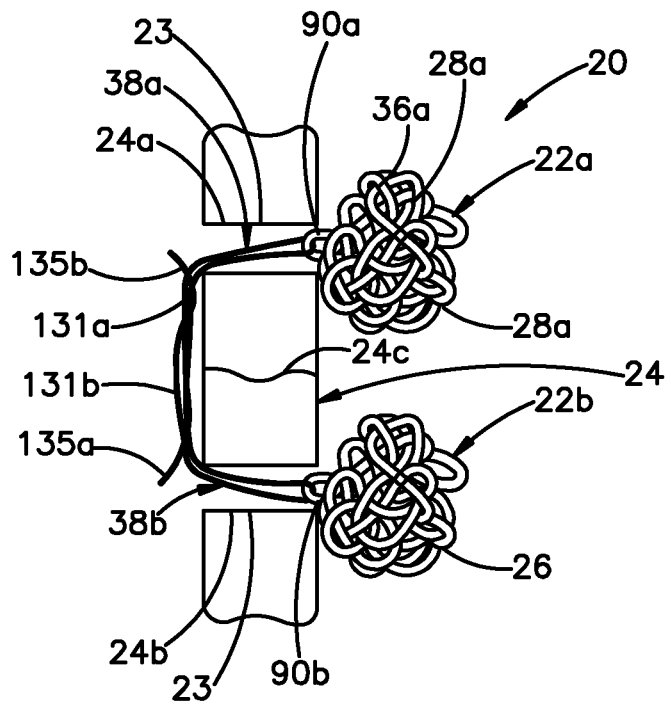
FIG. 39D is a side elevation view of the anchor assembly illustrated in FIG. 39C, showing the first and second anchors in respective expanded configurations.

Referring now to FIGS. 38A-C, the anchor assembly 20 as described above with reference to FIGS. 37A-D can include a plurality of connector members 63 that are configured to attach at least one or both of the actuation strands 38a and 38b. In accordance with the illustrated embodiment, the actuation strands 38a and 38b are defined by a common strand, such as the auxiliary strand 33, such that the respective attachment portions 133a and 133b are integral with each other. Thus, in accordance with the illustrated embodiment, the first and second actuation strands 38a and 38b are integral with each other. The anchor assembly 20 can include first and second connector members 63a and 63b that are configured to attach the actuation portions 131a and 131b to other locations of the common strand, and thus to each other. In accordance with the illustrated embodiment, the first connector member 63a can attach the corresponding first actuation portion 131a to another location of the auxiliary strand 33 that is spaced from the first actuation portion 131a. Likewise, the second connector member 63b can attach the corresponding second actuation portion 131b to another location of the auxiliary strand 33 that is spaced from the second actuation portion 131b. For instance, in accordance with the illustrated embodiment, the first connector member 63a attaches the first actuation portion 131a to the first attachment portion 133a, and the second connector member 63b attaches the second actuation portion 131b to the second attachment portion 133b.

Thus, it can be said that at least one connector member, such as the first and second connector members 63a and 63b, can attach the first and second actuation portions 131a and 131b to respective other locations of the auxiliary strand 33 so as to attach the first and second actuation portions 131a and 131b to each other, for instance indirectly through at least one or both of the attachment portions 133a and 133b. It can further be said that the first connector member 63a operably attaches one portion of the first actuation strand 38a to another location of the actuation strand 38a, and the second connector member 63b operably attaches one portion of the second actuation strand 38b to another location of the second actuation strand 38b.

In accordance the illustrated embodiment, each of the first and second connector members 63a and 63b can be configured as respective knot 66a and 66b that are defined by the auxiliary strand 33 at different locations along the auxiliary strands 33. The knots 66a and 66b can be constructed as described above with respect to FIGS. 4A-F, or can be alternatively constructed as desired. In accordance with the illustrated embodiment, the first knot 66a includes a post end 68, which can be defined by the actuation portion 131a of the first actuation strand 38a, and a free end 70, which can include a static portion 70a that is defined by a first end 137a of the first attachment portion 133a and a free portion 70b that is defined by a second end 139a of the first attachment portion 133a. The first end 137a can be disposed between the knot 66a and the first anchor body 28a, and the second end 139a can be disposed between the knot 66a and the second connector member 63b. Alternatively, the free portion 70b can be defined by the attachment portion 133b of the second actuation strand 38b.

In accordance with one embodiment, the second knot 66a includes a post end 68, which can be defined by the actuation portion 131b of the second actuation strand 38b, and a free end 70, which can include a static portion 70a that is defined by a first end 137b of the second attachment portion 133b and a free portion 70b that is defined by a second end 139b of the second attachment portion 133b. The first end 137b can be disposed between the knot 66b and the second anchor body 28b, and the second end 139b can be disposed between the knot 66b and the first connector member 63a. Alternatively, the free portion 70b can be defined by the attachment portion 133a of the first actuation strand 38a. The attachment portions 133a and 133b are illustrated as being integral with each other, though it should be appreciated that the attachment portions 133a and 133b be separate and attached to each other, for instance when the anchor assembly 20 defines first and second auxiliary strands 33a and 33b operably coupled to the first and second anchors 22a and 22b, respectively (see, e.g., FIGS. 30A-D).

Each of the first and second knots 66a and 66b can define respective sliding members 47 that allow the respective post ends 68 to translate therethrough relative to the free ends 70. Thus, the sliding members 47 allow the first and second actuation portions 131a and 131b to translate relative to the first and second attachment portions 133a and 133b, for instance in response to the applied actuation force F which can be applied to the terminal portions 135a and 135b when the knots 66a and 66b are in unlocked configurations, thereby actuating the respective anchor body 28a and 28b from the first configuration to the expanded configuration. Each knot 66 further defines a locking member 64 that can be actuated to a locked configuration so as to secure the at least one or both of the anchors 22a and 22b in their respective biased positions. For instance, a tensile locking force can be applied to the free portions 70b of the free ends of the knots 66a and 66b so as to prevent the actuation portions 131a and 131b from translating through the knots 66a and 66b relative to the attachment portions 133a and 133b.

The first and second knots 66a and 66b can be spaced apart a fixed distance L along the auxiliary strand 33, such that the gap 24c is maintained approximated when the anchor bodies 22a and 22b are inserted into the respective target anatomical locations 24a and 24b. For instance, the gap 24c can be approximated prior to injecting the knots 66a and 66b into the respective target anatomical locations 24a and 24b. During operation, once the first and second anchors 22a and 22b are implanted at the respective first and second target anatomical locations 24a and 24b, the knots 66a-b can be in an unlocked configuration such that application of the actuation force F to the respective actuation strands 38a-b, for instance the actuation portions 131a-b, causes the respective anchor bodies 28a-b to actuate from the first configuration to the expanded configuration. Next, a tensile locking force can be applied to the respective attachment portions 133a-b against the corresponding knots 66a-b, so as to actuate the knots 66a-b to their locked configurations and maintain the anchor 22a-b in their expanded configurations.

The distance L between the first and second knots 66a and 66b can be substantially equal to or less than the distance between the target anatomical locations 24a and 24b, such that the gap 24c is approximated when the first and second anchors 22a and 22b are expanded behind the anatomy and joined by the auxiliary strand 33, such that tension induced in the actuation strands 38a and 38b maintains the approximation of the gap 24c. While the first and second connector members 63a-b can be configured as respective knots 66, it should be appreciated that either or both of the first and second connector members 63a and 63b can be alternatively configured as any suitable locking member 63 of any type described herein or any suitable alternatively constructed locking member. For instance, at least one or both of the connector members 63a-b can define a splice, whereby one or both of the actuation strands 38a-b is spliced through itself or the other of the actuation strands 38a-b, and the connector strand is placed in tension after actuation of the anchors 22a and 22b so as to apply a compressive force that prevents translation of the anchor strands 38a-b. One example of such a splice is described above with respect to FIGS. 19D-H.

Referring now to FIGS. 39A-D, the auxiliary strand 33 can be inserted through, and thus extend through, the eyelets 90a and 90b of the first and second anchor bodies 28a and 28b as described above with respect to FIG. 37A, and can subsequently be spliced through itself at more than one location, such as two locations that are spaced apart from each other along a direction between the first and second anchor bodies 28a and 28b. Thus, the anchor assembly 20 can include at least one connector member 63, such as a pair of connector members 63a and 63b that join the first actuation strand 38a to the second actuation strand 38b.

For instance, each of the connector members 63a and 63b can be configured as a respective splice 134a and 134b that is defined by the first and second actuation strands 38a and 38b. In one example, one of the first and second actuation strands 38a and 38b can be woven or otherwise spliced through another location of the auxiliary strand 33, for instance through the other of the actuation strands 38a and 38b. In accordance with the illustrated embodiment, the first or actuation portion 131b of the second actuation strand 38b can be woven or otherwise spliced through at least one or both of the second or attachment portion 133b of the second actuation strand 38b and the second or attachment portion 133a of the first actuation strand 38a so as to define the first splice 134a. The second actuation strand 38b can enter the first actuation strand 38a and can extend along the first actuation strand 38a inside the first actuation strand 38a along a direction away from the corresponding second anchor body 28*b* so as to define the first splice 134*a* prior to exiting the first actuation strand 38*a* at the first terminal portion 135*b*. Thus, the first actuation strand 38*a* can circumscribe the second actuation strand 38*b* along a portion of the length of second actuation strand 38*b*.

Furthermore, the first actuation strand 38*a* can be woven or otherwise spliced through the second actuation strand 38*b* so as to define the second splice 134*b*. In accordance with the illustrated embodiment, the first or actuation portion 131*a* of the first actuation strand 38*a* can be woven or otherwise spliced through at least one or both of the second or attachment portion 133*a* of the first actuation strand 38*a* and the second or attachment portion 133*b* of the second actuation strand 38*b* so as to define the first splice 134*b*. The first and second attachment portions 133*a* and 133*b* can be attached, for instance integral or separately attached via a connector member, to each other. The first and second splices 134*a* and 134*b* can be spaced, such that the first splice 134*a* is disposed closer to the first anchor 22*a* than the second splice 134*b*, and the second splice 134*b* is disposed closer to the second anchor 22*b* than the first splice 134*a*. The first actuation strand 38*a* can enter the second actuation strand 38*b* and extend along the second actuation strand 38*b* inside the second actuation strand 38*b* along a direction away from the first anchor body 28*a* so as to define the second splice 134*b* prior to exiting the second actuation strand 38*b* at the first terminal portion 135*a*. Thus, the second actuation strand 38*b* can circumscribe the first actuation strand 38*a* along a portion of the length of the first actuation strand 38*a*.

During operation, the first and second actuation strands 38*a* and 38*b*, and in particular the first and second actuation ends 131*a* and 131*b*, can each receive a respective actuation force F that causes the anchor bodies 28*a* and 28*b* to actuate from their respective first configurations to their respective expanded configurations. The actuation force F can be applied directly to the first and second actuation strands 38*a* and 38*b* at the respective first and second actuation portions 131*a* and 131*b*, such as at the first and second terminal portions 135*a* and 135*b* as illustrated, or can be applied to the first and second actuation strands 38*a* and 38*b* at a location upstream of the respective splices 134*b* and 134*a*.

Next, each of the first and second actuation portions 131*a* and 131*b* of the first and second actuation strands 38*a* and 38*b*, respectively, can each receive an approximation force AF that biases at least one or both of the anchor bodies 28*a* and 28*b* toward the other of the anchor bodies 28*a* and 28*b* to a biased position so as to approximate the gap 24*c*. The approximation force AF can be a continuation of the actuation force F if, for instance, the actuation force F is applied to the actuation portions 131*a* and 131*b*. It should be appreciated that once both the first and second actuation strands 38*a* and 38*b* are placed under tension, the first actuation strand 38*a* applies a compressive force to the second actuation strand 38*b* at the first splice 134*a*, and the second actuation strand 38*b* applies a compressive force to the first actuation strand 38*a* at the second splice 134*b*. The first compressive force is sufficient to prevent the second actuation strand 38*b* from backing out of the first splice 134*a* along a direction toward the second anchor body 28*b*, and the second compressive force is sufficient to prevent the first actuation strand 38*a* from backing out of the second splice 134*b* along a direction toward the first anchor body 28*a*.

Accordingly, the first and second splices 134*a* and 134*b* each define a sliding member 47 that allows one of the first and second actuation strands 38*a* and 38*b* to slide with respect to the other of the first and second actuation strands 38*a* and 38*b* so as to approximate the gap 24*c*, and further define a locking member 64 that secures the first and second actuation strands 38*a* and 38*b* to each other, for example with respect to relative movement that would allow the first and second anchor bodies 28*a* and 28*b* to separate.

Figure 40A:
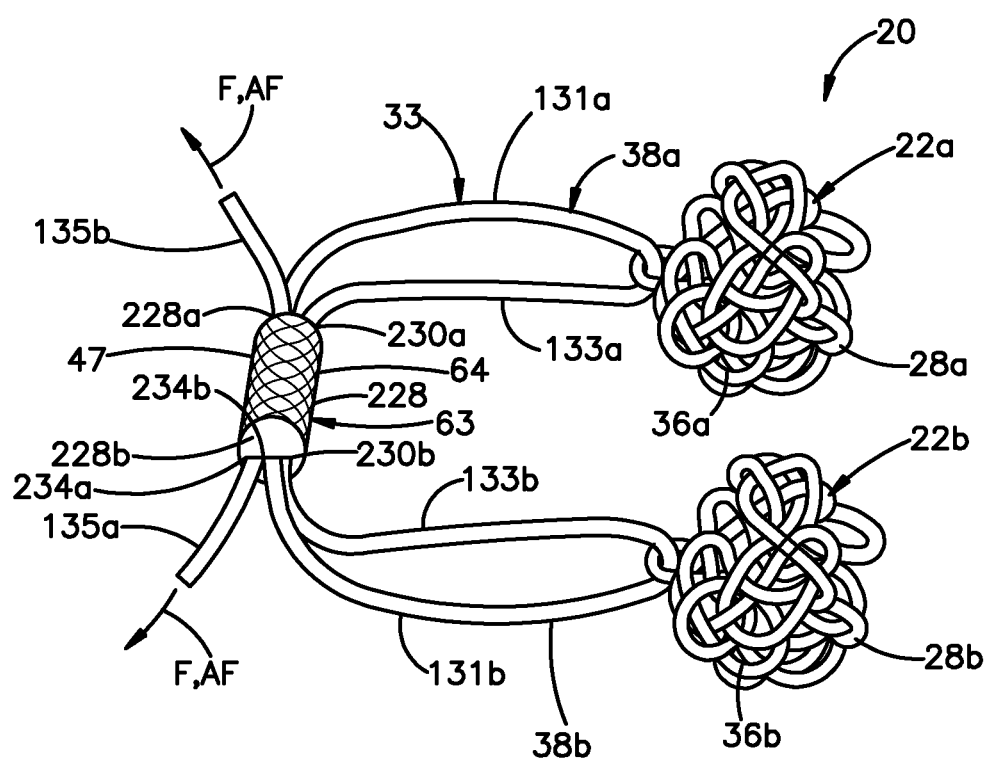
Figure 40B:
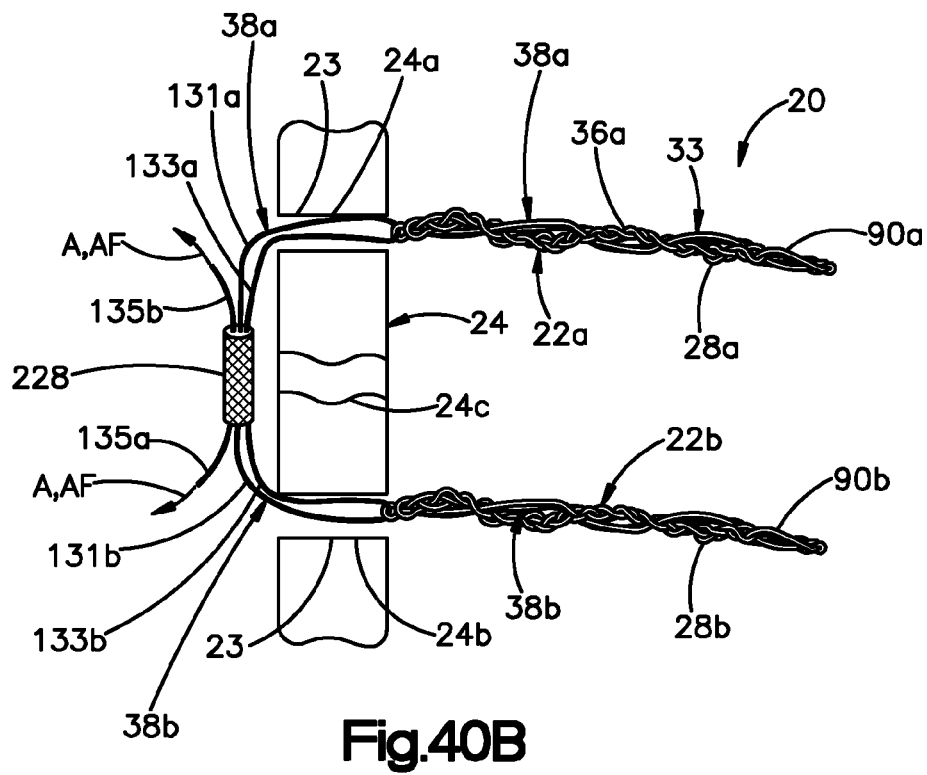
Figure 40C:
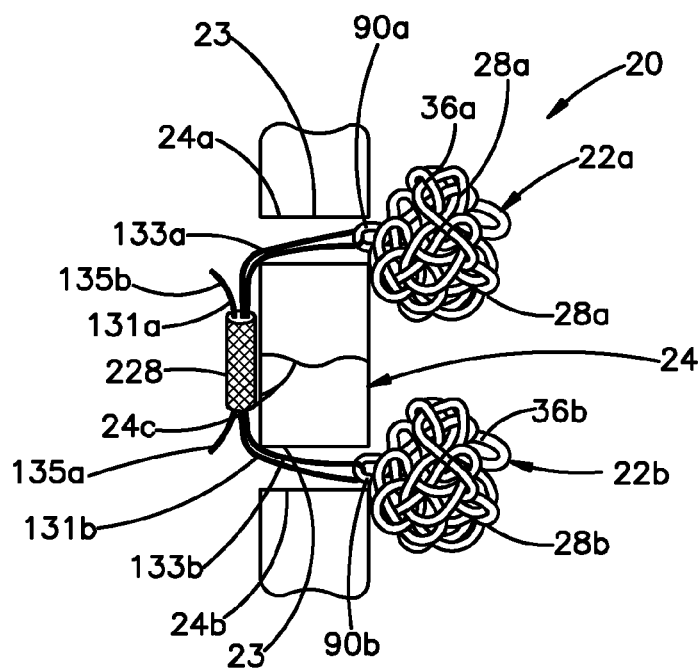

Referring now to FIGS. 40A-C, the auxiliary strand 33 can be inserted through, and thus extend through, the eyelets 90*a* and 90*b* of the first and second anchor bodies 28*a* and 28*b* as described above with respect to FIG. 37A prior to actuating the first and second anchor bodies to their first configurations., and can further be spliced through itself. For instance, the auxiliary strand 33 can include a compression member 228, which can define a woven structure such as a braid, a weave, a mesh, or a knit, or any suitable alternatively constructed member, such as a nonwoven structure, that defines at least one opening. The second or attachment portions 133*a* and 133*b* of the first and second actuation strands 38*a* and 38*b* can be attached to the compression member 228, for instance to opposed ends 228*a* and 228*b* of the compression member 228 at respective attachment locations 230*a* and 230*b* that are spaced apart along a direction between the first and second anchor bodies 28*a* and 28*b*. Thus, the auxiliary strand 33 can define a common strand for the first and second actuation strands 38*a* and 38*b*, and also for the compression member 228. In accordance with the one embodiment, the attachment portions 133*a* and 133*b* can be woven into the compression member 228, tied to the compression member 228, adhesively attached to the compression member 228, welded to the compression member 228, integral with the woven section, or otherwise attached to the compression member 228 in any manner desired. In this regard, it should be appreciated, for instance when the attachment portions 133*a* and 133*b* are integral with the compression member 228, that a substantial entirety of the auxiliary strand 33 can be a woven structure. It should be further appreciated that the compression member 228 can define a connector member 63 that is integral with the auxiliary strand 33, or can be separate and attached to the auxiliary strand.

Accordingly, the anchor assembly 20 can define first and second connector members 63*a* and 63*b* configured as respective splices 134*a* and 134*b* that are defined by the auxiliary strand 33, and in particular defined by the first and second actuation strands 38*a* and 38*b* and the compression member 228. In one example, the first actuation portion 131*a* of the first actuation strand 38*a* can extend through the compression member 228 so as to define a first splice 134*a*. The first actuation portion 131*a* can extend through the compression member 228 substantially along a first direction from the first anchor body 28*a* toward the second anchor body 28*b*. The compression member 228 can thus circumscribe a length of the actuation portion 131*a* of the first actuation strand 38*a*. The first actuation portion 131*a* can exit the compression member 228 at the first terminal portion 135*a*. Similarly, the second actuation portion 131*b* of the second actuation strand 38*b* can extend through the compression member 228 so as to define a second splice 134*b*. The compression member 228 can thus circumscribe a length of the actuation portion 131*b* of the second actuation strand 38*b*. The second actuation portion 131*b* can extend through the compression member 228 substantially along a second direction from the second anchor body 28*b* toward the first anchor body 28*a*. Thus, the second direction can be substantially opposite the first direction. The second actuation portion 131*b* can exit the compression member 228 at the second terminal portion 135*b*.

During operation, the first and second actuation strands 38*a* and 38*b*, and in particular the first and second actuation ends 131*a* and 131*b*, can each receive a respective tensile actuation force F that causes the anchor bodies 28a and 28b to actuate from their respective first configurations to their respective expanded configurations. The actuation force F can be applied directly to the first and second actuation strands 38a and 38b at the respective first and second actuation portions 131a and 131b, such as at the first and second terminal portions 135a and 135b as illustrated, or can be applied to the first and second actuation strands 38a and 38b at a location upstream of the respective splices 134b and 134a.

Next, each of the first and second actuation portions 131a and 131b of the first and second actuation strands 38a and 38b, respectively, can each receive a tensile approximation force AF that causes the first and second actuation portions 131a and 131b to translate through the compression member 228, which can define a connector 63, along a first direction that biases at least one or both of the anchor bodies 28a and 28b toward the other of the anchor bodies 28a and 28b to a biased position so as to approximate the gap 24c. The approximation force AF can be a continuation of the actuation force F if, for instance, the actuation force F is applied to the actuation portions 131a and 131b. It should be appreciated that the approximation force AF places the auxiliary strand 33 under tension, thereby causing the compression member 228 to apply a compressive force both to the first actuation strand 38a, and in particular to the first actuation portion 131a, at the first splice 134a, and to the second actuation strand 38b, and in particular to the second actuation portion 131b, at the second splice 134b. The compressive forces applied by the compression member 228 to the first and second actuation strands strand 38a and 38b prevent the first and second actuation strands 38a and 38b from backing out of compression member 228 along a second direction, opposite the first direction, toward the respective first and second anchor bodies 28b.

Accordingly, the first and second splices 134a and 134b each define a sliding member 47 that allows one of the first and second actuation strands 38a and 38b to slide with respect to the other of the first and second actuation strands 38a and 38b so as to approximate the gap 24c, and further define a locking member 64 that secures the first and second actuation strands 38a and 38b to each other, for example with respect with respect to relative movement along a second direction substantially opposite the first direction, which would allow the first and second anchor bodies 28a and 28b to separate.

Figure 41A:
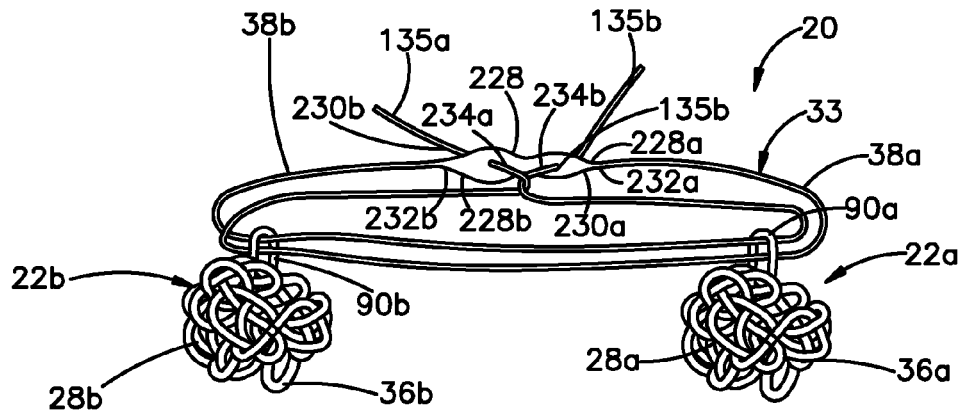
Figure 41B:
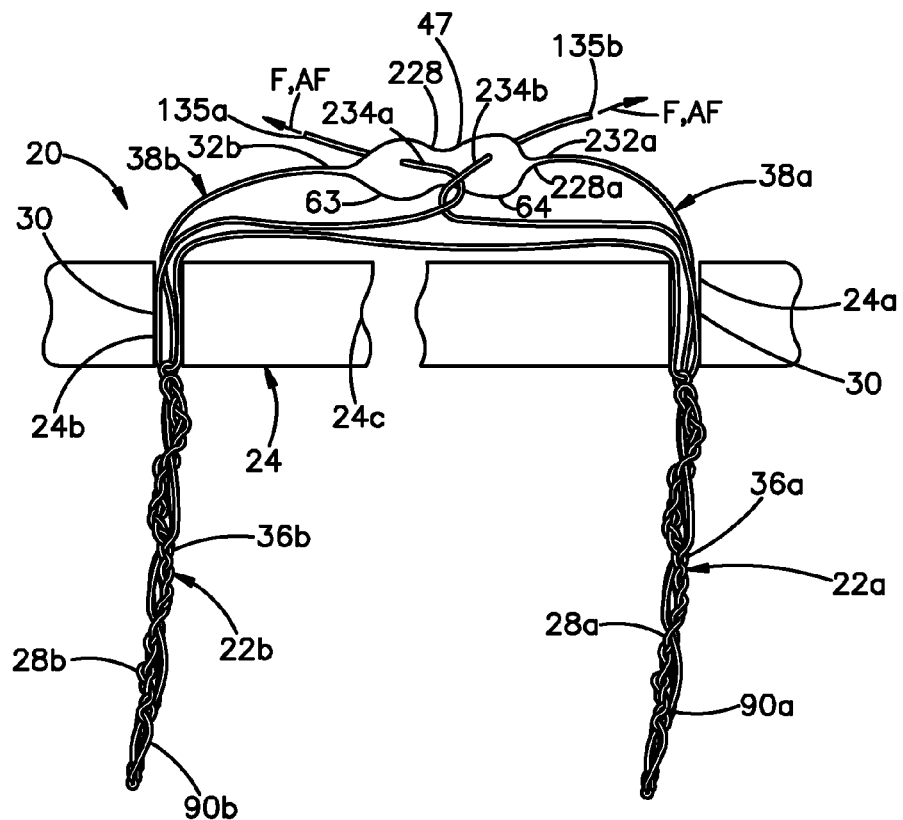
Figure 41C:
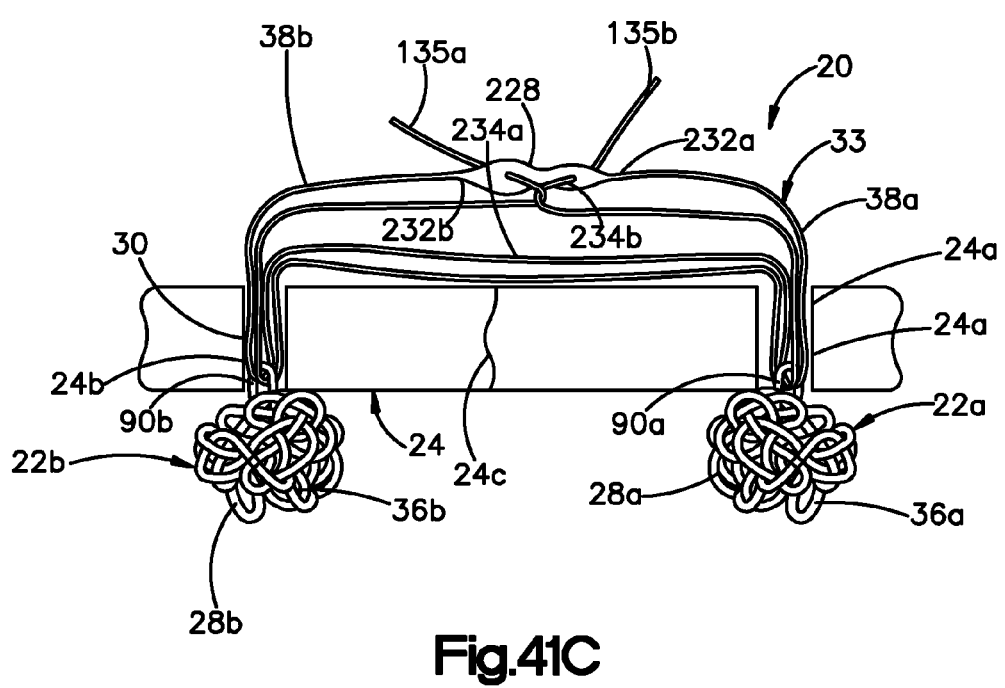

Referring now to FIGS. 41A-C, the auxiliary strand 33 can define the first and second actuation strands 38a and 38b. The first actuation strand 38a defines a first end 232a and an opposed second end 234a, and the second actuation strand 38b defines a first end 232b and an opposed second end 234b. The auxiliary strand 33 further defines a compression member 228, such that the first ends 232a and 232b of the first and second actuation strands 38a and 38b are attached to the compression member 228, for instance to opposed ends 228a and 228b of the compression member 228 at respective attachment locations 230a and 230b that are spaced apart along a direction between the first and second anchor bodies 28a and 28b. In accordance with the one embodiment, the attachment portions 133a and 133b can be woven into the compression member 228, tied to the compression member 228, adhesively attached to the compression member 228, welded to the compression member 228, integral with the woven section, or otherwise attached to the compression member 228 in any manner desired. It should thus be appreciated that the compression member 228 can define a connector member 63 that is integral with the auxiliary strand 33, or can be separate and attached to the auxiliary strand.

Each of the first and second actuation strands 38a and 38b can extend through both of the first and second eyelets 90a and 90 as described above with respect to FIG. 37A, prior to actuating the first and second anchor bodies to their first configurations. For instance, the first actuation strand 38a can extend from the first end 232a, through the first eyelet 90a, through the second eyelet 90b, and the second end 234a can extend through a corresponding opening 236a that extends through the compression member 228. Similarly, the second actuation strand 38b can extend from the second end 232a, through the second eyelet 90b, through the first eyelet 90a, and the second end 234b can extend through a corresponding opening 236b that extends through the compression member 228. The first and second actuation strands 38a and 38b can define respective terminal potions 135a and 135b that extend downstream of the compression member 228. The second ends 234a and 234b of first and second actuation strands 38a and 38b can further be folded around each other at a location proximate to the compression member 228, for instance upstream of the compression member, prior to entering the respective openings 236a and 236b of the compression member 228 and defining the respective terminal portions 135a and 135b. The first terminal portion 135a of the first actuation strand 38a exits the compression member 228 at a first location, and the second terminal portion 135b of the second actuation strand 38b exits the compression member 228 at a second location that can be disposed closer to the first anchor body 28a than the first location. It should be appreciated that the auxiliary strand 33 can define a common strand for the first and second actuation strands 38a and 38b, and also for the compression member 228.

Accordingly, the anchor assembly 20 can define first and second connector members 63a and 63b configured as respective splices 134a and 134b that are defined by the auxiliary strand 33, and in particular defined by the first and second actuation strands 38a and 38b and the compression member 228. In one example, the first splice 134a is defined by the second end 234a of the first actuation strand 38a extending through the compression member 228, for instance at the first opening 236a. The second splice 134b is defined by the second end 234b of the second actuation strand 38b extending through the compression member 228, for instance at the first opening 236a. Thus, the compression member 228 circumscribes a length of the first and second actuation strands 38a and 38b.

During operation, the first and second actuation strands 38a and 38b, and in particular the first and second terminal ends 135a and 135b, can each receive a respective tensile actuation force F that causes the anchor bodies 28a and 28b to actuate from their respective first configurations to their respective expanded configurations. The actuation force F can be applied directly to the first and second actuation strands 38a and 38b at the respective first and second terminal portions 135a and 135b as illustrated, or can be applied to the first and second actuation strands 38a and 38b at a location upstream of the respective splices 134b and 134a.

Next, each of the first and second terminal portions 135a and 135b of the first and second actuation strands 38a and 38b, respectively, can each receive a tensile approximation force AF that causes the first and second actuation strands 38a and 38b to translate through the compression member 228 along a first direction that biases at least one or both of the anchor bodies 28a and 28b toward the other of the anchor bodies 28a and 28b to a biased position so as to approximate the gap 24c. The approximation force AF can be a continuation of the actuation force F if, for instance, the actuation force F is applied to the terminal portions 135a and 135b. It should be appreciated that the approximation force AF places the auxiliary strand 33 under tension, thereby causing the compression member 228 to apply a compressive force both to the first actuation strand 38a at the first splice 134a, and to the second actuation strand 38b at the second splice 134b. The compressive forces applied by the compression member 228 to the first and second actuation strands strand 38a and 38b prevent the first and second actuation strands 38a and 38b from backing out of compression member 228 along a second direction, opposite the first direction, toward the respective first and second anchor bodies 28b.

Accordingly, the first and second splices 134a and 134b each define a sliding member 47 that allows one of the first and second actuation strands 38a and 38b to slide with respect to the other of the first and second actuation strands 38a and 38b so as to approximate the gap 24c, and further define a locking member 64 that secures the first and second actuation strands 38a and 38b to each other, for example with respect with respect to relative movement along a second direction substantially opposite the first direction, which would allow the first and second anchor bodies 28a and 28b to separate.

Figure 42A:
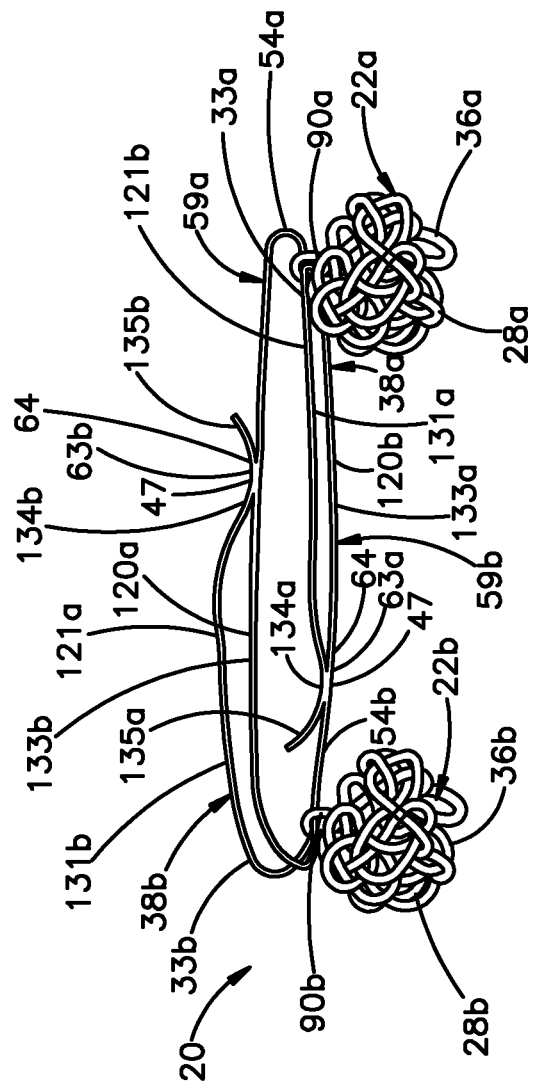
Figure 42B:
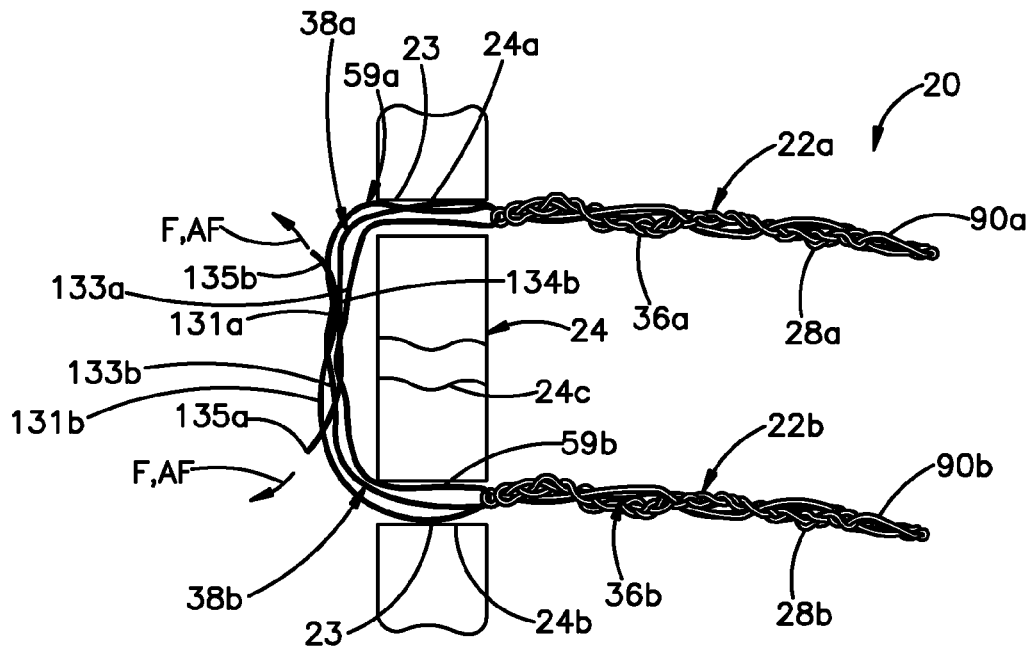
Figure 42C:
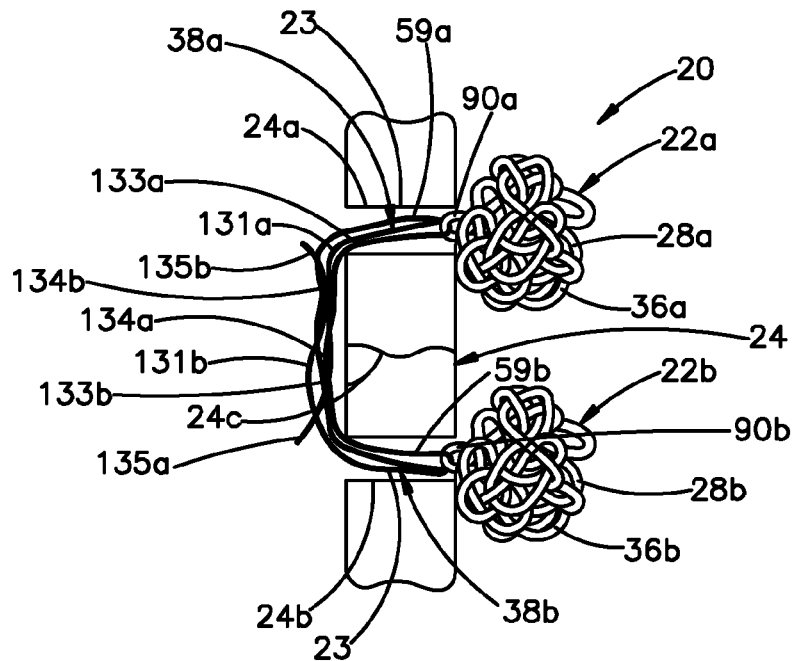

Referring now to FIGS. 42A-C, it should be appreciated that the anchor assembly can include at least one anchor, such as the first and second anchors 22a-b, that include eyelets 90 of the type described above, and can each further include a respective connector strand 59a and 59b that is defined by an end portion, such as the corresponding second end portion 54a and 54b, of the respective anchor body 28a and 28b. The connector strands 59a and 59b are thus integral with the anchor bodies 28a and 28b, and are configured to attach each of the first and second anchors 22a and 22b to the other of the first and second anchors 22a and 22b. For instance, the first connector strand 59a extends from the first anchor body 28a and can be woven through the second eyelet 90b of the second anchor 22b. Accordingly, the first connector strand 59a extends through the second eyelet 90b, and defines a first portion 120a that extends from the first anchor body 28a to the second eyelet 90b, and a second portion 121a that extends out from the second eyelet 90b at a location spaced from the first portion 120a. Likewise, the second connector strand 59b extends from the second anchor body 28b and can be woven through the first eyelet 90a of the first anchor 22a. Accordingly, the second connector strand 59b extends through the first eyelet 90a, and defines a first portion 120b that extends from the second anchor body 28b to the first eyelet 90a, and a second portion 121b that extends out from the first eyelet 90a at a location spaced from the first portion 120b.

Once the second connector strand 59b has been attached to the first eyelet 90a, thereby attaching the first anchor 22a to the second anchor 22b, the first anchor body 28a can be urged along the respective connector strand 59b, and in particular along the first and second portions 120b and 121b from its expanded configuration to its first configuration. Accordingly, the second connector strand 59b can define the first actuation strand 38a of the first anchor 22a. The first portion 120b of the second connector strand 59b can define the attachment portion 133a of the first actuation strand 38a, and the second portion 121b of the second connector strand can define the actuation portion 131a of the first actuation strand 38a. The first actuation strand 38a can therefore define an auxiliary strand 33a with respect to the first anchor body 28a, and can be integral with the second anchor body 28b.

Similarly, once the first connector strand 59a has been attached to the second eyelet 90b, thereby attaching the first anchor 22a to the second anchor 22b, the second anchor body 28b can be urged along the respective connector strand 59a, and in particular along the first and second portions 120a and 121a from its expanded configuration to its first configuration. Accordingly, the first connector strand 59a can define the second actuation strand 38b of the second anchor 22b. The first portion 120a of the first connector strand 59a can define the attachment portion 133b of the second actuation strand 38b, and the second portion 121a of the first connector strand 59a can define the actuation portion 131b of the second actuation strand 38b. The second actuation strand 38b can therefore define an auxiliary strand 33b with respect to the second anchor body 28b, and can be integral with the first anchor body 28a.

The anchor assembly 20 can include at least one connector member 63, such as a first connector member 63a that attaches the actuation portion 131a of the first actuation strand 38a to the attachment portion 133a of the first actuation strand 38a. The anchor assembly 20 can further include a second connector member 63b that attaches the actuation portion 131b of the second actuation strand 38b to the attachment portion 133b of the second actuation strand 38b. For instance, each of the connector members 63a and 63b can be configured as a respective splice 134a and 134b that is defined by the first and second actuation strands 38a and 38b. In one example, one of the attachment portion 133a and the actuation portion 131a of the first actuation strand 38a can be woven or otherwise spliced through the other. Likewise, one of the attachment portion 133b and the actuation portion 131b of the second actuation strand 38b can be woven or otherwise spliced through the other. In accordance with the illustrated embodiment, the actuation portion 131a of the first actuation strand 38a can be woven or otherwise spliced through the attachment portion 133a of the first actuation strand 38a, for instance along a direction from the first anchor body 28a toward the second anchor body 28b, and the actuation portion 131b of the second actuation strand 38b can be woven or otherwise spliced through the attachment portion 133b of the second actuation strand 38b, for instance along a direction from the second anchor body 28b toward the first anchor body 28a.

The actuation portion 131a of the first actuation strand 38a can thus extend through the attachment portion 133a of the first actuation strand 38a so as to define the first splice 134a, such that the attachment portion 133a circumscribes a length of the actuation portion 131a. Similarly, the actuation portion 131b of the second actuation strand 38b can thus extend through the attachment portion 133b of the second actuation strand 38b so as to define the second splice 134b, such that the attachment portion 133b circumscribes a length of the actuation portion 131b. The first and second actuation portions 131a and 131b define respective terminal portions 135a and 135b that extend downstream from the respective splices 134a and 134b.

During operation, the first and second actuation strands 38a and 38b, and in particular the first and second actuation ends 131a and 131b, can each receive a respective actuation force F that causes the anchor bodies 28a and 28b to actuate from their respective first configurations to their respective expanded configurations. The actuation force F can be applied directly to the first and second actuation strands 38a and 38b at the respective first and second actuation portions 131a and 131b, such as at the first and second terminal portions 135a and 135b as illustrated, or can be applied to the first and second actuation strands 38a and 38b at a location upstream of the respective splices 134b and 134a.

Next, each of the first and second actuation portions 131a and 131b of the first and second actuation strands 38a and 38b, respectively, can each receive an approximation force AF that biases at least one or both of the anchor bodies 28a and 28b toward the other of the anchor bodies 28a and 28b to a biased position so as to approximate the gap 24c. The approximation force AF can be a continuation of the actuation force F if, for instance, the actuation force F is applied to the actuation portions 131a and 131b. It should be appreciated that the approximation force AF applied to the first and second actuation portions 131a and 131b places the first and second actuation strands 38a and 38b under tension, such that the first attachment portion 133a applies a first compressive force to the first actuation portion 131a at the first splice 134a, and the second attachment portion 133b applies a second compressive force to the first attachment portion 131b at the second splice 134b. The first compressive force is sufficient to prevent the first actuation portion 131a from backing out of the first splice 134a along a direction toward the respective first anchor body 28a, and the second compressive force is sufficient to prevent the second actuation portion 131b from backing out of the second splice 134b along a direction toward the second anchor body 28b.

Accordingly, the first splice 134a can define a sliding member 47 that allows a first portion of the first actuation strand 38a to translate relative to a second portion of the first actuation strand 38a so as to actuate the respective anchor body 28a from the first configuration to the expanded configuration, and also to approximate the gap 24c, and can further define a locking member 64 that secures the first and second portions of the actuation strand 38a to each other, for example with respect to relative movement that would allow the first and second anchor bodies 28a and 28b to separate. Likewise, the second splice 134b can define a sliding member 47 that allows a first portion of the second actuation strand 38b to translate relative to a first portion of the second actuation strand 38b so as to actuate the respective anchor body 28b from the first configuration to the expanded configuration, and also to approximate the gap 24c, and can further define a locking member 64 that secures the first and second portions of the second actuation strand 38b to each other, for example with respect with respect to relative movement that would allow the first and second anchor bodies 28a and 28b to separate.

Referring now to FIGS. 43A-B, the anchor assembly 20 can include a first anchor 22a including the respective eyelet 90a as described above with reference to FIGS. 37A-D, and the second anchor 22b can include the respective anchor body 28b having an integral actuation strand 28b as described above with respect to FIGS. 36A-B. Thus, as described above, one of the actuation strands 38a and 38b can be integral with the respective anchor body 28a and 28b, and the other of the actuation strands 38b and 38b can be separate from and woven through the respective anchor body 28a and 28b so as to attach the actuation strand to the anchor body. In accordance with the illustrated embodiment, the integral actuation strand 38b of the second anchor 22b defines the auxiliary actuation strand 38a of the first anchor 22a. Thus, as described above with respect to FIGS. 7A-B, the first portion 41 of the second anchor body 22b can define both the respective actuation portion 131b and the attachment portion 133b.

The attachment portion 133b of the second actuation strand 38b can be integral with the attachment portion 133a of the first actuation strand 38a. The first actuation strand 38a can be woven through the anchor body in the manner described above with respect to FIGS. 9A-C, such that the first actuation strand 38a can define a path that the eyelet 90a can travel as the anchor body 28a is actuated from the first configuration to the expanded configuration. Furthermore, the first or actuation portion 131a and the second or attachment portion 133a extend out from the first anchor body 28a and are spaced from each other in the manner described above. The anchor assembly 20 can include a connector member 63 that attaches the first actuation portion 131a to another location of the auxiliary strand 33a, for instance to either or both of the first and second attachment portions 133a and 133b. In accordance with the illustrated embodiment, the connector member 63 attaches the first actuation portion 131a to the second attachment portion 133b. The connector member 63 can be configured in accordance with any of the embodiments described herein suitable to attach the first actuation portion 131a, directly or indirectly, to another target location of the auxiliary strand 33a, such as at least one or both of the first and second attachment portions 133a and 133b.

In accordance with the illustrated embodiment, the connector member 63 is configured as a knot 66 that is defined by the first actuation portion 131a and the target location of the auxiliary strand 33a, which can be the second attachment portion 133b as described above. The first actuation portion 131a can define the post end 68 of the knot 66, such that the terminal portion 135a extends out from the knot 66, and the second actuation strand 38b can define the free end 70 of the knot 66. For instance, the portion of the second actuation strand 38b that is disposed between the knot 66 and the anchor body 28b can define the static portion 70a of the free end 70, and the portion of the second actuation strand 38b that is disposed between the knot 66 and the first anchor body 28a can define the free portion 70b of the free end 70.

During operation, the knot 66 can be disposed in its unlocked configuration such that the post end 68, or the first actuation portion 131a, is slidable through the knot 66 with respect to the free end 70, or the second actuation strand 38b. Thus, the actuation force F can be applied to the first actuation portion 131a, and in particular to the first terminal portion 135a, which induces tension in the first and second actuation strands 38a and 38b, thereby actuating the first and second anchors 22a and 22b, respectively, from their first configurations to their expanded configurations. Application of the approximation force AF to the first actuation portion 131a, and in particular to the first terminal portion 135a, further induces tension in the first and second actuation strands 38a and 38b, thereby biasing the first and second anchors 22a and 22b toward each other and approximating the gap 24c. Thus, the approximation force AF can be a continuation of the actuation force F.

While the connector member 63 illustrated in FIGS. 43A-B is illustrated as a knot 66, it should be appreciated that the connector member 63 can be constructed in accordance with any suitable embodiment as described herein or any suitable alternative embodiment. For instance, as illustrated in FIGS. 43C-D, the connector member 63 can be configured as a splice 134 that is defined by the first and second actuation strands 38a and 38b. In accordance with the illustrated embodiment, the first actuation strand 38a is spliced through the second actuation strand 38b so as to define the splice 134.

In particular, the first actuation portion 131a is spliced through the second actuation strand 38b that extends out from the second anchor body 28b. Thus, as described above, a length of the second actuation strand 38b can circumscribe a length of the first actuation strand 38a. Alternatively, the first actuation strand 38a can be woven through the second actuation strand 38b as many times as desired so as to define the splice 134.

During operation, the first actuation strand 38a, and in particular the terminal portion 135a of the actuation portion 131a, can receive the actuation force F that causes the anchor body 28a to actuate from their respective first configuration to the expanded configurations, and also induces tension in the first and second actuation strands 38a-b. The tension induced in the second actuation strand 38b by the first actuation strand 38a applies an actuation force F to the second actuation strand 38b, thereby causing the respective second anchor body 28b to actuate from the first configuration to the expanded configuration. Next, the first terminal portion 135a can receive an approximation force AF that is communicated along the first actuation strand 38a to the second actuation strand 38b and biases at least one or both of the anchor bodies 28a and 28b toward the other of the anchor bodies 28a and 28b to a biased position so as to approximate the gap 24c. The approximation force AF can be a continuation of the actuation force F if, for instance, the actuation force F is applied to the terminal portions 135a. It should be appreciated that once both the first and second actuation strands 38a and 38b are placed under tension, the second actuation strand 38b applies a compressive force to the first actuation strand 38a at the splice 134 that is sufficient to prevent the first actuation strand 38a from backing out of the second splice 134b along a direction toward the first anchor body 28a.

Accordingly, the second splice 134 defines a sliding member 47 that allows the first actuation strand 38a to translate with respect to the second actuation strand 38b so as to approximate the gap 24c, and further define a locking member 64 that secures the first and second actuation strands 38a and 38b to each other, for example with respect with respect to relative movement that would allow the first and second anchor bodies 28a and 28b to separate.

While certain connector members 63 have been described as being integral with at least one or both of the actuation strands 38a and 38b such that the actuation strands 38a and 38b attach directly to each other, it should be appreciated that the anchor assembly 20 can alternatively or additionally include a connector member 63 configured as an auxiliary connector member 77 that is attached to one or both of the first and second actuation strands 38a and 38b so as to attach the first and second anchors 22 and 22b to each other. The auxiliary connector member 77 can alternatively or additionally attach at least one of the first and second actuation strands 38a and 38b to a connector strand, which can also define an auxiliary connector member 77, or can attach portions of the connector strand to itself so as to attach the first actuation strand 38a to the second actuation strand 38b, for instance when the actuation strands 38a and 38b define eyelets and the connector strand extends through the eyelets. The auxiliary connector member 77 can be made of metal, plastic, suture, or any suitable alternative material.

While the anchor assembly 20 has been described above in accordance with embodiments that illustrated a pair of anchors 22a and 22b attached across a defect, it should be appreciated that the anchor assembly 20 can include as many anchors as desired, that can be attached to each other in any manner and arrangement as desired. For instance, referring to FIG. 44A, the anchor assembly 20 can include multiple pairs of first and second anchors 22 and 22b attached on opposed sides of an gap 24c, which can be the same anatomical defect or different anatomical defects. The first and second anchors 22a and 22b of each pair of anchors can be attached in accordance with any of the embodiments described herein or any suitable alternative embodiment. Alternatively, referring to FIG. 44B, a plurality of pairs of first and second anchors 22a and 22b can be implanted in the target anatomical structure 24 across an gap 24c, and the anchor assembly 20 can include a connector member 63 configured to attach each of the anchors 22 and 22b to each other at a common hub 240. The connector member 63 can be configured as any suitable connector member of the type described herein or any suitable alternative connector member that can, for instance, attach at least one up to all of attachment portions of the anchors 22a and 22b and connector strands of the anchors 22a and 22b.

Referring now to FIG. 45A, a fixation kit 250 can include at least one anchor 22 and an insertion instrument 252 configured to inject the anchor 22 in the anatomical structure 24 as illustrated in FIGS. 1A-B. It should be appreciated that the fixation kit 250 can include at least one or more up to all of the anchors 22 described herein alone, attached to each other, or configured to be attached to each other in accordance with any of the embodiments describer herein. The insertion instrument 252 can include a cannula 254 with a central opening 256 and a plunger or push rod 258 which is coaxially insertable into the central opening 256. The cannula 254 has an acuminated tip 260 and a slot 268 extending axially from the tip 260.

Further, the insertion instrument 252 comprises a handle 262 with an operating lever 264. One end of the handle 262 is detachably attached to the cannula 254 and the operating lever 264 is detachably attached to the plunger 258. The outer diameter of the plunger 258 corresponds to the inner diameter of the central opening 256 of the cannula 254. At the rear end the central opening of the cannula 254 is conically configured in such a manner that it enlarges towards the rear end of the cannula 254 at an inlet 266. Thus, the anchor body 28 of the anchor 22 can be inserted in its first configuration through the conlical inlet 266 and into the central opening 256 of the cannula 254, such that the anchor body 28 can be compressed.

When the anchor body 28 is pressed out of the cannula 254 by pressing the plunger 258 forward the anchor body 28 can radially expand, for instance in the second direction 35 (see FIGS. 1A-B) in such a manner that it can be retained by the front face of the cannula 254 when a tensile force is exerted onto the actuation strand 38 in order to tighten the anchor body 28. The actuation strand 38 is led through the slot 268 so that it can be led alongside the cannula 254 when the cannula 254 is inserted into the anatomical structure 24. At the free end of the actuation strand 38 a needle 270 is attached that can be used for finishing a surgical procedure when the anchor body 28 of the anchor 22 has been actuated to the expanded configuration and secured to the anatomical structure 24.

Referring to FIG. 45B, the plunger 258 can have an outer diameter or alternative cross-sectional dimension that is less than the inner diameter or cross-sectional dimension of the central opening 256 of the cannula 254. The actuation strand 38 of the anchor 22 can thus be led through the central opening 256 of the cannula 254 when the plunger 258 is inserted in the central opening 256 of the cannula 254. By actuating the operating lever 264 at the handle 262, the plunger 258 can push the anchor 22 forward in the cannula 254 as far as the anchor body 28 exits from the central opening 256 at the tip 260 of the cannula 254. Once the anchor body 28 is positioned in the central opening 256 the actuation strand 38 can be pulled backward at the rear end of the cannula 254 so that the anchor body 28 can be actuated in the cavity 256 to its expanded configuration.

Referring to FIGS. 46A-D, the plunger 258 can define a central bore 272 where the actuation strand 38 of the anchor 22 can be led through. Further, the cannula 254 has a first longitudinal aperture 274 extending between the tip 260 and the rear end of the cannula 254 so that the cannula 254 is slotted over its entire length. A second longitudinal aperture 276 extends on the plunger 258 between the front end and the rear end of the plunger 258 so that the plunger 258 is slotted over its entire length as well. As shown in FIG. 46B when the cannula 254 is in a first rotative position relative to the plunger 258 the first longitudinal aperture 274 of the cannula 254 is diametrically opposite to the second longitudinal aperture 276 of the plunger 258. In the first rotative position of the cannula 254 the actuation strand 38 of the anchor 22 is retained by the central bore 272. Once the anchor body 28 of the anchor 22 has been fixed in a cavity of a patient's body by pulling the actuation strand 38 of the anchor 22 backward the cannula 254 can be rotated into a second rotative position relative to the plunger 258 (FIG. 46D). In this second rotative position of the cannula 254 the first longitudinal aperture 274 of the cannula 254 is aligned with the second longitudinal aperture 276 of the plunger 258 and the insertion instrument 252 can be released from the actuation strand 38 of the anchor 22.

FIGS. 47A-D illustrate the handle 262 and the attachment of the cannula 254 to the handle 262 of an embodiment of the insertion instrument 252 of FIG. 45A to 46D. The upper end portion of the handle 262 comprises a groove 278 into which the cannula 254 can be inserted and a spring member such as a leaf spring 279 so as to provide a releasable snap lock configured to releasably attach the cannula 254 to the handle 262. The rear end of the plunger 258 can be snapped into a resilient fork 280 arranged at the upper end of the operating lever 264.

Referring to FIG. 48, the insertion instrument 52 can include a depth control tube 282 slid over the cannula 254 and a clamping element 284. The insertion instrument 52 is pre-operatively prepared by inserting the anchor 22 into the cannula 254 and inserting the plunger 258. Once the anchor 22 and the plunger 258 have been inserted any one of a plurality of clamping elements 284 is attached to the rear end of the insertion instrument 252 by snapping a first tab 286 onto the rear portion of the cannula 254. To prevent an unintended displacement of the plunger 258 relative to the cannula 254 the clamping element 284 comprises a second tab 288 which abuts the rear end of the cannula 254 and a third tab 290 which abuts an enlarged portion at the rear end of the plunger 258. Before using the insertion instrument 252, the clamping element 284 is removed from the cannula 254 and the handle 262 is attached to the cannula 254, and the insertion instrument 252 can be operated in the manner described herein.

The embodiments described in connection with the illustrated embodiments have been presented by way of illustration, and the present invention is therefore not intended to be limited to the disclosed embodiments. Furthermore, the structure and features of each the embodiments described above can be applied to the other embodiments described herein, unless otherwise indicated. Accordingly, those skilled in the art will realize that the invention is intended to encompass all modifications and alternative arrangements included within the spirit and scope of the invention, for instance as set forth by the appended claims.

We claim:

1. An anchor assembly configured to be anchored to an anatomical location, the anchor assembly comprising:

an anchor including an anchor body that defines an expandable portion, the expandable portion defining a direction of elongation, the anchor body defining an eyelet and a plurality of loops that are spaced from the eyelet along the direction of elongation, the plurality of loops defining a respective plurality of openings that extend through the expandable portion and are spaced from each other substantially along the direction of elongation, the expandable portion configured to be actuated from a first configuration, wherein the expandable portion defines a first maximum thickness along a second direction that is angularly offset from the direction of elongation, to an expanded configuration, wherein the expandable portion defines a second maximum thickness along the second direction that is greater than the first maximum thickness; and the anchor further including an actuation member defining a connection location that is coupled to the eyelet when the expandable portion is in the first configuration, and first and second portions that extend from the connection location along the direction of elongation, the actuation member configured such that both of the first and second portions extend from the eyelet through each of at least two of the plurality of openings, thereby defining a path along which the actuation member extends through each of the at least two of the plurality of openings when the expandable portion is in the first configuration, and at least one of the first and second portions of the actuation member configured to receive an actuation force and, in response to the actuation force, pull the eyelet through the expandable portion body along the path, so as to actuate the expandable portion from the first configuration to the expanded configuration.

2. The anchor assembly as recited in claim 1, wherein the anchor body comprises a substrate that is at least one of braided, knitted and woven materials that define the plurality of openings.

3. The anchor assembly as recited in claim 2, wherein the substrate comprises an anchor body strand.

4. The anchor assembly as recited in claim 3, wherein the anchor body strand comprises a strand of suture.

5. The anchor assembly as recited in claim 3, wherein each of the first and second portions of the actuation member extend alternatingly through every other one of the plurality of the openings along the direction of elongation.

6. The anchor assembly as recited in claim 1, wherein the expandable portion collapses along the direction of elongation as the expandable portion is actuated from the first configuration to the expanded configuration.

7. The anchor assembly as recited in claim 1, wherein the actuation member comprises an actuation strand.

8. The anchor assembly as recited in claim 1, wherein the eyelet extends out the anchor body when the anchor is the expanded configuration.

9. The anchor assembly as recited in claim 8, wherein the eyelet is defined by a knot at one end of the anchor body.

10. The anchor assembly as recited in claim 8, wherein the anchor body is stitched through itself so as to define the eyelet.

11. The anchor assembly as recited in claim 8, wherein the anchor body is welded to itself so as to define the eyelet.

12. The anchor assembly as recited in claim 8, wherein the actuation member is an actuation strand that defines first and second ends, and the connection location is a fold disposed between the first and second ends, wherein the fold extends through the eyelet.

13. The anchor assembly as recited in claim 12, wherein each of the first and second ends extend alternatingly through every other one of the plurality of the openings along the direction of elongation.

14. The anchor assembly as recited in claim 12, wherein the actuation force comprises a tensile force applied to at least one of the first and second ends of the actuation strand that causes the eyelet to be pulled through the anchor body along the path and extend out the anchor body.

15. The anchor assembly as recited in claim 14, wherein the eyelet is configured to be attached to another strand that connects the anchor body to a second anchor body.

16. The anchor assembly as recited in claim 1, wherein the expandable portion defines opposed proximal and distal ends, and the direction of elongation extends linearly between the proximal and distal ends.

17. The anchor assembly as recited in claim 16, wherein the expandable portion is elongate along a central axis.

18. The anchor assembly as recited in claim 17, wherein at least a portion of the central axis is offset with respect to the direction of elongation.

19. The anchor assembly as recited in claim 1, wherein the anchor is a first anchor, the actuation member of the first anchor is a first actuation strand, the anchor body of the first anchor is a first anchor body, and the anchor assembly further comprises a second anchor including 1) a second anchor body that extends substantially along a second direction of elongation, the second anchor defining a second plurality of openings that extend through the second anchor body, the second plurality of openings spaced along the second direction of elongation, and 2) a second actuation strand that is woven through at least two of the second plurality of openings,
wherein an actuation force applied to the second actuation strand along a direction substantially along the second direction of elongation causes the second anchor body to collapse along the second direction of elongation and expand along a direction angularly offset with respect to the second direction of elongation, so as to expand the second anchor from a respective first configuration to a respective expanded configuration.

20. The anchor assembly as recited in claim 19, wherein the first actuation strand is attached to the second actuation strand.

21. The anchor assembly as recited in claim 20, wherein the first actuation strand is integral with the second actuation strand.

22. The anchor assembly as recited in claim 20, wherein the first actuation strand is separate from and attached to the second actuation strand.

23. The anchor assembly as recited in claim 19, further comprising a connector member that attaches the first anchor to the second anchor.

24. The anchor assembly as recited in claim 23, wherein the connector member defines a sliding member that allows one of the first and second actuation strands to translate relative to the other of the first and second actuation strands through the connector member.

25. The anchor assembly as recited in claim 23, wherein the connector member defines a locking member that prevents the first and second actuation strand translating relative to the other of the first and second actuation strands through the connector member.

26. The anchor assembly as recited in claim 23, wherein the connector member is defined by the first and second actuation strands.

27. The anchor assembly as recited in claim 23, wherein the eyelet of the first anchor body is a first eyelet, and the second anchor body comprises a second eyelet and a second plurality of loops that are spaced from the second eyelet along the second direction of elongation, the second plurality of loops defining the respective second plurality of openings, and the first and second actuation strands are woven through the respective first and second anchor bodies and attached to the first and second eyelets.

28. The anchor assembly as recited in claim 27, wherein the first actuation strand is integral with the second actuation strand.

29. The anchor assembly as recited in claim 27, wherein the first actuation strand comprises a first actuation portion and a first attachment portion that each extend out from the first anchor body, and the second actuation strand comprises a second actuation portion and a second attachment portion that each extend out from the second anchor body when in respective expandable portions of each anchor are in the respective expanded configurations.

30. The anchor assembly as recited in claim 29, wherein the first attachment portion is integral with the second attachment portion.

31. The anchor assembly as recited in claim 29, wherein the connector member attaches the first actuation portion and the second actuation portion.

32. The anchor assembly as recited in claim 31, wherein the connector member is defined by the first actuation portion and the second actuation portion.

33. The anchor assembly as recited in claim 32, wherein the connector member comprises a knot that is defined by the first actuation portion and the second actuation portion.

34. The anchor assembly as recited in claim 33, wherein the knot that can be actuated between an unlocked configuration whereby the at least one of the first and second actuation portions is translatable through the knot with respect to the other of the first and second actuation portions, and a locked configuration whereby the first and second actuation portions are translatably fixed to each other through the knot.

35. The anchor assembly as recited in claim 31, wherein the first and second actuation portions are each configured to receive respective actuation forces that causes the respective first and second anchors to actuate from the respective first configuration to the expanded configuration.

36. The anchor assembly as recited in claim 19, further comprising a connector strand attached between the first and second anchors.

37. The anchor assembly as recited in claim 36, wherein the connector strand defines a first portion and a second portion spaced from the first portion, the anchor assembly comprising a sliding member that allows one of the first and second portions to translate relative to the other of the first and second portions so as to apply a force to at least one of the anchors that biases the anchor toward the other anchor.

\* \* \* \* \*